US008252551B2

(12) United States Patent
Sleep et al.

(10) Patent No.: US 8,252,551 B2
(45) Date of Patent: Aug. 28, 2012

(54) 2-MICRON FAMILY PLASMID AND USE THEREOF

(75) Inventors: Darrell Sleep, West Bridgford (GB); Christopher John Arthur Finnis, Lenton (GB)

(73) Assignee: Novozymes Biopharma DK A/S, Bagsvaerd (DK)

( * ) Notice: Subject to any disclaimer, the term of this patent is extended or adjusted under 35 U.S.C. 154(b) by 770 days.

(21) Appl. No.: 10/584,486

(22) PCT Filed: Dec. 23, 2004

(86) PCT No.: PCT/GB2004/005435
§ 371 (c)(1),
(2), (4) Date: Apr. 9, 2007

(87) PCT Pub. No.: WO2005/061719
PCT Pub. Date: Jul. 7, 2005

(65) Prior Publication Data
US 2008/0261861 A1    Oct. 23, 2008

(30) Foreign Application Priority Data
Dec. 23, 2003 (GB) .................................. 0329722.3

(51) Int. Cl.
*C12P 21/02* (2006.01)
(52) U.S. Cl. ............... 435/69.1; 435/91.41; 435/91.42; 435/254.21; 435/320.1
(58) Field of Classification Search .................. None
See application file for complete search history.

(56) References Cited

U.S. PATENT DOCUMENTS

| | | | |
|---|---|---|---|
| 4,302,386 A | 11/1981 | Stevens | |
| 4,937,193 A | 6/1990 | Hinchliffe | |
| 5,571,691 A | 11/1996 | Conneely | |
| 5,637,504 A | 6/1997 | Hinchliffe | |
| 5,646,037 A | 7/1997 | Buxton | |
| 5,728,553 A | 3/1998 | Goodey | |
| 5,773,245 A | 6/1998 | Wittrup | |
| 5,783,385 A | 7/1998 | Treco | |
| 6,291,205 B1 | 9/2001 | Tuite | |
| 6,451,559 B1 | 9/2002 | Schreier | |
| 6,939,676 B2 | 9/2005 | Burke | |
| 2003/0221201 A1 | 11/2003 | Prior | |
| 2003/0226155 A1 | 12/2003 | Sadeghi | |
| 2007/0275889 A1 | 11/2007 | Sleep | |
| 2008/0206811 A1 | 8/2008 | Shodai | |
| 2008/0261861 A1 | 10/2008 | Sleep | |

FOREIGN PATENT DOCUMENTS

| | | |
|---|---|---|
| EP | 0060057 | 9/1982 |
| EP | 0251744 | 1/1988 |
| EP | 0286424 | 10/1988 |
| EP | 0293793 | 12/1988 |
| EP | 0073646 | 5/1989 |
| EP | 0319067 | 7/1989 |
| EP | 0366400 | 5/1990 |
| EP | 0464590 | 1/1992 |
| EP | 0509841 | 10/1992 |
| EP | 0258067 | 3/1993 |
| EP | 0746611 | 12/1993 |
| EP | 0431880 | 2/1996 |
| EP | 0387319 | 3/1996 |
| JP | 63-039576 | 1/1988 |
| JP | 01-503275 | 10/1988 |
| JP | 910114047 | 4/1991 |
| JP | 07-502723 | 8/1992 |
| JP | 08-504561 | 11/1993 |
| JP | 07-508881 | 12/1993 |
| JP | 10-127294 | 3/1998 |
| JP | 2001-514490 | 8/1998 |
| WO | WO 89/07140 | 8/1989 |
| WO | WO 90/01063 | 2/1990 |
| WO | WO 90/13653 | 11/1990 |
| WO | WO 92/04367 | 3/1992 |
| WO | 9403617 A1 | 2/1994 |
| WO | WO 94/04687 | 3/1994 |
| WO | WO 95/23857 | 9/1995 |
| WO | WO 95/33833 | 12/1995 |
| WO | WO 96/37515 | 11/1996 |
| WO | 9856928 A1 | 12/1998 |
| WO | WO 99/00504 | 1/1999 |
| WO | WO 00/41477 | 7/2000 |
| WO | WO 00/44772 | 8/2000 |
| WO | WO 01/79258 | 10/2001 |
| WO | WO 01/79271 | 10/2001 |
| WO | WO 01/79442 | 10/2001 |
| WO | WO 01/79443 | 10/2001 |
| WO | WO 01/79444 | 10/2001 |
| WO | WO 01/79480 | 10/2001 |
| WO | 03066085 A1 | 8/2003 |
| WO | WO 03/066824 | 8/2003 |
| WO | 2004015113 A2 | 2/2004 |

(Continued)

OTHER PUBLICATIONS

Jayaram et al., PNAS vol. 80, pp. 7264-7268 (1983).*
Sleep et al., "Yeast 2 mum plasmid copy number is elevated by a mutation in the nuclear gene UBC4", Yeast, vol. 18, No. 5, pp. 403-421 (2001).
Volkert et al., Microbiological Reviews, vol. 53, pp. 299-317 (1989).
Painting et al., Journal of Applied Bacteriology, vol. 56, pp. 331-335 (1984).
Futcher, Yeast, vol. 4, pp. 27-40 (1988).
Murray et al., J. Mol.Biol., vol. 200, No. 3, pp. 601-607 (1988).
Toh-e et al., Basic Life Science, vol. 40, p. 425 (1986).
Volkert & Broach, Cell, vol. 46, pp. 541-550 (1986).

(Continued)

*Primary Examiner* — Jim Ketter
(74) *Attorney, Agent, or Firm* — Michael W. Krenicky

(57) ABSTRACT

The present invention provides a 2 μm-family plasmid comprising a polynucleotide sequence insertion, deletion and/or substitution between the first base after the last functional codon of at least one of either a REP2 gene or an FLP gene and the last base before the FRT site in an inverted repeat adjacent to said gene.

51 Claims, 79 Drawing Sheets

FOREIGN PATENT DOCUMENTS

| | | |
|---|---|---|
| WO | WO 2004/042036 | 5/2004 |
| WO | 2004083245 A2 | 9/2004 |
| WO | 2005078105 A2 | 8/2005 |
| WO | 2006067511 A1 | 6/2006 |

OTHER PUBLICATIONS

Hartley and Donelson, Nature, vol. 286, pp. 860-865 (1980).
Cameron et al., Nucleic Acid Research, vol. 4, No. 5, pp. 1429-1448 (1977).
Kikuchi, Cell, vol. 35, pp. 487-493 (1983).
Livingston & Hahne, Proc. Natl. Acad. Sci. USA, vol. 76, No. 8, pp. 3727-3731 (1979).
Kerry-Williams et al., Yeast, vol. 14, pp. 161-169 (1998).
Mead et al., Molecular & General Genetics, vol. 205, pp. 417-421 (1986).
Futcher & Cox, J. Bacteriol., vol. 157, No. 1, pp. 283-290 (1984).
Bachmair & Ruis, Monatshefte fur Chemie, vol. 115, pp. 1229-1235 (1984).
Broach & Hicks, Cell, vol. 21, pp. 501-508 (1980).
Sutton & Broach, Mol. Cell. Biol., vol. 5, No. 10, pp. 2770-2780 (1985).
Senecoff et al., Proc. Natl. Sci. Acad. USA, vol. 82, pp. 7270-7274 (1985).
Rose & Broach, Methods Enzymol., vol. 185, p. 234-279 (1990).
Sengupta et al., J. Bacteriol., vol. 183, No. 7, pp. 2306-2315 (2001).
Reynolds et al., Mol. Cell. Biol., vol. 7, No. 10, pp. 3566-3573 (1987).
Jayaram, Proc. Natl. Sci. Acad. USA, vol. 82, pp. 5875-5879 (1985).
Meyer-Leon et al., Cold Spring Harbor Symposia on Quantitative Biology, vol. 49, p. 797 (1984).
Prasad et al., Proc. Natl. Sci. Acad. USA, vol. 84, pp. 2189-2193 (1987).
Chen et al., Cell, vol. 69, p. 647 (1992).
Grainge et al., J. Mol. Biol., vol. 314, pp. 717-733 (2001).
Chinery & Hinchliffe, Curr. Genet., vol. 16, pp. 21-25 (1989).
Sleep et al., Biotechnology, vol. 9, No. 2, pp. 183-187 (1991).
Bijvoet et al., Yeast, vol. 7, pp. 347-356 (1991).
Broach et al., Cell, vol. 16, pp. 827-839 (1985).
Robinson et al., Nature Bio/Technology, vol. 12, pp. 381-384 (1994).
Shusta et al., Nature Biotechnology, vo. 16, pp. 773-777 (1998).
Parekh & Wittrup, Biotechnol. Prog., vol. 13, pp. 117-122 (1997).
Bao et al., Yeast, vol. 16, pp. 329-341 (2000).
Bao & Fukuhara, Gene, vol. 272, pp. 103-110 (2001).
Gerbaud & Guerineau, Curr. Genet., vol. 1, pp. 219-228 (1980).
Holm, Cell, vol. 29, pp. 585-594 (1982).
Valkonen et al., Appl. Environ. Microbiol., vol. 69, pp. 2065-2072 (2003).
Hjelmqvist et al., Gen Biol. vol. 3, No. 6 (2002).
Hillson et al., Methods Enzymol., vol. 107, pp. 281-294 (1984).
Freedman, Trends Biochem Sci., vol. 9, No. 10, pp. 438-441 (1984).
Roth & Pierce, Biochemistry, vol. 26, No. 14, pp. 4179-4182 (1987).
Hayano et al., FEBS Letters vol. 377, pp. 505-511 (1995).
Solovyov et al., J Biol Chem., vol. 297, No. 33, pp. 34095-34100 (2004).
Scherens et al., Yeast, vol. 7, pp. 185-193 (1991).
Farquhar et al., Gene, vol. 108, pp. 81-89 (1991).
Freedman et al., Biochem. Soc. Symp., vol. 55, pp. 167-192 (1989).
Creighton et al., J. Mol. Biol., vol. 142, pp. 43-62 (1980).
Gilbert, Biochemistry, vol. 28, pp. 7298-7305 (1989).
Lundstrom & Holmgren, J. Biol. Chem., vol. 265, No. 16, pp. 9114-9120 (1990).
Edman et al., Nature, vol. 317, pp. 267-270 (1985).
Yamauchi et al., Biochem Biophys Res. Com., vol. 146, pp. 1485-1492 (1987).
Pihlajaniemi et al, EMBO J., vol. 6, No. 3, pp. 643-649 (1987).
Ngosuwan et al., J. Biol. Chem., vol. 278, No. 9, pp. 7034-7042 (2003).
Seedorf & Silver, Proc. Natl. Acad. Sci. USA, vol. 94, pp. 8590-8595 (1997).
Ueta et al., J. Biol. Chem., vol. 275, No. 50, pp. 50120-50127 (2003).
Mosammaparast et al., J. Biol. Chem. vol. 277, No. 1, pp. 862-868 (2002).
Chow et al., J. Cell. Sci, vol. 101, No. 3, pp. 709-719 (1992).
Peters, All Abuot Albumin Biochem. Gen. Med applns., Acad Press, pp. 170-181 (1996).
Dockal et al., J. Biol Chem, vol. 274, pp. 29303-29310 (1999).
Peters, All Abuot Albumin Biochem. Gen. Med applns., Acad Press, Table 2-4, p. 36 (1996).
Testa, Proteins of Iron Metabolism (2002).
Mason et al., Biochemistry, vol. 32, pp. 5472-5479 (1993).
Mason et al., J. Biochem, vol. 330, pp. 35-40 (1998).
Mason et al., Prot. Express Purif. vol. 8, pp. 119-125 (1996).
Mason et al., Prot. Express Purif. vol. 2, pp. 214-220 (1991).
Shin et al., Proc. Natl. Acad. Sci USA, vol. 92, pp. 2820-2824 (1995).
Ali et al., J. Biol. Chem., vol. 274, pp. 24066-24073 (1999).
Mason et al., Biochemistry, vol. 41, pp. 9448-9454 (2002).
Irie et al., Gene, vol. 108, No. 1, pp. 139-144 (1991).
Irie et al., Mol Gen Genet, vol. 225, No. 2, pp. 257-265 (1991).
Pemberton et al., Curr Op Biotechnol, vol. 10, pp. 392-399 (1998).
Kaska et al., J Biochem, vol. 268, pp. 63-68 (1990).
Parkkonen et al., J Biochem, vol. 256, pp. 1005-1011 (1998).
Ryan and Wente, Curr Op Cell Biol, vol. 12, pp. 361-371 (2000).
Cohen et al., Proc. Natl. Acad. Sci USA, vol. 69, No. 8, pp. 2110-2114 1972).
Beggs, Nature, vol. 275, pp. 104-109 (1978).
Piper and Curran, Curr Genet., vol. 17, pp. 119-123 (1990).
Southern, J. Mol Biol., vol. 98, pp. 503-517 (1975).
Ito et al., J Bacteriol., vol. 153, No. 1, pp. 163-168 (1983).
Crouzet and Tuite, Mol Gen Genet., vol. 210, pp. 581-583 (1987).
Gietz and Sugino, Gene, vol. 74, pp. 527-534 (1988).
Sleep, Biotechnology, vol. 8, pp. 42-46 (1990).
Rao et al., Antimic Agents Chemoth, vol. 24, No. 5, pp. 689-695 (1983).
Sun et al., Microbiology, vol. 145, pp. 2221-2227 (1999).
MacNeil et al., Gene, vol. 111, pp. 61-68 (1992).
Toyn et al., Yeast, vol. 16, pp. 553-560 (2000).
Freedman et al., Biochem Soc Transactions, vol. 16, pp. 96-99 (1988).
Thompson et al., Nucleic Acid Res, vol. 22, No. 22, pp. 4673-4680 (1994).
Chen et al., Cell, vol. 69, pp. 647-658 (1992).
Laboissiere et al., J Biol Chem., vol. 270, pp. 28006-28009 (1995).
Kramer et al., J Biochem, vol. 357, pp. 83-95 (2001).
Bulleid and Freedman, Nature, vol. 335, No. 13, pp. 649-651 (1988).
Rothman, Cell, vol. 59, pp. 591-601 (1989).
Kim et al., Proc Natl Acad Sci USA, vol. 95, pp. 12860-12865 (1998).
Glover and Lindquist, Cell, vol. 94, pp. 73-82 (1998).
Khan et al., Int J Biol Macromol., vol. 30, pp. 171-178 (2002).
Hoheisel, Biotechniques, vol. 17, pp. 456-460 (1994).
Isoyama et al., J Biol Chem, vol. 276, No. 24, pp. 21863-21869 (2001).
Vigentini et al., FEMS, vol. 5, pp. 647-652 (2005).
Vaux et al., Nature, vol. 345, pp. 495-502 (1990).
Semenza et al., Cell, vol. 61, pp. 1349-1357 (1990).
Schein, Nature Biotechnol., vol. 7, pp. 1141-1149 (1989).
Pelham, Trends Biotechnol., vol. 15, pp. 483-486 (1990).
Munro & Pelham, Cell, vol. 48, pp. 899-907 (1987).
Lewis & Pelham, Nature, vol. 348, pp. 162-163 (1990).
Fischer & Schmid, Biochemistry, vol. 29, pp. 2205-2212 (1990).
Freedman, Cell, vol. 57, pp. 1069-1072 (1989).
Freedman, Nature, vol. 329, pp. 196-197 (1987).
Reynolds et al., Mol. Cell Biol,. vol. 7, No. 10, pp. 3566-3573 (1987).
Hawkins and Freedman, J. Biochem., vol. 275, pp. 335-339 (1990).
Roth and Pierce, Biochemistry, vol. 26, pp. 4179-4182 (1987).
Cheng et al., J Biol Chem., vol. 262, No. 23, pp. 11221-11227 (1987).
Harris and Aisen, Iron Carrier and Iron Proteins, vol. 5 (1991).
Smith et al., Science, vol. 229, pp. 1219-1224 (1985).
Broach et al., Cold Spring Harbor Symp Quant Biol., vol. 47, pp. 1165-1174 (1982).
Williamson, Yeast, vol. 1, pp. 1-14 (1985).
Berent et al., Biotechniques, vol. 3, p. 208 (1985).
Becker and Craig, Eur J Biochem., vol. 219, pp. 11-23 (1994).
Becker and Guarente, Methods Enzymol., vol. 194, pp. 182-187 (1990).
Lee, Biotechniques, vol. 12, p. 677 (1992).

Geetha-Habib et al., Cell, vol. 54, pp. 1053-1060 (1988).
Kieser et al., Practical Streptomyces Genetics (2000).
Sambrook et al., Laboratory Manual, 3$^{rd}$ ed. (2001).
Utatsu et al., Journal of Bacteriology, vol. 169, No. 12, pp. 5537-5545 (1987).
Database NCBI—Accession No. X02398 *Zygosaccharomyces rouxii* plasmid pSR1 (Oct. 23, 2008).
Database NCBI—Accession No. X02608 *Zygosaccharomyces bisporus* plasmid pSB3 (Oct. 23, 2008).
Database NCBI—Accession No. M18274 Yeast (*Z.bailii*) plasmid pSB2, complete genome (Apr. 27, 1993).
Database NCBI—Accession No. X03961 *Kluyveromyces drosophilarum* circular plasmic pKD1 (B form) (Oct. 23, 2008).
Database NCBI—Accession No. NC002055 *Nosema ceranae* BRL01 Nc002055, whole genome shotgun sequence (Jun. 9, 2009).
Database NCBI—Accession No. NC002054 *Nosema ceranae* BRL01 Nc002054, whole genome shotgun sequence (Jun. 9, 2009).
Database NCBI—Accession No. NC001398 *Nosema ceranae* BRL01 Nc001398, whole genome shotgun sequence (Dec. 8, 2008).
Database NCBI—Accession No. J01347 *Saccharomyces cerevisiae* 2 micron circle plasmid, complete sequence (Oct. 18, 2007).
Database NCBI—Accession No. CAA38402 protein disulphide isomerase [*Saccharomyces cerevisiae*] (Apr. 18, 2005).
Database NCBI—Accession No. CAA42373 protein disulfide-isomerase precursor [*Saccharomyces cerevisiae*] (Oct. 23, 2008).
Database NCBI—Accession No. BAA00723 protein disulfide isomerase [*Saccharomyces cerevisiae*] (Jun. 7, 2009).
Database Swissprot—Accession No. P14639 Serum albumin precursor—*Ovis aries* (Sheep) (May 5, 2009).
Database Swissprot—Accession No. P02769 [ALBU_BOVIN] Serum albumin (Jun. 16, 2009).
Database Swissprot—Accession No. P08835 Serum albumin precursor—*Sus scrofa* (Pig) (May 5, 2009).
Database Swissprot—Accession No. P49822 Serum albumin precursor—*Canis familiaris* (Dog) (Jun. 16, 2009).
Database NCBI—Accession No. NC001135 *Nosema ceranae* BRL01 Nc001135, whole genome shotgun sequence (Jun. 9, 2009).
Database Swissprot—Accession No. O73860 [OVAL_MELGA] Ovalbumin (Jun. 16, 2009).
Database Swissprot—Accession No. P49064 Serum albumin precursor—*Felis silvestris catus* (Cat) (May 5, 2009).
Database Swissprot—Accession No. P19121 Serum albumin precursor—*Gallus gallus* (Chicken) (Jun. 16, 2009).
Database Swissprot—Accession No. P01012 Ovalbumin—*Gallus gallus* (Chicken) (Jun. 16, 2009).
Database Swissprot—Accession No. P39090 Alpha-1B-glycoprotein—*Equus asinus* (Donkey) (Jun. 16, 2009).
Database Swissprot—Accession No. P35747 Serum albumin precursor—*Equus caballus* (Horse) (Jun. 16, 2009).
Database Swissprot—Accession No. Q28522 Serum albumin precursor—*Macaca mulatta* (Rhesus macaque) (May 5, 2009).
Database Swissprot—Accession No. O89020 Afamin precursor—*Mus musculus* (Mouse) (Jun. 16, 2009).
Database Swissprot—Accession No. P36953 Afamin precursor—*Rattus norvegicus* (Rat) (Jun. 16, 2009).
Database Swissprot—Accession No. P49065 Serum albumin precursor—*Oryctolagus cuniculus* (Rabbit) (May 5, 2009).
Hollenberg, Current Topics in Microbiology and Immunobiology, vol. 96, p. 119 (1982).
Sadowski, Mechanisms of Yeast Recombination, Current Communications in Molecular Biology, pp. 7-10 (1986).
Sherman et al., Methods in Yeast Genetics, A Laboratory Manual (1986).
Weeke B, A Manual of Quantitative Immunoelectrophoresis, vol. 2 (1976).
Clements et al., "Secretion of human epidermal growth factor from *Saccharomyces cerevisiae* using synthetic leader Sequences", Gene, vol. 106, pp. 267-272 (1991).
Elble, BioTechniques, vol. 13, No. 1, pp. 18-20 (1992).
Harmsen et al 1996, Appl Microbiol Biotechnol 46, 365-370.
Ho et al 2002, Nature 415, 180-183.
Hochstrasser 1996, Annu Rev Genet 30, 405-439.
Hohenblum et al 2003, J Biotechnology 102, 281-290.
Huh 2003, Nature 425, 686-691.
Inan et al 2006, Biotechnol and Bioengineer 93(4), 771-778.
Jones et al 2003, Physiological Genomics 16, 107-.
Kauffman et al 2002, Biotechnol Prog 18, 942-950.
Kim et al 2003, J Biotechnology 101, 81-87.
Lambert et al 2001, PNAS 98(8), 4652-4657.
Lodi et al 2005, Appl Environ Microbiol 71(8), 4359-4363.
Ludwig et al 1991, Plasmid 25, 81-95.
Ludwig et al 1993, Gene 132, 33-40.
Lund et al 1985, J Biol Chem 260(12), 7609-7613.
Martzen et al 1999, Science 286, 1153-1155.
Mattanovich et al 2004, J Biotechnology 113, 121-135.
Moralejo et al 2001, Mol Genet Genomics 266, 246-253.
Norgaard et al 2001, J Cell Biology 152(3), 553-562.
Norgaard et al 2003, Yeast 20, 645-652.
Nutt et al 1988, J Biol Chem 263(21), 10162-10167.
Ozkaynak et al 1984, Nature 312, 663-666.
Ozkaynak et al 1987, EMBO Journal 6(5), 1429-1439.
Pelham et al 1988, EMBO Journal 7(6), 1757-1762.
pYEX4T-1 Vector information 1998.
Liang et al 1993, J Agric Food Chem 41, 1800-1807.
Qui et al 2006, Cell Mol Life Sci 63, 2560-2570.
Robinson et al 1995, Biotechnol Prog 11, 171-177.
Robinson et al 1996, J Biol Chem 271(17), 10017-10022.
Rosenberg et al 1984, Nature 312, 77-80.
Tong et al 2004, Science 303, 808-813.
Zealey et al 1988, Mol Gen Genet 211, 155-159.
Utatsu et al 1987, J Bacteriology 169(12), 5537-5545.
Breslow et al 2008, Nat Methods 5 (8), 711-718.
Dolinski 1997, Proc Natl Aad Sci USA 94, 13093-13098.
Jin et al 2008, Mol Biol Cell 19, 284-296.
Kurihara et al 1994, J Cell Biol 126 (4), 911-23.
Lawrence et al 2004, Mol Cel Biol 24 (8), 3307-3323.
Liang et al 2007, Mol Biol Cell 18, 4741-4749.
Palmer et al 2003, J Cell Sci 116, 2361-2373.
Yoshikawa et al 2008, FEMS Yeast Res 9 (1), 32-44.
AB Vector—ProFold—ERI 2004, Internet Article.
AB Vector Technol 2011, Internet Article.
Belanger et al 1994, Swissprot Acces No. P36953.
Boeke et al 1987, Methods enzymol 154, 164-175.
Brachmann et al 1998, Yeast 30 (14), 115-132.
Brown et al 1990, Swissprot acces No. P14639.
Cassady et al 1990, Swissprot Access No. P19121.
Fassler 2004, EMBO Rep 5 (1), 28-29.
Giaever et al 2002, Nature 418, 387-391.
Hilger 1996, Swissprot Access No. P49064.
Hilger 1996, Swissprot Access No. P49822.
Ho et al 1994, Swissprot access No. P35747.
Jones et al 2003, Physiol Genomics 16, 107-118.
McReynolds et al 1986, Swissprot Acess No. P01012.
Nishizawa et al 1989, Appl Microbiol Biotech 32, 317-322.
Panaretou et al 2002, Mol Cell 10, 1307-1318.
Patterson et al 1995, Swissprot Acess No. P39090.
Roberts et al 2005, Swissprot Acces No. O73860.
Rose et al 1987, Gene 60, 237-243.
Sahasrabudhe et al 1998, Prot Exp Purif 14, 425-433.
Schreuder et al 1996, Vaccine 14(5), 383-388.
Shevchuk et al 2004, Nucl Acids Res 32 (2), e19.
Syed et al 1996, Swissprot Access No. P49065.
Tonkool P 2001, Acta Biotechnol 21(2), 189-193.
Van Reeth 1999, Swissprot Acces No. O89020.
Vob et al, 2003, J Biotechnol 105, 205-213.
Watkins et al 1997, Swiss prot acces No. Q28522.
Wolkowicz et al 2004, Methods Mol Biol 246, 391-411.
NCB1 Accession No. NM001018416 (2005).
Accession No. P36424 (2010).
Accession No. Q5R9A4 (2010).
GenBank Accession No. U16761 (1994).
Finnis et al 1993, Eur J Biochem 212, 201-210.
Broach et al 1982, Cell 29, 227-234.
Cashmore et al 1986, Mol Gen Genet 203, 154-162.
Christis et al 2008, FEBS 275, 4700-4727.
Creasey et al 2003, Mol Microbiol 47(1), 209-221.

DeMolder et al 1994, J Biotechnology 32, 179-189.
Denecke et al 1991, The Plant Cell 3, 1025-1035.
Hamilton et al 1996, J Biol Chem 271(48), 30610-30613.
Lee et al 2001, J Biochem Mol Biology 34(2), 102-108.
BD pBridge three-Hybrid Vector 2003 Clontech Cat XP002325598.

Botstein et al 1979, Gene 8, 17-24.
Frand & Kaiser 1998, Mol Cell 1, 161-170.
Guenther et al 1993, J Bio Chem 268, (11), 7728-7732.

* cited by examiner

Figure 3
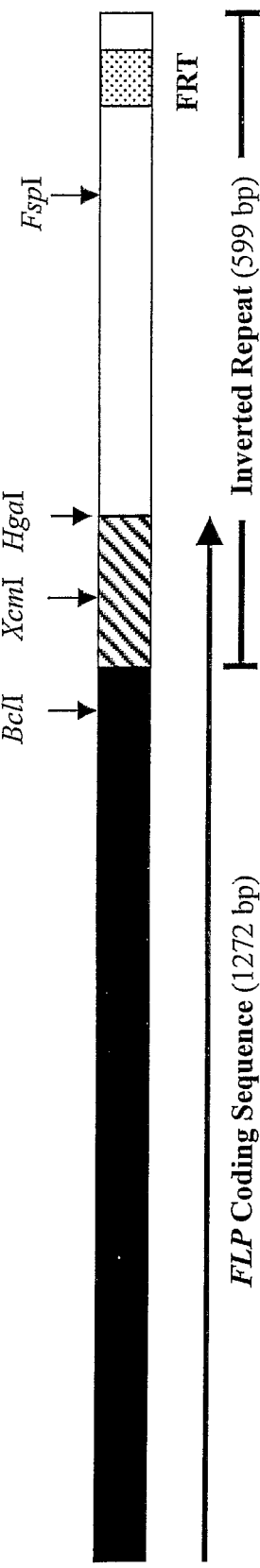
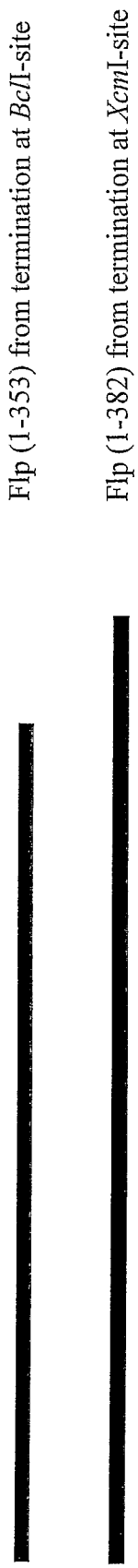
A) Restriction Endonuclease Sites used for DNA Insertions in *FLP* and the *FLP* Inverted Repeat
B) Flp Protein (423 amino acid residues)
C) Truncated FLP Protein Products mFL = modified HSA(pre)/MFα1(pro) fusion leader sequence

Figure 12

**A) Restriction Endonuclease Sites used for DNA Insertions in *REP2* and the *REP2* Inverted Repeat**

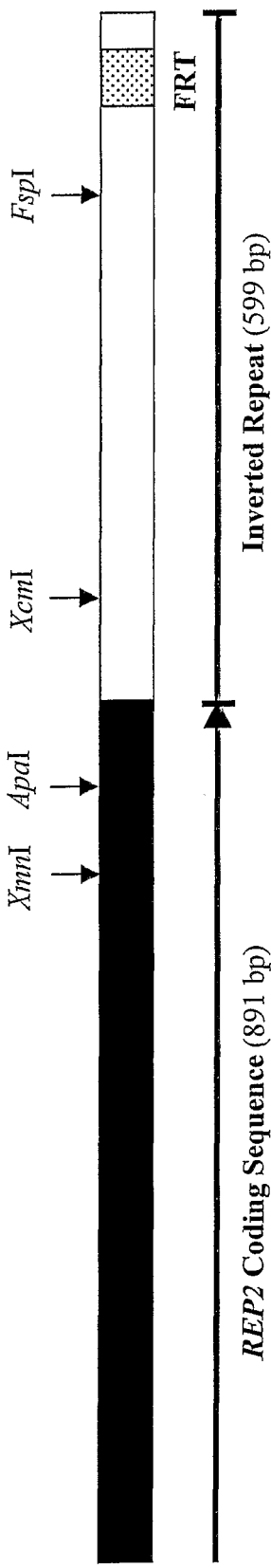

*REP2* Coding Sequence (891 bp)    Inverted Repeat (599 bp)

B) Rep2 Protein (296 amino acid residues)

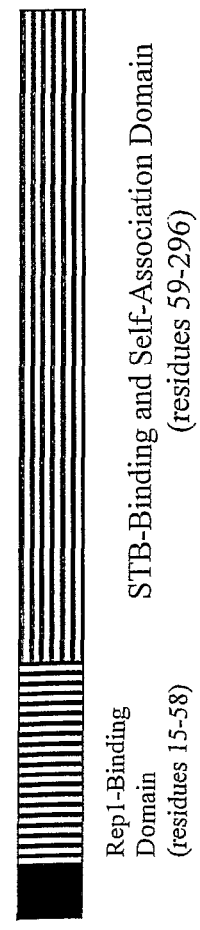

Rep1-Binding Domain (residues 15-58)    STB-Binding and Self-Association Domain (residues 59-296)

C) Truncated Rep2 Protein Products

Rep2 (1-244) from termination at *Xmn*I-site

Rep2 (1-269) from termination at *Apa*I-site digested by T4 DNA polymerase

Rep2 (1-271) from termination at *Apa*I-site

Figure 33A

Table 3 (part 1)

| Plasmid | Insertion Site | Insertion Site Details | 2μm Form | Initial OD$_{600}$ | Leucine Prototrophs | | |
|---|---|---|---|---|---|---|---|
| | | | | | Number | % | Average |
| pSAC35 | - | - | B | 0.074 | 100/100 | 100% | 99% |
| pSAC35 | - | - | B | 0.068 | 95/98 | 97% | |
| pDB2818 | *XmnI* | REP2 (1-244) | A | 0.062 | 32/100 | 32% | 42% |
| pDB2818 | *XmnI* | REP2 (1-244) | A | 0.059 | 52/100 | 52% | |
| pDB2787 | *ApaI*/T4 pol. | REP2 (1-269) | B | 0.054 | 34/100 | 34% | 45% |
| pDB2787 | *ApaI*/T4 pol. | REP2 (1-269) | B | 0.084 | 45/100 | 45% | |
| pDB2788 | *ApaI* | REP2 (1-271) | B | 0.066 | 23/100 | 23% | 33% |
| pDB2788 | *ApaI* | REP2 (1-271) | B | 0.051 | 43/100 | 43% | |

Figure 33B

Table 3 (part 2)

| Plasmid | Insertion Site | Insertion Site Details | 2μm Form | Initial OD$_{600}$ | Leucine Prototrophs | | |
|---|---|---|---|---|---|---|---|
| | | | | | Number | % | Average |
| pDB2688 | XcmI | Inverted Repeat | B | 0.055 | 100/100 | 100% | 100% |
| pDB2688 | XcmI | Inverted Repeat | B | 0.066 | 100/100 | 100% | |
| pDB2806 | FspI | Inverted Repeat | A | 0.073 | 100/100 | 100% | 100% |
| pDB2806 | FspI | Inverted Repeat | A | 0.070 | 100/100 | 100% | |
| pDB2817 | XmnI | REP2 (1-244) | B | 0.063 | 36/100 | 36% | 35% |
| pDB2817 | XmnI | REP2 (1-244) | B | 0.082 | 34/100 | 34% | |
| pDB2805 | FspI | Inverted Repeat | B | 0.069 | 100/100 | 100% | 100% |
| pDB2805 | FspI | Inverted Repeat | B | 0.078 | 100/100 | 100% | |
| pDB2814 | BclI | FLP (1-353), 1× Insert | B | 0.080 | 69/100 | 69% | 67% |
| pDB2814 | BclI | FLP (1-353), 1× Insert | B | 0.057 | 64/100 | 64% | |
| pDB2815 | BclI | FLP (1-353), 2× Insert | B | 0.067 | 70/100 | 70% | 67% |
| pDB2815 | BclI | FLP (1-353), 2× Insert | B | 0.068 | 64/100 | 64% | |

Figure 33C

Table 3 (part 3)

| Plasmid | Insertion Site | Insertion Site Details | 2μm Form | Initial OD$_{600}$ | Leucine Prototrophs | | |
|---|---|---|---|---|---|---|---|
| | | | | | Number | % | Average |
| pDB2816 | BclI | FLP (1-353), 3× Insert | B | 0.069 | 67/100 | 67% | 74% |
| pDB2816 | BclI | FLP (1-353), 3× Insert | B | 0.056 | 81/100 | 81% | |
| pDB2689 | XcmI | C-terminal FLP Mutant (FLP 1-384, plus 56 other residues) | B | 0.054 | 73/100 | 73% | 75% |
| pDB2689 | XcmI | C-terminal FLP Mutant (FLP 1-384, plus 56 other residues) | B | 0.056 | 77/100 | 77% | |
| pDB2786 | XcmI | C-terminal FLP Mutant (FLP 1-384, plus 14 other residues) | B | 0.079 | 73/100 | 73% | 67% |
| pDB2786 | XcmI | C-terminal FLP Mutant (FLP 1-384, plus 14 other residues) | B | 0.052 | 61/100 | 61% | |
| pDB2823 | XcmI | FLP (1-382) | B | 0.071 | 70/100 | 70% | 64% |
| pDB2823 | XcmI | FLP (1-382) | B | 0.055 | 57/100 | 57% | |

Figure 33D

Table 3 (part 4)

| Plasmid | Insertion Site | Insertion Site Details | 2μm Form | Initial OD$_{600}$ | Leucine Prototrophs | | |
|---|---|---|---|---|---|---|---|
| | | | | | Number | % | Average |
| pDB2813 | HgaI | Inverted Repeat | A | 0.057 | 100/100 | 100% | 100% |
| pDB2813 | HgaI | Inverted Repeat | A | 0.076 | 100/100 | 100% | |
| pDB2808 | FspI | Inverted Repeat | A | 0.058 | 100/100 | 100% | 100% |
| pDB2808 | FspI | Inverted Repeat | A | 0.060 | 100/100 | 100% | |
| pDB2812 | HgaI | Inverted Repeat | B | 0.062 | 100/100 | 100% | 100% |
| pDB2812 | HgaI | Inverted Repeat | B | 0.071 | 100/100 | 100% | |

Figure 34

SEQ ID NO:1

```
   1  ATGGACGACA TTGAAACAGC CAAGAATCTG ACGGTAAAAG CACGTACAGC TTATAGCGTC TGGGATGTAT GTCGGCTGTT TATTGAAATG ATTGCTCCTG
 101  ATGTAGATAT TGATATAGAG AGTAAACGTA AGATCTGATGA GCTACTCTTT CCAGGATATG TCATAAGGCC CATGGAATCT CTCACAACCG GTAGGCCGTA
 201  TGGTCTTGAT TCTAGCGCAG AAGATTCCAG CGTATCTTCT GACTCCAGTG CTGAGGTAAT TTTGCCTGCT GCGAAGATGG TTAAGGAAAG GTTTGATTCG
 301  ATTGGAAATG GTATGCTCTC TTCACAAGAA GCAAGTCAGG CTGCCATAGA TTTGATGCTA CAGAATAACA AGCTGTTAGA CAATAGAAAG CAACTATACA
 401  AATCTATTGC TATAATAATA GGAAGATTGC CCGAGAAAGA CAAGAAGAGA GCTACCGAAA TGCTCATGAG AAAAATGGAT TGTACACAGT TATTAGTCCC
 501  ACCAGCTCCA ACGGAAGAAG ATGTTATGAA GCTCGTTACC GTCGTTACCC AATTGCTTAC TTTAGTTCCA CCAGATCGTC AAGCTGCTTT AATAGGTGAT
 601  TTATTCATCC CGGAATCTCT AAAGGATATA TTCAATAGTT TCAATGAACT GGCGGCCAGAG AATCGTTTAC AGCAAAAAAA GAGTGAGTTG GAAGGAAGGA
 701  CTGAAGTGAA CCATGCTAAT ACAAATGAAG AAGTTCCCTC CAGGCGAACA AGAAGTAGAG ACACAAATGC AAGAGGAGCA TATAAATTAC AAAACACCAT
 801  CACTGAGGGC CCTAAAGCGG TTCCCACGAA AAAAAGGAGA GTAGCAACGA GGGTAAGGGG CAGAAAATCA CGTAATACTT CTAGGGTATG ATCCAATATC
 901  AAAGGAAATG ATAGCATTGA AGGATGAGAC TAATCCAATT GAGGAGTGGC AGCAGTAAAG ACAGCTAAAG GGTAGTGCTG AAGGAAGCAT ACGATACCCC
1001  GCATGGAATG GGATAATATC ACAGGAGGTA CTAGACTACC TTTCATCCTA CATAAATAGA CGCATATAAG TACGCATTTA AGCATAAAACA CGCACTATGC
1101  CGTTCTTCTC ATGTATATAT ATATACAGGC AACACGCAGA AACGTGAACAG TATAGGTGCG ACGTGAACAG TGTGCGCAGCT GTGCCGCAGCT TTTCGGAAAC
1201  GCTCGTTTTC GGAAACGCTT TGAAGTTCCT ATTCCGAAGT TCCTATTCTC TAGAAAGTAT AGGAACTTCA GAGCGCTTTT GAAAACCAAA AGCGCTCTGA
1301  AGACGCACTT TCAAAAAAAC AAAAACGCAC CGGACTGTAA CGAGCTACTA AAATATTGCG AATACCGCTT CCACAAACAT TGCTCAAAAG TATCTCTTTG
1401  CTATATATCT CTGTGCTATA TCCCTATATA ACCTACCCAT CCACCTTTCG CTCCTTGAAC TTGCATCTAA ACTCGACCTC TACAT
```

Figure 35

SEQ ID NO:2

```
   1 ATGCCACAAT TTGGTATATT ATGTAAAAACA CCACCTAAGG TGCTTGTGTCG TCAGTTTGTG GAAAGGTTTG AAAGACCTTC AGGTGAGAAA ATAGCATTAT
 101 GTGCTGCTGA ACTAACCTAT TTATGTTGGA TGATTACACA TAACGGAACA GCAATCAAGA GAGCCACATT CATGAGCTAT AATACTATCA TAAGCAATTC
 201 GCTGAGTTTC GATATTGTCA ATAAATCACT CCAGTTTAAA TACAAGACGC AAAAAGCAAC AATTCTGAAA GCCTCATTAA AGAAATTGAT TCCTGCTTGG
 301 GAATTTACAA TTATTCCTTA CTATGGACAA AAACATCAAT CTGATATCAC TGATATTGTA AGTAGTTTGC AATTACAGTT CGAATCATCG GAAGAAGCAG
 401 ATAAGGGAAA TAGCCACAGT AAAAAAAATGC TTAAAGCACT TCTAAGTGAG GGTGAAAGCA TCTGGGAGAT CACTGAGAAA ATACTAAATT CGTTTGAGTA
 501 TACTTCGAGA TTTACAAAAA CAAAAACTTT ATACCAATTC CTCTTCCTAG CTACTTTCAT CAATTGTGGA AGATTCAGCG ATATTAAGAA CGTTGATCCG
 601 AAATCATTTA AATTAGTCCA AAATAAGTAT CTGGGAGTAA TAATCCAGTG TTTAGTGACA GAGACAAAGA CAAGCGTTAG TAGGCACATA TACTTCTTTA
 701 GCGCAAGGGG TAGGATCGAT CCACTTGTAT ATTTGGATGA AATTTTTGAGG AATTCTGAAC CAGTCCTAAA ACGAGTAAAT AGGACCCGCA ATTCTTCAAG
 801 CAATAAACAG GAATACCAAT TATTAAAAGA TAACTTAGTC AGATCGTACA ATAAAGCTTT GAAGAAAAAT GCGCCTTATT CAATCTTTGC TATAAAAAAT
 901 GGCCCAAAAT CTCACATTGG AAGACATTTG ATGACCTCAT TTCTTTCAAT AACAGCAATA CCTGATCACT AGTTCGCACT ACTTCGCACT ATGATCCAAT
1001 GTGCTTCTGC CGTGGCCAGG ACAACGTATA CTCATCAGAT ATTGAGGAGT GGCAGCATAT CTACATAAAT AGAACAGCTA AAGGGTAGTG AGCGATAAGC
1101 ATCAAAGGAA ATGATAGCAT TGAAGGATGA GACTAATCCA ACCTTTCATC AGATATAGGT GCGACGTGAA CAGTGAGCTG TATGTGCGCA CTGAAGGAAG CATACGATAC
1201 CCCGCATGGA ATGGGATAAT ATCACAGGAG GTACTAGACT GTACTAGACT GGCAACACGC CTACATAAAT AGACGCATAT AAGTACGCAT TTAAGCATAA ACACGCACTA
1301 TGCCGTTCTT CTCATGTATA TATATATACA TTTGAAGTT CCTATTCCGA AGTTCCTATT CTCTAGAAAG GCGACGTGAA CAGTGAGCTG GCTCGCGTTG CATTTTCGGA
1401 AGCGCTCGTT TTCGAAACG CTTTGAAGTT ACCAAAAACG CACCGGACTG TAACGAGCTA CTAAAATATT TCAGAGGAACT TATAGGAACT TCAGAGGCGCT TTTGAAAACC AAAAGCGCTC
1501 TGAAGACGCA CTTTCAAAAA ACCAAAAACG CACCGGACTA ATAACCTACC CATCCACCTT GCGAATACCG CTTCCACAAA CATTGCTCAA AAGTATCTCT
1601 TTGCTATATA TCTCTGTGCT ATATCCCTAT ATAACCTACC TCGCTCCTTG AACTTGCATC TAAACTCGAC CTCTACAT
```

Figure 43

PCR Primers DS248 and DS250 for amplification of *S. cerevisiae PDI1* genes

DS248 (SEQ ID NO:65)

```
     EcoRI   SacI   SnaBI   PacI              SfiI           FseI    SmaI
5'-GTCAGAATTC GAGCTCTACG TATTAATTAA GGCCGGCCAG GCCCGGGCTA GTCTCTTTTT CCAATTTGCC ACCGTGTAGC ATTTGTTGT-3'
                                                                                        >>........'YCL044c'........>>
```

DS250 (SEQ ID NO:67)

```
     BamHI   SmaI   SnaBI
5'-GTCAGGATCC TACGTACCCG GGTAAGGGCGT TCGTGCAGTG TGACGAATAT AGCG-3'
```

2-MICRON FAMILY PLASMID AND USE THEREOF

CROSS-REFERENCE TO RELATED APPLICATIONS

This application is a National Stage application based on International Application No. PCT/GB2004/005435, filed Dec. 23, 2004, which claims priority to Great Britain Application No. 0329722.3, filed Dec. 23, 2003, the disclosures of which are incorporated herein by reference.

FIELD OF THE INVENTION

The present application relates to modified plasmids and uses thereof.

BACKGROUND OF THE INVENTION

Certain closely related species of budding yeast have been shown to contain naturally occurring circular double stranded DNA plasmids. These plasmids, collectively termed 2 µm-family plasmids, include pSR1, pSB3 and pSB4 from *Zygosaccharomyces rouxii* (formerly classified as *Zygosaccharomyces bisporus*), plasmids pSB1 and pSB2 from *Zygosaccharomyces bailii*, plasmid pSM1 from *Zygosaccharomyces fermentati*, plasmid pKD1 from *Kluyveromyces drosphilarum*, an un-named plasmid from *Pichia membranaefaciens* (hereinafter referred to as "pPM1") and the 2 µm plasmid and variants (such as Scp1, Scp2 and Scp3) from *Saccharomyces cerevisiae* (Volkert, et al., 1989, *Microbiological Reviews*, 53, 299; Painting, et al., 1984, *J. Applied Bacteriology*, 56, 331) and other *Saccharomyces* species, such as *S. carlsbergensis*. As a family of plasmids these molecules share a series of common features in that they possess two inverted repeats on opposite sides of the plasmid, have a similar size around 6-kbp (range 4757 to 6615-bp), at least three open reading frames, one of which encodes for a site specific recombinase (such as FLP in 2 µm) and an autonomously replicating sequence (ARS), also known as an origin of replication (ori), located close to the end of one of the inverted repeats. (Futcher, 1988, *Yeast*, 4, 27; Murray et al., 1988, *J. Mol. Biol.* 200, 601 and Toh-e et al., 1986, *Basic Life Sci.* 40, 425). Despite their lack of discernible DNA sequence homology, their shared molecular architecture and the conservation of function of the open reading frames have demonstrated a common link between the family members.

The 2 µm plasmid (FIG. 1) is a 6,318-bp double-stranded DNA plasmid, endogenous in most *Saccharomyces cerevisiae* strains at 60-100 copies per haploid genome. The 2 µm plasmid comprises a small-unique (US) region and a large unique (UL) region, separated by two 599-bp inverted repeat sequences. Site-specific recombination of the inverted repeat sequences results in inter-conversion between the A-form and B-form of the plasmid in vivo (Volkert & Broach, 1986, *Cell*, 46, 541). The two forms of 2 µm differ only in the relative orientation of their unique regions.

While DNA sequencing of a cloned 2 µm plasmid (also known as Scp1) from *Saccharomyces cerevisiae* gave a size of 6,318-bp (Hartley and Donelson, 1980, *Nature*, 286, 860), other slightly smaller variants of 2 µm, Scp2 and Scp3, are known to exist as a result of small deletions of 125-bp and 220-bp, respectively, in a region known as STB (Cameron et al., 1977, *Nucl. Acids Res.*, 4, 1429: Kikuchi, 1983, *Cell*, 35, 487 and Livingston & Hahne, 1979, *Proc. Natl. Acad. Sci. USA*, 76, 3727). In one study about 80% of natural *Saccharomyces* strains from around the world contained DNA homologous to 2 µm (by Southern blot analysis) (Hollenberg, 1982, *Current Topics in Microbiology and Immunobiology*, 96, 119). Furthermore, variation (genetic polymorphism) occurs within the natural population of 2 µm plasmids found in *S. cerevisiae* and *S. carlsbergensis*, with the NCBI sequence (accession number NC_001398) being one example.

The 2 µm plasmid has a nuclear localisation and displays a high level of mitotic stability (Mead et al, 1986, *Molecular & General Genetics*, 205, 417). The inherent stability of the 2 µm plasmid results from a plasmid-encoded copy number amplification and partitioning mechanism, which is easily compromised during the development of chimeric vectors (Futcher & Cox, 1984, *J. Bacteriol.*, 157, 283; Bachmair & Ruis, 1984, *Monatshefte für Chemie*, 115, 1229). A yeast strain, which contains a 2 µm plasmid is known as [cir$^+$], while a yeast strain which does not contain a 2 µm plasmid is known as [cir$^0$].

The US-region contains the REP2 and FLP genes, and the UL-region contains the REP1 and D (also known as RAF) genes, the STB-locus and the origin of replication (Broach & Hicks, 1980, *Cell*, 21, 501; Sutton & Broach, 1985, *Mol. Cell. Biol.*, 5, 2770). The Flp recombinase binds to FRT-sites (Flp Recognition Target) within the inverted repeats to mediate site-specific recombination, which is essential for natural plasmid amplification and control of plasmid copy number in vivo (Senecoff et al, 1985, *Proc. Natl. Acad. Sci. U.S.A.*, 82, 7270; Jayaramn, 1985, *Proc. Natl. Acad. Sci. U.S.A.*, 82, 5875). The copy number of 2 µm-family plasmids can be significantly affected by changes in Flp recombinase activity (Sleep et al, 2001, *Yeast*, 18, 403; Rose & Broach, 1990, *Methods Enzymol.*, 185, 234). The Rep1 and Rep2 proteins mediate plasmid segregation, although their mode of action is unclear (Sengupta et al, 2001, *J. Bacteriol.*, 183, 2306). They also repress transcription of the FLP gene (Reynolds et al, 1987, *Mol. Cell. Biol.*, 7, 3566).

The FLP and REP2 genes are transcribed from divergent promoters, with apparently no intervening sequence defined between them. The FLP and REP2 transcripts both terminate at the same sequence motifs within the inverted repeat sequences, at 24-bp and 178-bp respectively after their translation termination codons (Sutton & Broach, 1985, *Mol. Cell. Biol.*, 5, 2770).

In the case of FLP, the C-terminal coding sequence also lies within the inverted repeat sequence. Furthermore, the two inverted repeat sequences are highly conserved over 599-bp, a feature considered advantageous to efficient plasmid replication and amplification in vivo, although only the FRT-sites (less than 65-bp) are essential for site-specific recombination in vitro (Senecoff et al, 1985, *Proc. Natl. Acad. Sci. U.S.A.*, 82, 7270; Jayararm, 1985, *Proc. Natl. Acad. Sci. U.S.A.*, 82, 5875; Meyer-Leon et al, 1984, *Cold Spring Harbor Symposia On Quantitative Biology*, 49, 797). The key catalytic residues of Flp are arginine-308 and tyrosine-343 (which is essential) with strand-cutting facilitated by histidine-309 and histidine 345 (Prasad et al, 1987, *Proc. Natl. Acad. Sci. U.S.A.*, 84, 2189; Chen et al, 1992, *Cell*, 69, 647; Grainge et al, 2001, *J. Mol. Biol.*, 314, 717).

Two functional domains are described in Rep2. Residues 15-58 form a Rep1-binding domain, and residues 59-296 contain a self-association and STB-binding region (Sengupta et al, 2001, *J. Bacteriol.*, 183, 2306).

Chimeric or large deletion mutant derivatives of 2 µm which lack many of the essential functional regions of the 2 µm plasmid but retain functional the cis element ARS and STB, cannot effectively partition between mother and daughter cells at cell division. Such plasmids can do so if these functions are supplied in traces, by for instance the provision of a functional 2 μm plasmid within the host, a so called [cir⁺] host.

Genes of interest have previously been inserted into the UL-region of the 2 μm plasmid. For example, see plasmid pSAC3U1 in EP 0 286 424. However, there is likely to be a limit to the amount of DNA that can usefully be inserted into the UL-region of the 2 μm plasmid without generating excessive asymmetry between the US and UL-regions. Therefore, the US-region of the 2 μm plasmid is particularly attractive for the insertion of additional DNA sequences, as this would tend to equalise the length of DNA fragments either side of the inverted repeats.

This is especially true for expression vectors, such as that shown in FIG. 2, in which the plasmid is already crowded by the introduction of a yeast selectable marker and adjacent DNA sequences. For example, the plasmid shown in FIG. 2 includes a β-lactamase gene (for ampicillin resistance), a LEU2 selectable marker and an oligonucleotide linker, the latter two of which are inserted into a unique SnaBI-site within the UL-region of the 2 μm-family disintegration vector, pSAC3 (see EP 0 286 424). The *E. coli* DNA between the XbaI-sites that contains the ampicillin resistance gene is lost from the plasmid shown in FIG. 2 after transformation into yeast. This is described in Chinery & Hinchliffe, 1989, *Curr. Genet.*, 16, 21 and EP 0 286 424, where these types of vectors are designated "disintegration vectors". In the crowded state shown in FIG. 2, it is not readily apparent where further polynucleotide insertions can be made. A NotI-site within the linker has been used for the insertion of additional DNA fragments, but this contributes to further asymmetry between the UL and US regions (Sleep et al, 1991, *Biotechnology (N Y)*, 9, 183).

We had previously attempted to insert additional DNA into the US-region of the 2 μm plasmid and maintain its high inherent plasmid stability. In the 2 μm-family disintegration plasmid pSAC300, a 1.1-kb DNA fragment containing the URA3 gene was inserted into EagI-site between REP2 and FLP in US-region in such a way that transcription from the URA3 gene was in same direction as REP2 transcription (see EP 0 286 424). When S150-2B [cir⁰] was transformed to uracil prototrophy by pSAC300, it was shown to be considerably less stable (50% plasmid loss in under 30 generations) than comparable vectors with URA3 inserted into the UL-region of 2 μm (0-10% plasmid loss in under 30 generations) (Chinery & Hinchliffe, 1989, *Curr. Genet.*, 16, 21; EP 0 286 424). Thus, insertion at the EagI site may have interfered with FLP expression and it was concluded that the insertion position could have a profound effect upon the stability of the resultant plasmid, a conclusion confirmed by Bijvoet et al., 1991, *Yeast*, 7, 347.

It is desirable to insert further polynucleotide sequences into 2 μm-family plasmids. For example, the insertion of polynucleotide sequences that encode host derived proteins, recombinant proteins, or non-coding antisense or RNA interference (RNAi) transcripts may be desirable. Moreover, it is desirable to introduce multiple further polynucleotide sequences into 2 μm-family plasmids, thereby to provide a plasmid which encodes, for example, multiple separately encoded multi-subunit proteins, different members of the same metabolic pathway, additional selective markers or a recombinant protein (single or multi-subunit) and a chaperone to aid the expression of the recombinant protein.

However, the 6,318-bp 2 μm plasmid, and other 2 μm-family plasmids, are crowded with functional genetic elements (Sutton & Broach, 1985, *Mol. Cell. Biol.*, 5, 2770; Broach et al, 1979, *Cell*, 16, 827), with no obvious positions existing for the insertion of additional DNA sequences without a concomitant loss in plasmid stability. In fact, except for the region between the origin of replication and the D gene locus, the entire 2 μm plasmid genome is transcribed into at least one poly(A)⁺ species and often more (Sutton & Broach, 1985, *Mol. Cell. Biol.*, 5, 2770). Consequently, most insertions might be expected to have a detrimental impact on plasmid function in vivo.

Indeed, persons skilled in the art have given up on inserting heterologous polynucleotide sequences into 2 μm-family plasmids.

Robinson et al, 1994, *Bio/Technology*, 12, 381-384 reported that a recombinant additional PDI gene copy in *Saccharomyces cerevisiae* could be used to increase the recombinant expression of human platelet derived growth factor (PDGF) B homodimer by ten-fold and *Schizosaccharomyces pombe* acid phosphatase by four-fold. Robinson obtained the observed increases in expression of PDGF and *S. pombe* acid phosphatase using an additional chromosomally integrated PDI gene copy. Robinson reported that attempts to use the multi-copy 2 μm expression vector to increase PDI protein levels had had a detrimental effect on heterologous protein secretion.

Shusta et al, 1998, *Nature Biotechnology*, 16, 773-777 described the recombinant expression of single-chain antibody fragments (scFv) in *Saccharomyces cerevisiae*. Shusta reported that in yeast systems, the choice between integration of a transgene into the host chromosome versus the use of episomal expression vectors can greatly affect secretion and, with reference to Parekh & Wittrup, 1997, *Biotechnol. Prog.*, 13, 117-122, that stable integration of the scFv gene into the host chromosome using a δ integration vector was superior to the use of a 2 μm-based expression plasmid. Parekh & Wittrup, op. cit., had previously taught that the expression of bovine pancreatic trypsin inhibitor (BPTI) was increased by an order of magnitude using a δ integration vector rather than a 2 μm-based expression plasmid. The 2 μm-based expression plasmid was said to be counter-productive for the production of heterologous secreted protein.

Bao et al, 2000, *Yeast*, 16, 329-341, reported that the KlPDI1 gene had been introduced into *K. lactis* on a multi-copy plasmid, pKan707, and that the presence of the plasmid caused the strain to grow poorly. In the light of the earlier findings in Bao et al, 2000, Bao & Fukuhara, 2001, *Gene*, 272, 103-110, chose to introduce a single duplication of KlPDI1 on the host chromosome.

Accordingly, the art teaches the skilled person to integrate transgenes into the yeast chromosome, rather than into a multicopy vector. There is, therefore, a need for alternative ways of transforming yeast.

DESCRIPTION OF THE INVENTION

The present invention relates to recombinantly modified versions of 2 μm-family plasmids.

A 2 μm-family plasmid is a circular, double stranded, DNA plasmid. It is typically small, such as between 3,000 to 10,000 bp, preferably between 4,500 to 7000 bp, excluding recombinantly inserted sequences. Preferred 2 μm-family plasmids for use in the present invention comprise sequences derived from one or more of plasmids pSR1, pSB3, or pSB4 as obtained from *Zygosaccharomyces rouxii*, pSB1 or pSB2 both as obtained from *Zygosaccharomyces bailli*, pSM1 as obtained from *Zygosaccharomyces fermentati*, pKD1 as obtained from *Kluyveromyces drosophilarum*, pPM1 as obtained from *Pichia membranaefaciens* and the 2 μm plasmid and variants (such as Scp1, Scp2 and Scp3) as obtained from *Saccharomyces cerevisiae*, for example as described in Volkert et al, 1989, *Microbiological Reviews*, 53 (3), 299-317, Murray et al, 1988, *Mol. Biol.*, 200, 601-607 and Painting, et al., 1984, *J. Applied Bacteriology*, 56, 331.

A 2 μm-family plasmid is capable of stable multicopy maintenance within a yeast population, although not necessarily all 2 μm-family plasmids will be capable of stable multicopy maintenance within all types of yeast population. For example, the 2 μm plasmid is capable of stable multicopy maintenance, inter alia, within *Saccharomyces cerevisiae* and *Saccharomyces carlsbergensis*.

By "multicopy maintenance" we mean that the plasmid is present in multiple copies within each yeast cell. A yeast cell comprising 2 μm-family plasmid is designated [cir⁺], whereas a yeast cell that does not comprise 2 μm-family plasmid is designated [cir⁰]. A [cir⁺] yeast cell typically comprises 10-100 copies of 2 μm-family plasmid per haploid genome, such as 20-90, more typically 30-80, preferably 40-70, more preferably 50-60 copies per haploid genome. Moreover, the plasmid copy number can be affected by the genetic background of the host which can increase the plasmid copy number of 2 μm-like plasmid to above 100 per haploid genome (Gerbaud and Guerineau, 1980, *Curr. Genetics*, 1, 219, Holm, 1982, *Cell*, 29, 585, Sleep et al., 2001, *Yeast*, 18, 403 and WO99/00504). Multicopy stability is defined below.

A 2 μm-family plasmid typically comprises at least three open reading frames ("ORFs") that each encode a protein that functions in the stable maintenance of the 2 μm-family plasmid as a multicopy plasmid. The proteins encoded by the three ORFs can be designated FLP, REP1 and REP2. Where a 2 μm-family plasmid comprises not all three of the ORFs encoding FLP, REP1 and REP2 then ORFs encoding the missing protein(s) should be supplied in trans, either on another plasmid or by chromosomal integration.

A "FLP" protein is a protein capable of catalysing the site-specific recombination between inverted repeat sequences recognised by FLP. The inverted repeat sequences are termed FLP recombination target (FRT) sites and each is typically present as part of a larger inverted repeat (see below). Preferred FLP proteins comprise the sequence of the FLP proteins encoded by one of plasmids pSR1, pSB1, pSB2, pSB3, pSB4, pSM1, pKD1, pPM1 and the 2 μm plasmid, for example as described in Volkert et al, op. cit., Murray et al, op. cit and Painting et al, op. cit. Variants and fragments of these FLP proteins are also included in the present invention. "Fragments" and "variants" are those which retain the ability of the native protein to catalyse the site-specific recombination between the same FRT sequences. Such variants and fragments will usually have at least 50%, 60%, 70%, 80%, 90%, 95%, 98%, 99%, or more, homology with an FLP protein encoded by one of plasmids pSR1, pSB1, pSB2, pSB3, pSM1, pKD1 and the 2 μm plasmid. Different FLP proteins can have different FRT sequence specificities. A typical FRT site may comprise a core nucleotide sequence flanked by inverted repeat sequences. In the 2 μm plasmid, the FRT core sequence is 8 nucleotides in length and the flanking inverted repeat sequences are 13 nucleotides in length (Volkert et al, op. cit.). However the FRT site recognised by any given FLP protein may be different to the 2 μm plasmid FRT site.

REP1 and REP2 are proteins involved in the partitioning of plasmid copies during cell division, and may also have a role in the regulation of FLP expression. Considerable sequence divergence has been observed between REP1 proteins from different 2 μm-family plasmids, whereas no sequence alignment is currently possible between REP2 proteins derived from different 2 μm-family plasmids. Preferred REP1 and REP2 proteins comprise the sequence of the REP1 and REP2 proteins encoded by one of plasmids pSR1, pSB1, pSB2, pSB3, pSB4, pSM1, pKD1, pPM1 and the 2 μm plasmid, for example as described in Volkert et al, op. cit., Murray et al, op. cit. and Painting et al, op. cit. Variants and fragments of these REP1 and REP2 proteins are also included in the present invention. "Fragments" and "variants" of REP1 and REP2 are those which, when encoded by the plasmid in place of the native ORF, do not disrupt the stable multicopy maintenance of the plasmid within a suitable yeast population. Such variants and fragments of REP1 and REP2 will usually have at least 5%, 10%, 20%, 30%, 40%, 50%, 60%, 70%, 80%, 90%, 95%, 98%, 99%, or more, homology with a REP1 and REP2 protein, respectively, as encoded by one of plasmids pSR1, pSB1, pSB2, pSB3, pSB4, pSM1, pKD1, pPM1 and the 2 μm plasmid.

The REP1 and REP2 proteins encoded by the ORFs on the plasmid must be compatible. REP1 and REP2 are compatible if they contribute, in combination with the other functional elements of the plasmid, towards the stable multicopy maintenance of the plasmid which encodes them. Whether or not a REP1 and REP2 ORF contributes towards the stable multicopy maintenance of the plasmid which encodes them can be determined by preparing mutants of the plasmid in which each of the REP1 and REP2 ORFs are specifically disrupted. If the disruption of an ORF impairs the stable multicopy maintenance of the plasmid then the ORF can be concluded to contribute towards the stable multicopy maintenance of the plasmid in the non-mutated version. It is preferred that the REP1 and REP2 proteins have the sequences of REP1 and REP2 proteins encoded by the same naturally occurring 2 μm-family plasmid, such as pSR1, pSB1, pSB2, pSB3, pSB4, pSM1, pKD1, pPM1 and the 2 μm plasmid, or variant or fragments thereof.

A 2 μm-family plasmid comprises two inverted repeat sequences. The inverted repeats may be any size, so long as they each contain an FRT site (see above). The inverted repeats are typically highly homologous. They may share greater than 50%, 60%, 70%, 80%, 90%, 95%, 96%, 97%, 98%, 99%, 99.5% or more sequence identity. In a preferred embodiment they are identical. Typically the inverted repeats are each between 200 to 1000 bp in length. Preferred inverted repeat sequences may each have a length of from 200 to 300 bp, 300 to 400 bp, 400 to 500 bp, 500 to 600 bp, 600 to 700 bp, 700 to 800 bp, 800 to 900 bp, or 900 to 1000 bp. Particularly preferred inverted repeats are those of the plasmids pSR1 (959 bp), pSB1 (675 bp), pSB2 (477 bp), pSB3 (391 bp), pSM1 (352 bp), pKD1 (346 bp), the 2 μm plasmid (599 bp), pSB4 and pPM1.

The sequences of the inverted repeats may be varied. However, the sequences of the FRT site in each inverted repeat should be compatible with the specificity of the FLP protein encoded by the plasmid, thereby to enable the encoded FLP protein to act to catalyse the site-specific recombination between the inverted repeat sequences of the plasmid. Recombination between inverted repeat sequences (and thus the ability of the FLP protein to recognise the FRT sites with the plasmid) can be determined by methods known in the art. For example, a plasmid in a yeast cell under conditions that favour FLP expression can be assayed for changes in the restriction profile of the plasmid which would result from a change in the orientation of a region of the plasmid relative to another region of the plasmid. The detection of changes in restriction profile indicate that the FLP protein is able to recognise the FRT sites in the plasmid and therefore that the FRT site in each inverted repeat are compatible with the specificity of the FLP protein encoded by the plasmid.

In a particularly preferred embodiment, the sequences of inverted repeats, including the FRT sites, are derived from the same 2 μm-family plasmid as the ORF encoding the FLP protein, such as pSR1, pSB1, pSB2, pSB3, pSB4, pSM1, pKD1, pPM1 or the 2 μm plasmid.

The inverted repeats are typically positioned within the 2 μm-family plasmid such that the two regions defined between the inverted repeats (e.g. such as defined as UL and US in the 2 μm plasmid) are of approximately similar size, excluding exogenously introduced sequences such as transgenes. For example, one of the two regions may have a length equivalent to at least 40%, 50%, 60%, 70%, 80%, 90%, 95% or more, up to 100%, of the length of the other region.

A 2 μm-family plasmid comprises the ORF that encodes FLP and one inverted repeat (arbitrarily termed "IR1" to distinguish it from the other inverted repeat mentioned in the next paragraph) juxtaposed in such a manner that IR1 occurs at the distal end of the FLP ORF, without any intervening coding sequence, for example as seen in the 2 μm plasmid. By "distal end" in this context we mean the end of the FLP ORF opposite to the end from which the promoter initiates its transcription. In a preferred embodiment, the distal end of the FLP ORF overlaps with IR1.

A 2 μm-family plasmid comprises the ORF that encodes REP2 and the other inverted repeat (arbitrarily termed "IR2" to distinguish it from IR1 mentioned in the previous paragraph) juxtaposed in such a manner that IR2 occurs at the distal end of the REP2 ORF, without any intervening coding sequence, for example as seen in the 2 μm plasmid. By "distal end" in this context we mean the end of the REP2 ORF opposite to the end from which the promoter initiates its transcription.

In one embodiment, the ORFs encoding REP2 and FLP may be present on the same region of the two regions defined between the inverted repeats of the 2 μm-family plasmid, which region may be the bigger or smaller of the regions (if there is any inequality in size between the two regions).

In one embodiment, the ORFs encoding REP2 and FLP may be transcribed from divergent promoters.

Typically, the regions defined between the inverted repeats (e.g. such as defined as UL and US in the 2 μm plasmid) of a 2 μm-family plasmid may comprise not more than two endogenous genes that encode a protein that functions in the stable maintenance of the 2 μm-family plasmid as a multicopy plasmid. Thus in a preferred embodiment, one region of the plasmid defined between the inverted repeats may comprise not more than the ORFs encoding FLP and REP2; FLP and REP1; or REP1 and REP2, as endogenous coding sequence.

A 2 μm-family plasmid comprises an origin of replication (also known as an autonomously replicating sequence—"ARS"), which is typically bidirectional. Any appropriate ARS sequence can be present. Consensus sequences typical of yeast chromosomal origins of replication may be appropriate (Broach et al, 1982, *Cold Spring Harbor Symp. Quant. Biol.*, 47, 1165-1174; Williamson, *Yeast*, 1985, 1, 1-14). Preferred ARSs include those isolated from pSR1, pSB1, pSB2, pSB3, pSB4, pSM1, pKD1, pPM1 and the 2 μm plasmid.

Thus, a 2 μm-family plasmid typically comprises at least ORFs encoding FLP and REP2, two inverted repeat sequences each inverted repeat comprising an FRT site compatible with FLP protein, and an ARS sequence. Preferably the plasmid also comprises an ORF encoding REP1, although it may be supplied in trans, as discussed above. Preferably the FRT sites are derived from the same 2 μm-family plasmid as the sequence of the encoded FLP protein. Preferably the sequences of the encoded REP1 and REP2 proteins are derived from the same 2 μm-family plasmid as each other. More preferably, the FRT sites are derived from the same 2 μm-family plasmid as the sequence of the encoded FLP, REP1 and REP2 proteins. Even more preferably, the sequences of the ORFs encoding FLP, REP1 and REP2, and the sequence of the inverted repeats (including the FRT sites) are derived from the same 2 μm-family plasmid. Yet more preferably, the ARS site is obtained from the same 2 μm-family plasmid as one or more of the ORFs of FLP, REP1 and REP2, and the sequence of the inverted repeats (including the FRT sites). Preferred plasmids include plasmids pSR1, pSB3 and pSB4 as obtained from *Zygosaccharomyces rouxii*, pSB1 or pSB2 both as obtained from *Zygosaccharomyces bailli*, pSM1 as obtained from *Zygosaccharomyces fermentati*, pKD1 as obtained from *Kluyveromyces drosophilarum*, pPM1 as obtained from *Pichia membranaefaciens*, and the 2 μm plasmid as obtained from *Saccharomyces cerevisiae*, for example as described in Volkert et al, 1989, op. cit., Murray et al, op. cit. and Painting et al, op. cit.

Optionally, a 2 μm-family plasmid may comprise a region equivalent to the STB region (also known as REP3) of the 2 μm plasmid, as defined in Volkert et al, op. cit. The STB region in a 2 μm-family plasmid of the invention may comprise two or more tandem repeat sequences, such as three, four, five or more. Alternatively, no tandem repeat sequences may be present. The tandem repeats may be any size, such as 10, 20, 30, 40, 50, 60, 70, 80, 90, 100 bp or more in length. The tandem repeats in the STB region of the 2 μm plasmid are 62 bp in length. It is not essential for the sequences of the tandem repeats to be identical. Slight sequence variation can be tolerated. It may be preferable to select an STB region from the same plasmid as either or both of the REP1 and REP2 ORFs. The STB region is thought to be a cis-acting element and preferably is not transcribed.

Optionally, a 2 μm-family plasmid may comprise an additional ORF that encodes a protein that functions in the stable maintenance of the 2 μm-family plasmid as a multicopy plasmid. The additional protein can be designated RAF or D. ORFs encoding the RAF or D gene can be seen on, for example, the 2 μm plasmid and pSM1. Thus a RAF or D ORF can comprise a sequence suitable to encode the protein product of the RAF or D gene ORFs encoded by the 2 μm plasmid or pSM1, or variants and fragments thereof. Thus variants and fragments of the protein products of the RAF or D genes of the 2 μm plasmid or pSM1 are also included in the present invention. "Fragments" and "variants" of the protein products of the RAF or D genes of the 2 μm plasmid or pSM1 are those which, when encoded by the 2 μm plasmid or pSM1 in place of the native ORF, do not disrupt the stable multicopy maintenance of the plasmid within a suitable yeast population. Such variants and fragments will usually have at least 5%, 10%, 20%, 30%, 40%, 50%, 60%, 70%, 80%, 90%, 950%, 98%, 99%, or more, homology with the protein product of the RAF or D gene ORFs encoded by the 2 μm plasmid or pSM1.

The present invention provides a 2 μm-family plasmid comprising a polynucleotide sequence insertion, deletion and/or substitution between the first base after the last functional codon of at least one of either a REP2 gene or an FLP gene and the last base before the FRT site in an inverted repeat adjacent to said gene.

A polynucleotide sequence insertion is any additional polynucleotide sequence inserted into the plasmid. Preferred polynucleotide sequence insertions are described below. A deletion is removal of one or more base pairs, such as the removal of up to 2, 3, 4, 5, 6, 7, 8, 9, 10, 20, 30, 40, 50, 60, 70, 80, 90, 100, 200, 300, 400, 500, 600, 700, 800, 900, 1000 or more base pairs, which may be as a single contiguous sequence or from spaced apart regions within a DNA sequence. A substitution is the replacement of one or more base pairs, such as the replacement of up to 2, 3, 4, 5, 6, 7, 8, 9, 10, 20, 30, 40, 50, 60, 70, 80, 90, 100, 200, 300, 400, 500, 600, 700, 800, 900, 1000 or more base pairs, which may be as a single contiguous sequence or from spaced apart regions within a DNA sequence. It is possible for a region to be modified by any two of insertion, deletion or substitution, or even all three.

The last functional codon of either a REP2 gene or a FLP gene is the codon in the open reading frame of the gene that is furthest downstream from the promoter of the gene whose replacement by a stop codon will lead to an unacceptable loss of multicopy stability of the plasmid, when determined by a test such as defined in Chinery & Hinchliffe (1989, *Curr. Genet.*, 16, 21-25). It may be appropriate to modify the test defined by Chinery & Hinchcliffe, for example to maintain exponential logarithmic growth over the desired number of generations, by introducing modifications to the inocula or sub-culturing regime. This can help to account for differences between the host strain under analysis and *S. cerevisiae* S150-2B used by Chinery & Hinchcliffe, and/or to optimise the test for the individual characteristics of the plasmid(s) under assay, which can be determined by the identity of the insertion site within the small US-region of the 2 μm-like plasmid, and/or other differences in the 2 μm-like plasmid, such as the size and nature of the inserted sequences within the 2 μm-like plasmid and/or insertions elsewhere in the 2 μm-like plasmid. For yeast that do not grow in the non-selective medium (YPD, also designated YEPD) defined in Chinery & Hinchliffe (1989, *Curr. Genet.*, 16, 21-25) other appropriate non-selective media might be used. A suitable alternative non-selective medium typically permits exponential logarithmic growth over the desired number of generations. For example, sucrose or glucose might be used as alternative carbon sources. Plasmid stability may be defined as the percentage cells remaining prototrophic for the selectable marker after a defined number of generations. The number of generations will preferably be sufficient to show a difference between a control plasmid, such as pSAC35 or pSAC310, or to show comparable stability to such a control plasmid. The number of generations may be 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100 or more. Higher numbers are preferred. The acceptable plasmid stability might be 1%, 2%, 3%, 4%, 5%, 10%, 15%, 20%, 25%, 30%, 40%, 500%, 60%, 70%, 75%, 80%, 85%, 90%, 95%, 96%, 97%, 98%, 99%, 99.9% or substantially 100%. Higher percentages are preferred. The skilled person will appreciate that, even though a plasmid may have a stability less than 100% when grown on non-selective media, that plasmid can still be of use when cultured in selective media. For example plasmid pDB2711 as described in the examples is only 10% stable when the stability is determined accordingly to Example 1, but provides a 15-fold increase in recombinant transferrin productivity in shake flask culture under selective growth conditions.

Thus, disruption of the REP2 or FLP genes at any point downstream of the last functional codon in either gene, by insertion of a polynucleotide sequence insertion, deletion or substitution will not lead to an unacceptable loss of multicopy stability of the plasmid. We have surprisingly found that the REP2 gene of the 2 μm plasmid can be disrupted after codon 59 and that the FLP gene of the 2 μm plasmid can be disrupted after codon 344, each without leading to an unacceptable loss of multicopy stability of the plasmid. The last functional codon in equivalent genes in other 2 μm-family plasmids can be determined routinely by modifying the relevant genes and determining stability as described above. Typically, therefore, modified plasmids of the present invention are stable, in the sense that the modifications made thereto do not lead to an unacceptable loss of multicopy stability of the plasmid.

The REP2 and FLP genes in a 2 μm plasmid of the invention each have an inverted repeat adjacent to them. The inverted repeat can be identified because (when reversed) it matches the sequence of another inverted repeat within the same plasmid. By "adjacent" is meant that the FLP or REP2 gene and its inverted repeat are juxtaposed in such a manner that the inverted repeat occurs at the distal end of the gene, without any intervening coding sequence, for example as seen in the 2 μm plasmid. By "distal end" in this context we mean the end of the gene opposite to the end from which the promoter initiates its transcription. In a preferred embodiment, the distal end of the gene overlaps with the inverted repeat.

In a first preferred aspect of the invention, the polynucleotide sequence insertion, deletion and/or substitution occurs between the first base after the last functional codon of the REP2 gene and the last base before the FRT site in an inverted repeat adjacent to said gene, preferably between the first base of the inverted repeat and the last base before the FRT site, even more preferably at a position after the translation termination codon of the REP2 gene and before the last base before the FRT site.

The term "between", in this context, includes the defined outer limits and so, for example, an insertion, deletion and/or substitution "between the first base after the last functional codon of the REP2 gene and the last base before the FRT site" includes insertions, deletions and/or substitutions at the first base after the last functional codon of the REP2 gene and insertions, deletions and/or substitutions at the last base before the FRT site.

In a second preferred aspect of the invention, the polynucleotide sequence insertion, deletion and/or substitution occurs between the first base after the last functional codon of the FLP gene and the last base before the FRT site in an inverted repeat adjacent to said gene, preferably between the first base of the inverted repeat and the last base before the FRT site, more preferably between the first base after the end of the FLP coding sequence and the last base before the FRT site, such as at the first base after the end of the FLP coding sequence. The polynucleotide sequence insertion, deletion and/or substitution may occur between the last base after the end of FLP and the FspI-site in the inverted repeat, but optionally not within the FspI-site.

In one embodiment, other than the polynucleotide sequence insertion, deletion and/or substitution, the FLP gene and/or the REP2 gene has the sequence of a FLP gene and/or a REP2 gene, respectively, derived from a naturally occurring 2 μm-family plasmid.

The term "derived from" includes sequences having an identical sequence to the sequence from which they are derived. However, variants and fragments thereof, as defined above, are also included. For example, an FLP gene having a sequence derived from the FLP gene of the 2 μm plasmid may have a modified promoter or other regulatory sequence compared to that of the naturally occurring gene. Alternatively, an FLP gene having a sequence derived from the FLP gene of the 2 μm plasmid may have a modified nucleotide sequence in the open reading frame which may encode the same protein as the naturally occurring gene, or may encode a modified FLP protein. The same considerations apply to REP2 genes having a sequence derived from a particular source.

A naturally occurring 2 μm-family plasmid is any plasmid having the features defined above as being essential features for a 2 μm-family plasmid, which plasmid is found to naturally exist in yeast, i.e. has not been recombinantly modified to include heterologous sequence. Preferably the naturally occurring 2 μm-family plasmid is selected from pSR1 (Accession No. X02398), pSB3 (Accession No. X02608) or pSB4 as obtained from *Zygosaccharomyces rouxii*, pSB1 or pSB2 (Accession No. NC_002055 or M18274) both as obtained from *Zygosaccharomyces bailli*, pSM1 (Accession No. NC_002054) as obtained from *Zygosaccharomyces fermentati*, pKD1 (Accession No. X03961) as obtained from *Kluyveromyces drosophilarum*, pPM1 as obtained from *Pichia membranaefaciens*, or, most preferably, the 2 μm plasmid (Accession No. NC_001398 or J01347) as obtained from *Saccharomyces cerevisiae*. Accession numbers refer to deposits at the NCBI.

Preferably, other than the polynucleotide sequence insertion, deletion and/or substitution, the sequence of the inverted repeat adjacent to said FLP and/or REP2 gene is derived from the sequence of the corresponding inverted repeat in the same naturally occurring 2 μm-family plasmid as the sequence from which the gene is derived. Thus, for example, if the FLP gene is derived from the 2 μm plasmid as obtained from *S. cerevisiae*, then it is preferred that the inverted repeat adjacent to the FLP gene has a sequence derived from the inverted repeat that is adjacent to the FLP gene in the 2 μm plasmid as obtained from *S. cerevisiae*. If the REP2 gene is derived from the 2 μm plasmid as obtained from *S. cerevisiae*, then it is preferred that the inverted repeat adjacent to the REP2 gene has a sequence derived from the inverted repeat that is adjacent to the REP2 gene in the 2 μm plasmid as obtained from *S. cerevisiae*.

Where, in the first preferred aspect of the invention, other than the polynucleotide sequence insertion, deletion and/or substitution, the REP2 gene and the inverted repeat sequence have sequences derived from the corresponding regions of the 2 μm plasmid as obtained from *S. cerevisiae*, then it is preferred that the polynucleotide sequence insertion, deletion and/or substitution occurs at a position between the first base of codon 59 of the REP gene and the last base before the FRT site in the adjacent inverted repeat, more preferably at a position between the first base of the inverted repeat and the last base before the FRT site, even more preferably at a position after the translation termination codon of the REP2 gene and before the last base before the FRT site, such as at the first base after the end of the REP2 coding sequence.

Where, other than the polynucleotide sequence insertion, deletion and/or substitution, the REP2 gene and the inverted repeat sequence have sequences derived from the corresponding regions of the 2 μm plasmid as obtained from *S. cerevisiae*, then in one embodiment, other than the polynucleotide sequence insertion, deletion and/or substitution, the sequence of the REP2 gene and the adjacent inverted repeat is as defined by SEQ ID NO:1 or variant thereof. In SEQ ID NO:1, the first base of codon 59 of the REP2 gene is represented by base number 175 and the last base before the FRT site is represented by base number 1216. The FRT sequence given here is the 55-base-pair sequence from Sadowski et al, 1986, pp 7-10, *Mechanisms of Yeast Recombination* (Current Communications in Molecular Biology) CSHL. Ed. Klar, A. Strathern, J. N. In SEQ ID NO:1, the first base of the inverted repeat is represented by base number 887 and the first base after the translation termination codon of the REP2 gene is represented by base number 892.

In an even more preferred embodiment of the first aspect of the invention, other than the polynucleotide sequence insertion, deletion and/or substitution, the REP2 gene and the inverted repeat sequence have sequences derived from the corresponding regions of the 2 μm plasmid as obtained from *S. cerevisiae* and, in the absence of the interruption the polynucleotide sequence insertion, deletion and/or substitution, comprise an XcmI site or an FspI site within the inverted repeat and the polynucleotide sequence insertion, deletion and/or substitution occurs at the XcmI site, or at the FspI site. In SEQ ID NO:1, the XcmI site is represented by base numbers 935-949 and the FspI site is represented by base numbers 1172-1177.

Where, in the second preferred aspect of the invention, other than the polynucleotide sequence insertion, deletion and/or substitution, the FLP gene and the adjacent inverted repeat sequence have sequences derived from the corresponding regions of the 2 μm plasmid as obtained from *S. cerevisiae*, then it is preferred that the polynucleotide sequence insertion, deletion and/or substitution occurs at a position between the first base of codon 344 of the FLP gene and the last base before the FRET site, more preferably between the first base of the inverted repeat and the last base before the FRT site, yet more preferably between the first base after the end of the FLP coding sequence and the last base before the FRT site, such as at the first base after the end of the FLP coding sequence. The FspI site between the FLP gene and the FRT site can be avoided as an insertion site.

Where, other than the polynucleotide sequence insertion, deletion and/or substitution, the FLP gene and the adjacent inverted repeat sequence have sequences derived from the corresponding regions of the 2 μm plasmid as obtained from *S. cerevisiae*, then in one embodiment, other than the polynucleotide sequence insertion, deletion and/or substitution, the sequence of the FLP gene and the inverted repeat that follows the FLP gene is as defined by SEQ ID NO:2 or variant thereof. In SEQ ID NO:2, the first base of codon 344 of the FLP gene is represented by base number 1030 and the last base before the FRT site is represented by base number 1419, the first base of the inverted repeat is represented by base number 1090, and the first base after the end of the FLP coding sequence is represented by base number 1273.

In an even more preferred embodiment of the second preferred aspect of the invention, other than the polynucleotide sequence insertion, deletion and/or substitution, the FLP gene and the adjacent inverted repeat sequence have sequences derived from the corresponding regions of the 2 μm plasmid as obtained from *S. cerevisiae* and, in the absence of the polynucleotide sequence insertion, deletion and/or substitution, comprise an HgaI site or an FspI site within the inverted repeat and the polynucleotide sequence insertion, deletion and/or substitution occurs at the cut formed by the action of HgaI on the HgaI site (HgaI cuts outside the 5 bp sequence that it recognises), or at the FspI. In SEQ ID NO:2, the HgaI site is represented by base numbers 1262-1266 and the FspI site is represented by base numbers 1375-1380.

The skilled person will appreciate that the features of the plasmid defined by the first and second preferred aspects of the present invention are not mutually exclusive. Thus, a plasmid according to a third preferred aspect of the present invention may comprise polynucleotide sequence insertions, deletions and/or substitutions between the first bases after the last functional codons of both of the REP2 gene and the FLP gene and the last bases before the FRT sites in the inverted repeats adjacent to each of said genes, which polynucleotide sequence insertions, deletions and/or substitutions can be the same or different. For example, a plasmid according to a third aspect of the present invention may, other than the polynucleotide sequence insertions, deletions and/or substitutions, comprise the sequence of SEQ ID NO:1 or variant thereof and the sequence of SEQ ID NO:2 or variant thereof, each comprising a polynucleotide sequence insertion, deletion and/or substitution at a position as defined above for the first and second preferred aspects of the invention, respectively.

The skilled person will appreciate that the features of the plasmid defined by the first, second and third preferred aspects of the present invention do not exclude the possibility of the plasmid also having other sequence modifications. Thus, for example, a 2 μm-family plasmid of the first, second and third preferred aspects of the present invention may additionally comprise a polynucleotide sequence insertion, deletion and/or substitution which is not at a position as defined above. Accordingly, the plasmid may additionally carry transgenes at a site other than the insertion sites of the invention.

Alternative insertion sites in 2 μm plasmids are known in the art, but do not provide the advantages of using the insertion sites defined by the present invention. Nevertheless, plasmids which already include a polynucleotide sequence insertion, deletion and/or substitution at a site known in the art can be further modified by making one or more further modifications at one or more of the sites defined by the first, second and third preferred aspects of the present invention. The skilled person will appreciate that, as discussed in the introduction to this application, there are considerable technical limitations placed on the insertion of transgenes at sites of 2 µm-family plasmids other than as defined by the first and second aspects of the invention.

Typical modified 2 µm plasmids known in the art include those described in Rose & Broach (1990, Methods Enzymol., 185, 234-279), such as plasmids pCV19, pCV20, $CV_{neo}$, which utilise an insertion at EcoRI in FLP, plasmids pCV21, pGT41 and pYE which utilise EcoRI in D as the insertion site, plasmid pHKB52 which utilises PstI in D as the insertion site, plasmid pJDB248 which utilises an insertion at PstI in D and EcoRI in D, plasmid pJDB219 in which PstI in D and EcoRI in FLP are used as insertion sites, plasmid G18, plasmid pAB18 which utilises an insertion at ClaI in FLP, plasmids pGt39 and pA3, plasmids pYT11, pYT14 and pYT11-LEU which use PstI in D as the insertion site, and plasmid PTY39 which uses EcoRI in FLP as the insertion site. Other 2 µm plasmids include pSAC3, pSAC3U1, pSAC3U2, pSAC300, pSAC310, pSAC3C1, pSAC3PL1, pSAC3SL4, and pSAC3SC1 are described in EP 0 286 424 and Chinery & Hinchliffe (1989, Curr. Genet., 16, 21-25) which also described PstI, EagI or SnaBI as appropriate 2 µm insertion sites. Further 2 µm plasmids include pAYE255, pAYE316, pAYE443, pAYE522 (Kerry-Williams et al, 1998, Yeast, 14, 161-169), pDB2244 (WO 00/44772) and pAYE329 (Sleep et al, 2001, Yeast, 18, 403-421).

In one preferred embodiment, a 2 µm-like plasmid as defined by the first, second and third preferred aspects of the present invention additionally comprises a polynucleotide sequence insertion, deletion and/or substitution which occurs within an untranscribed region around the ARS sequence. For example, in the 2 µm plasmid obtained from S. cerevisiae, the untranscribed region around the ARS sequence extends from end of the D gene to the beginning of ARS sequence. Insertion into SnaBI (near the origin of replication sequence ARS) is described in Chinery & Hinchliffe, 1989, Curr. Genet., 16, 21-25. The skilled person will appreciate that an additional polynucleotide sequence insertion, deletion and/or substitution can also occur within the untranscribed region at neighbouring positions to the SnaBI site described by Chinery & Hinchliffe.

A plasmid according to any of the first, second or third aspects of the present invention may be a plasmid capable of autonomous replication in yeast, such as a member of the Saccharomyces, Kluyveromyces, Zygosaccharomyces, or Pichia genus, such Saccharomyces cerevisiae, Saccharomyces carlsbergensis, Kluyveromyces lactis, Pichia pastoris and Pichia membranaefaciens, Zygosaccharomyces rouxii, Zygosaccharomyces bailii, Zygosaccharomyces fermentati, or Kluyveromyces drosphilarum. S. cerevisiae and S. carlsbergensis are thought to provide a suitable host cell for the autonomous replication of all known 2 µm plasmids.

In a preferred embodiment, the, or at least one, polynucleotide sequence insertion, deletion and/or substitution included in a 2 µm-family plasmid of the invention is a polynucleotide sequence insertion. Any polynucleotide sequence insertion may be used, so long as it is not unacceptably detrimental to the stability of the plasmid, by which we mean that the plasmid is at least 1%, 2%, 3%, 4%, 5%, 10%, 15%, 20%, 25%, 30%, 40% 50%, 60%, 70%, 75%, 80%, 85%, 90%, 95%, 96%, 97%, 98%, 99%, 99.9% or substantially 100% stable on non-selective media such as YEPD media compared to the unmodified plasmid, the latter of which is assigned a stability of 100%. Preferably, the above mentioned level of stability is seen after separately culturing yeast cells comprising the modified and unmodified plasmids in a culture medium for one, two, three, four, five, six, seven, eight, nine ten, 11, 12, 13, 14, 15, 16, 17, 18, 19, 20, 25, 30, 35, 40, 45, 50, 60, 70, 80, 90, 100 or more generations.

Where the plasmid comprises a selectable marker, higher levels of stability can be obtained when transformants are grown under selective conditions (e.g. in minimal medium), since the medium can place a selective pressure on the host to retain the plasmid.

Stability in non-selective and selective (e.g. minimal) media can be determined using the methods set forth above. Stability in selective media can be demonstrated by the observation that the plasmids can be used to transform yeast to prototrophy.

Typically, the polynucleotide sequence insertion will be at least 4, 6, 8, 10, 20, 30, 40, 50, 60, 70, 80, 90, 100, 150, 200, 250, 300, 350, 400, 450, 500 or more base pairs in length. Usually, the polynucleotide sequence insertion will be up to 1 kb, 2 kb, 3 kb, 4 kb, 5 kb, 6 kb, 7 kb, 8 kb, 9 kb, 10 kb or more in length. The skilled person will appreciate that the 2 µm plasmid of the present invention may comprise multiple polynucleotide sequence insertions at different sites within the plasmid. Typically, the total length of polynucleotide sequence insertions is no more than 5 kb, 10 kb, 15 kb, 20 kb, 25 kb or 30 kb although greater total length insertion may be possible.

The polynucleotide sequence may or may not be a linker sequence used to introduce new restriction sites. For example a synthetic linker may or may not be introduced at the FspI site after the FLP gene, such as to introduce a further restriction site (e.g. BamHI).

The polynucleotide sequence insertion may contain a transcribed region or may contain no transcribed region. A transcribed region may encode an open reading frame, or may be non-coding. The polynucleotide sequence insertion may contain both transcribed and non-transcribed regions.

A transcribed region is a region of DNA that can be transcribed by RNA polymerase, typically yeast RNA polymerase. A transcribed region can encode a functional RNA molecule, such as ribosomal or transfer RNA or an RNA molecule that can function as an antisense or RNA interference ("RNAi") molecule. Alternatively a transcribed region can encode a messenger RNA molecule (mRNA), which mRNA can contain an open reading frame (ORF) which can be translated in vivo to produce a protein. The term "protein" as used herein includes all natural and non-natural proteins, polypeptides and peptides. Preferably, the ORF encodes a heterologous protein. By "heterologous protein" we mean a protein that is not naturally encoded by a 2 µm-family plasmid (i.e. a "non-2 µm-family plasmid protein"). For convenience the terms "heterologous protein" and "non-2 µm-family plasmid protein" are used synonymously throughout this application. Preferably, therefore, the heterologous protein is not a FLP, REP1, REP2, or a RAF/D protein as encoded by any one of pSR1, pSB3 or pSB4 as obtained from Z. rouxii, pSB1 or pSB2 both as obtained from Z. bailli, pSM1 as obtained from Z. fermentati, pKD1 as obtained from K. drosophilarum, pPM1 as obtained from P. membranaefaciens and the 2 µm plasmid as obtained from S. cerevisiae.

Where the polynucleotide sequence insertion encodes an open reading frame, then it may additionally comprise some polynucleotide sequence that does not encode an open reading frame (termed "non-coding region").

Non-coding region in the polynucleotide sequence insertion may contain one or more regulatory sequences, operatively linked to the open reading frame, which allow for the transcription of the open reading frame and/or translation of the resultant transcript.

The term "regulatory sequence" refers to a sequence that modulates (i.e., promotes or reduces) the expression (i.e., the transcription and/or translation) of an open reading frame to which it is operably linked. Regulatory regions typically include promoters, terminators, ribosome binding sites and the like. The skilled person will appreciate that the choice of regulatory region will depend upon the intended expression system. For example, promoters may be constitutive or inducible and may be cell- or tissue-type specific or non-specific.

Where the expression system is yeast, such as *Saccharomyces cerevisiae*, suitable promoters for *S. cerevisiae* include those associated with the PGK1 gene, GAL1 or GAL10 genes, TEF1, TEF2, PYK1, PMA1, CYC1, PHO5, TRP1, ADH1, ADH2, the genes for glyceraldehyde-3-phosphate dehydrogenase, hexokinase, pyruvate decarboxylase, phosphofructokinase, triose phosphate isomerase, phosphoglucose isomerase, glucokinase, α-mating factor pheromone, a-mating factor pheromone, the PRB1 promoter, the PRA1 promoter, the GPD1 promoter, and hybrid promoters involving hybrids of parts of 5' regulatory regions with parts of 5' regulatory regions of other promoters or with upstream activation sites (e.g. the promoter of EP-A-258 067).

Suitable transcription termination signals are well known in the art. Where the host cell is eukaryotic, the transcription termination signal is preferably derived from the 3' flanking sequence of a eukaryotic gene, which contains proper signals for transcription termination and polyadenylation. Suitable 3' flanking sequences may, for example, be those of the gene naturally linked to the expression control sequence used, i.e. may correspond to the promoter. Alternatively, they may be different. In that case, and where the host is a yeast, preferably *S. cerevisiae*, then the termination signal of the *S. cerevisiae* ADH1, ADH2, CYC1, or PGK1 genes are preferred.

It may be beneficial for the promoter and open reading frame of the heterologous gene, such as the those of the chaperone PDI1, to be flanked by transcription termination sequences so that the transcription termination sequences are located both upstream and downstream of the promoter and open reading frame, in order to prevent transcriptional read-through into neighbouring genes, such as 2 µm genes, and vice versa.

In one embodiment, the favoured regulatory sequences in yeast, such as *Saccharomyces cerevisiae*, include: a yeast promoter (e.g. the *Saccharomyces cerevisiae* PRB1 promoter), as taught in EP 431 880; and a transcription terminator, preferably the terminator from *Saccharomyces* ADH1, as taught in EP 60 057.

It may be beneficial for the non-coding region to incorporate more than one DNA sequence encoding a translational stop codon, such as UAA, UAG or UGA, in order to minimise translational read-through and thus avoid the production of elongated, non-natural fusion proteins. The translation stop codon UAA is preferred. Preferably, at least two translation stop codons are incorporated.

The term "operably linked" includes within its meaning that a regulatory sequence is positioned within any non-coding region such that it forms a relationship with an open reading frame that permits the regulatory region to exert an effect on the open reading frame in its intended manner. Thus a regulatory region "operably linked" to an open reading frame is positioned in such a way that the regulatory region is able to influence transcription and/or translation of the open reading frame in the intended manner, under conditions compatible with the regulatory sequence.

Where the polynucleotide sequence insertion as defined by the first, second or third aspects of the present invention includes an open reading frame that encodes a protein, then it may be advantageous for the encoded protein to be secreted. In that case, a sequence encoding a secretion leader sequence may be included in the open reading frame.

For production of proteins in eukaryotic species such as the yeasts *Saccharomyces cerevisiae, Zygosaccharomyces* species, *Kluyveromyces lactis* and *Pichia pastoris*, known leader sequences include those from the *S. cerevisiae* acid phosphatase protein (Pho5p) (see EP 366 400), the invertase protein (Suc2p) (see Smith et al. (1985) *Science,* 229, 1219-1224) and heat-shock protein-150 (Hsp150p) (see WO 95/33833). Additionally, leader sequences from the *S. cerevisiae* mating factor alpha-1 protein (MFα-1) and from the human lysozyme and human serum albumin (HSA) protein have been used, the latter having been used especially, although not exclusively, for secreting human albumin. WO 90/01063 discloses a fusion of the MFα-1 and HSA leader sequences, which advantageously reduces the production of a contaminating fragment of human albumin relative to the use of the MFα-1 leader sequence. In addition, the natural transferrin leader sequence may be used to direct secretion of transferrin and other heterologous proteins.

Alternatively, the encoded protein may be intracellular.

In one preferred embodiment, at least one polynucleotide sequence insertion as defined by the first, second or third aspects of the present invention includes an open reading frame comprising a sequence that encodes a yeast protein. In another preferred embodiment, at least one polynucleotide sequence insertion as defined by the first, second or third aspects of the present invention includes an open reading frame comprising a sequence that encodes a yeast protein from the same host from which the 2 µm-like plasmid is derived.

In another preferred embodiment, at least one polynucleotide sequence insertion as defined by the first, second or third aspects of the present invention includes an open reading frame comprising a sequence that encodes a protein involved in protein folding, or which has chaperone activity or is involved in the unfolded protein response (Stanford Genome Database (SGD), http://db.yeastgenome.org). Preferred proteins may be selected from protein encoded by AHA1, CCT2, CCT3, CCT4, CCT5, CCT6, CCT7, CCT8, CNS1, CPR3, CPR6, ERO1, EUG1, FMO1, HCH1, HSP10, HSP12, HSP104, HSP26, HSP30, HSP42, HSP60, HSP78, HSP82, JEM1, MDJ1, MDJ2, MPD1, MPD2, PDI1, PFD1, ABC1, APJ1, ATP11, ATP12, BTT1, CDC37, CNS1, CPR6, CPR7, HSC82, KAR2, LHS1, MGE1, MRS11, NOB1, ECM10, SSA1, SSA2, SSA3, SSA4, SSC1, SSE2, SIL1, SLS1, ORM1, UBI4, ORM2, PER1, PTC2, PSE1 and HAC1 or a truncated intronless HAC1 (Valkonen et al. 2003, *Applied Environ. Micro.* 69, 2065).

A preferred protein involved in protein folding, or protein with chaperone activity or a protein involved in the unfolded protein response may be:
  a heat shock protein, such as a protein that is a member of the hsp70 family of proteins (including Kar2p, SSA and SSB proteins, for example proteins encoded by SSA1, SSA2, SSA3, SSA4, SSB1 and SSB2), a protein that is a member of the HSP90-family, or a protein that is a member of the HSP40-family or proteins involved in their modulation (e.g. Sil1p), including DNA-J and DNA-J-like proteins (e.g. Jem1p, Mdj2p);
  a protein that is a member of the karyopherin/importin family of proteins, such as the alpha or beta families of karyopherin/importin proteins, for example the karyopherin beta protein encoded by PSE1;
  a protein that is a member of the ORMDL family described by Hjelmqvist et al, 2002, *Genome Biology,* 3 (6), research 0027.1-0027.16, such as Orm2p.
  a protein that is naturally located in the endoplasmic reticulum or elsewhere in the secretory pathway, such as the golgi. For example, a protein that naturally acts in the lumen of the endoplasmic reticulum (ER), particularly in secretory cells, such as PDI a protein that is a transmembrane protein anchored in the ER, such as a member of the ORMDL family described by Hjelmqvist et al, 2002, supra, (for example, Orm2p);

a protein that acts in the cytosol, such as the hsp70 proteins, including SSA and SSB proteins, for example proteins encoded by SSA1, SSA2, SSA3, SSA4, SSB1 and SSB2;

a protein that acts in the nucleus, the nuclear envelope and/or the cytoplasm, such as Pse1p;

a protein that is essential to the viability of the cell, such as PDI or an essential karyopherin protein, such as Pse1p;

a protein that is involved in sulphydryl oxidation or disulphide bond formation, breakage or isomerization, or a protein that catalyses thiol:disulphide interchange reactions in proteins, particularly during the biosynthesis of secretory and cell surface proteins, such as protein disulphide isomerases (e.g. Pdi1p, Mpd1p), homologues (e.g. Eug1p) and/or related proteins (e.g. Mpd2p, Fmo1p, Ero1p);

a protein that is involved in protein synthesis, assembly or folding, such as PDI and Ssa1p;

a protein that binds preferentially or exclusively to unfolded, rather than mature protein, such as the hsp70 proteins, including SSA and SSB proteins, for example proteins encoded by SSA1, SSA2, SSA3, SSA4, SSB1 and SSB2;

a protein that prevents aggregation of precursor proteins in the cytosol, such as the hsp70 proteins, including SSA and SSB proteins, for example proteins encoded by SSA1, SSA2, SSA3, SSA4, SSB1 and SSB2;

a protein that binds to and stabilises damaged proteins, for example Ssa1p;

a protein that is involved in the unfolded protein response or provides for increased resistance to agents (such as tunicamycin and dithiothreitol) that induce the unfolded protein response, such as a member of the ORMDL family described by Hjelmqvist et al, 2002, supra (for example, Orm2p) or a protein involved in the response to stress (e.g. Ubi4p);

a protein that is a co-chaperone and/or a protein indirectly involved in protein folding and/or the unfolded protein response (e.g. hsp104p, Mdj1p);

a protein that is involved in the nucleocytoplasmic transport of macromolecules, such as Pse1p;

a protein that mediates the transport of macromolecules across the nuclear membrane by recognising nuclear location sequences and nuclear export sequences and interacting with the nuclear pore complex, such as Pse1p;

a protein that is able to reactivate ribonuclease activity against RNA of scrambled ribonuclease as described in as described in EP 0 746 611 and Hillson et al, 1984, *Methods Enzymol.*, 107, 281-292, such as PDI;

a protein that has an acidic pI (for example, 4.0-4.5), such as PDI;

a protein that is a member of the Hsp70 family, and preferably possesses an N-terminal ATP-binding domain and a C-terminal peptide-binding domain, such as Ssa1p.

a protein that is a peptidyl-prolyl cis-trans isomerases (e.g. Cpr3p, Cpr6p);

a protein that is a homologues of known chaperones (e.g. Hsp10p);

a protein that is a mitochondrial chaperone (e.g. Cpr3p);

a protein that is a cytoplasmic or nuclear chaperone (e.g. Cns1p);

a protein that is a membrane-bound chaperone (e.g. Orm2p, Fmo1p);

a protein that has chaperone activator activity or chaperone regulatory activity (e.g. Aha1p, Hac1p, Hch1p);

a protein that transiently binds to polypeptides in their immature form to cause proper folding transportation and/or secretion, including proteins required for efficient translocation into the endoplasmic reticulum (e.g. Lhs1p) or their site of action within the cell (e.g. PseIp);

a protein that is a involved in protein complex assembly and/or ribosome assembly (e.g. Atp11p, PseIp, Nob1p);

a protein of the chaperonin T-complex (e.g. Cct2p); or a protein of the prefoldin complex (e.g. Pfd1p).

One preferred chaperone is protein disulphide isomerase (PDI) or a fragment or variant thereof having an equivalent ability to catalyse the formation of disulphide bonds within the lumen of the endoplasmic reticulum (ER). By "PDI" we include any protein having the ability to reactivate the ribonuclease activity against RNA of scrambled ribonuclease as described in EP 0 746 611 and Hillson et al, 1984, *Methods Enzymol.* 107, 281-292.

Protein disulphide isomerase is an enzyme which typically catalyzes thiol:disulphide interchange reactions, and is a major resident protein component of the E.R. lumen in secretory cells. A body of evidence suggests that it plays a role in secretory protein biosynthesis (Freedman, 1984, *Trends Biochem. Sci.*, 9, 438-41) and this is supported by direct cross-linking studies in situ (Roth and Pierce, 1987, *Biochemistry*, 26, 4179-82). The finding that microsomal membranes deficient in PDI show a specific defect in cotranslational protein disulphide formation (Bulleid and Freedman, 1988, *Nature*, 335, 649-51) implies that the enzyme functions as a catalyst of native disulphide bond formation during the biosynthesis of secretory and cell surface proteins. This role is consistent with what is known of the enzyme's catalytic properties in vitro; it catalyzes thiol:disulphide interchange reactions leading to net protein disulphide formation, breakage or isomerization, and can typically catalyze protein folding and the formation of native disulphide bonds in a wide variety of reduced, unfolded protein substrates (Freedman et al., 1989, *Biochem. Soc. Symp.*, 55, 167-192). PDI also functions as a chaperone since mutant PDI lacking isomerase activity accelerates protein folding (Hayano et al, 1995, *FEBS Letters*, 377, 505-511). Recently, sulphydryl oxidation, not disulphide isomerisation was reported to be the principal function of Protein Disulphide Isomerase in *S. cerevisiae* (Solovyov et al., 2004, J. Biol. Chem., 279 (33) 34095-34100). The DNA and amino acid sequence of the enzyme is known for several species (Scherens et al, 1991, *Yeast*, 7, 185-193; Farquhar et al, 1991, *Gene*, 108, 81-89; EP074661; EP0293793; EP0509841) and there is increasing information on the mechanism of action of the enzyme purified to homogeneity from mammalian liver (Creighton et al, 1980, *J. Mol. Biol.*, 142, 43-62; Freedman et al, 1988, *Biochem. Soc. Trans.*, 16, 96-9; Gilbert, 1989, *Biochemistry*, 28, 7298-7305; Lundstrom and Holmgren, 1990, *J. Biol. Chem.*, 265, 9114-9120; Hawkins and Freedman, 1990, *Biochem. J*, 275, 335-339). Of the many protein factors currently implicated as mediators of protein folding, assembly and translocation in the cell (Rothman, 1989, *Cell*, 59, 591-601), PDI has a well-defined catalytic activity.

The deletion or inactivation of the endogenous PDI gene in a host results in the production of an inviable host. In other words, the endogenous PDI gene is an "essential" gene.

PDI is readily isolated from mammalian tissues and the homogeneous enzyme is a homodimer (2×57 kD) with characteristically acidic pI (4.0-4.5) (Hillson et al, 1984, *Methods Enzymol.,* 107, 281-292). The enzyme has also been purified from wheat and from the alga *Chlamydomonas reinhardii* (Kaska et al, 1990, *Biochem. J,* 268, 63-68), rat (Edman et al, 1985, *Nature,* 317, 267-270), bovine (Yamauchi et al, 1987, *Biochem. Biophys. Res. Comm.,* 146, 1485-1492), human (Pihlajaniemi et al, 1987, *EMBO. J,* 6, 643-9), yeast (Scherens et al, supra; Farquhar et al, supra) and chick (Parkkonen et al, 1988, *Biochem. J,* 256, 1005-1011). The proteins from these vertebrate species show a high degree of sequence conservation throughout and all show several overall features first noted in the rat PDI sequence (Edman et al., 1985, op. cit.).

A yeast protein disulphide isomerase precursor, PDI1, can be found as Genbank accession no. CAA42373 or BAA00723. It has the following sequence of 522 amino acids (SEQ ID NO: 3):

```
  1 mkfsagavls wsslllassv faqqeavape dsavvklatd sfneyiqshd lvlaeffapw 61 cghcknmape yvkaaetlve knitlaqidc tenqdlcmeh nipgfpslki fknsdvnnsi 121 dyegprtaea ivqfmikqsq pavavvadlp aylanetfvt pvivqsgkid adfnatfysm 181 ankhfndydf vsaenadddf kisiylpsam depvvyngkk adiadadvfe kwlqvealpy 241 fgeidgsvfa qyvesglplg ylfyndeeel eeykplftel akknrglmnf vsidarkfgr 301 hagnlnmkeq fplfaihdmt edlkyglpql seeafdelsd kivleskaie slvkdflkgd 361 aspivksqei fengdssvfq lvgknhdeiv ndpkkdvlvl yyapwcghck rlaptyqela 421 dtyanatsdv liakldhten dvrgvviegy ptivlypggk ksesvvyqgs rsldslfdfi 481 kenghfdvdg kalyeeaqek aaeeadadae ladeedaihd el
```

An alternative PDI sequence can be found as Genbank accession no. CAA38402. It has the following sequence of 530 amino acids (SEQ ID NO: 4):

```
  1 mkfsagavls wsslllassv faqqeavape dsavvklatd sfneyiqshd lvlaeffapw 61 cghcknmape yvkaaetlve knitlaqidc tenqdlcmeh nipgfpslki fknrdvnnsi 121 dyegprtaea ivqfmikqsq pavavvadlp aylanetfvt pvivqsgkid adfnatfysm 181 ankhfndydf vsaenadddf klsiylpsam depvvyngkk adiadadvfe kwlqvealpy 241 fgeidgsvfa qyvesglplg ylfyndeeel eeykplftel akknrglmnf vsidarkfgr 301 hagnlnmkeq fplfaihdmt edlkyglpql seeafdelsd kivleskaie slvkdflkgd 361 aspivksqei fenqdssvfq lvgknhdeiv ndpkkdvlvl yyapwcghck rlaptyqela 421 dtyanatsdv liakldhten dvrgvviegy ptivlypggk ksesvvyqgs rsldslfdfi 481 kenghfdvdg kalyeeaqek aaeeaeadae aeadadaela deedaihdel
```

Variants and fragments of the above PDI sequences, and variants of other naturally occurring PDI sequences are also included in the present invention. A "variant", in the context of PDI, refers to a protein wherein at one or more positions there have been amino acid insertions, deletions, or substitutions, either conservative or non-conservative, provided that such changes result in a protein whose basic properties, for example enzymatic activity (type of and specific activity), thermostability, activity in a certain pH-range (pH-stability) have not significantly been changed. "Significantly" in this context means that one skilled in the art would say that the properties of the variant may still be different but would not be unobvious over the ones of the original protein.

By "conservative substitutions" is intended combinations such as Val, Ile, Leu, Ala, Met; Asp, Glu; Asn, Gln; Ser, Thr, Gly, Ala; Lys, Arg, His; and Phe, Tyr, Trp. Preferred conservative substitutions include Gly, Ala; Val, Ile, Leu; Asp, Glu; Asn, Gln; Ser, Thr; Lys, Arg; and Phe, Tyr.

A "variant" typically has at least 25%, at least 50%, at least 60% or at least 70%, preferably at least 80%, more preferably at least 90%, even more preferably at least 95%, yet more preferably at least 99%, most preferably at least 99.5% sequence identity to the polypeptide from which it is derived.

The percent sequence identity between two polypeptides may be determined using suitable computer programs, as discussed below. Such variants may be natural or made using the methods of protein engineering and site-directed mutagenesis as are well known in the art.

A "fragment", in the context of PDI, refers to a protein wherein at one or more positions there have been deletions. Thus the fragment may comprise at most 5, 10, 20, 30, 40 or 50%, typically up to 60%, more typically up to 70%, preferably up to 80%, more preferably up to 90%, even more preferably up to 95%, yet more preferably up to 99% of the complete sequence of the full mature PDI protein. Particularly preferred fragments of PDI protein comprise one or more whole domains of the desired protein.

A fragment or variant of PDI may be a protein that, when expressed recombinantly in a host cell, such as *S. cerevisiae*, can complement the deletion of the endogenously encoded PDI gene in the host cell and may, for example, be a naturally occurring homolog of PDI, such as a homolog encoded by another organism, such as another yeast or other fungi, or another eukaryote such as a human or other vertebrate, or animal or by a plant.

Another preferred chaperone is SSA1 or a fragment or variant thereof having an equivalent chaperone-like activity. SSA1, also known as YG100, is located on chromosome I of the *S. cerevisiae* genome and is 1.93-kbp in size.

One published protein sequence of SSA1 is as follows (SEQ ID NO: 5):

MSKAVGIDLGTTYSCVAHFANDRVDIIANDQGNRTTPSFVAFTDTERLIG

DAAKNQAAMNPSNTVFDAKRLIGRNFNDPEVQADMKHFPFKLIDVDGKPQ

IQVEFKGETKNFTPEQISSMVLGKMKETAESYLGAKVNDAVVTVPAYFND

SQRQATKDAGTIAGLNVLRIINEPTAAAIAYGLDKKGKEEHVLIFDLGGG

TFDVSLLFIEDGIFEVKATAGDTHLGGEDFDNRLVNHFIQEFKRKNKKDL

STNQRALRRLRTACERAKRTLSSSAQTSVEIDSLFEGIDFYTSITRARFE

ELCADLFRSTLDPVEKVLRDAKLDKSQVDEIVLVGGSTRIPKVQKLVTDY

FNGKEPNRSINPDEAVAYGAAVQAAILTGDESSKTQDLLLLDVAPLSLGI

ETAGGVMTKLIPRNSTISTKKFEIFSTYADNQPGVLIQVFEGERAKTKDN

NLLGKFELSGIPPAPRGVPQIEVTFDVDSNGILNVSAVEKGTGKSNKITI

TNDKGRLSKEDIEKMVAEAEKFKEEDEKESQRIASKNQLESIAYSLKNTI

SEAGDKLEQADKDTVTKKAEETISWLDSNTTASKEEFDDKLKELQDIANP

IMSKLYQAGGAPGGAAGGAPGGFPGGAPPAPEAEGPTVEEVD

A published coding sequence for SSA1 is a follows, although it will be appreciated that the sequence can be modified by degenerate substitutions to obtain alternative nucleotide sequences which encode an identical protein product (SEQ ID NO: 6):

ATGTCAAAAGCTGTCGGTATTGATTTAGGTACAACATACTCGTGTGTTGC

TCACTTTGCTAATGATCGTGTGGACATTATTGCCAACGATCAAGGTAACA

GAACCACTCCATCTTTTGTCGCTTTCACTGACACTGAAAGATTGATTGGT

GATGCTGCTAAGAATCAAGCTGCTATGAATCCTTCGAATACCGTTTTCGA

CGCTAAGCGTTTGATCGGTAGAAACTTCAACGACCCAGAAGTGCAGGCTG

ACATGAAGCACTTCCCATTCAAGTTGATCGATGTTGACGGTAAGCCTCAA

ATTCAAGTTGAATTTAAGGGTGAAACCAAGAACTTTACCCCAGAACAAAT

CTCCTCCATGGTCTTGGGTAAGATGAAGGAAACTGCCGAATCTTACTTGG

GAGCCAAGGTCAATGACGCTGTCGTCACTGTCCCAGCTTACTTCAACGAT

TCTCAAAGACAAGCTACCAAGGATGCTGGTACCATTGCTGGTTTGAATGT

CTTGCGTATTATTAACGAACCTACCGCCGCTGCCATTGCTTACGGTTTGG

ACAAGAAGGGTAAGGAAGAACACGTCTTGATTTTCGACTTGGGTGGTGGT

ACTTTCGATGTCTCTTTGTTGTTCATTGAAGACGGTATCTTTGAAGTTAA

GGCCACCGCTGGTGACACCCATTTGGGTGGTGAAGATTTTGACAACAGAT

TGGTCAACCACTTCATCCAAGAATTCAAGAGAAAGAACAAGAAGGACTTG

TCTACCAACCAAAGAGCTTTGAGAAGATTAAGAACCGCTTGTGAAAGAGC

CAAGAGAACTTTGTCTTCCTCCGCTCAAACTTCCGTTGAAATTGACTCTT

TGTTCGAAGGTATCGATTTCTACACTTCCATCACCAGAGCCAGATTCGAA

GAATTGTGTGCTGACTTGTTCAGATCTACTTTGGACCCAGTTGAAAAGGT

CTTGAGAGATGCTAAATTGGACAAATCTCAAGTCGATGAAATTGTCTTGG

TCGGTGGTTCTACCAGAATTCCAAAGGTCCAAAAATTGGTCACTGACTAC

TTCAACGGTAAGGAACCAAACAGATCTATCAACCCAGATGAAGCTGTTGC

TTACGGTCCTGCTGTTCAAGCTGCTATTTTGACTGGTGACGAATCTTCCA

AGACTCAAGATCTATTGTTGTTGGATGTCGCTCCATTATCCTTGGGTATT

GAAACTGCTGGTGGTGTCATGACCAAGTTGATTCCAAGAAACTCTACCAT

TTCAACAAAGAAGTTCGAGATCTTTTCCACTTATGCTGATAACCAACCAG

GTGTCTTGATTCAAGTCTTTGAAGGTGAAAGAGCCAAGACTAAGGACAAC

AACTTGTTGGGTAAGTTCGAATTGAGTGGTATTCCACCAGCTCCAAGAGG

TGTCCCACAAATTGAAGTCACTTTCGATGTCGACTCTAACGGTATTTTGA

ATGTTTCCGCCGTCGAAAAGGGTACTGGTAAGTCTAACAAGATCACTATT

ACCAACGACAAGGGTAGATTGTCCAAGGAAGATATCGAAAAGATGGTTGC

TGAAGCCGAAAAATTCAAGGAAGAAGATGAAAAGGAATCTCAAAGAATTG

CTTCCAAGAACGAATTGGAATCCATTGCTTACTCTTTGAAGAACACCATT

TCTGAAGCTGGTGACAAATTGGAACAAGCTGACAAGGACACCGTCACCAA

GAAGGCTGAAGAGACTATTTCTTGGTTAGACAGCAACACCACTGCCAGCA

AGGAAGAATTCGATGACAAGTTGAAGGAGTTGCAAGACATTGCCAACCCA

ATCATGTCTAAGTTGTACCAAGCTGGTGGTGCTCCAGGTGGCGCTGCAGG

TGGTGCTCCAGGCGGTTTCCCAGGTGGTGCTCCTCCAGCTCCAGAGGCTG

AAGGTCCAACCGTTGAAGAAGTTGATTAA

The protein Ssa1p belongs to the Hsp70 family of proteins and is resident in the cytosol. Hsp70s possess the ability to perform a number of chaperone activities; aiding protein synthesis, assembly and folding; mediating translocation of polypeptides to various intracellular locations, and resolution of protein aggregates (Becker & Craig, 1994, *Eur. J. Biochem.* 219, 11-23). Hsp70 genes are highly conserved, possessing an N-terminal ATP-binding domain and a C-terminal peptide-binding domain. Hsp70 proteins interact with the peptide backbone of, mainly unfolded, proteins. The binding and release of peptides by hsp70 proteins is an ATP-dependent process and accompanied by a conformational change in the hsp70 (Becker & Craig, 1994, supra).

Cytosolic hsp70 proteins are particularly involved in the synthesis, folding and secretion of proteins (Becker & Craig, 1994, supra). In *S. cerevisiae* cytosolic hsp70 proteins have been divided into two groups; SSA (SSA 1-4) and SSB (SSB 1 and 2) proteins, which are functionally distinct from each other. The SSA family is essential in that at least one protein from the group must be active to maintain cell viability (Becker & Craig, 1994, supra). Cytosolic hsp70 proteins bind preferentially to unfolded and not mature proteins. This suggests that they prevent the aggregation of precursor proteins, by maintaining them in an unfolded state prior to being assembled into multimolecular complexes in the cytosol and/or facilitating their translocation to various organelles (Becker & Craig, 1994, supra). SSA proteins are particularly involved in post-translational biogenesis and maintenance of precursors for translocation into the endoplasmic reticulum and mitochondria (Kim et al., 1998, *Proc. Natl. Acad. Sci. USA*. 95, 12860-12865; Ngosuwan et al., 2003, *J. Biol. Chem.* 278 (9), 7034-7042). Ssa1p has been shown to bind damaged proteins, stabilising them in a partially unfolded form and allowing refolding or degradation to occur (Becker & Craig, 1994, supra; Glover & Lindquist, 1998, *Cell.* 94, 73-82).

Variants and fragments of SSA1 are also included in the present invention. A "variant", in the context of SSA1, refers to a protein having the sequence of native SSA1 other than for at one or more positions where there have been amino acid insertions, deletions, or substitutions, either conservative or non-conservative, provided that such changes result in a protein whose basic properties, for example enzymatic activity (type of and specific activity), thermostability, activity in a certain pH-range (pH-stability) have not significantly been changed. "Significantly" in this context means that one skilled in the art would say that the properties of the variant may still be different but would not be unobvious over the ones of the original protein.

By "conservative substitutions" is intended combinations such as Val, Ile, Leu, Ala, Met; Asp, Glu; Asn, Gln; Ser, Thr, Gly, Ala; Lys, Arg, His; and Phe, Tyr, Trp. Preferred conservative substitutions include Gly, Ala; Val, Ile, Leu; Asp, Glu; Asn, Gln; Ser, Thr; Lys, Arg; and Phe, Tyr.

A "variant" of SSA1 typically has at least 25%, at least 50%, at least 60% or at least 70%, preferably at least 80%, more preferably at least 90%, even more preferably at least 95%, yet more preferably at least 99%, most preferably at least 99.5% sequence identity to the sequence of native SSA1.

The percent sequence identity between two polypeptides may be determined using suitable computer programs, as discussed below. Such variants may be natural or made using the methods of protein engineering and site-directed mutagenesis as are well known in the art.

A "fragment", in the context of SSA1, refers to a protein having the sequence of native SSA1 other than for at one or more positions where there have been deletions. Thus the fragment may comprise at most 5, 10, 20, 30, 40 or 50%, typically up to 60%, more typically up to 70%, preferably up to 80%, more preferably up to 90%, even more preferably up to 95%, yet more preferably up to 99% of the complete sequence of the full mature SSA1 protein. Particularly preferred fragments of SSA1 protein comprise one or more whole domains of the desired protein.

A fragment or variant of SSA1 may be a protein that, when expressed recombinantly in a host cell, such as *S. cerevisiae*, can complement the deletion of the endogenously encoded SSA1 gene in the host cell and may, for example, be a naturally occurring homolog of SSA1, such as a homolog encoded by another organism, such as another yeast or other fungi, or another eukaryote such as a human or other vertebrate, or animal or by a plant.

Another preferred chaperone is PSE1 or a fragment or variant thereof having equivalent chaperone-like activity.

PSE1, also known as KAP121, is an essential gene, located on chromosome XIII.

A published protein sequence for the protein pse1p is a follows (SEQ ID NO: 7):

MSALPEEVNRTLLQIVQAFASPDNQIRSVAEKALSEEWITENNIEYLLTF

LAEQAAFSQDTTVAALSAVLFRKLALKAPPSSKLMIMSKNITHIRKEVLA

QIRSSLLKGFLSERADSIRHKLSDAIAECVQDDLPAWPELLQALIESLKS

GNPNFRESSFRILTTVPYLITAVDINSILPIFQSGFTDASDNVKIAAVTA

FVGYFKQLPKSEWSKLGILLPSLLNSLPRFLDDGKDDALASVFESLIELV

ELAPKLFKDMFDQIIQFTDMVIKNKDLEPPARTTALELLTVFSENAPQMC

-continued
KSNQNYGQTLVMVTLIMMTEVSIDDDDAAEWIESDDTDDEEEVTYDHARQ

ALDRVALKLGGEYLAAPLFQYLQQMITSTEWRERFAAMMALSSAAEGCAD

VLIGEIPKILDMVIPLINDPHPRVQYGCCNVLGQISTDFSPFIQRTAHDR

ILPALISKLTSECTSRVQTHAAAALVNFSEFASKDILEPYLDSLLTNLLV

LLQSNKLYVQEQALTTIAFIAEAAKNKFIKYYDTLMPLLLNVLKVNNKDN

SVLKGKCMECATLIGFAVGKEKFHEHSQELISILVALQNSDIDEDDALRS

YLEQSWSRICRILGDDFVPLLPIVIPPLLITAKATQDVGLIEEEEAANFQ

QYPDWDVVQVQGKHIAIHTSVLDDKVSAMELLQSYATLLRGQFAVYVKEV

MEEIALPSLDFYLHDGVRAAGATLIPILLSCLLAATGTQNEELVLLWHKA

SSKLIGGLMSEPMPEITQVYHNSLVNGIKVMGDNCLSEDQLAAFTKGVSA

NLTDTYERMQDRHGDGDEYNENIDEEEDFTDEDLLDEINKSIAAVLKTTN

GHYLKNLENIWPMINTFLLDNEPILVIFALVVIGDLIQYGGEQTASMKNA

FIPKVTECLISPDARIRQAASYIIGVCAQYAPSTYADVCIPTLDTLVQIV

DFPGSKLEENRSSTENASAAIAKILYAYNSNIPNVDTYTANWFKTLPTIT

DKEAASFNYQFLSQLIENNSPIVCAQSNISAVVDSVIQALNERSLTEREG

QTVISSVKKLLGFLPSSDAMAIFNRYPADIMEKVHKWFA*

A published nucleotide coding sequence of PSE1 is a follows, although it will be appreciated that the sequence can be modified by degenerate substitutions to obtain alternative nucleotide sequences which encode an identical protein product (SEQ ID NO: 8):

ATGTCTGCTTTACCGGAAGAAGTTAATAGAACATTACTTCAGATTGTCCA

GGCGTTTGCTTCCCCTGACAATCAAATACGTTCTGTAGCTGAGAAGGCTC

TTAGTGAAGAATGGATTACCGAAAACAATATTGAGTATCTTTTAACTTTT

TTGGCTGAACAAGCCGCTTTCTCCCAAGATACAACAGTTGCAGCATTATC

TGCTGTTCTGTTTAGAAAATTAGCATTAAAAGCTCCCCCTTCTTCGAAGC

TTATGATTATGTCCAAAAATATCACACATATTAGGAAAGAAGTTCTTGCA

CAAATTCGTTCTTCATTGTTAAAAGGGTTTTTGTCGGAAAGAGCTGATTC

AATTAGGCACAAACTATCTGATGCTATTGCTGAGTGTGTTCAAGACGACT

TACCAGCATGGCCAGAATTACTACAAGCTTTAATAGAGTCTTTAAAAAGC

GGTAACCCAAATTTTAGAGAATCCAGTTTTAGAATTTTGACGACTGTACC

TTATTTAATTACCGCTGTTGACATCAACAGTATCTTACCAATTTTTCAAT

CAGGCTTTACTGATGCAAGTGATAATGTCAAAATTGCTGCAGTTACGGCT

TTCGTGGGTTATTTTAAGCAACTACCAAAATCTGAGTGGTCCAAGTTAGG

TATTTTATTACCAAGTCTTTTGAATAGTTTACCAAGATTTTTAGATGATG

GTAAGGACGATGCCCTTGCATCAGTTTTTGAATCGTTAATTGAGTTGGTG

GAATTGGCACCAAAACTATTCAAGGATATGTTTGACCAAATAATACAATT

CACTGATATGGTTATAAAAAATAAGGATTTAGAACCTCCAGCAAGAACCA

CAGCACTCGAACTGCTAACCGTTTTCAGCGAGAACGCTCCCCAAATGTGT

AAATCGAACCAGAATTACGGGCAAACTTTAGTGATGGTTACTTTAATCAT

GATGACGGAGGTATCCATAGATGATGATGATGCAGCAGAATGGATAGAAT

```
CTGACGATACCGATGATGAAGAGGAAGTTACATATGACCACGCTCGTCAA

GCTCTTGATCGTGTTGCTTTAAAGCTGGGTGGTGAATATTTGGCTGCACC

ATTGTTCCAATATTTACAGCAAATGATCACATCAACCGAATGGAGAGAAA

GATTCGCGGCCATGATGGCACTTTCCTCTGCAGCTGAGGGTTGTGCTGAT

GTTCTGATCGGCGAGATCCCAAAAATCCTGGATATGGTAATTCCCCTCAT

CAACGATCCTCATCCAAGAGTACAGTATGGATGTTGTAATGTTTTGGGTC

AAATATCTACTGATTTTTCACCATTCATTCAAGAACTGCACACGATAGAA

TTTTGCCGGCTTTAATATCTAAAACTAACGTCAGAATGCACCTCAAGAGT

TCAAACGCACGCCGCAGCGGCTCTGGTTAACTTTTCTGAATTCGCTTCGA

AGGATATTCTTGAGCCTTACTTGGATAGTCTATTGACAAATTTATTAGTT

TTATTACAAAGCAACAAACTTTACGTACAGGAACAGGCCCTAACAACCAT

TGCATTTATTGCTGAAGCTGCAAAGAATAAATTTATCAAGTATTACGATA

CTCTAATGCCATTATTATTAAATGTTTTGAAGGTTAACAATAAAGATAAT

AGTGTTTTGAAAGGTAAATGTATGGAATGTGCAACTCTGATTGGTTTTGC

CGTTGGTAAGGAAAAATTTCATGAGCACTCTCAAGAGCTGATTTCTATAT

TGGTCGCTTTACAAAACTCAGATATCGATGAAGATGATGCGCTCAGATCA

TACTTAGAACAAAGTTGGAGCAGGATTTGCCGAATTCTGGGTGATGATTT

TGTTCCGTTGTTACCGATTGTTATACCACCCCTGCTAATTACTGCCAAAG

CAACGCAAGACGTCGGTTTAATTGAAGAAGAAGAAGCAGCAAATTTCCAA

CAATATCCAGATTGGGATGTTGTTCAAGTTCAGGGAAAACACATTGCTAT

TCACACATCCGTCCTTGACGATAAAGTATCAGCAATGGAGCTATTACAAA

GCTATGCGACACTTTTAAGAGGCCAATTTGCTGTATATGTTAAAGAAGTA

ATGGAAGAAATAGCTCTACCATCGCTTGACTTTTACCTACATGACGGTGT

TCGTGCTGCAGGAGCAACTTTAATTCCTATTCTATTATCTTGTTTACTTG

CAGCCACCGGTACTCAAAACCGAGGAATTGGTATTGTTGTGGCATAAAGC

TTCGTCTAAACTAATCGGAGGCTTAATGTCAGAACCAATGCCAGAAATCA

CGCAAGTTTATCACAACTCGTTAGTGAATGGTATTAAAGTCATGGGTGAC

AATTGCTTAAGCGAAGACCAATTAGCGGCATTTACTAAGGGTGTCTCCGC

CAACTTAACTGACACTTACGAAAGGATGCAGGATCGCCATGGTGATGGTG

ATGAATATAATGAAAATATTGATGAAGAGGAAGACTTTACTGACGAAGAT

CTTCTCGATGAAATCAACAAGTCTATCGCGGCCGTTTTGAAAACCACAAA

TGGTCATTATCTAAAGAATTTGGAGAATATATGGCCTATGATAAACACAT

TCCTTTTAGATAATGAACCAATTTTAGTCATTTTTGCATTAGTAGTGATT

GGTGACTTGATTCAATATGGTGGCGAACAAACTGCTAGCATGAAGAACGC

ATTTATTCCAAAGGTTACCGAGTGCTTGATTTCTCCTGACGCTCGTATTC

GCCAAGCTGCTTCTTATATAATCGGTGTTTGTGCCCAATACGCTCCATCT

ACATATGCTGACGTTTGCATACCGACTTTAGATACACTTGTTCAGATTGT

CGATTTTCCAGGCTCCAAACTGGAAGAAAATCGTTCTTCAACAGAGAATG

CCAGTGCAGCCATCGCCAAAATTCTTTATGCATACAATTCCAACATTCCT

AACGTAGACACGTACACGGCTAATTGGTTCAAAACGTTACCAACAATAAC

TGACAAAGAAGCTGCCTCATTCAACTATCAATTTTTGAGTCAATTGATTG

AAAATAATTCGCCAATTGTGTGTGCTCAATCTAATATCTCCGCTGTAGTT

GATTCAGTCATACAAGCCTTGAATGAGAGAAGTTTGACCGAAAGGGAAGG

CCAAACGGTGATAAGTTCAGTTAAAAAGTTGTTGGGATTTTTGCCTTCTA

GTGATGCTATGGCAATTTTCAATAGATATCCAGCTGATATTATGGAGAAA

GTACATAAATGGTTTGCATAA
```

The PSE1 gene is 3.25-kbp in size. Pse1p is involved in the nucleocytoplasmic transport of macromolecules (Seedorf & Silver, 1997, *Proc. Natl. Acad. Sci. USA.* 94, 8590-8595). This process occurs via the nuclear pore complex (NPC) embedded in the nuclear envelope and made up of nucleoporins (Ryan & Wente, 2000, *Curr. Opin. Cell Biol.* 12, 361-371). Proteins possess specific sequences that contain the information required for nuclear import, nuclear localisation sequence (NLS) and export, nuclear export sequence (NES) (Pemberton et al., 1998, *Curr. Opin. Cell Biol.* 10, 392-399). Pse1p is a karyopherin/importin, a group of proteins, which have been divided up into α and β families. Karyopherins are soluble transport factors that mediate the transport of macromolecules across the nuclear membrane by recognising NLS and NES, and interact with and the NPC (Seedorf & Silver, 1997, supra; Pemberton et al., 1998, supra; Ryan & Wente, 2000, supra). Translocation through the nuclear pore is driven by GTP hydrolysis, catalysed by the small GTP-binding protein, Ran (Seedorf & Silver, 1997, supra). Pse1p has been identified as a karyopherin β. 14 karyopherin β proteins have been identified in *S. cerevisiae*, of which only 4 are essential. This is perhaps because multiple karyopherins may mediate the transport of a single macromolecule (Isoyama et al., 2001, *J. Biol. Chem.* 276 (24), 21863-21869). Pse1p is localised to the nucleus, at the nuclear envelope, and to a certain extent to the cytoplasm. This suggests the protein moves in and out of the nucleus as part of its transport function (Seedorf & Silver, 1997, supra). Pse1p is involved in the nuclear import of transcription factors (Isoyama et al., 2001, supra; Ueta et al., 2003, *J. Biol. Chem.* 278 (50), 50120-50127), histones (Mosammaparast et al., 2002, *J. Biol. Chem.* 277 (1), 862-868), and ribosomal proteins prior to their assembly into ribosomes (Pemberton et al., 1998, supra). It also mediates the export of mRNA from the nucleus. Karyopherins recognise and bind distinct NES found on RNA-binding proteins, which coat the RNA before it is exported from the nucleus (Seedorf & Silver, 1997, Pemberton et al., 1998, Supra).

As nucleocytoplasmic transport of macromolecules is essential for proper progression through the cell cycle, nuclear transport factors, such as pse1p are novel candidate targets for growth control (Seedorf & Silver, 1997, supra).

Overexpression of Pse1p (protein secretion enhancer) on a multicopy plasmid in *S. cerevisiae* has also been shown to increase protein secretion levels of a repertoire of biologically active proteins (Chow et al., 1992; *J. Cell. Sci.* 101 (3), 709-719).

Variants and fragments of PSE1 are also included in the present invention. A "variant", in the context of PSE1, refers to a protein having the sequence of native PSE1 other than for at one or more positions where there have been amino acid insertions, deletions, or substitutions, either conservative or non-conservative, provided that such changes result in a protein whose basic properties, for example enzymatic activity (type of and specific activity), thermostability, activity in a certain pH-range (pH-stability) have not significantly been changed. "Significantly" in this context means that one skilled in the art would say that the properties of the variant may still be different but would not be unobvious over the ones of the original protein.

By "conservative substitutions" is intended combinations such as Val, Ile, Leu, Ala, Met; Asp, Glu; Asn, Gln; Ser, Thr, Gly, Ala; Lys, Arg, His; and Phe, Tyr, Trp. Preferred conservative substitutions include Gly, Ala; Val, Ile, Leu; Asp, Glu; Asn, Gln; Ser, Thr; Lys, Arg; and Phe, Tyr.

A "variant" of PSE1 typically has at least 25%, at least 50%, at least 60% or at least 70%, preferably at least 80%, more preferably at least 90%, even more preferably at least 95%, yet more preferably at least 99%, most preferably at least 99.5% sequence identity to the sequence of native PSE1.

The percent sequence identity between two polypeptides may be determined using suitable computer programs, as discussed below. Such variants may be natural or made using the methods of protein engineering and site-directed mutagenesis as are well known in the art.

A "fragment", in the context of PSE1, refers to a protein having the sequence of native PSE1 other than for at one or more positions where there have been deletions. Thus the fragment may comprise at most 5, 10, 20, 30, 40 or 50%, typically up to 60%, more typically up to 70%, preferably up to 80%, more preferably up to 90%, even more preferably up to 95%, yet more preferably up to 99% of the complete sequence of the full mature PSE1 protein. Particularly preferred fragments of PSE1 protein comprise one or more whole domains of the desired protein.

A fragment or variant of PSE1 may be a protein that, when expressed recombinantly in a host cell, such as *S. cerevisiae*, can complement the deletion of the endogenous PSE1 gene in the host cell and may, for example, be a naturally occurring homolog of PSE1, such as a homolog encoded by another organism, such as another yeast or other fungi, or another eukaryote such as a human or other vertebrate, or animal or by a plant.

Another preferred chaperone is ORM2 or a fragment or variant thereof having equivalent chaperone-like activity.

ORM2, also known as YLR350W, is located on chromosome XII (positions 828729 to 829379) of the *S. cerevisiae* genome and encodes an evolutionarily conserved protein with similarity to the yeast protein Orm1p. Hjelmqvist et al, 2002, *Genome Biology*, 3 (6), research 0027.1-0027.16 reports that ORM2 belongs to gene family comprising three human genes (ORMDL1, ORMDL2 and ORMDL3) as well as homologs in microsporidia, plants, *Drosophila*, urochordates and vertebrates. The ORMDL genes are reported to encode transmembrane proteins anchored in the proteins endoplasmic reticulum (ER).

The protein Orm2p is required for resistance to agents that induce the unfolded protein response. Hjelmqvist et al, 2002 (supra) reported that a double knockout of the two *S. cerevisiae* ORMDL homologs (ORM1 and ORM2) leads to a decreased growth rate and greater sensitivity to tunicamycin and dithiothreitol.

One published sequence of Orm2p is as follows (SEQ ID NO: 9):

```
MIDRTKNESPAFEESPLTPNVSNLKPFPSQSNKISTPVTDHRRRRSSSVI

SHVEQETFEDENDQQMLPNMNATWVDQRGAWLIHIVVIVLLRLFYSLFGS

TPKWTWTLTNMTYIIGFYIMFHLVKGTPFDFNGGAYDNLTMWEQINDETL

YTPTRKFLLIVPIVLFLISNQYYRNDMTLFLSNLAVTVLIGVVPKLGITH

RLRISIPGITGRAQIS*
```

The above protein is encoded in *S. cerevisiae* by the following coding nucleotide sequence, although it will be appreciated that the sequence can be modified by degenerate substitutions to obtain alternative nucleotide sequences which encode an identical protein product (SEQ ID NO: 10):

```
ATGATTGACCGCACTAAAAACGAATCTCCAGCTTTTGAAGAGTCTCCGCT

TACCCCCAATGTGTCTAACCTGAAACCATTCCCTTCTCAAAGCAACAAAA

TATCCACTCCAGTGACCGACCATAGGAGAAGACGGTCATCCAGCGTAATA

TCACATGTGGAACAGGAAACCTTCGAAGACGAAAATGACCAGCAGATGCT

TCCCAACATGAACGCTACGTGGGTCGACCAGCGAGGCGCGTGGTTGATTC

ATATCGTCGTAATAGTACTCTTGAGGCTCTTCTACTCCTTGTTCGGGTCG

ACGCCCAAATGGACGTGGACTTTAACAAACATGACCTACATCATCGGATT

CTATATCATGTTCCACCTTGTCAAAGGTACGCCCTTCGACTTTAACGGTG

GTGCGTACGACAACCTGACCATGTGGGAGCAGATTAACGATGAGACTTTG

TACACACCCACTAGAAAATTTCTGCTGATTGTACCCATTGTGTTGTTCCT

GATTAGCAACCAGTACTACCGCAACGACATGACACTATTCCTCTCCAACC

TCGCCGTGACGGTGCTTATTGGTGTCGTTCCTAAGCTGGGAATTACGCAT

AGACTAAGAATATCCATCCCTGGTATTACGGGCCGTGCTCAAATTAGTTA

G
```

Variants and fragments of ORM2 are also included in the present invention. A "variant", in the context of ORM2, refers to a protein having the sequence of native ORM2 other than for at one or more positions where there have been amino acid insertions, deletions, or substitutions, either conservative or non-conservative, provided that such changes result in a protein whose basic properties, for example enzymatic activity (type of and specific activity), thermostability, activity in a certain pH-range (pH-stability) have not significantly been changed. "Significantly" in this context means that one skilled in the art would say that the properties of the variant may still be different but would not be unobvious over the ones of the original protein.

By "conservative substitutions" is intended combinations such as Val, Ile, Leu, Ala, Met; Asp, Glu; Asn, Gln; Ser, Thr, Gly, Ala; Lys, Arg, His; and Phe, Tyr, Trp. Preferred conservative substitutions include Gly, Ala; Val, Ile, Leu; Asp, Glu; Asn, Gln; Ser, Thr; Lys, Arg; and Phe, Tyr.

A "variant" of ORM2 typically has at least 25%, at least 50%, at least 60% or at least 70%, preferably at least 80%, more preferably at least 90%, even more preferably at least 95%, yet more preferably at least 99%, most preferably at least 99.5% sequence identity to the sequence of native ORM2.

The percent sequence identity between two polypeptides may be determined using suitable computer programs, as discussed below. Such variants may be natural or made using the methods of protein engineering and site-directed mutagenesis as are well known in the art.

A "fragment", in the context of ORM2, refers to a protein having the sequence of native ORM2 other than for at one or more positions where there have been deletions. Thus the fragment may comprise at most 5, 10, 20, 30, 40 or 50%, typically up to 60%, more typically up to 70%, preferably up to 80%, more preferably up to 90%, even more preferably up to 95%, yet more preferably up to 99% of the complete sequence of the full mature ORM2 protein. Particularly preferred fragments of ORM2 protein comprise one or more whole domains of the desired protein.

A fragment or variant of ORM2 may be a protein that, when expressed recombinantly in a host cell, such as *S. cerevisiae*, can complement the deletion of the endogenous ORM2 gene in the host cell and may, for example, be a naturally occurring homolog of ORM2, such as a homolog encoded by another organism, such as another yeast or other fungi, or another eukaryote such as a human or other vertebrate, or animal or by a plant.

It is particularly preferred that a plasmid according to a first, second or third aspects of the invention includes, either within a polynucleotide sequence insertion, or elsewhere on the plasmid, an open reading frame encoding a protein comprising the sequence of albumin or a fragment or variant thereof. Alternatively, the host cell into which the plasmid is transformed may include within its genome a polynucleotide sequence encoding a protein comprising the sequence of albumin or a fragment or variant thereof, either as an endogenous or heterologous sequence.

By "albumin" we include a protein having the sequence of an albumin protein obtained from any source. Typically the source is mammalian. In one preferred embodiment the serum albumin is human serum albumin ("HSA"). The term "human serum albumin" includes the meaning of a serum albumin having an amino acid sequence naturally occurring in humans, and variants thereof. Preferably the albumin has the amino acid sequence disclosed in WO 90/13653 or a variant thereof. The HSA coding sequence is obtainable by known methods for isolating cDNA corresponding to human genes, and is also disclosed in, for example, EP 73 646 and EP 286 424.

In another preferred embodiment the "albumin" has the sequence of bovine serum albumin. The term "bovine serum albumin" includes the meaning of a serum albumin having an amino acid sequence naturally occurring in cows, for example as taken from Swissprot accession number P02769, and variants thereof as defined below. The term "bovine serum albumin" also includes the meaning of fragments of full-length bovine serum albumin or variants thereof, as defined below.

In another preferred embodiment the albumin is an albumin derived from (i.e. has the sequence of) one of serum albumin from dog (e.g. see Swissprot accession number P49822), pig (e.g. see Swissprot accession number P08835), goat (e.g. as available from Sigma as product no. A2514 or A4164), turkey (e.g. see Swissprot accession number O73860), baboon (e.g. as available from Sigma as product no. A1516), cat (e.g. see Swissprot accession number P49064), chicken (e.g. see Swissprot accession number P19121), ovalbumin (e.g. chicken ovalbumin) (e.g. see Swissprot accession number P01012), donkey (e.g. see Swissprot accession number P39090), guinea pig (e.g. as available from Sigma as product no. A3060, A2639, O5483 or A6539), hamster (e.g. as available from Sigma as product no. A5409), horse (e.g. see Swissprot accession number P35747), rhesus monkey (e.g. see Swissprot accession number Q28522), mouse (e.g. see Swissprot accession number O89020), pigeon (e.g. as defined by Khan et al, 2002, *Int. J. Biol. Macromol.*, 30 (3-4), 171-8), rabbit (e.g. see Swissprot accession number P49065), rat (e.g. see Swissprot accession number P36953) and sheep (e.g. see Swissprot accession number P14639) and includes variants and fragments thereof as defined below.

Many naturally occurring mutant forms of albumin are known. Many are described in Peters, (1996, *All About Albumin: Biochemistry Genetics and Medical Applications*, Academic Press, Inc., San Diego, Calif., p. 170-181). A variant as defined above may be one of these naturally occurring mutants.

A "variant albumin" refers to an albumin protein wherein at one or more positions there have been amino acid insertions, deletions, or substitutions, either conservative or non-conservative, provided that such changes result in an albumin protein for which at least one basic property, for example binding activity (type of and specific activity e.g. binding to bilirubin), osmolarity (oncotic pressure, colloid osmotic pressure), behaviour in a certain pH-range (pH-stability) has not significantly been changed. "Significantly" in this context means that one skilled in the art would say that the properties of the variant may still be different but would not be unobvious over the ones of the original protein.

By "conservative substitutions" is intended combinations such as Gly, Ala; Val, Ile, Leu; Asp, Glu; Asn, Gln; Ser, Thr; Lys, Arg; and Phe, Tyr. Such variants may be made by techniques well known in the art, such as by site-directed mutagenesis as disclosed in U.S. Pat. No. 4,302,386 issued 24 Nov. 1981 to Stevens, incorporated herein by reference.

Typically an albumin variant will have more than 40%, usually at least 50%, more typically at least 60%, preferably at least 70%, more preferably at least 80%, yet more preferably at least 90%, even more preferably at least 95%, most preferably at least 98% or more sequence identity with naturally occurring albumin. The percent sequence identity between two polypeptides may be determined using suitable computer programs, for example the GAP program of the University of Wisconsin Genetic Computing Group and it will be appreciated that percent identity is calculated in relation to polypeptides whose sequence has been aligned optimally. The alignment may alternatively be carried out using the Clustal W program (Thompson et al., 1994). The parameters used may be as follows:

Fast pairwise alignment parameters: K-tuple (word) size; 1, window size; 5, gap penalty; 3, number of top diagonals; 5. Scoring method: x percent. Multiple alignment parameters: gap open penalty; 10, gap extension penalty; 0.05. Scoring matrix: BLOSUM.

The term "fragment" as used above includes any fragment of full-length albumin or a variant thereof, so long as at least one basic property, for example binding activity (type of and specific activity e.g. binding to bilirubin), osmolarity (oncotic pressure, colloid osmotic pressure), behaviour in a certain pH-range (pH-stability) has not significantly been changed.

"Significantly" in this context means that one skilled in the art would say that the properties of the variant may still be different but would not be unobvious over the ones of the original protein. A fragment will typically be at least 50 amino acids long. A fragment may comprise at least one whole sub-domain of albumin. Domains of HSA have been expressed as recombinant proteins (Dockal, M. et al., 1999, *J. Biol. Chem.*, 274, 29303-29310), where domain I was defined as consisting of amino acids 1-197, domain II was defined as consisting of amino acids 189-385 and domain III was defined as consisting of amino acids 381-585. Partial overlap of the domains occurs because of the extended α-helix structure (h10-h1) which exists between domains I and II, and between domains II and III (Peters, 1996, op. cit., Table 2-4). HSA also comprises six sub-domains (sub-domains IA, IB, IIA, IIB, IIIA and IIIB). Sub-domain IA comprises amino acids 6-105, sub-domain IB comprises amino acids 120-177, sub-domain IIA comprises amino acids 200-291, sub-domain IIB comprises amino acids 316-369, sub-domain IIIA comprises amino acids 392-491 and sub-domain IIIB comprises amino acids 512-583. A fragment may comprise a whole or part of one or more domains or sub-domains as defined above, or any combination of those domains and/or sub-domains.

Thus the polynucleotide insertion may comprise an open reading frame that encodes albumin or a variant or fragment thereof.

Alternatively, it is preferred that a plasmid according to a first, second or third aspects of the invention includes, either within a polynucleotide sequence insertion, or elsewhere on the plasmid, an open reading frame encoding a protein comprising the sequence of transferrin or a variant or fragment thereof. Alternatively, the host cell into which the plasmid is transformed may include within its genome a polynucleotide sequence encoding a protein comprising the sequence of transferrin or a variant or fragment thereof, either as an endogenous or heterologous sequence.

The term "transferrin" as used herein includes all members of the transferrin family (Testa, *Proteins of iron metabolism*, CRC Press, 2002; Harris & Aisen, *Iron carriers and iron proteins*, Vol. 5, Physical Bioinorganic Chemistry, VCH, 1991) and their derivatives, such as transferrin, mutant transferrins (Mason et al, 1993, *Biochemistry*, 32, 5472; Mason et al, 1998, *Biochem. J.*, 330 (1), 35), truncated transferring, transferrin lobes (Mason et al, 1996, *Protein Expr. Purif.*, 8, 119; Mason et al, 1991, *Protein Expr. Purif.*, 2, 214), lactoferrin, mutant lactoferrins, truncated lactoferrins, lactoferrin lobes or fusions of any of the above to other peptides, polypeptides or proteins (Shin et al, 1995, *Proc. Natl. Acad. Sci. USA*, 92, 2820; Ali et al, 1999, *J. Biol. Chem.*, 274, 24066; Mason et al, 2002, *Biochemistry*, 41, 9448).

The transferrin may be human transferrin. The term "human transferrin" is used herein to denote material which is indistinguishable from transferrin derived from a human or which is a variant or fragment thereof. A "variant" includes insertions, deletions and substitutions, either conservative or non-conservative, where such changes do not substantially alter the useful ligand-binding or immunogenic properties of transferrin.

Mutants of transferrin are included in the invention. Such mutants may have altered immunogenicity. For example, transferrin mutants may display modified (e.g. reduced) glycosylation. The N-linked glycosylation pattern of a transferrin molecule can be modified by adding/removing amino acid glycosylation consensus sequences such as N-X-S/T, at any or all of the N, X, or S/T position. Transferrin mutants may be altered in their natural binding to metal ions and/or other proteins, such as transferrin receptor. An example of a transferrin mutant modified in this manner is exemplified below.

We also include naturally-occurring polymorphic variants of human transferrin or human transferrin analogues. Generally, variants or fragments of human transferrin will have at least 50% (preferably at least 80%, 90% or 95%) of human transferrin's ligand binding activity (for example iron-binding), weight for weight. The iron binding activity of transferrin or a test sample can be determined spectrophotometrically by 470 nm:280 nm absorbance ratios for the proteins in their iron-free and fully iron-loaded states. Reagents should be iron-free unless stated otherwise. Iron can be removed from transferrin or the test sample by dialysis against 0.1M citrate, 0.1M acetate, 10 nm EDTA pH4.5. Protein should be at approximately 20 mg/mL in 100 mM HEPES, 10 mM NaHCO$_3$ pH8.0. Measure the 470 nm:280 nm absorbance ratio of apo-transferrin (Calbiochem, CN Biosciences, Nottingham, UK) diluted in water so that absorbance at 280 nm can be accurately determined spectrophotometrically (0% iron binding). Prepare 20 mM iron-nitrilotriacetate (FeNTA) solution by dissolving 191 mg nitrotriacetic acid in 2 mL 1M NaOH, then add 2 mL 0.5M ferric chloride. Dilute to 50 mL with deionised water. Fully load apo-transferrin with iron (100% iron binding) by adding a sufficient excess of freshly prepared 20 mM FeNTA, then dialyse the holo-transferrin preparation completely against 100 mM HEPES, 10 mM NaHCO$_3$ pH8.0 to remove remaining FeNTA before measuring the absorbance ratio at 470 nm:280 nm. Repeat the procedure using test sample, which should initially be free from iron, and compare final ratios to the control.

Additionally, single or multiple heterologous fusions comprising any of the above; or single or multiple heterologous fusions to albumin, transferrin or immunoglobins or a variant or fragment of any of these may be used. Such fusions include albumin N-terminal fusions, albumin C-terminal fusions and co-N-terminal and C-terminal albumin fusions as exemplified by WO 01/79271, and transferrin N-terminal fusions, transferrin C-terminal fusions, and co-N-terminal and C-terminal transferrin fusions.

The skilled person will also appreciate that the open reading frame of any other gene or variant, or part or either, can be utilised to form a whole or part of an open reading frame in forming a polynucleotide sequence insertion for use with the present invention. For example, the open reading frame may encode a protein comprising any sequence, be it a natural protein (including a zymogen), or a variant, or a fragment (which may, for example, be a domain) of a natural protein; or a totally synthetic protein; or a single or multiple fusion of different proteins (natural or synthetic). Such proteins can be taken, but not exclusively, from the lists provided in WO 01/79258, WO 01/79271, WO 01/79442, WO 01/79443, WO 01/79444 and WO 01/79480, or a variant or fragment thereof, the disclosures of which are incorporated herein by reference. Although these patent applications present the list of proteins in the context of fusion partners for albumin, the present invention is not so limited and, for the purposes of the present invention, any of the proteins listed therein may be presented alone or as fusion partners for albumin, the Fc region of immunoglobulin, transferrin, lactoferrin or any other protein or fragment or variant of any of the above, including fusion proteins comprising any of the above, as a desired polypeptide. Further examples of transferrin fusions are given in US patent applications US2003/0221201 and US2003/0226155.

Preferred other examples of desirable proteins for expression by the present invention includes sequences comprising the sequence of a monoclonal antibody, an etoposide, a serum protein (such as a blood clotting factor), antistasin, a tick anticoagulant peptide, transferrin, lactoferrin, endostatin, angiostatin, collagens, immunoglobulins or immunoglobulin-based molecules or fragment of either (e.g. a Small Modular ImmunoPharmaceutical™ ("SMIP") or dAb, Fab' fragments, F(ab')2, scAb, scFv or scFv fragment), a Kunitz domain protein (such as those described in WO 03/066824, with or without albumin fusions) interferons, interleukins, IL10, IL11, IL2, interferon α species and sub-species, interferon β species and sub-species, interferon γ species and sub-species, leptin, CNTF, CNTF$_{Ax15}$, IL1-receptor antagonist, erythropoetin (EPO) and EPO mimics, thrombopoetin (TPO) and TPO mimics, prosaptide, cyanovirin-N, 5-helix, T20 peptide, T1249 peptide, HIV gp41, HIV gp120, urokinase, prourokinase, tPA (tissue plasminogen activator), hirudin, platelet derived growth factor, parathyroid hormone, proinsulin, insulin, glucagon, glucagon-like peptides, insulin-like growth factor, calcitonin, growth hormone, transforming growth factor β, tumour necrosis factor, G-CSF, GM-CSF, M-CSF, FGF, coagulation factors in both pre and active forms, including but not limited to plasminogen, fibrinogen, thrombin, pre-thrombin, pro-thrombin, von Willebrand's factor, α$_1$-antitrypsin, plasminogen activators, Factor VII, Factor VIII, Factor IX, Factor X and Factor XIII, nerve growth factor, LACI (lipoprotein associated coagulation inhibitor, also known as tissue factor pathway inhibitor or extrinsic pathway inhibitor), platelet-derived endothelial cell growth factor (PD-ECGF), glucose oxidase, serum cholinesterase, aprotinin, amyloid precursor, inter-alpha trypsin inhibitor, antithrombin III, apo-lipoprotein species, Protein C, Protein S, a variant or fragment or fusion protein of any of the above. The protein may or may not be hirudin.

A "variant", in the context of the above-listed proteins, refers to a protein wherein at one or more positions there have been amino acid insertions, deletions, or substitutions, either conservative or non-conservative, provided that such changes result in a protein whose basic properties, for example enzymatic activity or receptor binding (type of and specific activity), thermostability, activity in a certain pH-range (pH-stability) have not significantly been changed. "Significantly" in this context means that one skilled in the art would say that the properties of the variant may still be different but would not be unobvious over the ones of the original protein.

By "conservative substitutions" is intended combinations such as Val, Ile, Leu, Ala, Met; Asp, Glu; Asn, Gln; Ser, Thr; Gly, Ala; Lys, Arg, His; and Phe, Tyr, Trp. Preferred conservative substitutions include Gly, Ala; Val, Ile, Leu; Asp, Glu; Asn, Gln; Ser, Thr; Lys, Arg; and Phe, Tyr.

A "variant" typically has at least 25%, at least 50%, at least 60% or at least 70%, preferably at least 80%, more preferably at least 90%, even more preferably at least 95%, yet more preferably at least 99%, most preferably at least 99.5% sequence identity to the polypeptide from which it is derived.

The percent sequence identity between two polypeptides may be determined using suitable computer programs, for example the GAP program of the University of Wisconsin Genetic Computing Group and it will be appreciated that percent identity is calculated in relation to polypeptides whose sequence has been aligned optimally.

The alignment may alternatively be carried out using the Clustal W program (Thompson et al., (1994) *Nucleic Acids Res.,* 22 (22), 4673-80). The parameters used may be as follows:

Fast pairwise alignment parameters: K-tuple (word) size; 1, window size; 5, gap penalty; 3, number of top diagonals; 5. Scoring method: x percent.

Multiple alignment parameters: gap open penalty; 10, gap extension penalty; 0.05.

Scoring matrix: BLOSUM.

Such variants may be natural or made using the methods of protein engineering and site-directed mutagenesis as are well known in the art.

A "fragment", in the context of the above-listed proteins, refers to a protein wherein at one or more positions there have been deletions. Thus the fragment may comprise at most 5, 10, 20, 30, 40 or 50% of the complete sequence of the full mature polypeptide. Typically a fragment comprises up to 60%, more typically up to 70%, preferably up to 80%, more preferably up to 90%, even more preferably up to 95%, yet more preferably up to 99% of the complete sequence of the full desired protein. Particularly preferred fragments of a desired protein comprise one or more whole domains of the desired protein.

It is particularly preferred that a plasmid according to a first, second or third aspects of the invention includes, either within a polynucleotide sequence insertion, or elsewhere on the plasmid, an open reading frame encoding a protein comprising the sequence of albumin or a fragment or variant thereof, or any other protein take from the examples above (fused or unfused to a fusion partner) and at least one other heterologous sequence, wherein the at least one other heterologous sequence may contain a transcribed region, such as an open reading frame. In one embodiment, the open reading frame may encode a protein comprising the sequence of a yeast protein. In another embodiment the open reading frame may encode a protein comprising the sequence of a protein involved in protein folding, or which has chaperone activity or is involved in the unfolded protein response, preferably protein disulphide isomerase.

The resulting plasmids may or may not have symmetry between the US and UL regions. For example, a size ratio of 1:1, 5:4, 5:3, 5:2, 5:1 or 5:<1 can be achieved between US and UL or between UL and US regions. The benefits of the present invention do not rely on symmetry being maintained.

The present invention also provides a method of preparing a plasmid of the invention, which method comprises—
  (a) providing a 2 μm-family plasmid comprising a REP2 gene or an FLP gene and an inverted repeat adjacent to said gene;
  (b) providing a polynucleotide sequence and inserting the polynucleotide sequence into the plasmid at a position according to the first, second or third preferred aspects of the invention; and/or
  (c) additionally or as an alternative to step (b), deleting some or all of the nucleotide bases at the positions according to the first, second or third preferred aspects of the invention; and/or
  (d) additionally or as an alternative to either of steps (b) and (c), substituting some or all of the nucleotide bases at the positions according to the first, second or third preferred aspects of the invention with alternative nucleotide bases.

Steps (b), (c) and (d) can be achieved using techniques well known in the art, including cloning techniques, site-directed mutagenesis and the like, such as are described in by Sambrook et al., Molecular Cloning: A Laboratory Manual, 2001, 3rd edition, the contents of which are incorporated herein by reference. For example, one such method involves ligation via cohesive ends. Compatible cohesive ends can be generated on a DNA fragment for insertion and plasmid by the action of suitable restriction enzymes. These ends will rapidly anneal through complementary base pairing and remaining nicks can be closed by the action of DNA ligase.

A further method uses synthetic double stranded oligonucleotide linkers and adaptors. DNA fragments with blunt ends are generated by bacteriophage T4 DNA polymerase or *E. coli* DNA polymerase I which remove protruding 3' termini and fill in recessed 3' ends. Synthetic linkers and pieces of blunt-ended double-stranded DNA, which contain recognition sequences for defined restriction enzymes, can be ligated to blunt-ended DNA fragments by T4 DNA ligase. They are subsequently digested with appropriate restriction enzymes to create cohesive ends and ligated to an expression vector with compatible termini. Adaptors are also chemically synthesised DNA fragments which contain one blunt end used for ligation but which also possess one preformed cohesive end. Alternatively a DNA fragment or DNA fragments can be ligated together by the action of DNA ligase in the presence or absence of one or more synthetic double stranded oligonucleotides optionally containing cohesive ends.

Synthetic linkers containing a variety of restriction endonuclease sites are commercially available from a number of sources including Sigma-Genosys Ltd, London Road, Pampisford, Cambridge, United Kingdom.

Accordingly, the present invention also provides a plasmid obtainable by the above method.

The present invention also provides a host cell comprising a plasmid as defined above. The host cell may be any type of cell. Bacterial and yeast host cells are preferred. Bacterial host cells may be useful for cloning purposes. Yeast host cells may be useful for expression of genes present in the plasmid.

In one embodiment the host cell is a cell in which the plasmid is stable as a multicopy plasmid. Plasmids obtained from one yeast type can be maintained in other yeast types (Irie et al, 1991, *Gene*, 108 (1), 139-144; Irie et al, 1991, *Mol. Gen. Genet.*, 225 (2), 257-265). For example, pSR1 from *Zygosaccharomyces rouxii* can be maintained in *Saccharomyces cerevisiae*. Where the plasmid is based on pSR1, pSB3 or pSB4 the host cell may be *Zygosaccharomyces rouxii*, where the plasmid is based on pSB1 or pSB2 the host cell may be *Zygosaccharomyces bailli*, where the plasmid is based on pPM1 the host cell may be *Pichia membranaefaciens*, where the plasmid is based on pSM1 the host cell may be *Zygosaccharomyces fermentati*, where the plasmid is based on pKD1 the host cell may be *Kluyveromyces drosophilarum* and where the plasmid is based on the 2 μm plasmid the host cell may be *Saccharomyces cerevisiae* or *Saccharomyces carlsbergensis*. A 2 μm-family plasmid of the invention can be said to be "based on" a naturally occurring plasmid if it comprises one, two or preferably three of the genes FLP, REP1 and REP2 having sequences derived from that naturally occurring plasmid.

A plasmid as defined above, may be introduced into a host through standard techniques. With regard to transformation of prokaryotic host cells, see, for example, Cohen et al (1972) *Proc. Natl. Acad. Sci. USA* 69, 2110 and Sambrook et al (2001) *Molecular Cloning, A Laboratory Manual*, 3$^{rd}$ Ed. Cold Spring Harbor Laboratory, Cold Spring Harbor, N.Y. Transformation of yeast cells is described in Sherman et al (1986) *Methods In Yeast Genetics, A Laboratory Manual*, Cold Spring Harbor, N.Y. The method of Beggs (1978) *Nature* 275, 104-109 is also useful. Methods for the transformation of *S. cerevisiae* are taught generally in EP 251 744, EP 258 067 and WO 90/01063, all of which are incorporated herein by reference. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA.

Electroporation is also useful for transforming cells and is well known in the art for transforming yeast cell, bacterial cells and vertebrate cells. Methods for transformation of yeast by electroporation are disclosed in Becker & Guarente (1990) *Methods Enzymol* 194, 182.

Generally, the plasmid will transform not all of the hosts and it will therefore be necessary to select for transformed host cells. Thus, a plasmid according to any one of the first, second or third aspects of the present invention may comprise a selectable marker, either within a polynucleotide sequence insertion, or elsewhere on the plasmid, including but not limited to bacterial selectable marker and/or a yeast selectable marker. A typical bacterial selectable marker is the β-lactamase gene although many others are known in the art. Suitable yeast selectable marker include LEU2 (or an equivalent gene encoding a protein with the activity of β-lactamase malate dehydrogenase), TRP1, HIS3, HIS4, URA3, URA5, SFA1, ADE2, MET15, LYS5, LYS2, ILV2, FBA1, PSE1, PDI1 and PGK1. In light of the different options available, the most suitable selectable markers can be chosen. If it is desirable to do so, URA3 and/or LEU2 can be avoided. Those skilled in the art will appreciate that any gene whose chromosomal deletion or inactivation results in an inviable host, so called essential genes, can be used as a selective marker if a functional gene is provided on the plasmid, as demonstrated for PGK1 in a pgk1 yeast strain (Piper and Curran, 1990, *Curr. Genet.* 17, 119). Suitable essential genes can be found within the Stanford Genome Database (SGD), http://db.yeastgenome.org).

Additionally, a plasmid according to any one of the first, second or third aspects of the present invention may comprise more than one selectable marker, either within a polynucleotide sequence insertion, or elsewhere on the plasmid.

One selection technique involves incorporating into the expression vector a DNA sequence marker, with any necessary control elements, that codes for a selectable trait in the transformed cell. These markers include dihydrofolate reductase, G418 or neomycin resistance for eukaryotic cell culture, and tetracyclin, kanamycin or ampicillin (i.e. β-lactamase) resistance genes for culturing in *E. coli* and other bacteria. Alternatively, the gene for such selectable trait can be on another vector, which is used to co-transform the desired host cell.

Another method of identifying successfully transformed cells involves growing the cells resulting from the introduction of a plasmid of the invention, optionally to allow the expression of a recombinant polypeptide (i.e. a polypeptide which is encoded by a polynucleotide sequence on the plasmid and is heterologous to the host cell, in the sense that that polypeptide is not naturally produced by the host). Cells can be harvested and lysed and their DNA or RNA content examined for the presence of the recombinant sequence using a method such as that described by Southern (1975) *J. Mol. Biol.* 98, 503 or Berent et al (1985) *Biotech.* 3, 208, or other methods of DNA and RNA analysis common in the art. Alternatively, the presence of a polypeptide in the supernatant of a culture of a transformed cell can be detected using antibodies.

In addition to directly assaying for the presence of recombinant DNA, successful transformation can be confirmed by well known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies.

Thus, in addition to the transformed host cells themselves, the present invention also contemplates a culture of those cells, preferably a monoclonal (clonally homogeneous) culture, or a culture derived from a monoclonal culture, in a nutrient medium. Alternatively, transformed cells may themselves represent an industrially/commercially or pharmaceutically useful product and can be purified from a culture medium and optionally formulated with a carrier or diluent in a manner appropriate to their intended industrial/commercial or pharmaceutical use, and optionally packaged and presented in a manner suitable for that use. For example, whole cells could be immobilised; or used to spray a cell culture directly on to/into a process, crop or other desired target. Similarly, whole cell, such as yeast cells can be used as capsules for a huge variety of applications, such as fragrances, flavours and pharmaceuticals.

Transformed host cells may then be cultured for a sufficient time and under appropriate conditions known to those skilled in the art, and in view of the teachings disclosed herein, to permit the expression of any ORF(s) in the one or more polynucleotide sequence insertions within the plasmid.

The present invention thus also provides a method for producing a protein comprising the steps of (a) providing a plasmid according to the first, second or third aspects of the invention as defined above; (b) providing a suitable host cell; (c) transforming the host cell with the plasmid; and (d) culturing the transformed host cell in a culture medium, thereby to produce the protein.

Many expression systems are known, including bacteria (for example *E. coli* and *Bacillus subtilis*), yeasts, filamentous fungi (for example *Aspergillus*), plant cells, whole plants, animal cells and insect cells.

In one embodiment the preferred host cells are the yeasts in which the plasmid is capable of being maintained as a stable multicopy plasmid. Such yeasts include *Saccharomyces cerevisiae*, *Kluyveromyces lactis*, *Pichia pastoris*, *Zygosaccharomyces rouxii*, *Zygosaccharomyces bailli*, *Zygosaccharomyces fermentati*, and *Kluyveromyces drosophilarum*.

A plasmid is capable of being maintained as a stable multicopy plasmid in a host, if the plasmid contains, or is modified to contain, a selectable (e.g. LEU2) marker, and stability, as measured by the loss of the marker, is at least 1%, 2%, 3%, 4%, 5%, 10%, 15%, 20%, 25%, 30%, 40%, 50%, 60%, 70%, 75%, 80%, 85%, 90%, 95%, 96%, 97%, 98%, 99%, 99.9% or substantially 100% after one, two, three, four, five, six, seven, eight, nine ten, 11, 12, 13, 14, 15, 16, 17, 18, 19, 20, 25, 30, 35, 40, 45, 50, 60, 70, 80, 90, 100 or more generations. Loss of a marker can be assessed as described above, with reference to Chinery & Hinchliffe (1989, Curr. Genet., 16, 21-25).

It is particularly advantageous to use a yeast deficient in one or more protein mannosyl transferases involved in O-glycosylation of proteins, for instance by disruption of the gene coding sequence.

Recombinantly expressed proteins can be subject to undesirable post-translational modifications by the producing host cell. For example, the albumin protein sequence does not contain any sites for N-linked glycosylation and has not been reported to be modified, in nature, by O-linked glycosylation. However, it has been found that recombinant human albumin ("rHA") produced in a number of yeast species can be modified by O-linked glycosylation, generally involving mannose. The mannosylated albumin is able to bind to the lectin Concanavalin A. The amount of mannosylated albumin produced by the yeast can be reduced by using a yeast strain deficient in one or more of the PMT genes (WO94/04687). The most convenient way of achieving this is to create a yeast which has a defect in its genome such that a reduced level of one of the Pmt proteins is produced. For example, there may be a deletion, insertion or transposition in the coding sequence or the regulatory regions (or in another gene regulating the expression of one of the PMT genes) such that little or no Pmt protein is produced. Alternatively, the yeast could be transformed to produce an anti-Pmt agent, such as an anti-Pmt antibody.

If a yeast other than S. cerevisiae is used, disruption of one or more of the genes equivalent to the PMT genes of S. cerevisiae is also beneficial, e.g. in Pichia pastoris or Kluyveromyces lactis. The sequence of PMT1 (or any other PMT gene) isolated from S. cerevisiae may be used for the identification or disruption of genes encoding similar enzymatic activities in other fungal species. The cloning of the PMT1 homologue of Kluyveromyces lactis is described in WO 94/04687.

The yeast will advantageously have a deletion of the HSP150 and/or YAP3 genes as taught respectively in WO 95/33833 and WO 95/23857.

The present application also provides a method of producing a protein comprising the steps of providing a host cell as defined above, which host cell comprises a plasmid of the present invention and culturing the host cell in a culture medium thereby to produce the protein. The culture medium may be non-selective or place a selective pressure on the stable multicopy maintenance of the plasmid.

A method of producing a protein expressed from a plasmid of the invention preferably further comprise the step of isolating the thus produced protein from the cultured host cell or the culture medium.

The thus produced protein may be present intracellularly or, if secreted, in the culture medium and/or periplasmic space of the host cell. The protein may be isolated from the cell and/or culture medium by many methods known in the art. For example purification techniques for the recovery of recombinantly expressed albumin have been disclosed in: WO 92/04367, removal of matrix-derived dye; EP 464 590, removal of yeast-derived colorants; EP 319 067, alkaline precipitation and subsequent application of the albumin to a lipophilic phase; and WO 96/37515, U.S. Pat. No. 5,728,553 and WO 00/44772, which describe complete purification processes; all of which are incorporated herein by reference.

Proteins other than albumin may be purified from the culture medium by any technique that has been found to be useful for purifying such proteins.

Such well-known methods include ammonium sulphate or ethanol precipitation, acid or solvent extraction, anion or cation exchange chromatography, phosphocellulose chromatography, hydrophobic interaction chromatography, affinity chromatography, hydroxylapatite chromatography, lectin chromatography, concentration, dilution, pH adjustment, diafiltration, ultrafiltration, high performance liquid chromatography ("HPLC"), reverse phase HPLC, conductivity adjustment and the like.

In one embodiment, any one or more of the above mentioned techniques may be used to further purifying the thus isolated protein to a commercially acceptable level of purity. By commercially acceptable level of purity, we include the provision of the protein at a concentration of at least 0.01 $g \cdot L^{-1}$, 0.02 $g \cdot L^{-1}$, 0.03 $g \cdot L^{-1}$, 0.04 $g \cdot L^{-1}$, 0.05 $g \cdot L^{-1}$, 0.06 $g \cdot L^{-1}$, 0.07 $g \cdot L^{-1}$, 0.08 $g \cdot L^{-1}$, 0.09 $g \cdot L^{-1}$, 0.1 $g \cdot L^{-1}$, 0.2 $g \cdot L^{-1}$, 0.3 $g \cdot L^{-1}$, 0.4 $g \cdot L^{-1}$, 0.5 $g \cdot L^{-1}$, 0.6 $g \cdot L^{-1}$, 0.7 $g \cdot L^{-1}$, 0.8 $g \cdot L^{-1}$, 0.9 $g \cdot L^{-1}$, 1 $g \cdot L^{-1}$, 2 $g \cdot L^{-1}$, 3 $g \cdot L^{-1}$, 4 $g \cdot L^{-1}$, 5 $g \cdot L^{-1}$, 6 $g \cdot L^{-1}$, 7 $g \cdot L^{-1}$, 8 $g \cdot L^{-1}$, 9 $g \cdot L^{-1}$, 10 $g \cdot L^{-1}$, 15 $g \cdot L^{-1}$, 20 $g \cdot L^{-1}$, 25 $g \cdot L^{-1}$, 30 $g \cdot L^{-1}$, 40 $g \cdot L^{-1}$, 50 $g \cdot L^{-1}$, 60 $g \cdot L^{-1}$, 70 $g \cdot L^{-1}$, 70 $g \cdot L^{-1}$, 90 $g \cdot L^{-1}$, 100 $g \cdot L^{-1}$, 150 $g \cdot L^{-1}$, 200 $g \cdot L^{-1}$, 250 $g \cdot L^{-1}$, 300 $g \cdot L^{-1}$, 350 $g \cdot L^{-1}$, 400 $g \cdot L^{-1}$, 500 $g \cdot L^{-1}$, 600 $g \cdot L^{-1}$, 700 $g \cdot L^{-1}$, 800 $g \cdot L^{-1}$, 900 $g \cdot L^{-1}$, 1000 $g \cdot L^{-1}$, or more.

The thus purified protein may be lyophilised. Alternatively it may be formulated with a carrier or diluent, and optionally presented in a unit form.

It is preferred that the protein is isolated to achieve a pharmaceutically acceptable level of purity. A protein has a pharmaceutically acceptable level of purity if it is essentially pyrogen free and can be administered in a pharmaceutically efficacious amount without causing medical effects not associated with the activity of the protein.

The resulting protein may be used for any of its known utilities, which, in the case of albumin, include i.v. administration to patients to treat severe burns, shock and blood loss, supplementing culture media, and as an excipient in formulations of other proteins.

Although it is possible for a therapeutically useful desired protein obtained by a process of the invention to be administered alone, it is preferable to present it as a pharmaceutical formulation, together with one or more acceptable carriers or diluents. The carrier(s) or diluent(s) must be "acceptable" in the sense of being compatible with the desired protein and not deleterious to the recipients thereof. Typically, the carriers or diluents will be water or saline which will be sterile and pyrogen free.

Optionally the thus formulated protein will be presented in a unit dosage form, such as in the form of a tablet, capsule, injectable solution or the like.

We have also demonstrated that a plasmid-borne gene encoding a protein comprising the sequence of an "essential" protein can be used to stably maintain the plasmid in a host cell that, in the absence of the plasmid, does not produce the essential protein. A preferred essential protein is an essential chaperone, which can provide the further advantage that, as well as acting as a selectable marker to increase plasmid stability, its expression simultaneously increases the expression of a heterologous protein encoded by a recombinant gene within the host cell. This system is advantageous because it allows the user to minimise the number of recombinant genes that need to be carried by a plasmid. For example, typical prior art plasmids carry marker genes (such as those as described above) that enable the plasmid to be stably maintained during host cell culturing process. Such marker genes need to be retained on the plasmid in addition to any further genes that are required to achieve a desired effect. However, the ability of plasmids to incorporate exogenous DNA sequences is limited and it is therefore advantageous to minimise the number of sequence insertions required to achieve a desired effect. Moreover, some marker genes (such as auxotrophic marker genes) require the culturing process to be conducted under specific conditions in order to obtain the effect of the marker gene. Such specific conditions may not be optimal for cell growth or protein production, or may require inefficient or unduly expensive growth systems to be used.

Thus, it is possible to use a gene that recombinantly encodes a protein comprising the sequence of an "essential protein" as a plasmid-borne gene to increase plasmid stability, where the plasmid is present within a cell that, in the absence of the plasmid, is unable to produce the "essential protein".

It is preferred that the "essential protein" is one that, when its encoding gene(s) in a host cell are deleted or inactivated, does not result in the host cell developing an auxotrophic (biosynthetic) requirement. By "auxotrophic (biosynthetic) requirement" we include a deficiency that can be complemented by additions or modifications to the growth medium. Therefore, an "essential marker gene" which encodes an "essential protein", in the context of the present invention is one that, when deleted or inactivated in a host cell, results in a deficiency which cannot be complemented by additions or modifications to the growth medium. The advantage of this system is that the "essential marker gene" can be used as a selectable marker on a plasmid in host cell that, in the absence of the plasmid, is unable to produce that gene product, to achieve increased plasmid stability without the disadvantage of requiring the cell to be cultured under specific selective (e.g. selective nutrient) conditions. Therefore, the host cell can be cultured under conditions that do not have to be adapted for any particular marker gene, without losing plasmid stability. For example, host cells produced using this system can be cultured in non-selective media such as complex or rich media, which may be more economical than the minimal media that are commonly used to give auxotrophic marker genes their effect.

The cell may, for example, have its endogenous gene or genes deleted or otherwise inactivated.

It is particularly preferred if the "essential protein" is an "essential" chaperone, as this can provide the dual advantage of improving plasmid stability without the need for selective growth conditions and increasing the production of proteins, such as endogenously encoded or a heterologous proteins, in the host cell. This system also has the advantage that it minimises the number of recombinant genes that need to be carried by the plasmid if one chooses to use over-expression of an essential chaperone to increase protein production by the host cell.

Preferred "essential proteins" for use in this aspect of the invention include the "essential" chaperones PDI1 and PSE1, and other "essential" gene products such as PGK1 or FBA1 which, when the endogenous gene(s) encoding these proteins are deleted or inactivated in a host cell, do not result in the host cell developing an auxotrophic (biosynthetic) requirement.

Accordingly, in a fourth aspect, the present invention also provides a host cell comprising a plasmid (such as a plasmid according to any of the first, second or third aspects of the invention), the plasmid comprising a gene that encodes an essential chaperone wherein, in the absence of the plasmid, the host cell is unable to produce the chaperone. Preferably, in the absence of the plasmid, the host cell is inviable. The host cell may further comprise a recombinant gene encoding a heterologous (or homologous, in the sense that the recombinant gene encodes a protein identical in sequence to a protein encoded by the host cell) protein, such as those described above in respect of earlier aspects of the invention.

The present invention also provides, in a fifth aspect, a plasmid comprising, as the sole selectable marker, a gene encoding an essential chaperone. The plasmid may further comprise a gene encoding a heterologous protein. The plasmid may be a 2 μm-family plasmid and is preferably a plasmid according to any of the first, second or third aspects of the invention.

The present invention also provides, in a sixth aspect, a method for producing a heterologous protein comprising the steps of: providing a host cell comprising a plasmid, the plasmid comprising a gene that encodes an essential chaperone wherein, in the absence of the plasmid, the host cell is unable to produce the chaperone and wherein the host cell further comprises a recombinant gene encoding a heterologous protein; culturing the host cell in a culture medium under conditions that allow the expression of the essential chaperone and the heterologous protein; and optionally purifying the thus expressed heterologous protein from the cultured host cell or the culture medium; and further optionally, lyophilising the thus purified protein.

The method may further comprise the step of formulating the purified heterologous protein with a carrier or diluent and optionally presenting the thus formulated protein in a unit dosage form, in the manner discussed above. In one preferred embodiment, the method involves culturing the host cell in non-selective media, such as a rich media.

BRIEF DESCRIPTION OF THE FIGURES

FIG. 3 shows some exemplified FLP insertion sites.
FIG. 12 shows some exemplified REP2 insertion sites.
FIG. 33 shows table 3 as referred to in the Examples.
FIG. 34 shows the sequence of SEQ ID NO: 1.
FIG. 35 shows the sequence of SEQ ID NO: 2.
FIG. 43 shows the sequence of PCR primers DS248 and DS250.

EXAMPLES

Figure 1:
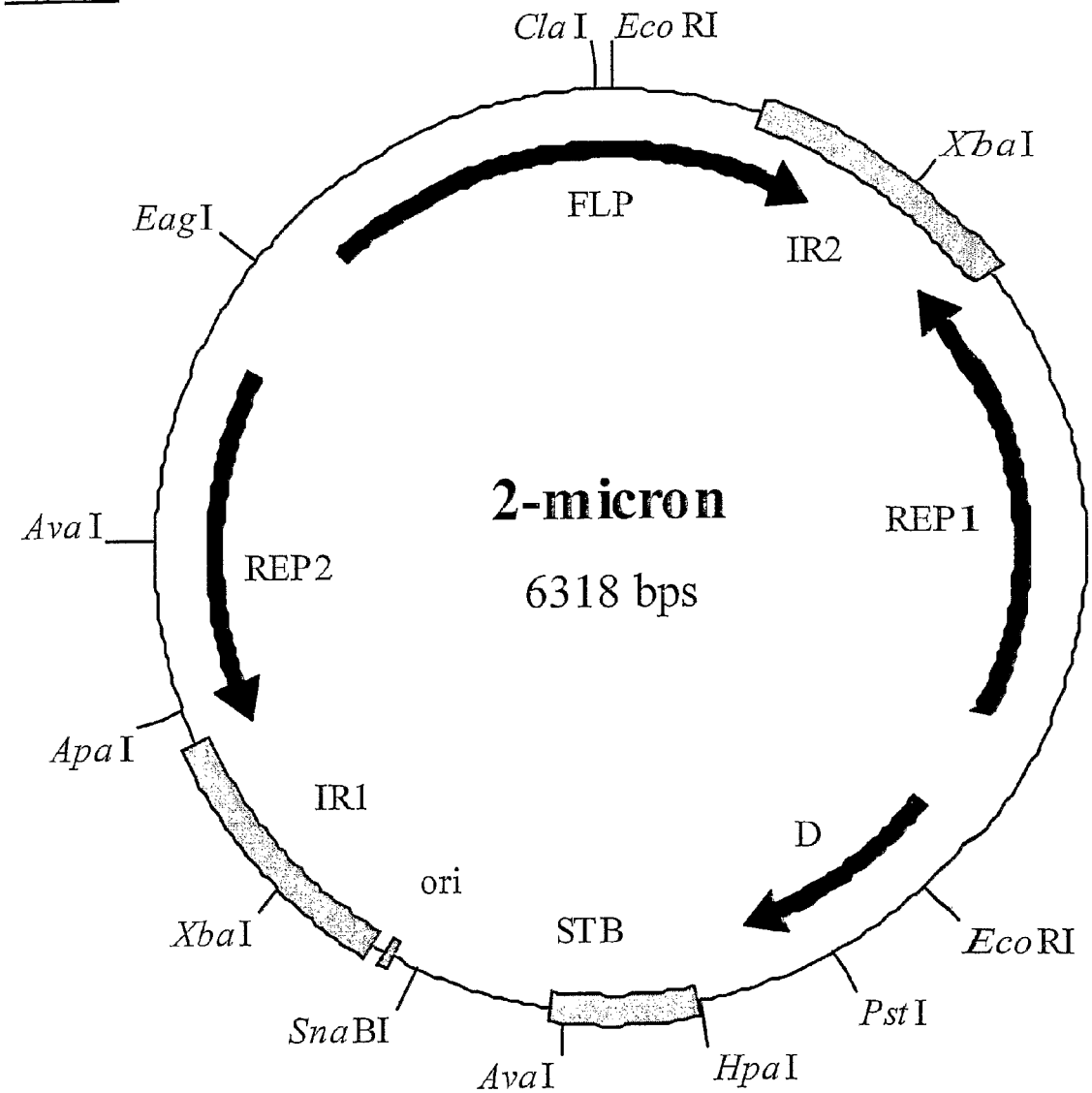
FIG. 1 shows a plasmid map of the 2 μm plasmid.
Figure 2:
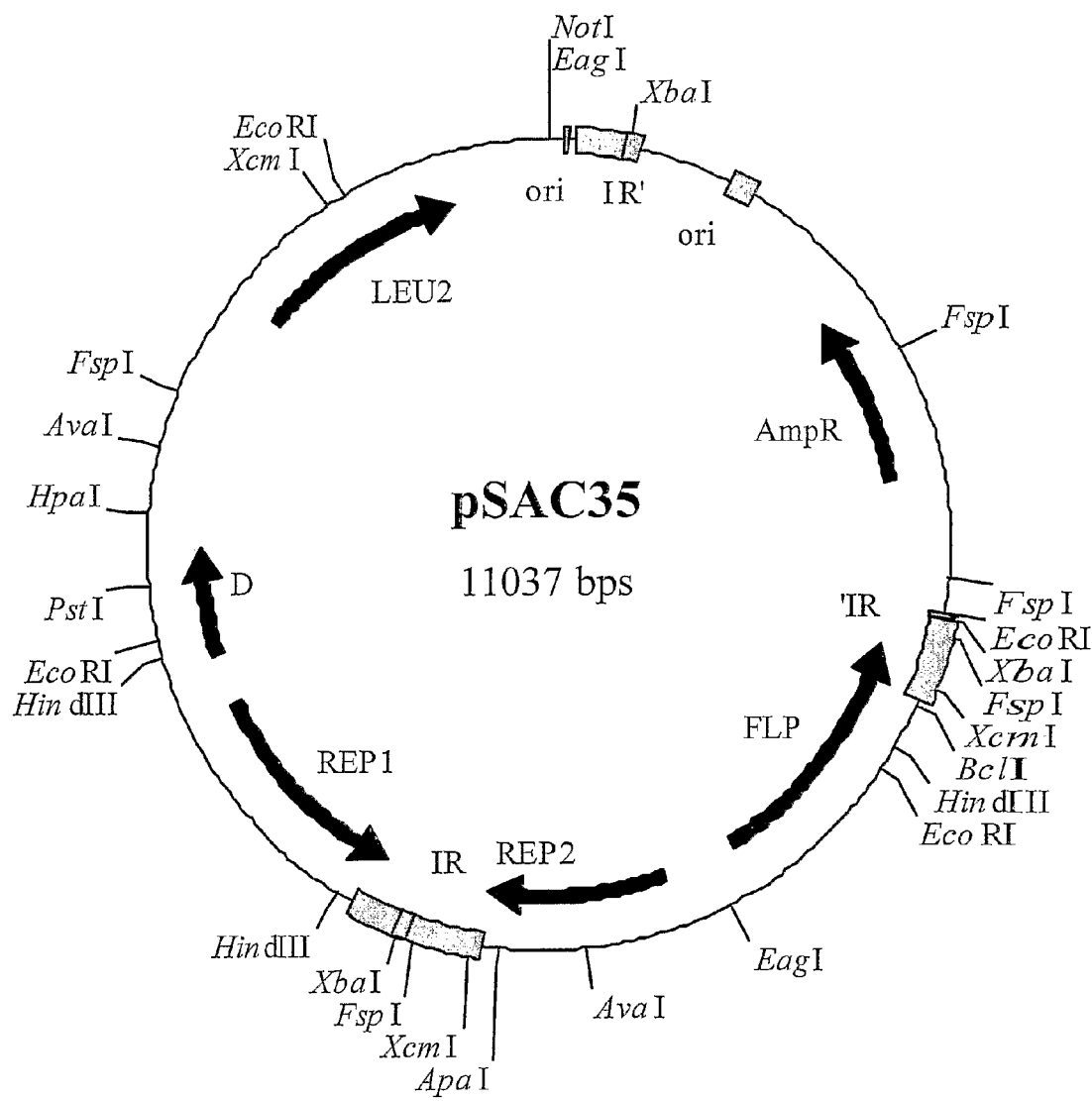
FIG. 2 shows a plasmid map of pSAC35.

These example describes the insertion of additional DNA sequences into a number of positions, defined by restriction endonuclease sites, within the US-region of a 2 μm-family plasmid, of the type shown in FIG. 2 and generally designated pSAC35, which includes a β-lactamase gene (for ampicillin resistance, which is lost from the plasmid following transformation into yeast), a LEU2 selectable marker and an oligonucleotide linker, the latter two of which are inserted into a unique SnaBI-site within the UL-region of the 2 μm-family disintegration vector, pSAC3 (see EP 0 286 424). The sites chosen were towards the 3'-ends of the REP2 and FLP coding regions or in the downstream inverted repeat sequences. Short synthetic DNA linkers were inserted into each site, and the relative stabilities of the modified plasmids were compared during growth on non-selective media. Preferred sites for DNA insertions were identified. Insertion of larger DNA fragments containing "a gene of interest" was demonstrated by inserting a DNA fragment containing the PDI1 gene into the XcmI-site after REP2.

Example 1

Insertion of Synthetic DNA Linker into XcmI-Sites in the Small Unique Region of pSAC35

Sites assessed initially for insertion of additional DNA into the US-region of pSAC35, were the XcmI-sites in the 599-bp inverted repeats. One XcmI-site cuts 51-bp after the REP2 translation termination codon, whereas the other XcmI-site cuts 127-bp before the end of the FLP coding sequence, due to overlap with the inverted repeat (see FIG. 3).

The sequence inserted was a 52-bp linker made by annealing 0.5 mM solutions of oligonucleotides CF86 and CF87. This DNA linker contained a core region "SnaBI-PacI-FseI/SfiI-SmaI-SnaBI", which encoded restriction sites absent from pSAC35.

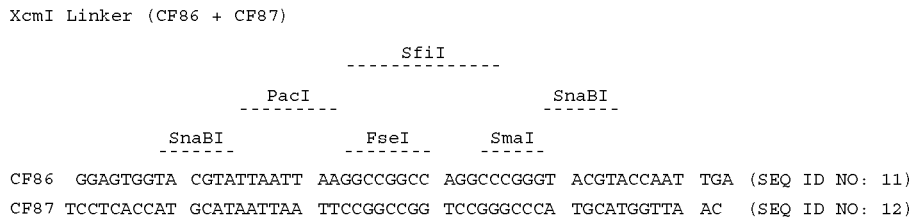

Figure 4:
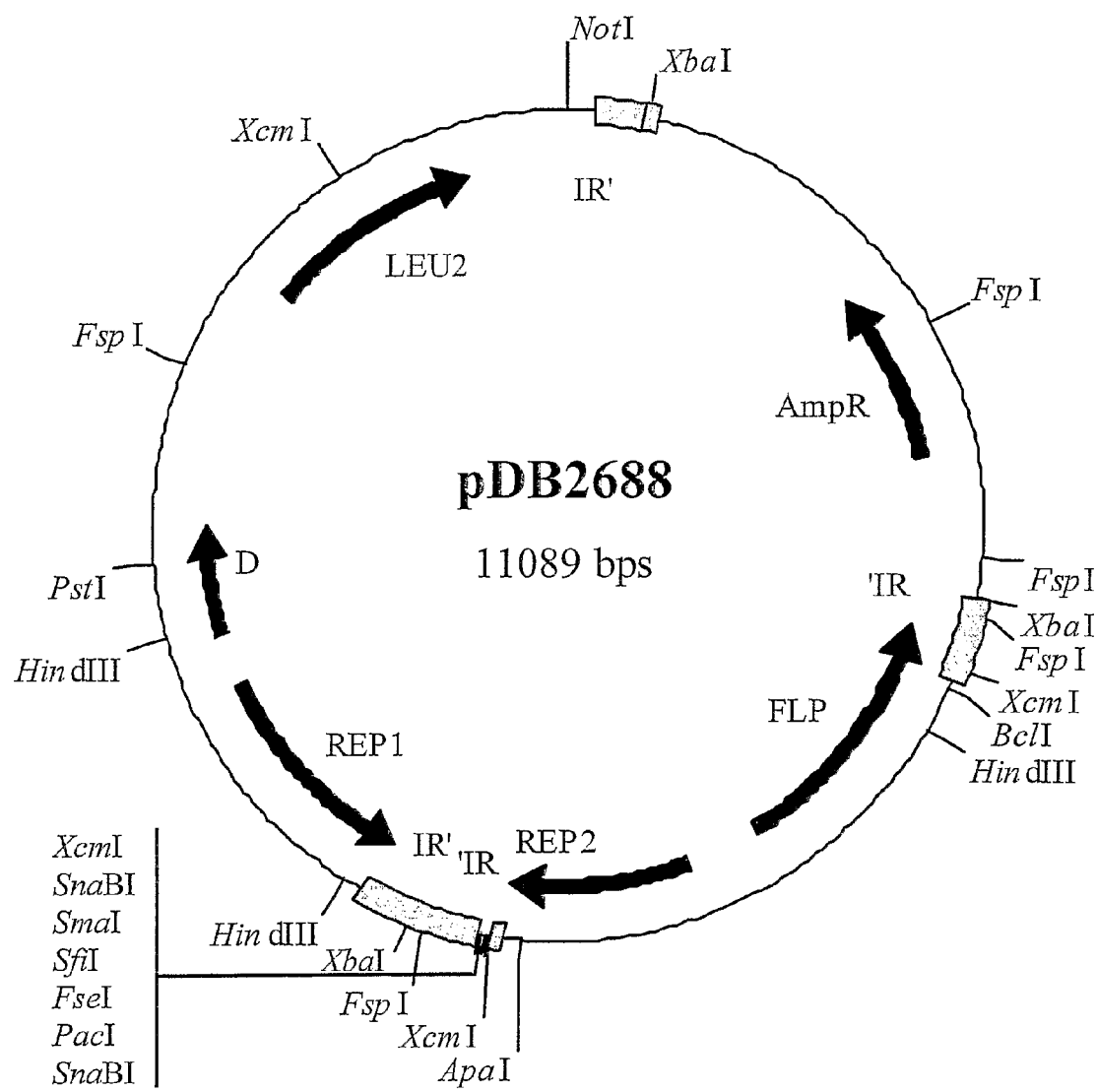
FIGS. 4 to 8, 10, 11, 13 to 32, 36 to 42, 44 to 46, 48 to 54 and 57 to 76 show maps of various plasmids.

Plasmid pSAC35 was partially digested with XcmI, the linear 11-kb fragment was isolated from a 0.7% (w/v) agarose gel, ligated with the CF86/CF87 XcmI linker (neat, $10^{-1}$ and $10^{-2}$ dilutions) and transformed into E. coli DH5α. Ampicillin resistant transformants were selected and screened for the presence of plasmids that could be linearised by SmaI digestion. Restriction enzyme analysis identified pDB2688 (FIG. 4) with the linker cloned into the XcmI-site after REP2. DNA sequencing using oligonucleotides primers CF88, CF98 and CF99 (Table 1) confirmed the insertion contained the correct lifer sequence.

TABLE 1

Oligonucleotide sequencing printers:

| Primer | Description | Sequence |
|---|---|---|
| CF88 (SEQ ID NO: 13) | REP2 primer, 20 mer | 5'-ATCACGTAATACTTCTAGGG-3' |
| CF98 (SEQ ID NO: 14) | REP2 primer, 20 mer | 5'-AGAGTGAGTTGGAAGGAAGG-3' |
| CF99 (SEQ ID NO: 15) | REP2 primer, 20 mer | 5'-AGCTCGTAAGCGTCGTTACC-3' |
| CF90 (SEQ ID NO: 16) | FLP primer, 20 mer | 5'-CTAGTTTCTCGGTACTATGC-3' |
| CF91 (SEQ ID NO: 17) | FLP primer, 20 mer | 5'-GAGTTGACTAATGTTGTGGG-3' |

TABLE 1-continued

Oligonucleotide sequencing printers:

| Primer | Description | Sequence |
|---|---|---|
| CF100 (SEQ ID NO: 18) | FLP primer, 20 mer | 5'-AAAGCTTTGAAGAAAAATGC-3' |
| CF101 (SEQ ID NO: 19) | FLP primer, 20 mer | 5'-GCAAGGGGTAGGATCGATCC-3' |
| CF123 (SEQ ID NO: 20) | pDB2783 MCS, 24 mer | 5'-ATTCGAGCTCGGTACCTACGTACT-3' |
| CF126 (SEQ ID NO: 21) | pDB2783 MCS, 24 mer | 5'-CCCGGGCACGTGGGATCCTCTAGA-3' |
| M13-Forward (SEQ ID NO: 22) | pDB2783 MCS, 17 mer | 5'-GTAAAACGACGGCCAGT-3' |
| M13-Reverse (SEQ ID NO: 23) | pDB2783 MCS, 16 mer | 5'-AACAGCTATGACCATG-3' |
| CF129 (SEQ ID NO: 24) | Inverted repeat primer, 19 mer | 5'-GTGTTTATGCTTAAATGCG-3' |
| CF130 (SEQ ID NO: 25) | REP2 primer, 20 mer | 5'-TCCTCTTGCATTTGTGTCTC-3' |
| CF131 (SEQ ID NO: 26) | REP2 primer, 19 mer | 5'-ATCTTCCTATTATTATAGC-3' |

Figure 5:
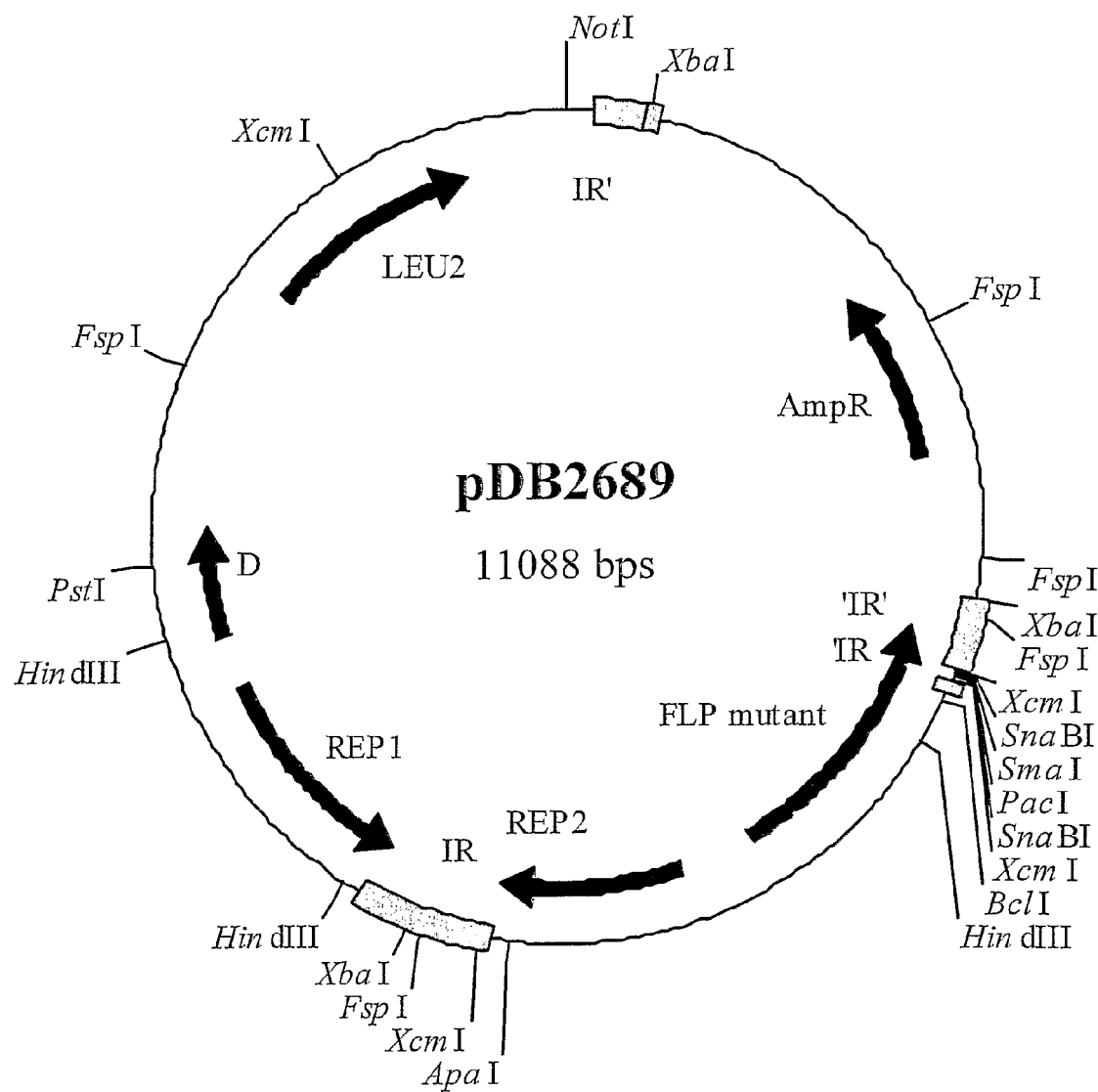

Restriction enzyme analysis also identified pDB2689 (FIG. 5), with the linker cloned into the XcmI-site in the FLP gene. However, the linker in pDB2689 was shown by DNA sequencing using primers CF90 and CF91 to have a missing G:C base-pair within the FseI/SfiI site (marked above in bold in the CF86+CF87 linker). This generated a coding sequence for a mutant Flp-protein, with 39 C-terminal amino acid residues replaced by 56 different amino acids before the translation termination codon.

Figure 6:
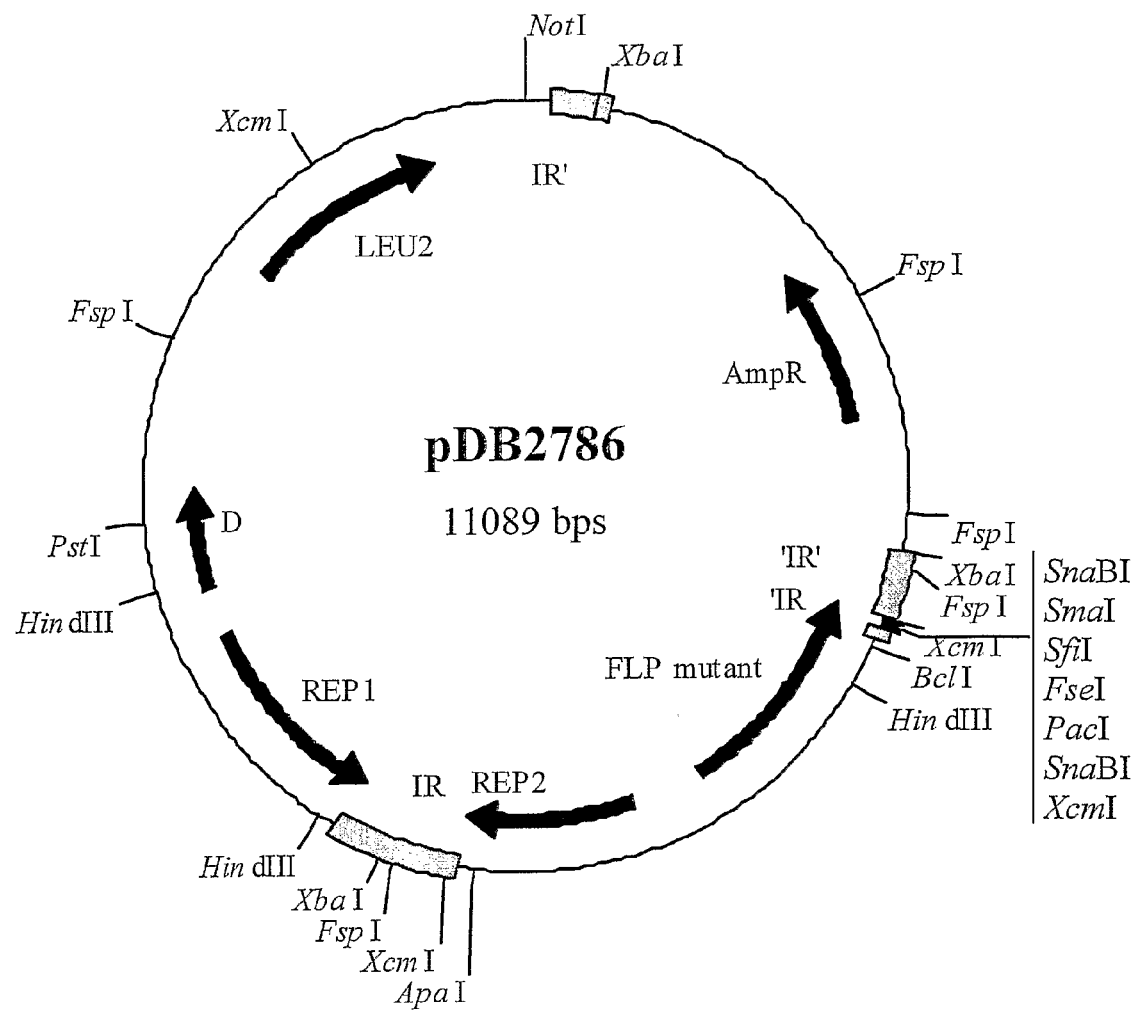

The missing base-pair in the pDB2689 tinker sequence was corrected to produce pDB2786 (FIG. 6). To achieve this, a 31-bp 5'-phosphorylated SnaBI-linker was made from oligonucleotides CF104 and CF105. This was ligated into the SnaBI site of pDB2689, which had previously been treated with calf intestinal alkaline phosphatase. DNA sequencing with primers CF90, CF91, CF100 and CF101 confirmed the correct DNA linker sequence in pDB2786. This generated a coding sequence for a mutant Flp-protein, with 39 C-terminal residues replaced by 14 different residues before translation termination.

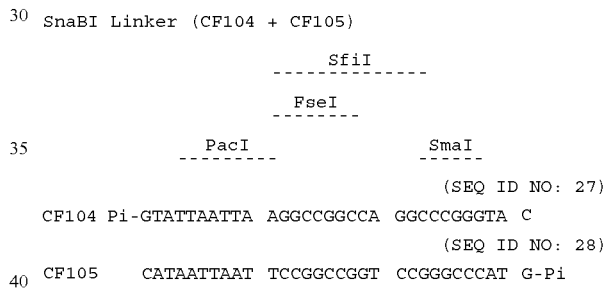

(SEQ ID NO: 27)
CF104 Pi-GTATTAATTA AGGCCGGCCA GGCCCGGGTA C
(SEQ ID NO: 28)
CF105    CATAATTAAT TCCGGCCGGT CCGGGCCCAT G-Pi

Figure 7:
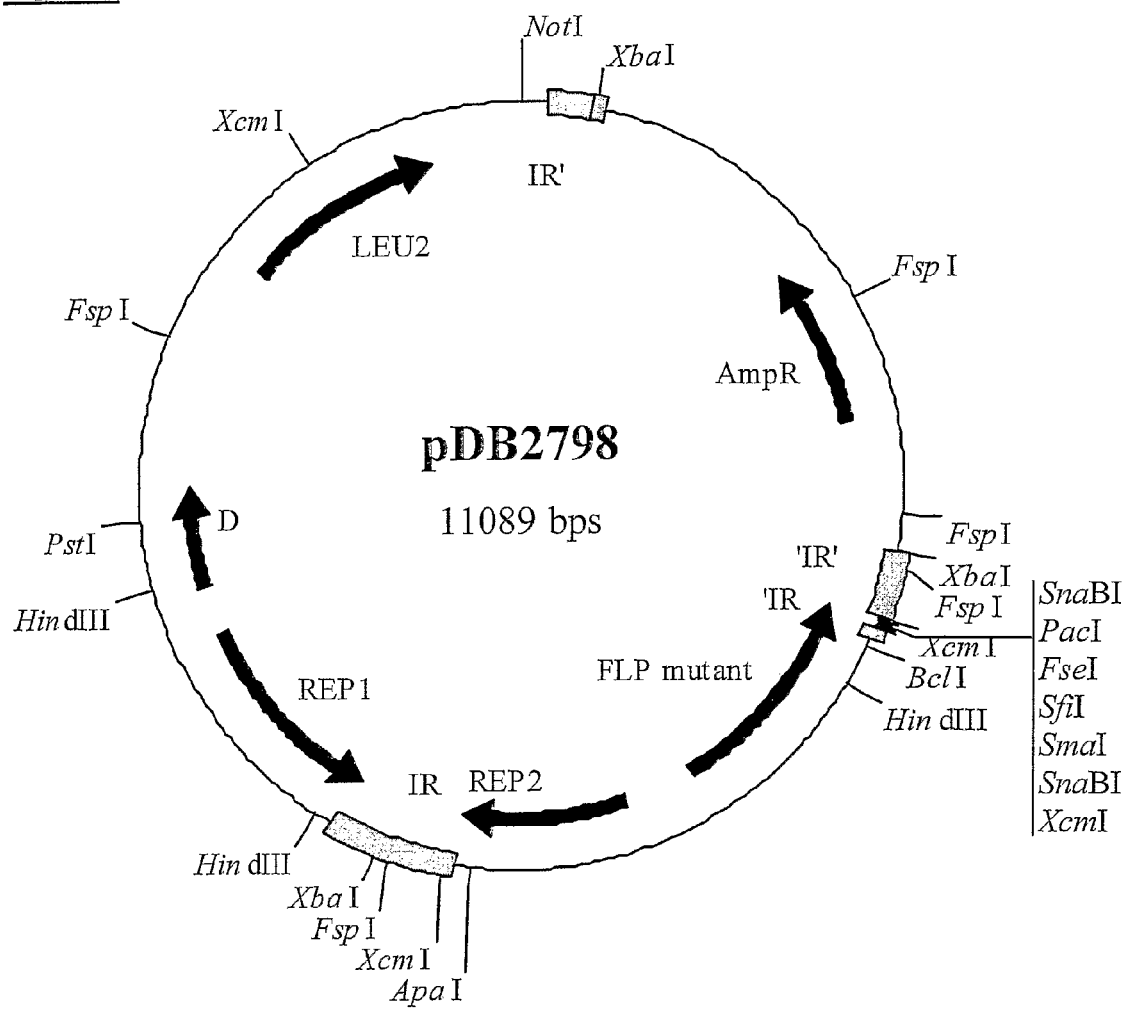

An additional plasmid, pDB2798 (FIG. 7), was also produced by ligation of the SnaBI linker in the opposite direction to pDB2786. The linker sequence in pDB2798 was confirmed by DNA sequencing. Plasmid pDB2798 contained a coding sequence for a mutant Flp-protein, with 39 C-terminal residues replaced by 8 different residues before translation termination.

A linker was also cloned into the XcmI-site in the FLP gene to truncate the Flp protein at the site of insertion. The linker used was a 45-bp 5'-phosphorylated XcmI-linker made from oligonucleotides CF120 and CF121.

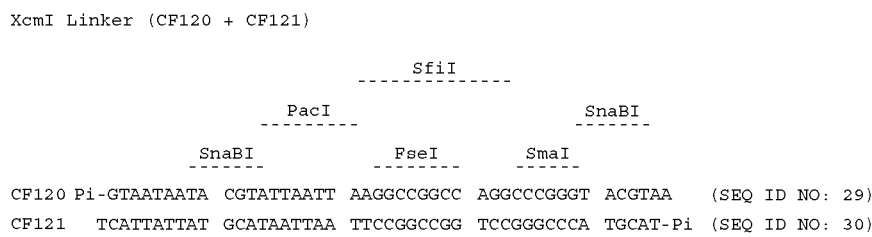

Figure 8:
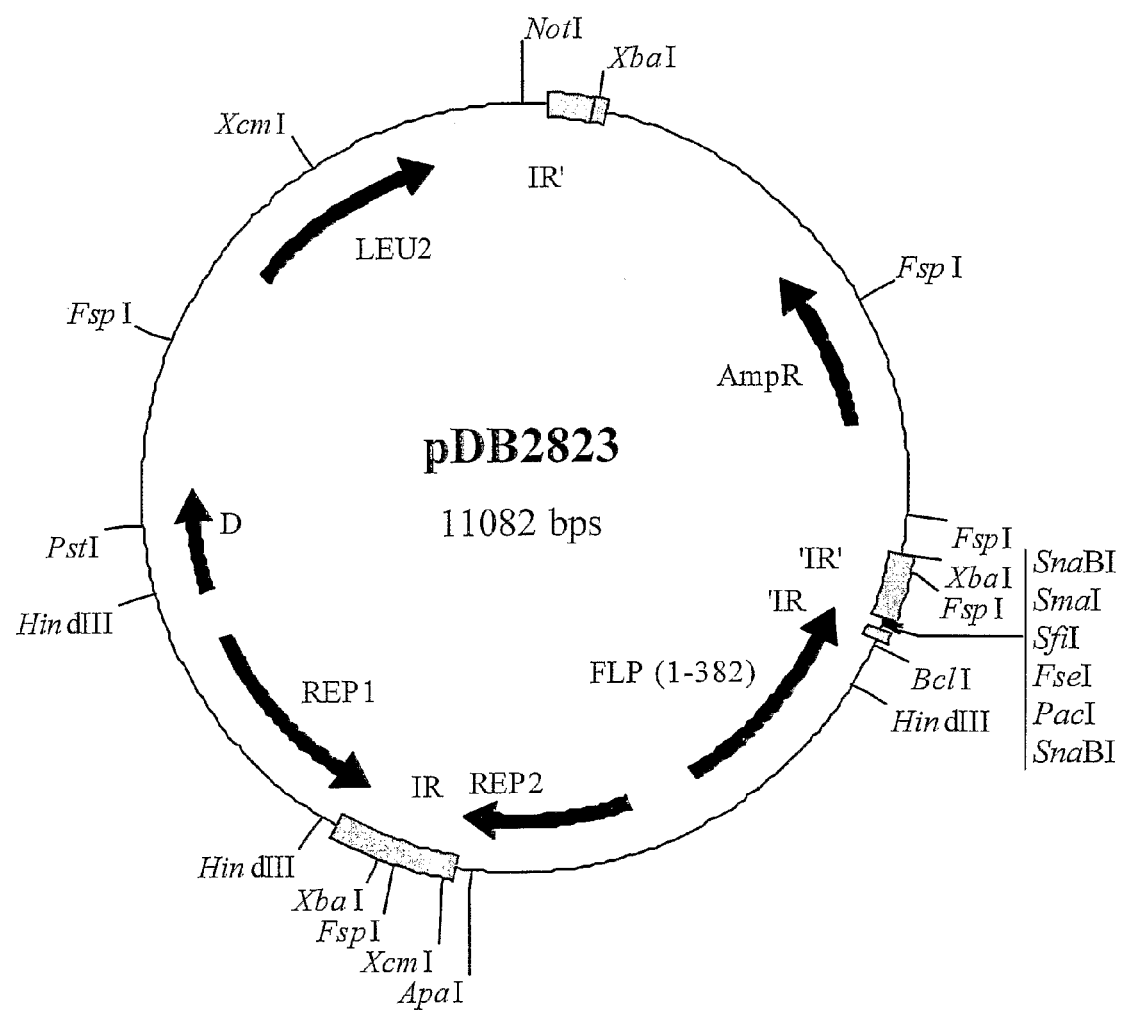

This CF120/CF121 XcmI linker was ligated with 11-kb pSAC35 fragments produced by partial digestion with XcmI, followed by treatment with calf intestinal alkaline phosphatase. Analysis of ampicillin resistant *E. coli* DH5α transformants identified clones containing pDB2823 (FIG. 8). DNA sequencing with primers CF90, CF91, CF100 and CF101 confirmed the linker sequence in pDB2823. Translation termination within the linker inserted would result in the production of Flp (1-382), which lacked 41 C-terminal residues.

The impact on plasmid stability from insertion of linker sequences into the XcmI-sites within the US-region of pSAC35 was assessed for pDB2688 and pDB2689. Plasmid stability was determined in a *S. cerevisiae* strain by loss of the LEU2 marker during non-selective grown on YEPS. The same yeast strain, transformed with pSAC35, which is structurally similar to pSAC3, but contains additional DNA inserted at the SnaBI site that contained a LEU2 selectable marker (Chinery & Hinchliffe, 1989, *Curr. Genet.*, 16, 21), was used as the control.

The yeast strain was transformed to leucine prototrophy using a modified lithium acetate method (Sigma yeast transformation kit, YEAST-1, protocol 2; (Ito et al, 1983, *J. Bacteriol.*, 153, 163; Elble, 1992, *Biotechniques*, 13, 18)). Transformants were selected on BMMD-agar plates, and were subsequently patched out on BMMD-agar plates. Cryopreserved trehalose stocks were prepared from 10 mL BMMD shake flask cultures (24 hrs, 30° C., 200 rpm).

The composition of YEPD and BMMD is described by Sleep et al., 2002, *Yeast* 18, 403. YEPS and BMMS are similar in composition to YEPD and BMMD accept that 2% (w/v) sucrose was substituted for the 2% (w/v) glucose as the sole initial carbon source.

For the determination of plasmid stability a 1 mL cryopreserved stock was thawed and inoculated into 100 mL YEPS (initial $OD_{600}$≈0.04-0.09) in a 250 mL conical flask and grow for approximately 72 hours (70-74 hrs) at 30° C. in an orbital shaker (200 rpm, Innova 4300 incubator shaker, New Brunswick Scientific).

Samples were removed from each flask, diluted in YEPS-broth ($10^{-2}$ to $10^{-5}$ dilution), and 100 μL aliquots plated in duplicate onto YEPS-agar plates. Cells were grown at 30° C. for 3-4 days to allow single colonies to develop. For each yeast stock analysed, 100 random colonies were patched in replica onto BMMS-agar plates followed by YEPS-agar plates. After growth at 30° C. for 3-4 days the percentage of colonies growing on both BMMS-agar plates and YEPS-agar plates was determined as the measure of plasmid stability.

In the above analysis to measure the loss of the LEU2 marker from transformants, pSAC35 and pDB2688 appeared to be 100% stable, whereas pDB2689 was 72% stable. Hence, insertion of the linker into the XcmI-site after REP2 had no apparent effect on plasmid stability, despite altering the transcribed sequence and disrupting the homology between the 599-bp inverted repeats. Insertion of the linker at the XcmI-site in FLP also resulted in a surprisingly stable plasmid, despite both disruption of the inverted repeat and mutation of the Flp protein.

Example 2

Insertion of the PDI1 Gene into the XcmI Linker of pDB2688

Figure 9:
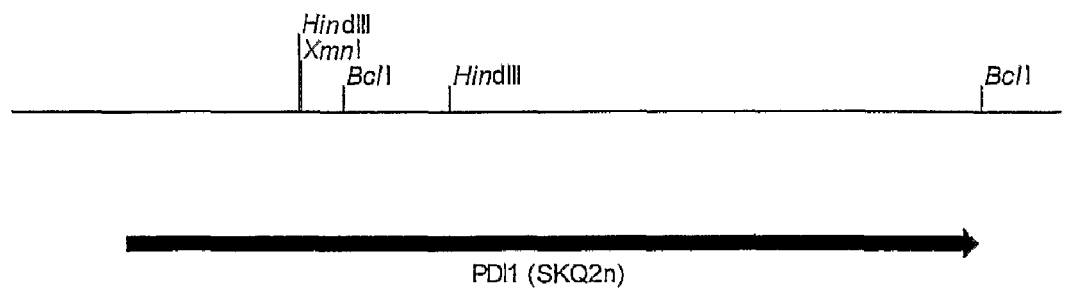
FIG. 9 shows the DNA fragment from pDB2429 containing the PDI1 gene.
Figure 10:
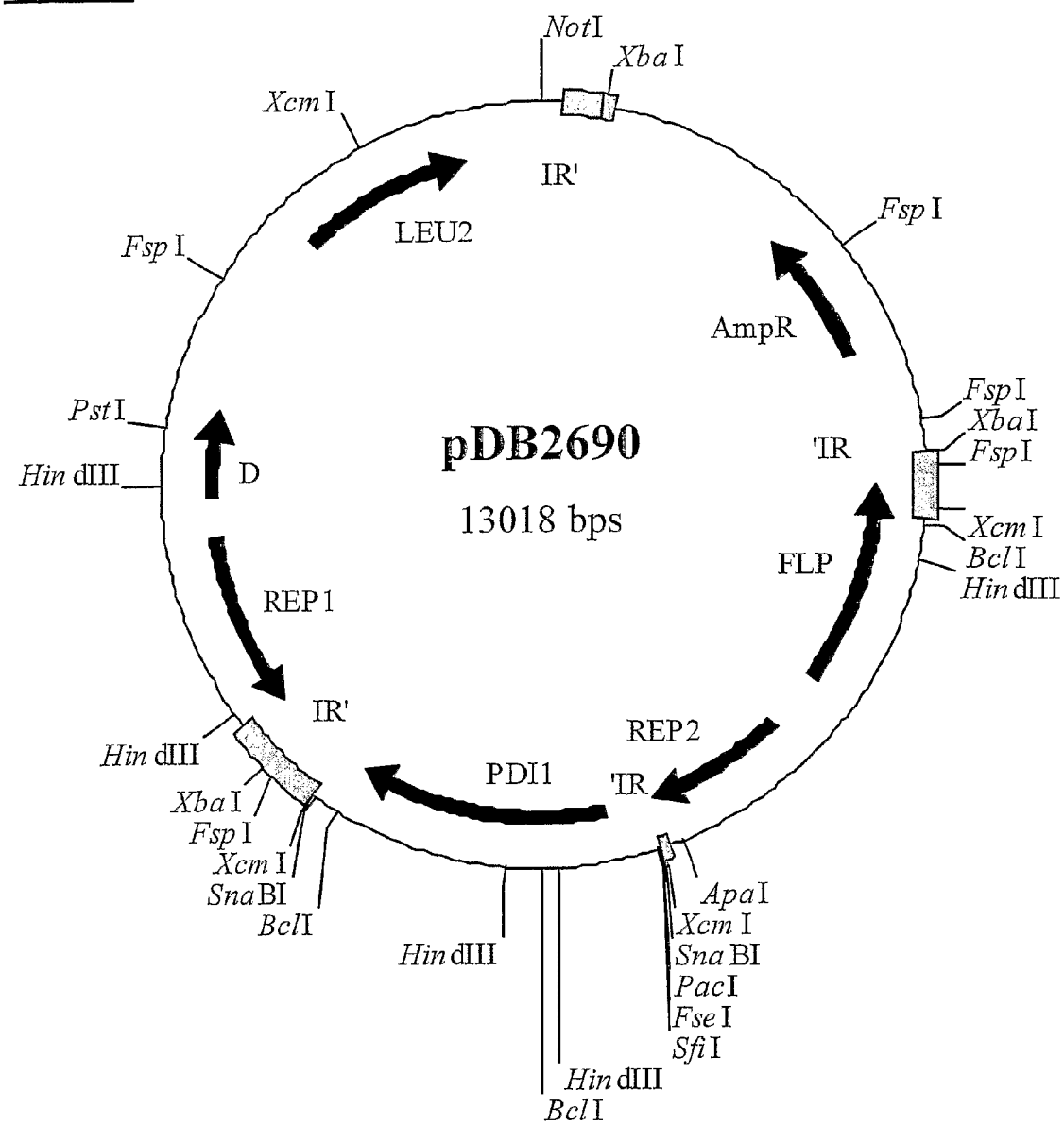

The insertion of a large DNA fragment into the US-region of 2 μm-like vectors was demonstrated by cloning the *S. cerevisiae* PDI1 gene into the XcmI-linker of pDB2688. The PDI1 gene (FIG. 9) was cloned on a 1.9-kb SacI-SpeI fragment from a larger *S. cerevisiae* SKQ2n genomic DNA fragment containing the PDI1 gene (as provided in the plasmid pMA3a:C7 that is described in U.S. Pat. No. 6,291,205 and also described as Clone C7 in Crouzet & Tuite, 1987, *Mol. Gen. Genet.*, 210, 581-583 and Farquhar et al, 1991, supra), which had been cloned into YIplac211 (Gietz & Sugino, 1988, *Gene*, 74, 527-534) and had a synthetic DNA linker containing a SacI restriction site inserted at a unique Bsu36I-site in the 3' untranslated region of the PDI1 gene. The 1.9-kb SacI-SpeI fragment was treated with T4 DNA polymerase to fill the SpeI 5'-overhang and remove the SacI 3'-overhang. This PDI1 fragment included 212-bp of the PDI1 promoter upstream of the translation initiation codon, and 148-bp downstream of the translation termination codon. This was ligated with SmaI linearised/calf intestinal alkaline phosphatase treated pDB2688, to create plasmid pDB2690 (FIG. 10), with the PDI1 gene transcribed in the same direction as REP2. A *S. cerevisiae* strain was transformed to leucine prototrophy with pDB2690.

Figure 11:
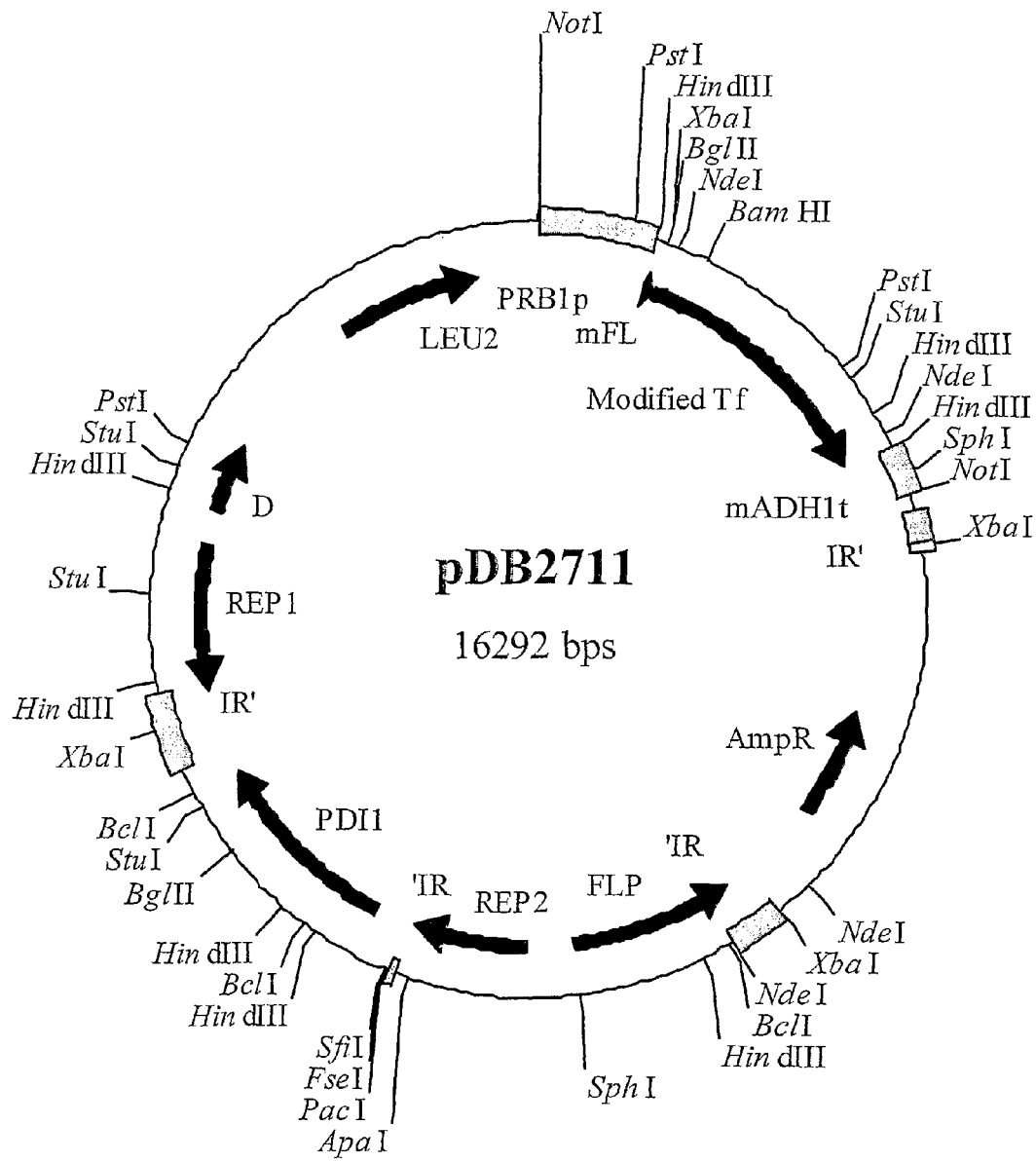
Figure 36:
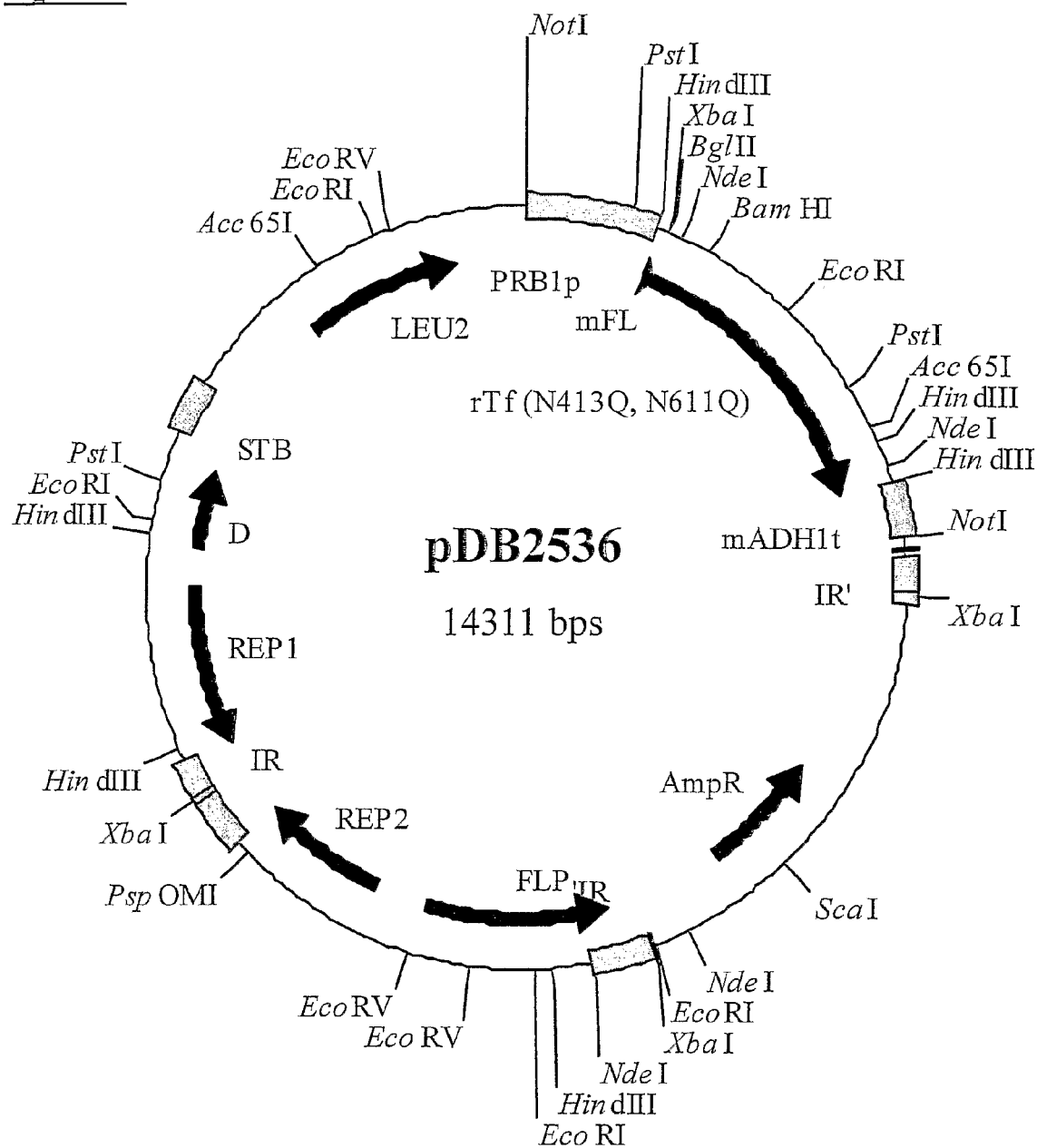

An expression cassette for a human transferrin mutant (N413Q, N611Q) was subsequently cloned into the NotI-site of pDB2690 to create pDB2711 (FIG. 11). The expression cassette in pDB2711 contains the *S. cerevisiae* PRB1 promoter, an HSA/MFα fusion leader sequence (EP 387319; Sleep et al, 1990, *Biotechnology (N.Y.)*, 8, 42) followed by a coding sequence for the human transferrin mutant (N413Q, N611Q) and the *S. cerevisiae* ADH1 terminator. Plasmid pDB2536 (FIG. 36) was constructed similarly by insertion of the same expression cassette into the NotI-site of pSAC35.

The advantage of inserting "genes of interest" into the US-region of 2 μm-vectors was demonstrated by the approximate 7-fold increase in recombinant transferrin N413Q, N611Q secretion during fermentation of yeast transformed with pDB2711, compared to the same yeast transformed with pDB2536. An approximate 15-fold increase in recombinant transferrin N413Q, N611Q secretion was observed in shake flask culture (data not shown).

The relative stabilities of plasmids pDB2688, pDB2690, pDB2711, pDB2536 and pSAC35 were determined in the same yeast strain grown in YEPS media, using the method described above (Table 2).

In this analysis, pDB2690 was 32% stable, compared to 100% stability for pDB2688 without the PDI1 insert. This decrease in plasmid stability was less than the decrease in plasmid stability observed with pDB2536, due to insertion of the rTF (N413Q, N611Q) expression cassette into the NotI-site within the large unique region of pSAC35 (Table 2).

Furthermore, selective growth in minimal media during high cell density fermentations could overcome the increased plasmid instability due to the PDI1 insertion observed in YEPS medium, as the rTF (N413Q, N611Q) yield from the same yeast transformed with pDB2711 did not decrease compared to that achieved from the same yeast transformed with pDB2536.

TABLE 2

Summary of plasmid stability data for PDI1 insertion into the small unique region of pSAC35. Data from 3 days growth in non-selective shake flask culture before plating on YEPS-agar.

| Plasmid | Insertion Site(s) | Additional Details | Relative Stability |
|---|---|---|---|
| pSAC35 | — | — | 100% |
| pDB2688 | XcmI | Linker in Inverted Repeat | 100% |

TABLE 2-continued

Summary of plasmid stability data for PDI1 insertion into the small unique region of pSAC35. Data from 3 days growth in non-selective shake flask culture before plating on YEPS-agar.

| Plasmid | Insertion Site(s) | Additional Details | Relative Stability |
|---|---|---|---|
| pDB2690 | XcmI | PDI1 in XcmI Linker | 32% |
| pDB2711 | XcmI, NotI | PDI1 in XcmI Linker, rTf Cassette at NotI | 10% |
| pDB2536 | NotI | rTf Cassette at NotI | 17% |

Example 3

Insertion of DNA Linkers into the REP2 Gene and Downstream Sequences in the Inverted Repeat of pSAC35

To define the useful limits for insertion of additional DNA into the REP2 gene and sequences in the inverted repeat downstream of it, further linkers were inserted into pSAC35. FIG. 12 indicates the restriction sites used for these insertions and the effects on the Rep2 protein of translation termination at these sites.

The linker inserted at the XmnI-site in REP2 was a 44-bp sequence made from oligonucleotides CF108 and CF109.

```
XmnI Linker (CF108 + CF109)
                              SfiI
                              ----------------
                    PacI                       SnaBI
                    ---------                  -------

SnaBI             FseI       SmaI
          -------           --------   ------
CF108 ATAATAATAC GTATTAATTA AGGCCGGCCA GGCCCGGGTA CGTA (SEQ ID NO: 31)
CF109 TATTATTATG CATAATTAAT TCCGGCCGGT CCGGGCCCAT GCAT (SEQ ID NO: 32)
```

Figure 13:
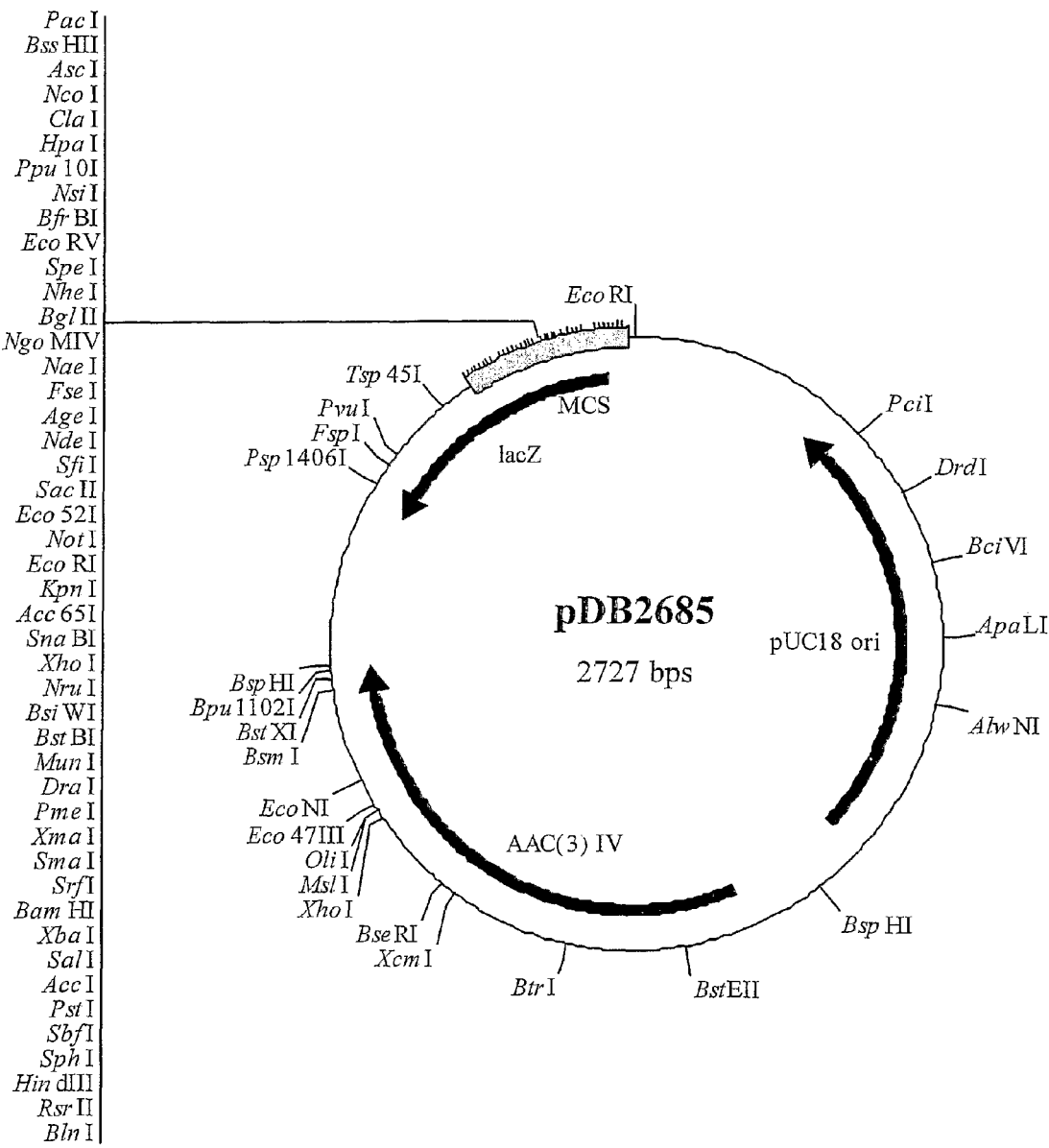
Figure 14:
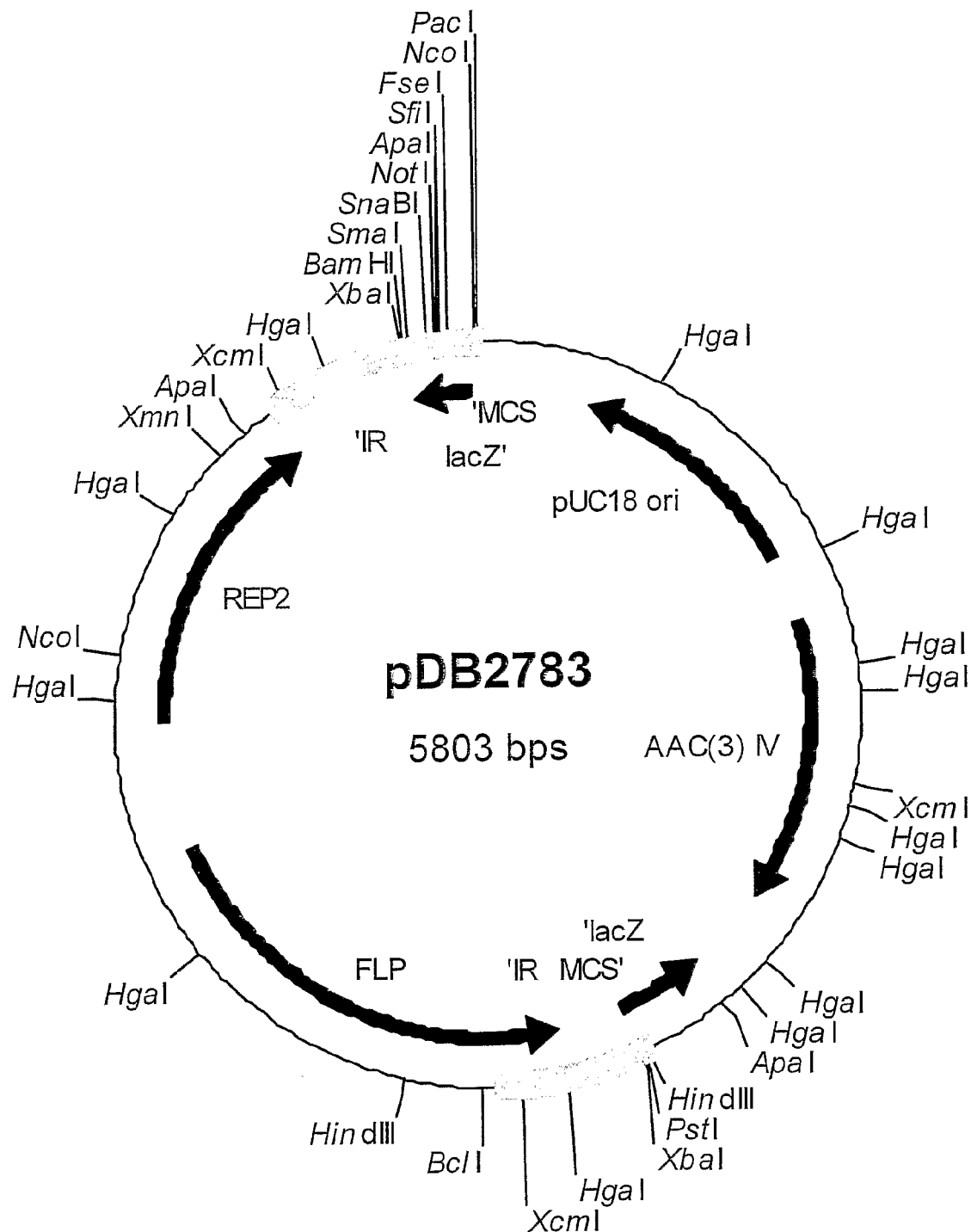

To avoid insertion into other XmnI-sites in pSAC35, the 3,076-bp XbaI fragment from pSAC35 that contained the REP2 and FLP genes was first sub-cloned into the *E. coli* cloning vector pDB2685 (FIG. 13) to produce pDB2783 (FIG. 14).

Plasmid pDB2685 is a pUC18-like cloning vector derived from pCF17 containing apramycin resistance gene aac(3)IV from *Klebsiella pneumoniae* (Rao et al, 1983, *Antimicrob. Agents Chemother.*, 24, 689) and multiple cloning site from pMCS5 (Hoheisel, 1994, *Biotechniques*, 17, 456). pCF17 was made from pIJ8600 (Sun et al., 1999, *Microbiology*, 145 (9), 2221-7) by digestion with EcoRI, NheI and the Klenow fragment of DNA polymerase I, and self-ligation, followed by isolation from the reaction products by transformation of competent *E. coli* DH5α cells and selection with apramycin sulphate. Plasmid pDB2685 was constructed by cloning a 439 bp SspI-SwaI fragment from pMCS5 into pCF17, which had been cut with MscI and treated with calf intestinal alkaline phosphatase. Blue/white selection is not dependant on IPTG induction.

Figure 15:
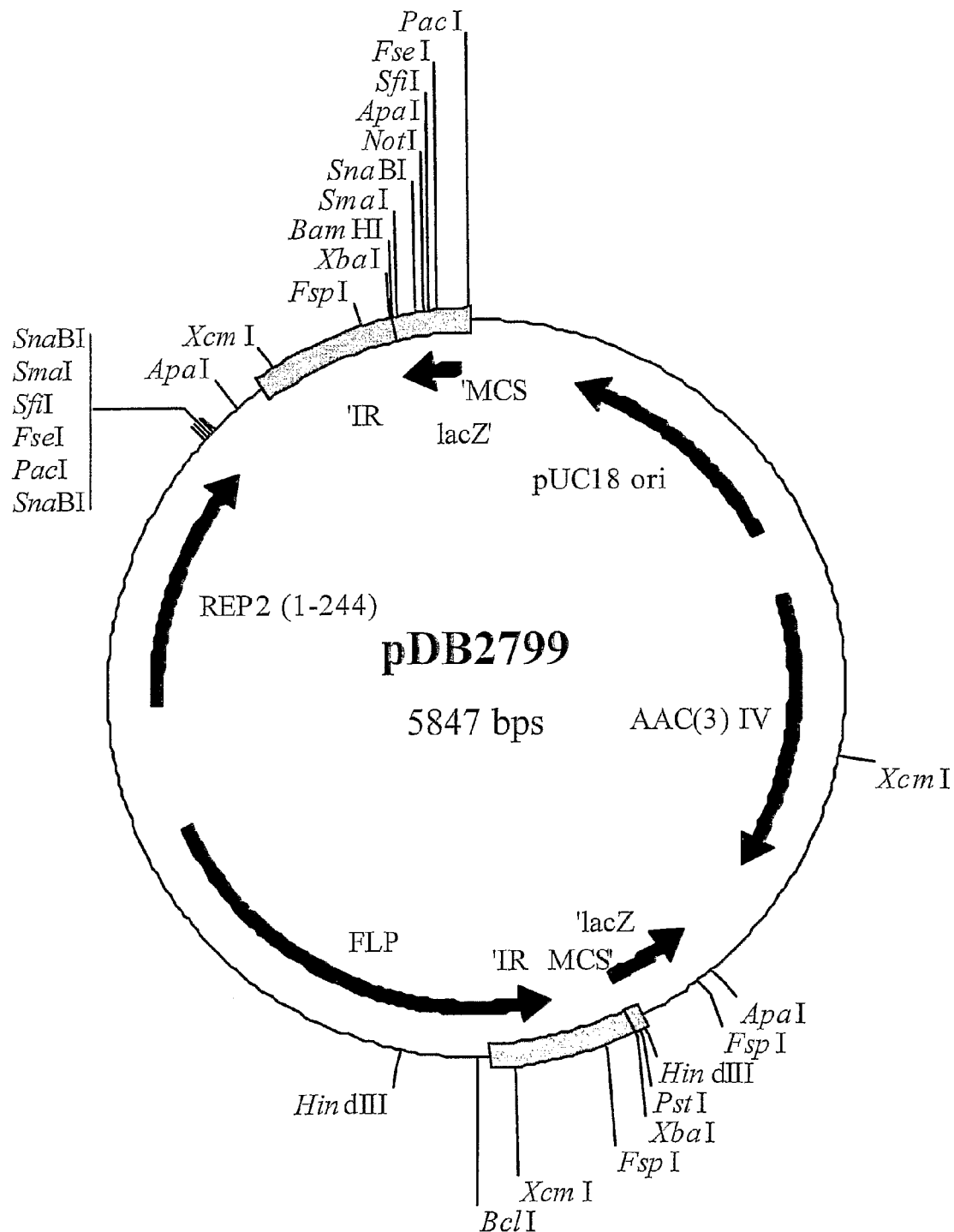

Plasmid pDB2783 was linearised with XmnI and ligated with the CF108/CF109 XmnI-linker to produce pDB2799 (FIG. 15) and pDB2780 (not shown). Plasmid pDB2799 contained the CF108/CF109 XmnI linker in the correct orientation for translation termination at the insertion site to produce Rep2 (1-244), whereas pDB2780 contained the linker cloned in the opposite orientation. DNA sequencing with primers CF98 and CF99 confirmed the correct linker sequences.

Figure 16:
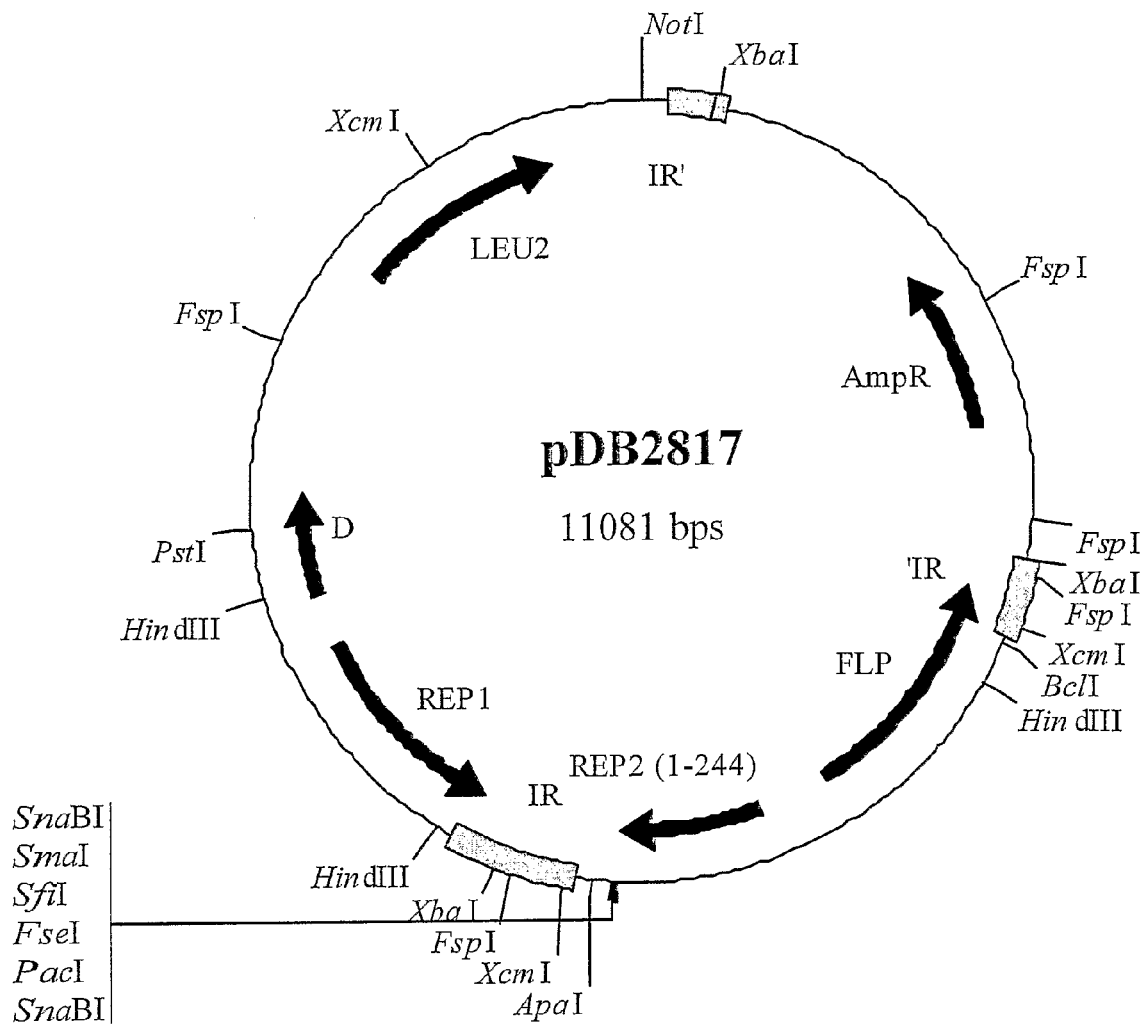
Figure 17:
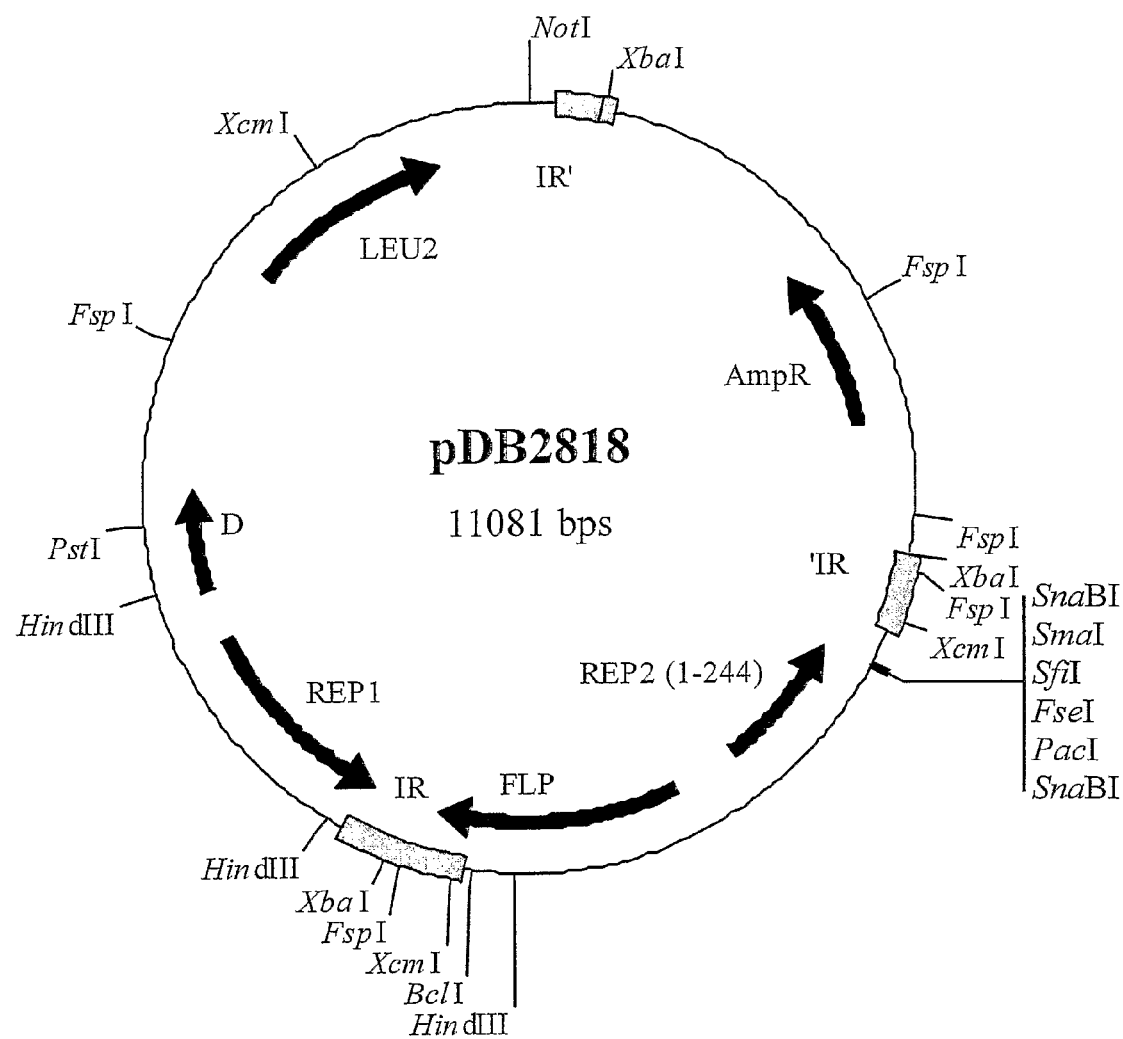

The 3,120 bp XbaI fragment from pDB2799 was subsequently ligated with a 7,961-bp pSAC35 fragment which had been produced by partial XbaI digestion and treatment with calf intestinal alkaline phosphatase, to create plasmid pDB2817 (B-form) and pDB2818 (A-form) disintegration vectors (FIGS. 16 and 17 respectively).

Insertion of linkers at the ApaI-site in pSAC35 was performed with and without 3'-5' exonuclease digestion by T4 DNA polymerase. This produced coding sequences for either Rep2 (1-271) or Rep2 (1-269) before translation termination. In the following figure, the sequence GGCC marked with diagonal lines was deleted from the 3'-overhang produced after ApaI digestion resulting in removal of nucleotides from the codons for Glycine-170 (GGC) and Proline-171.

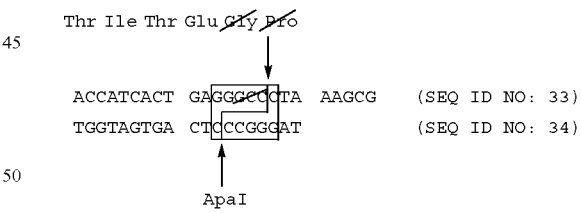

The linker inserted at the ApaI-site without exonuclease digestion was a 50-bp 5'-phosphorylated linker made from oligonucleotides CF116 and CF117.

```
ApaI Linker (CF116 + CF117)
                                  SfiI
                                  ----------------
                        PacI                       SnaBI
                        ---------                  ------

SnaBI             FseI       SmaI
              -------           --------   -------
CF116  Pi-CTTAAT AATACGTATT AATTAAGGCC GGCCAGGCCC GGGTACGTAG GGCC    (SEQ ID NO: 35)
CF117  CCGGGAATTA TTATGCATAA TTAATTCCGG CCGGTCCGGG CCCATGCATC-Pi    (SEQ ID NO: 36)
```

Figure 18:
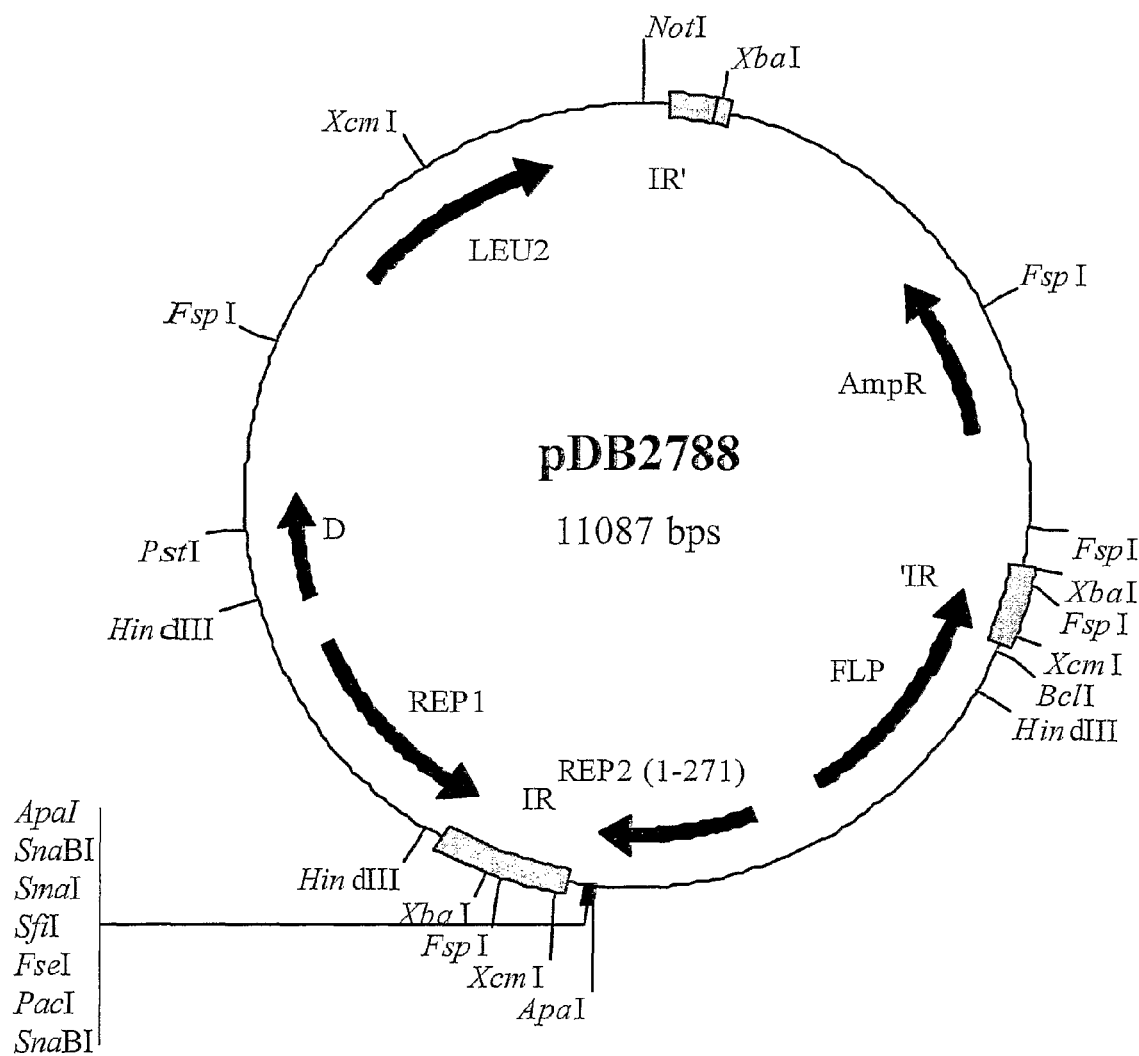

This was ligated with pSAC35, which had been linearised with ApaI and treated with calf intestinal alkaline phosphatase, to produce pDB2788 (FIG. 18) and pDB2789 (not shown). Within pDB2788, the linker was in the correct orientation for translation termination after proline-271, whereas in pDB2789 the linker was in the opposite orientation.

The linker inserted at the ApaI-site with exonuclease digestion by T4 DNA polymerase was a 43-bp 5'-phosphorylated linker made from oligonucleotides CF106 and CF107, which was called the core termination linker.

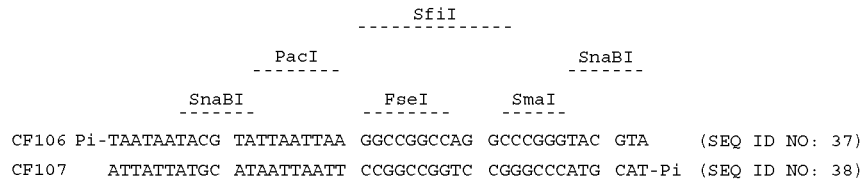

```
Core Termination-Linker (CF106 + CF107)
                                       SfiI
                                    ---------------
                    PacI                            SnaBI
                  --------                         -------
          SnaBI              FseI        SmaI
         -------           --------     ------
CF106 Pi-TAATAATACG TATTAATTAA GGCCGGCCAG GCCCGGGTAC GTA      (SEQ ID NO: 37)
CF107    ATTATTATGC ATAATTAATT CCGGCCGGTC CGGGCCCATG CAT-Pi  (SEQ ID NO: 38)
```

Figure 19:
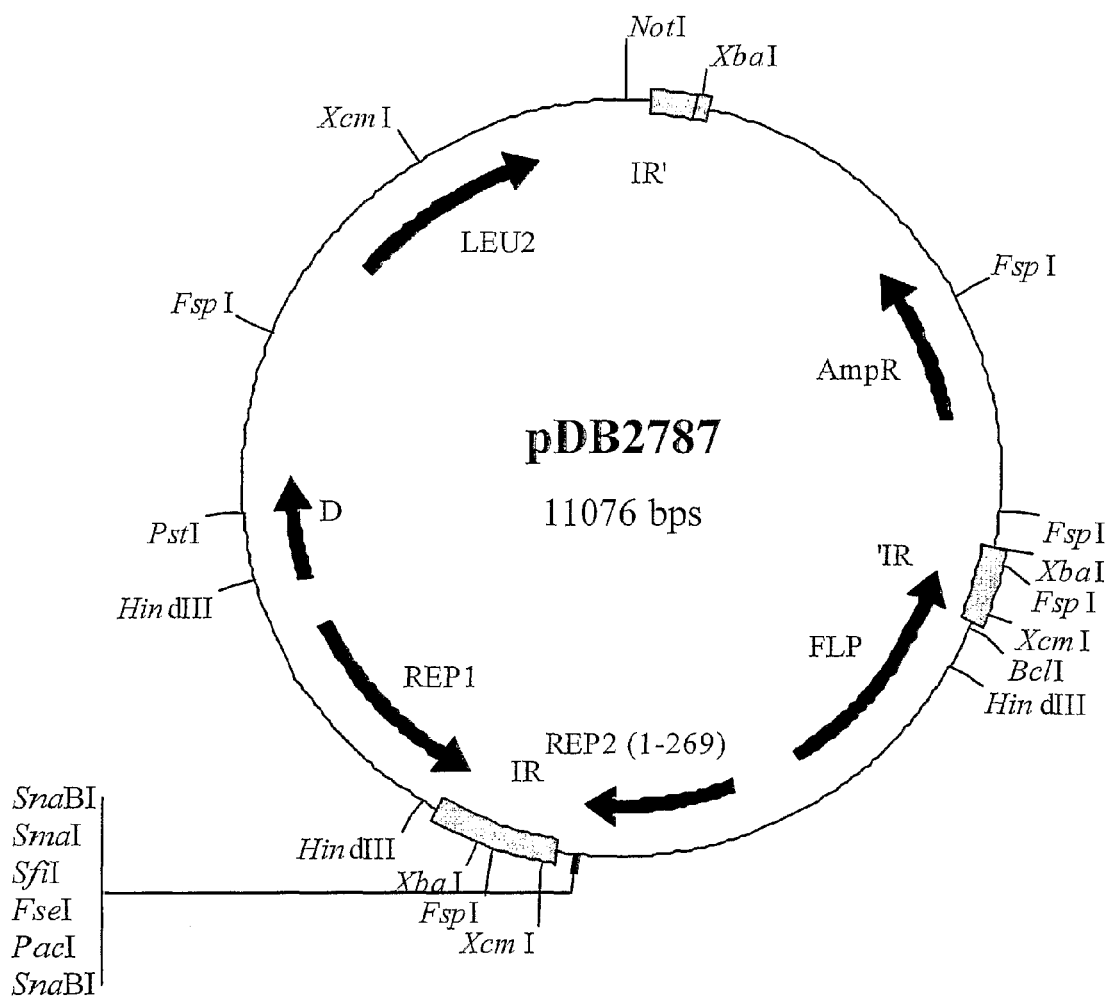

The core termination linker was ligated with pSAC35, which had been linearised with ApaI, digested with T4 DNA polymerase and treated with calf intestinal alkaline phosphatase. This ligation produced pDB2787 (FIG. 19) with the linker cloned in the correct orientation for translation termination after glutamate-269.

The correct DNA sequences were confirmed in all clones containing the ApaI-linkers, using oligonucleotide primers CF98 and CF99.

The core termination linker (CF106+CF107) was also used for insertion into the FspI-sites of pDB2783 (FIG. 14). The core termination linker (CF106+CF107) was ligated into pDB2783 linearised by partial FspI digestion, which had been treated with calf intestinal alkaline phosphatase. Plasmids isolated from apramycin resistant *E. coli* DH5α transformants were screened by digestion with FspI, and selected clones were sequenced with M13 forward and reverse primers.

Figure 20:
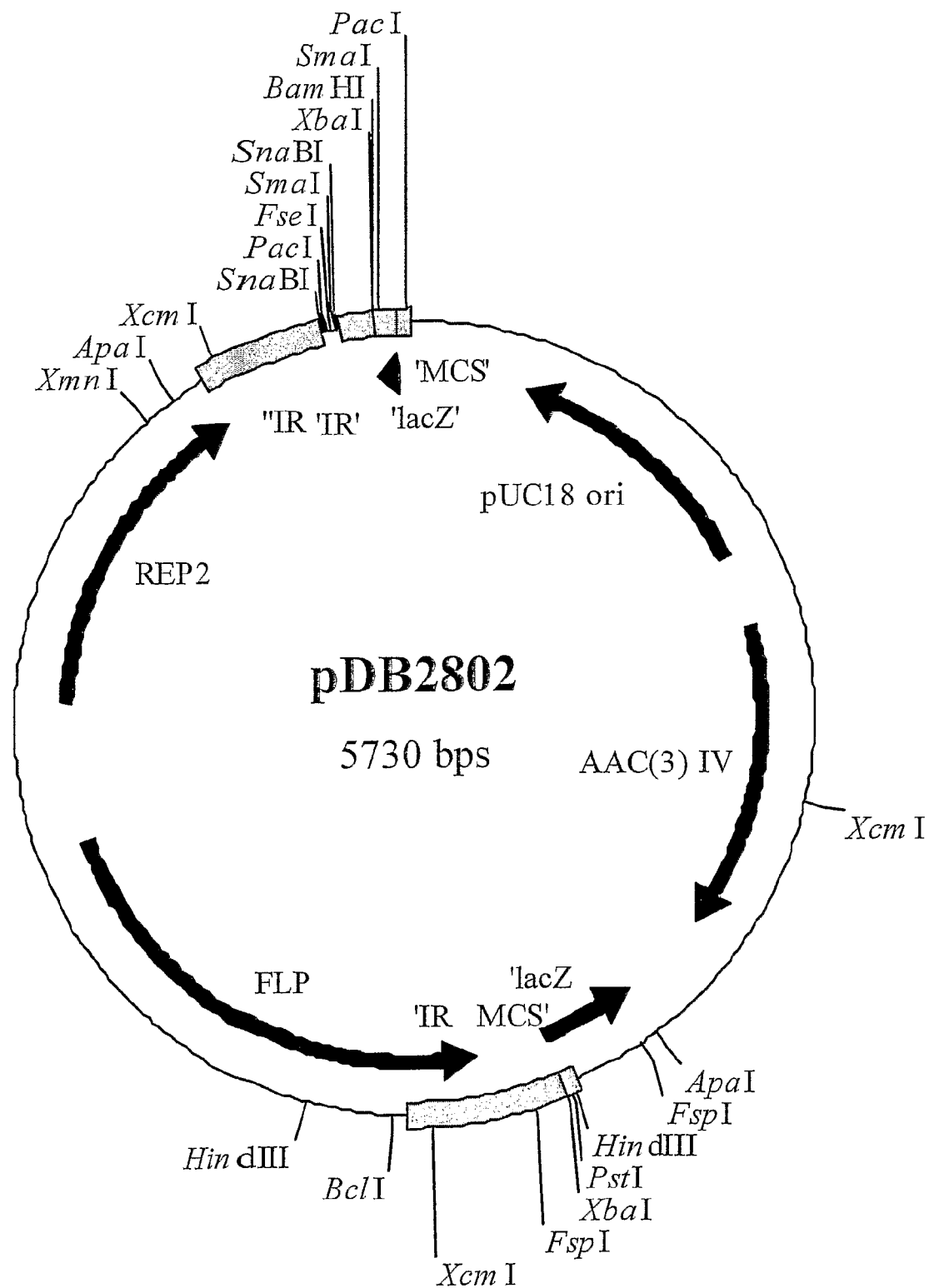

Plasmid pDB2801 (not shown) was identified containing two copies of the linker cloned in the correct orientation (with the PacI-site nearest the REP2 gene). The extra copy of the linker was subsequently removed by first deleting a 116-bp NruI-HpaI fragment containing an FseI-site from the multiple cloning site region, followed by digestion with FseI and re-ligation to produce pDB2802 (FIG. 20). DNA sequencing using oligonucleotide CF126 confirmed the correct linker sequence.

Figure 21:
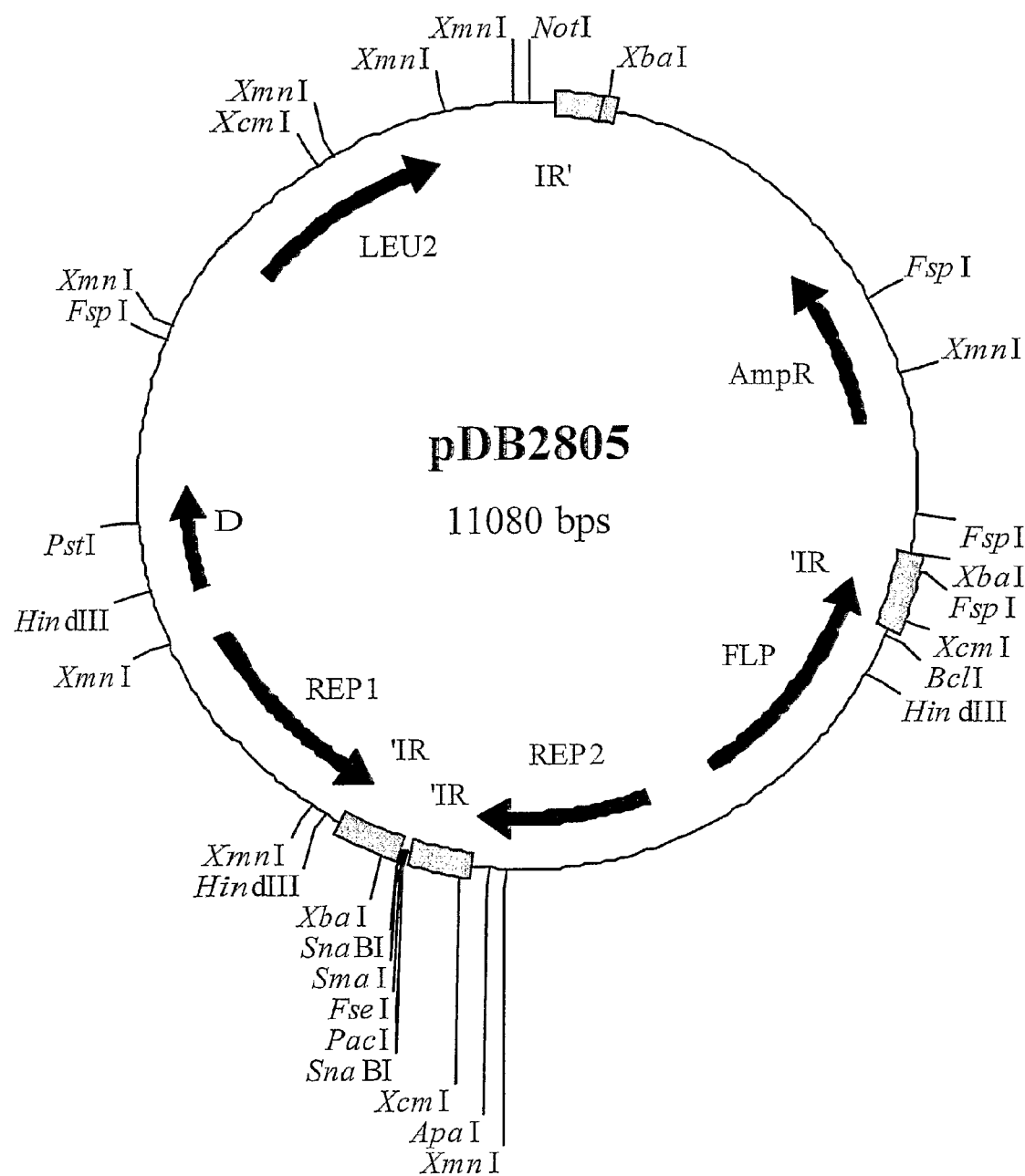
Figure 22:
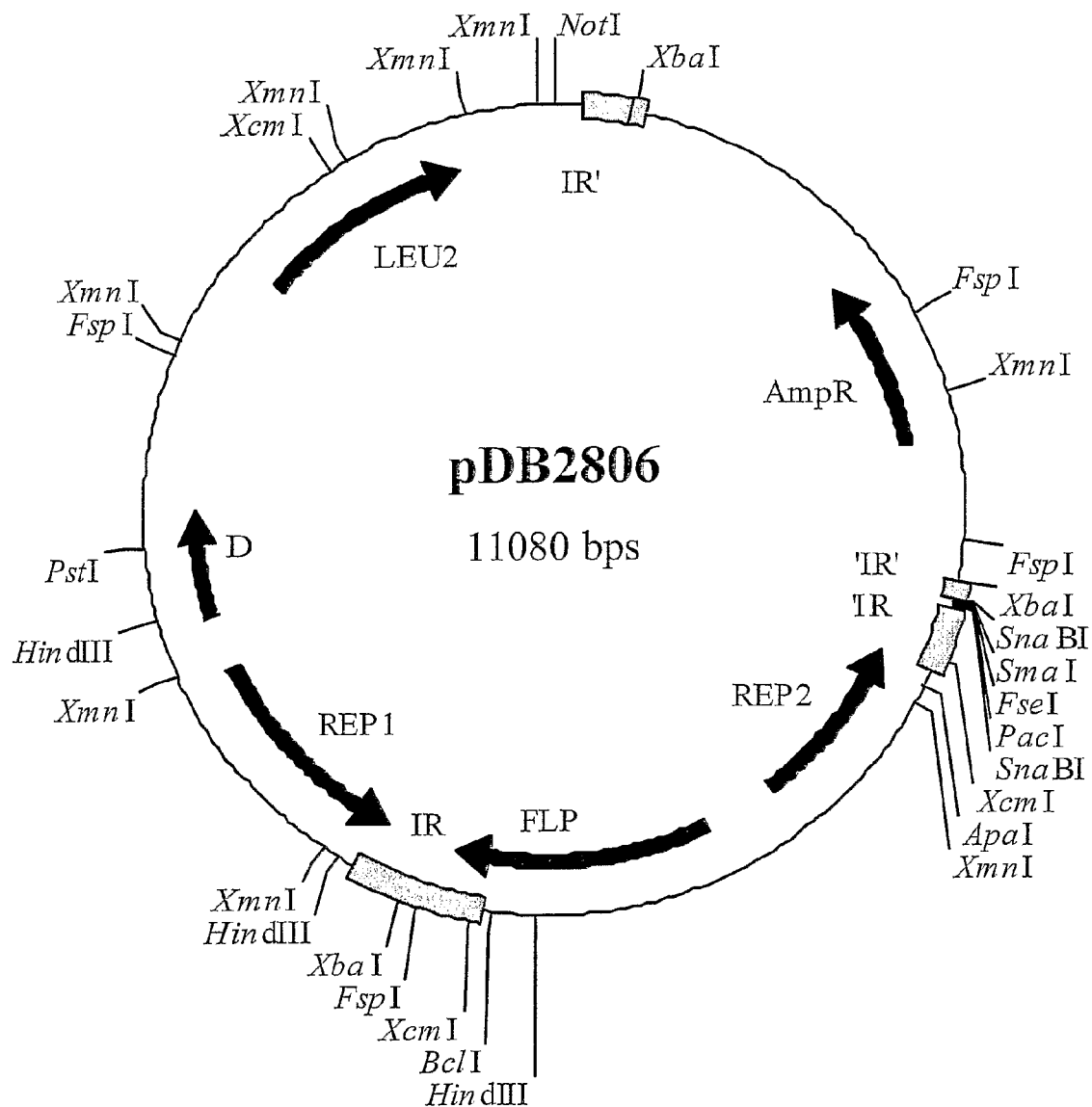

The 3,119-bp pDB2802 XbaI fragment was subsequently ligated with a 7,961-bp pSAC35 fragment produced by partial XbaI digestion and treatment with calf intestinal alkaline phosphatase to create pDB2805 (B-form) and pDB2806 (A-form) disintegration vectors (FIGS. 21 and 22, respectively).

Example 4

Insertion of DNA Linkers into the FLP Gene and Downstream Sequences in the Inverted Repeat of pSAC35

DNA linkers were inserted into pSAC35 to define the useful limits for insertion of additional DNA into the FLP gene and sequences downstream in the inverted repeat. FIG. 3 indicates the restriction sites used for these insertions and the affects on the Flp protein of translation termination at these sites.

The linker inserted at the BclI-site was a 49-bp 5'-phosphorylated linker made from oligonucleotides CF18 and CF119.

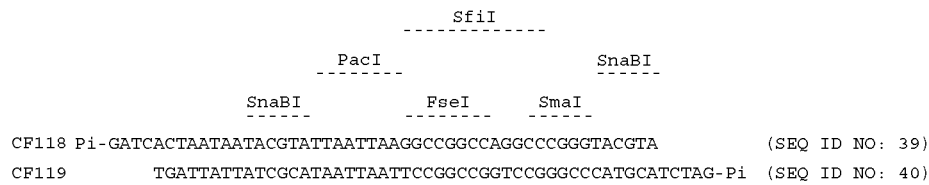

```
BclI Linker (CF118 + CF119)
                                                 SfiI
                                              ---------------
                                    PacI                      SnaBI
                                  --------                   ------
                       SnaBI                 FseI      SmaI
                      ------               --------   ------
       CF118 Pi-GATCACTAATAATACGTATTAATTAAGGCCGGCCAGGCCCGGGTACGTA           (SEQ ID NO: 39)
       CF119          TGATTATTATCGCATAATTAATTCCGGCCGGTCCGGGCCCATGCATCTAG-Pi (SEQ ID NO: 40)
```

Figure 23:
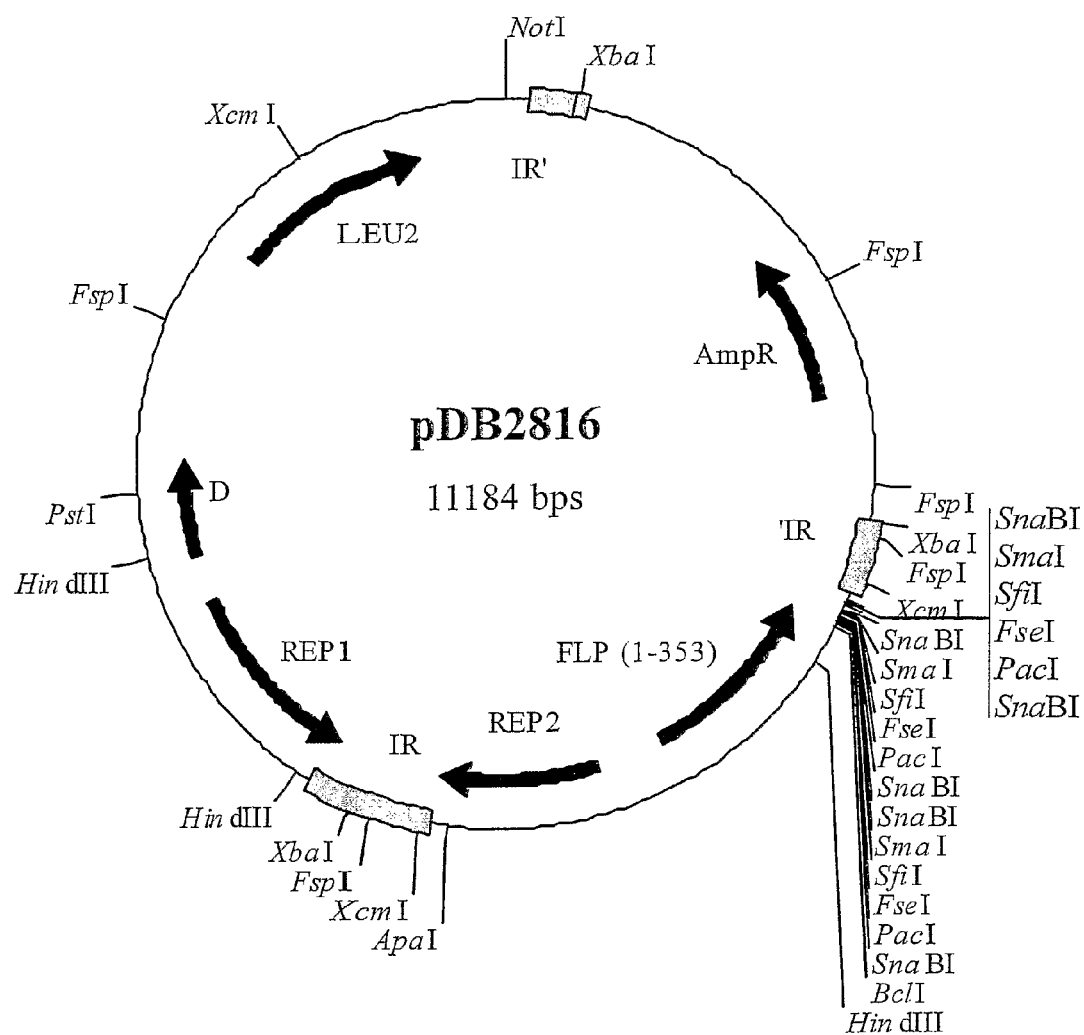

Due to Dam-methylation of the BclI-site in pSAC35, the BclI-linker was cloned into non-methylated pSAC35 DNA, which had been isolated from the *E. coli* strain ET12567 pUZ8002 (MacNeil et al, 1992, *Gene,* 111, 61; Kieser et al, 2000, *Practical Streptomyces Genetics,* The John Innes Foundation, Norwich). Plasmid pSAC35 was linearised with BclI, treated with calf intestinal alkaline phosphatase, and ligated with the BclI-linker to create pDB2816 (FIG. 23). DNA sequencing with oligonucleotide primers CF91 and CF100 showed that three copies of the BclI-linker were present in pDB2816, which were all in the correct orientation for translational termination of Flp after histidine-353.

Figure 24:
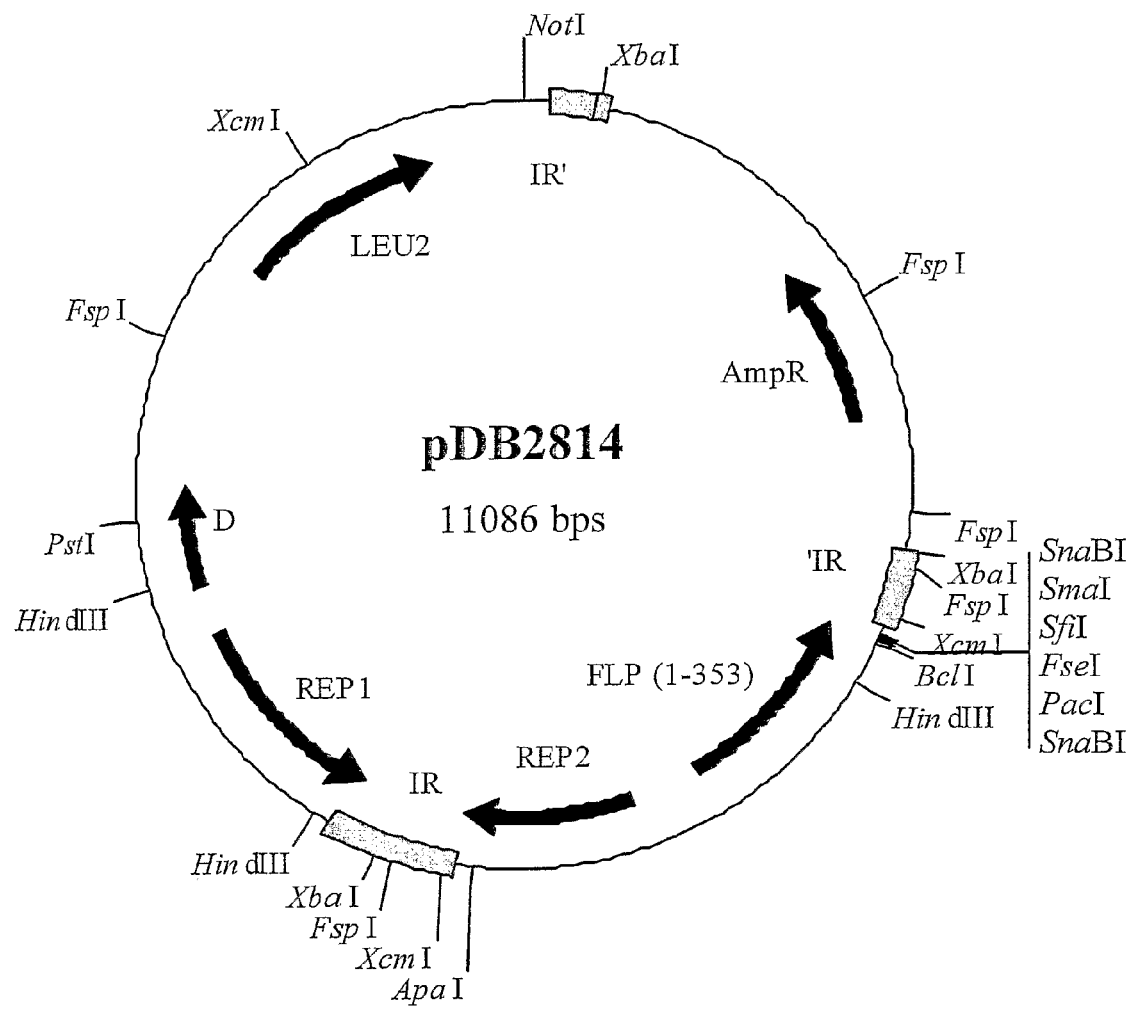
Figure 25:
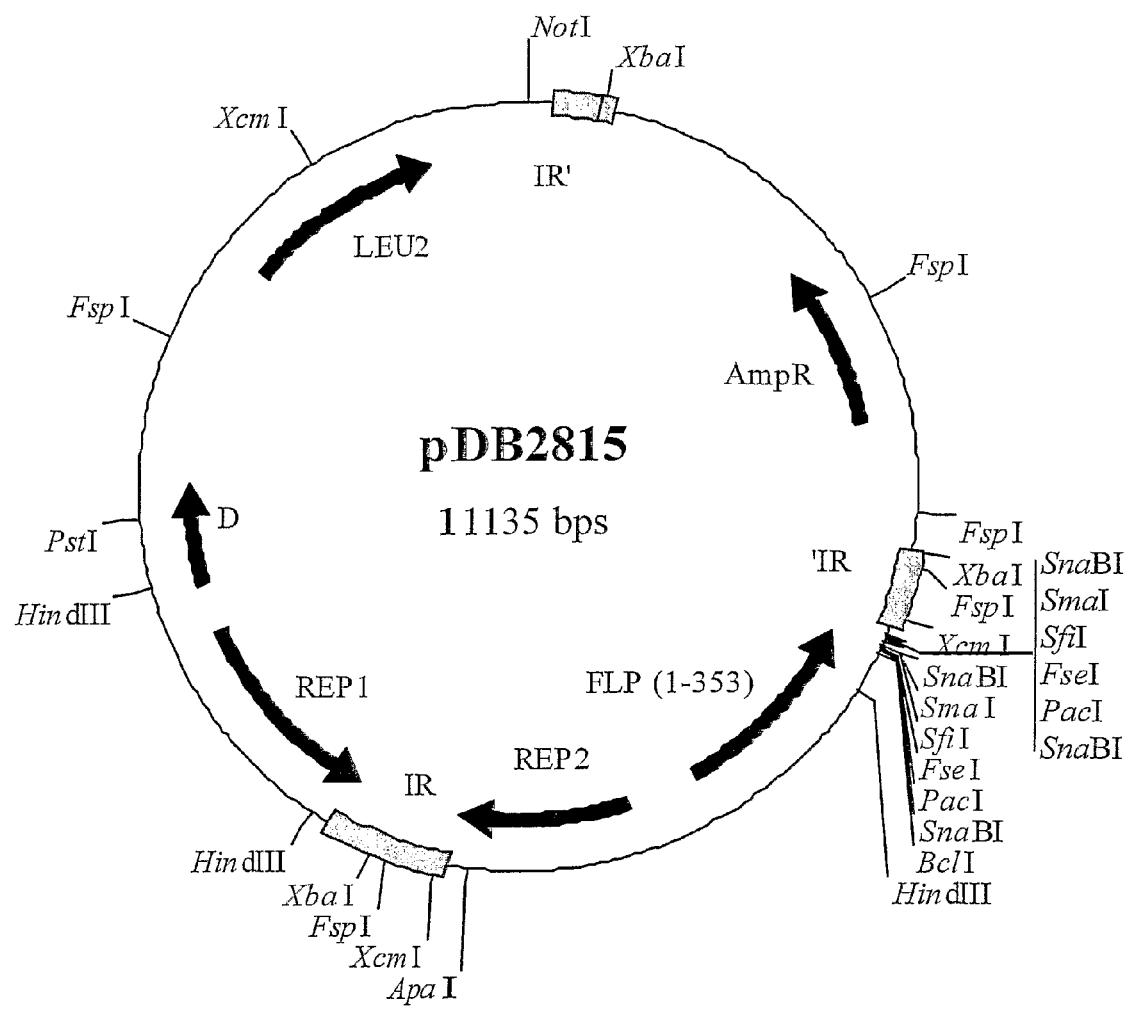

Digestion of pDB2816 with PacI followed by self-ligation, was performed to produce pDB2814 and pDB2815, containing one and two copies of the BclI-linker respectively (FIGS. 24 and 25). The DNA sequences of the linkers were confirmed using primers CF91 and CF100. In *S. cerevisiae* a truncated Flp (1-353) protein will be produced by yeast transformed with pDB2814, pDB2815 or pDB2816.

An additional plasmid pDB2846 (data not shown) was also produced by ligation of a single copy of the BclI-linker in the opposite orientation to pDB2814. This has the coding sequence for the first 352-residues from Flp followed by 14 different residues before translation termination.

The linker inserted at the HgaI-site was a 47-bp 5'-phosphorylated linker made from oligonucleotides CF114 and CF115.

HgaII Linker (CF114 + CF115)

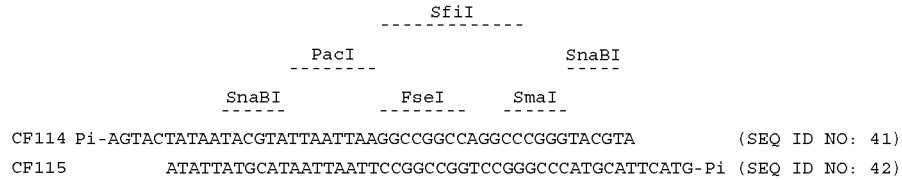

```
CF114 Pi-AGTACTATAATACGTATTAATTAAGGCCGGCCAGGCCCGGGTACGTA        (SEQ ID NO: 41)
CF115            ATATTATGCATAATTAATTCCGGCCGGTCCGGGCCCATGCATTCATG-Pi (SEQ ID NO: 42)
```

Figure 26:
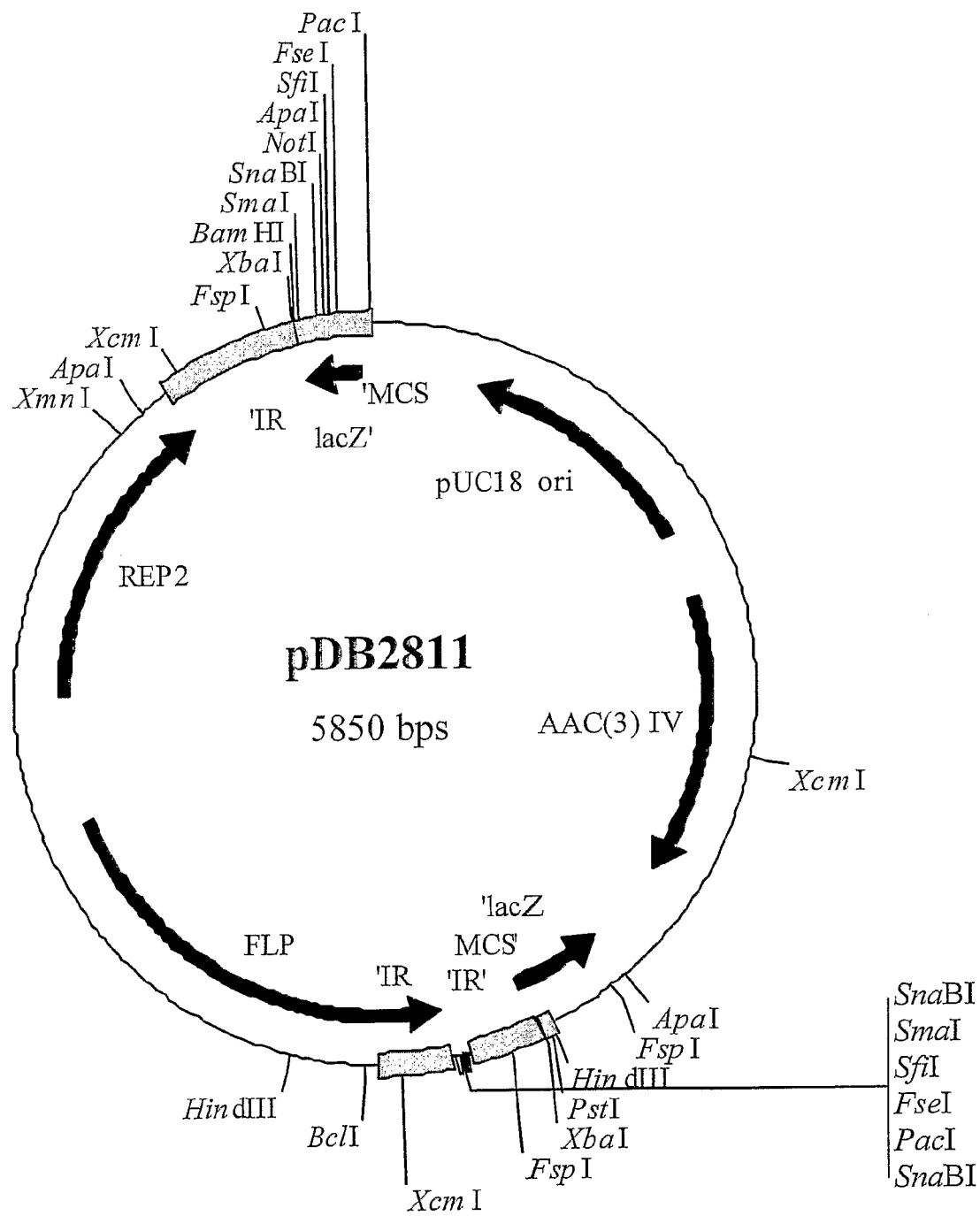

The HgaI-linker was ligated with pDB2783, which had been linearised by partial HgaI digestion and treated with calf intestinal alkaline phosphatase to create pDB281 (FIG. 26). DNA sequencing with oligonucleotides CF90, CF91 and CF100 confirmed the correct linker insertion.

Figure 27:
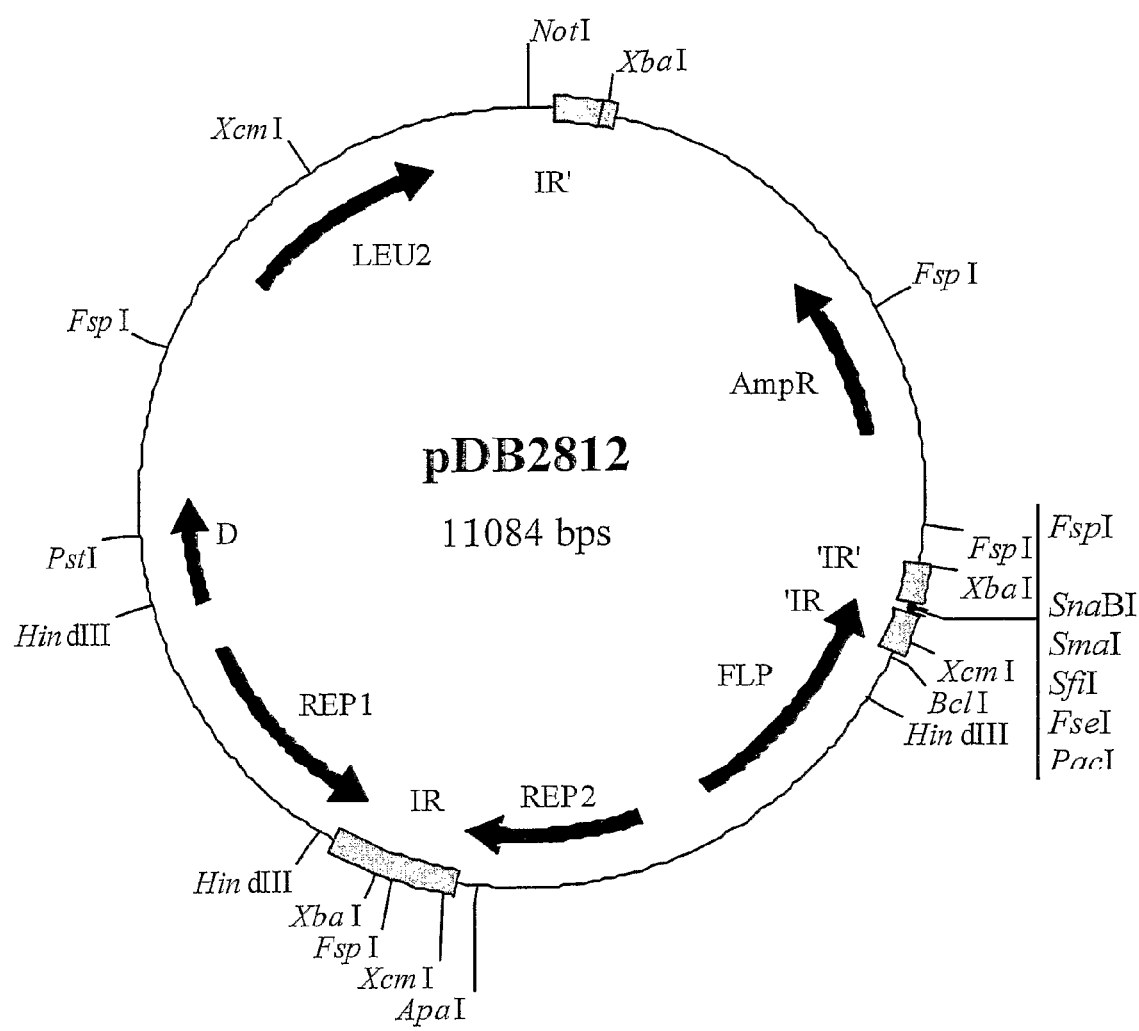
Figure 28:
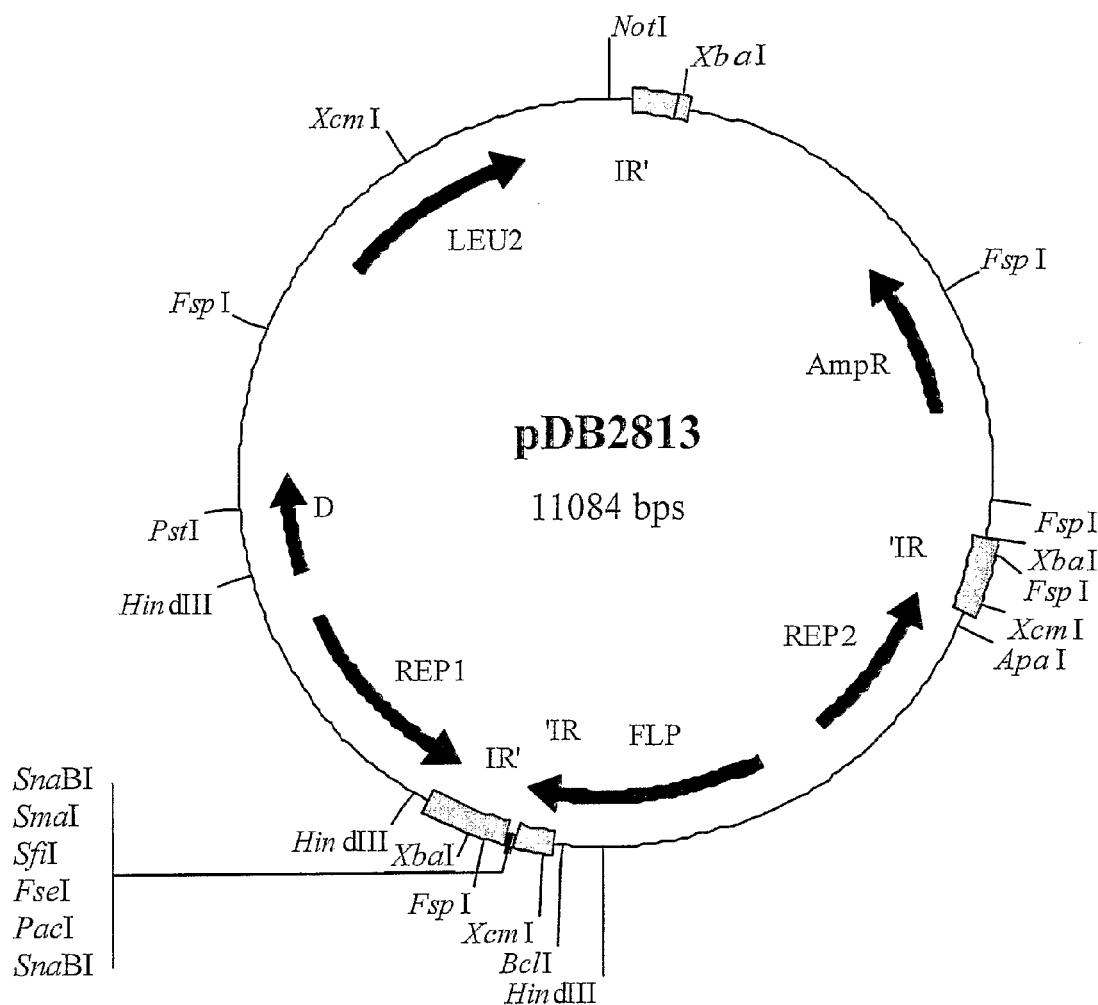

The 3,123-bp XbaI fragment from pDB2811 was subsequently ligated with the 7,961-bp pSAC35 fragment, produced by partial XbaI digestion and treatment with calf intestinal alkaline phosphatase to produce pDB2812 (B-form) and pDB2813 (A-form) disintegration vectors containing DNA inserted at the HgaI-site (FIGS. 27 and 28, respectively).

Figure 29:
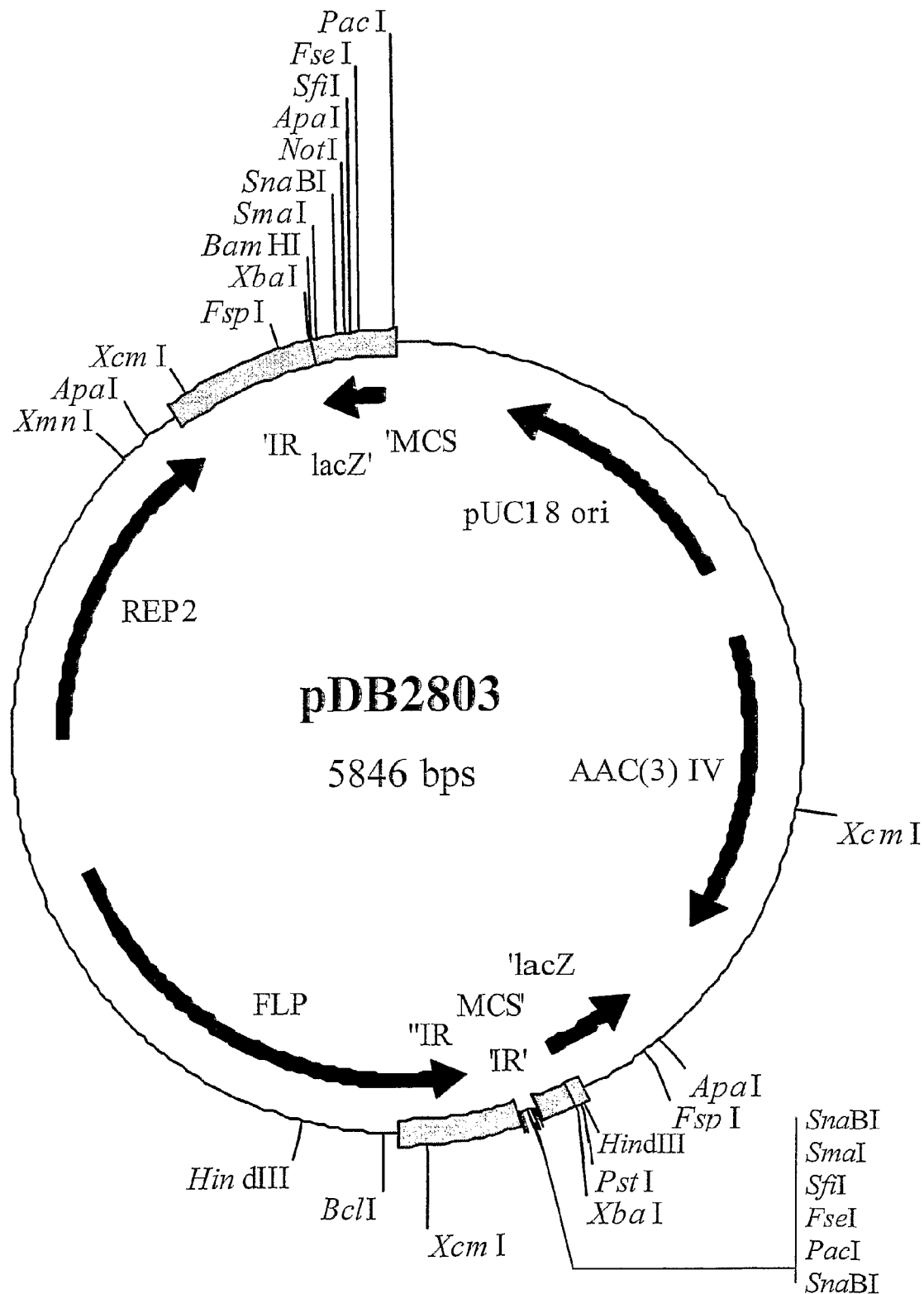
Figure 30:
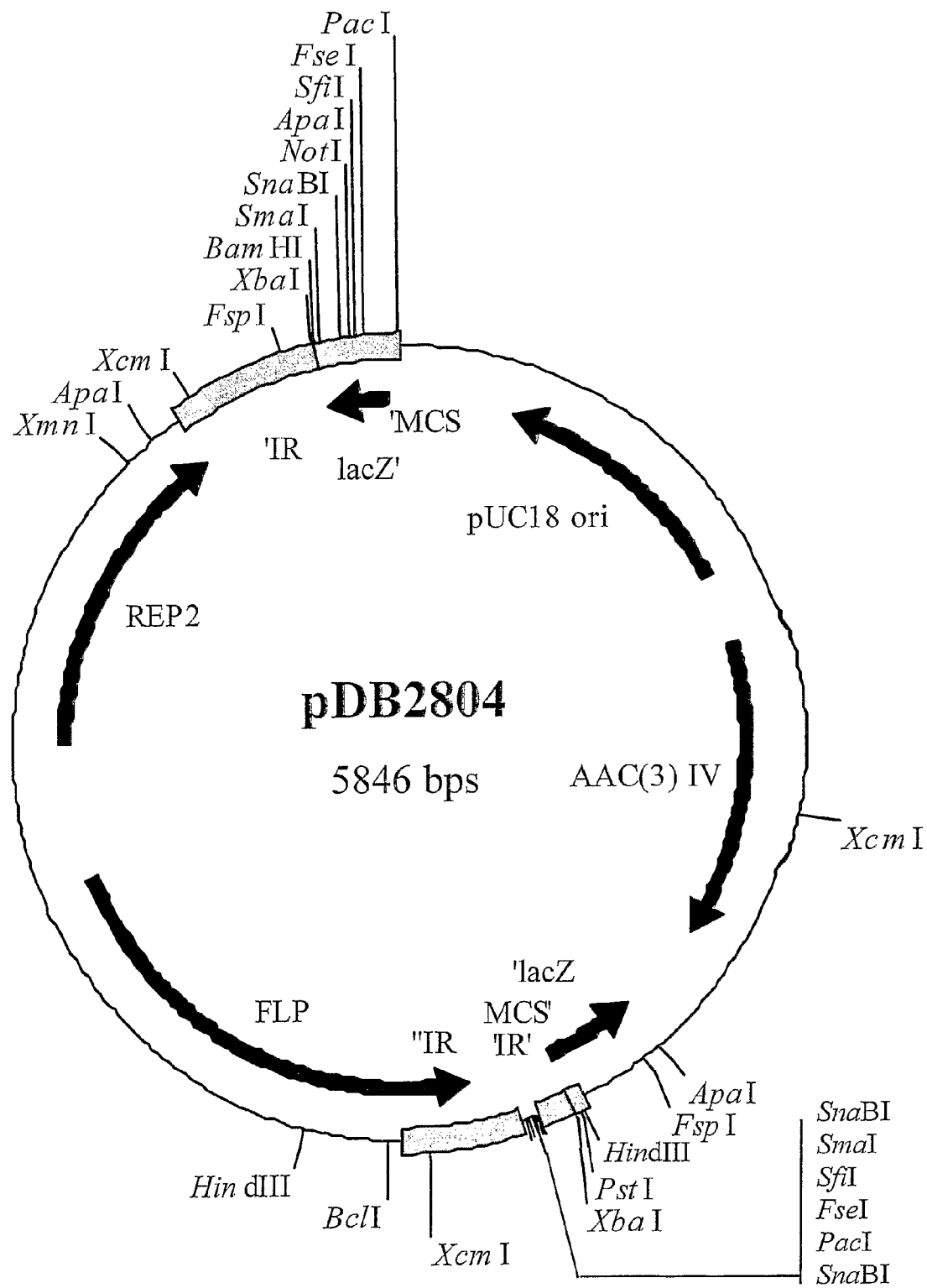

Plasmids pDB2803 and pDB2804 (FIGS. 29 and 30, respectively) with the core termination linker (CF106+CF107) inserted at the FspI after FLP, were isolated by the same method used to construct pDB2801. The correct linker insertions were confirmed by DNA sequencing. Plasmid pDB2804 contained the linker inserted in the correct orientation (with the PacI-site closest to the FLP gene), whereas pDB2803 contained the linker in the opposite orientation.

Figure 31:
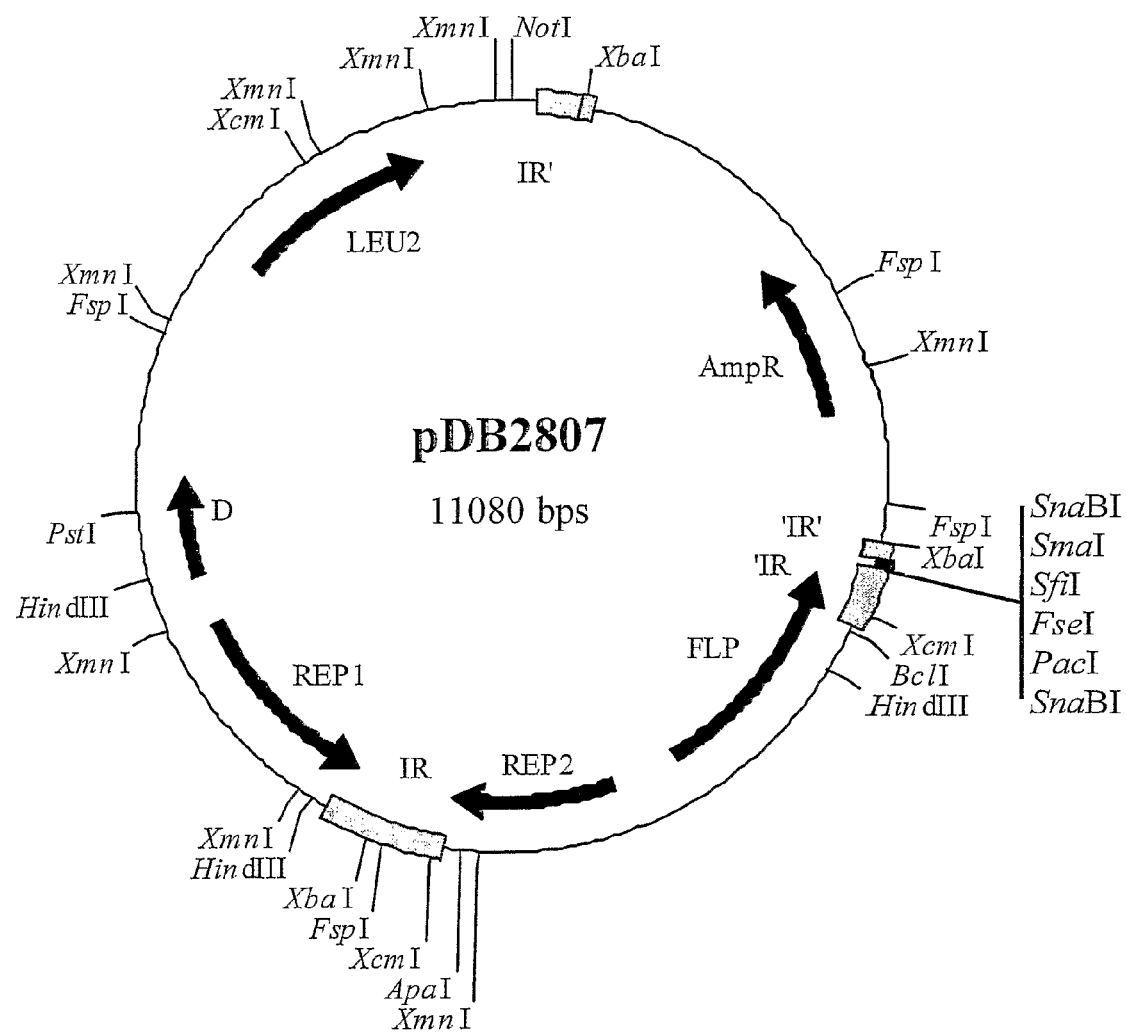
Figure 32:
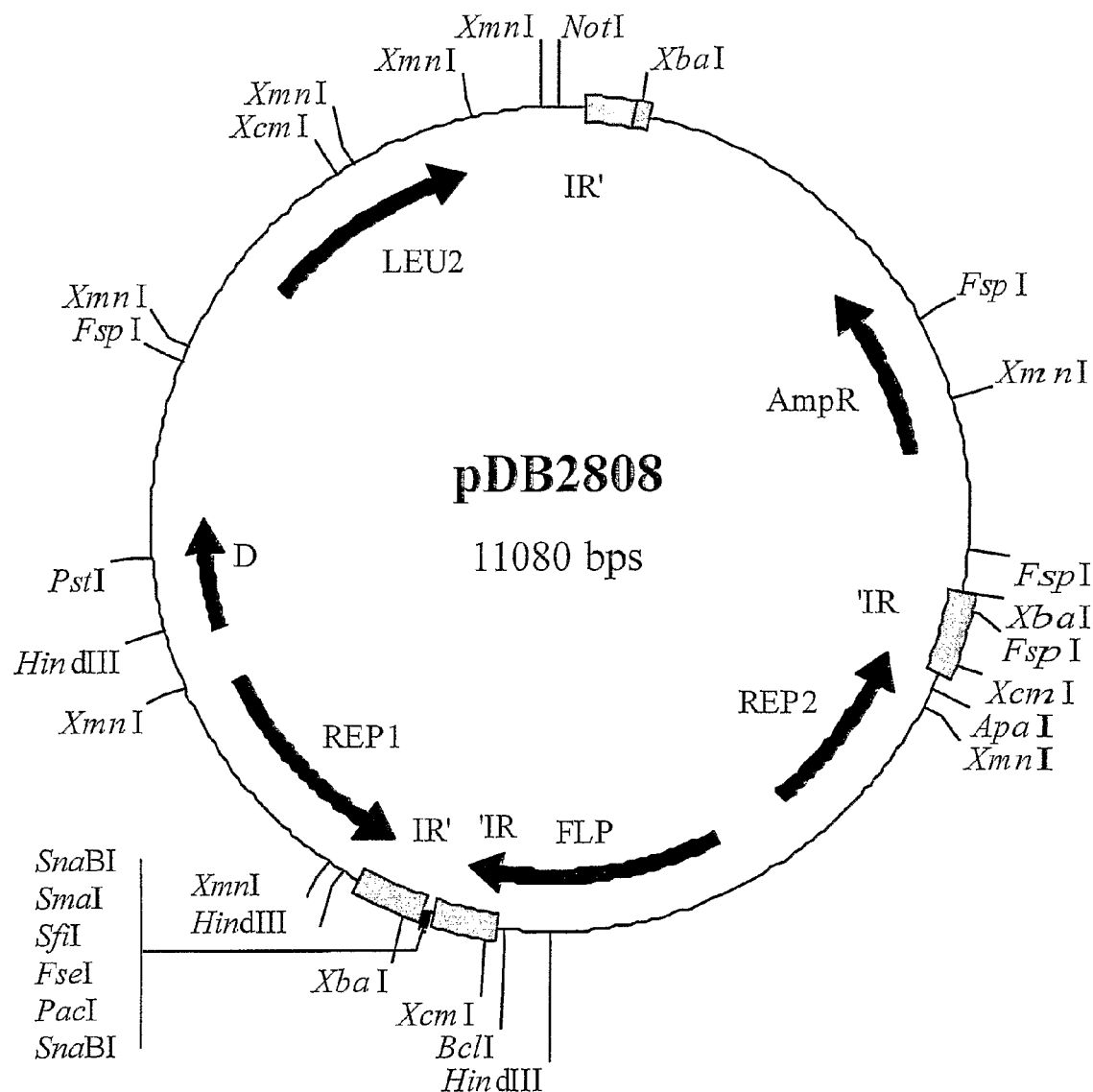

The pDB28043,119-bp XbaI fragment was ligated with the 7,961-bp pSAC35 fragment produced by partial XbaI digestion and treatment with calf intestinal alkaline phosphatase to create pDB2807 (B-form) and pDB2808 (A-form) disintegration vectors containing DNA inserted at the FspI-site after FLP (FIGS. 31 and 32 respectively).

Example 5

Relative Stabilities of the LEU2 Marker in Yeast Transformed with pSAC35-Like Plasmids Containing DNA Linkers Inserted into the Small Unique Region and Inverted Repeats A *S. cerevisiae* strain was transformed with the pSAC35-like plasmids containing DNA linkers inserted into the US-region and inverted repeats. Cryopreserved trehalose stocks were prepared for testing plasmid stabilities (Table 3). Plasmid stabilities were analysed as described above for linkers inserted at the XcmI-sites in pSAC35. Duplicate flasks were set up for each insertion site analysed. In addition, to the analysis of colonies derived from cells after 3-days in shake flake culture, colonies were grown and analysed from cells with a further 4-days shake flask culture. For this, 100 µL samples were removed from each 3-day old flask and subcultured in 100 mL YEPS broth for a further period of approximately 96 hours (94-98 hrs) at 30.0° C. in an orbital shaker, after which single colonies were obtained and analysed for loss of the LEU2 marker. In this case analysis was restricted to a single flask from selected strains, for which 50 colonies were picked. The overall results are summarised in Table 4.

TABLE 4

Summary of plasmid stability data for DNA insertions into pSAC35
Set 1 represents data from 3 days in non-selective shake flask culture.
Set 2 represents data from 7 days in non-selective shake flask culture.

| Plasmid(s) | Insertion Site | Additional Details | Relative Stability Set 1 | Set 2 |
|---|---|---|---|---|
| A) REP2 Insertion Sites | | | | |
| pSAC35 | — | Control | 99% | 100% |
| pDB2817 & pDB2818 | XmnI | REP2 (1-244) | 39% | 16% |
| pDB2787 | ApaI/T4 pol. | REP2 (1-269) | 45% | 0% |
| pDB2788 | ApaI | REP2 (1-271) | 33% | 0% |
| pDB2688 | XcmI | Inverted Repeat | 100% | 100% |
| pDB2805 & pDB2806 | FspI | Inverted Repeat | 100% | 100% |
| B) FLP Insertion Sites | | | | |
| pDB2814 | BclI | FLP (1-353) | 67% | 64% |
| pDB2823 | XcmI | FLP (1-382) | 64% | 53% |
| pDB2812 & pDB2813 | HgaI | Inverted Repeat | 100% | 100% |
| pDB2808 | FspI | Inverted Repeat | 100% | 100% |

All of the modified pSAC35 plasmids were able to transform yeast to leucine prototrophy, indicating that despite the additional DNA inserted within the functionally crowded regions of 2 µm DNA, all could replicate and partition in *S. cerevisiae*. This applied to plasmids with 43-52 base-pair linkers inserted at all the sites in the 2 µm US-region, as well as the larger DNA insertion containing the PDI1 gene.

For the linker insertion sites, data was reproducible between both experiments and duplicates. All sites outside REP2 or FLP open reading frames, but within inverted repeats appeared to be 100% stable under the test conditions used. Plasmid instability (i.e. plasmid loss) was observed for linkers inserted into sites within the REP2 or FLP open reading frames. The observed plasmid instability of REP2 insertions was greater than for FLP insertions. For the REP2 insertions, loss of the LEU2 marker continued with the extended growth period in non-selective media, whereas there was little difference for the FLP insertions.

Insertions into the REP2 gene produced Rep2 polypeptides truncated within a region known to function in self-association and binding to the STB-locus of 2 µm (Sengupta et al, 2001, *J. Bacteriol.*, 183, 2306).

Insertions into the FLP gene resulted in truncated Flp proteins. All the insertion sites were after tyrosine-343 in the C-terminal domain, which is essential for correct functioning of the Flp protein (Prasad et al, 1987, *Proc. Natl. Acad. Sci. U.S.A.*, 84, 2189; Chen et al, 1992, *Cell*, 69, 647; Grainge et al, 2001, *J. Mol. Biol.*, 314, 717).

None of the insertions into the inverted repeat regions resulted in plasmid instability being detected, except for the insertion into the FLP XcmI-site, which also truncated the Flp protein product. The insertions at the FspI-sites in the inverted repeat regions were the closest to the FRT (Flp recognition target) regions, important for plasmid replication.

pSAC35-like plasmids have been constructed with 43-52 base-pair DNA linkers inserted into the REP2 open reading frame, or the FLP open reading frame or the inverted repeat sequences. In addition, a 1.9-kb DNA fragment containing the PDI1 gene was inserted into a DNA linker at the XcmI-site after REP2.

All of the pSAC35-like vectors with additional DNA inserted were able to transform yeast to leucine prototrophy. Therefore, despite inserting DNA into functionally crowded regions of 2 μm plasmid DNA, the plasmid replication and partitioning mechanisms had not been abolished.

Determination of plasmid stability by measuring loss of the LEU2 selectable marker during growth in non-selective medium indicated that inserting DNA linkers into the inverted repeats had not destabilised the plasmid, whereas plasmid stability had been reduced by insertions into the REP2 and FLP open reading frames. However, despite a reduction in plasmid stability under non-selective media growth conditions when insertions were made into the REP2 and FLP open reading frames at some positions defined by the first and second aspects of the invention, the resulting plasmid nevertheless has a sufficiently high stability for use in yeast when grown on selective media.

Example 6

Insertion of DNA Sequences Immediately after the Rep2 Gene in the Small Unique Region of pSAC35

Figure 37:
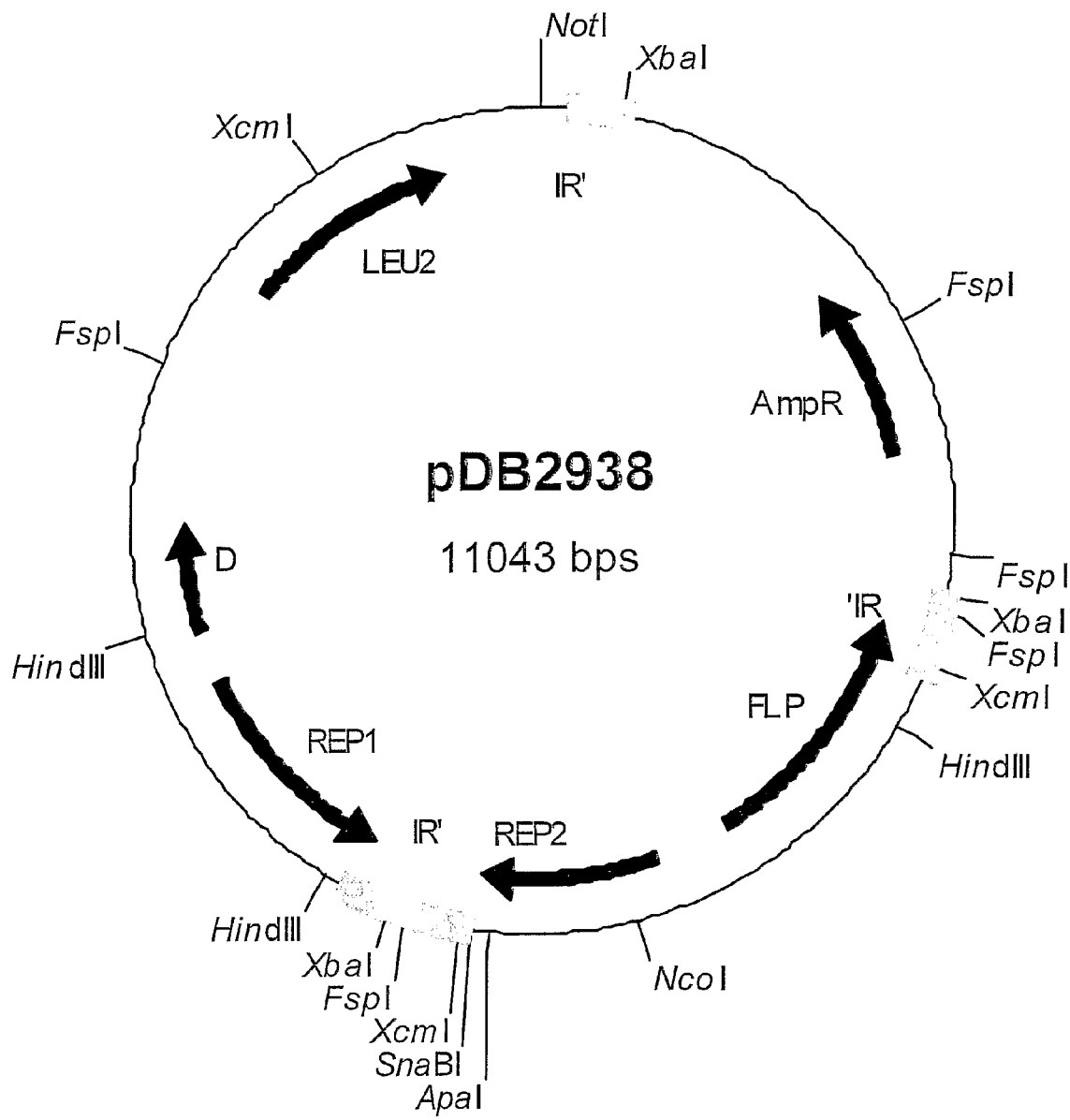
Figure 38:
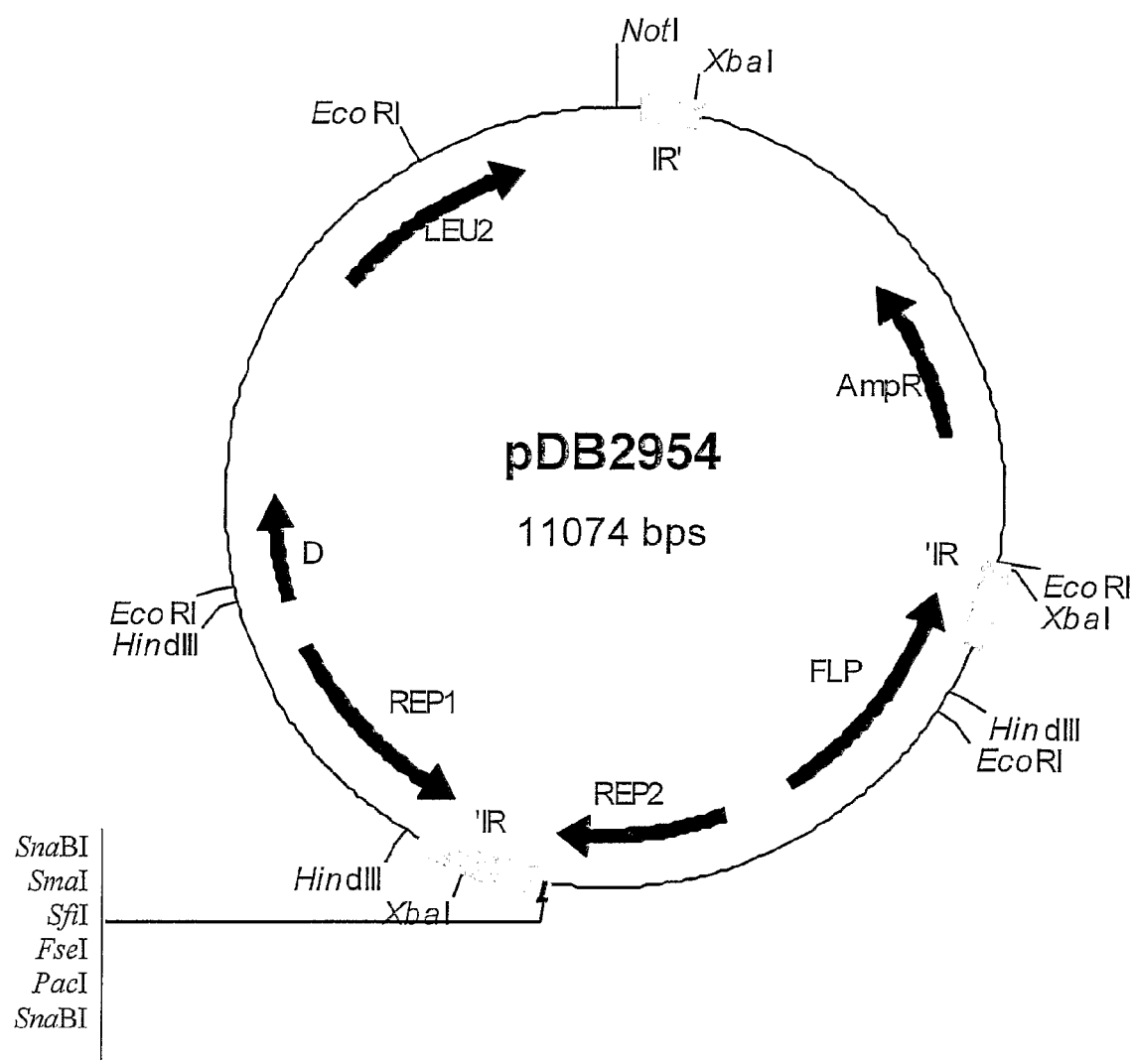

To further define the useful limits for insertion of additional DNA into the REP2 gene and sequences in the inverted repeat downstream of it, a synthetic DNA linker was inserted into pSAC35 immediately after the REP2 translation termination codon (TGA). As there were no naturally occurring restriction endonuclease sites conveniently located immediately after the REP2 coding sequence in 2 μm (or pSAC35), a SnaBI-site was introduced at this position by oligonucleotide directed mutagenesis. The pSAC35 derivative with a unique SnaBI-site immediately downstream of REP2 was named pDB2938 (FIG. 37). In pDB2938, the end of the inverted repeat was displaced from the rest of the inverted repeat by insertion of the SnaBI-site. pDB2954 (FIG. 38) was subsequently constructed with a 31-bp sequence identical to the SnaBI-linker made from oligonucleotides CF104 and CF105 (supra) inserted into the unique SnaBI site of pDB2938, such that the order of restriction endonuclease sites located immediately after the TGA translation termination codon of REP2 was SnaBI-PacI-FseI/SfiI-SmaI-SnaBI.

Figure 39:
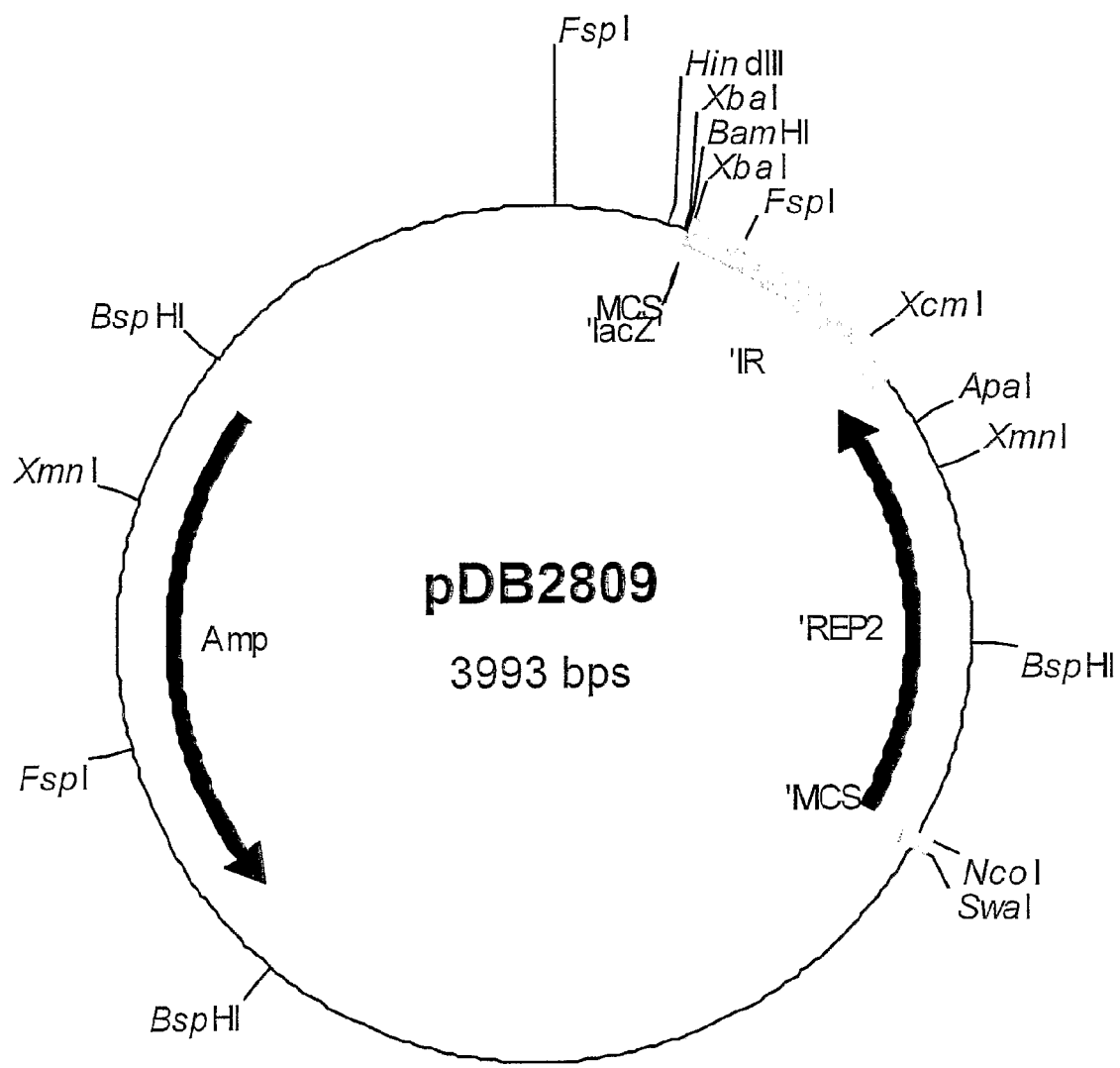
Figure 40:
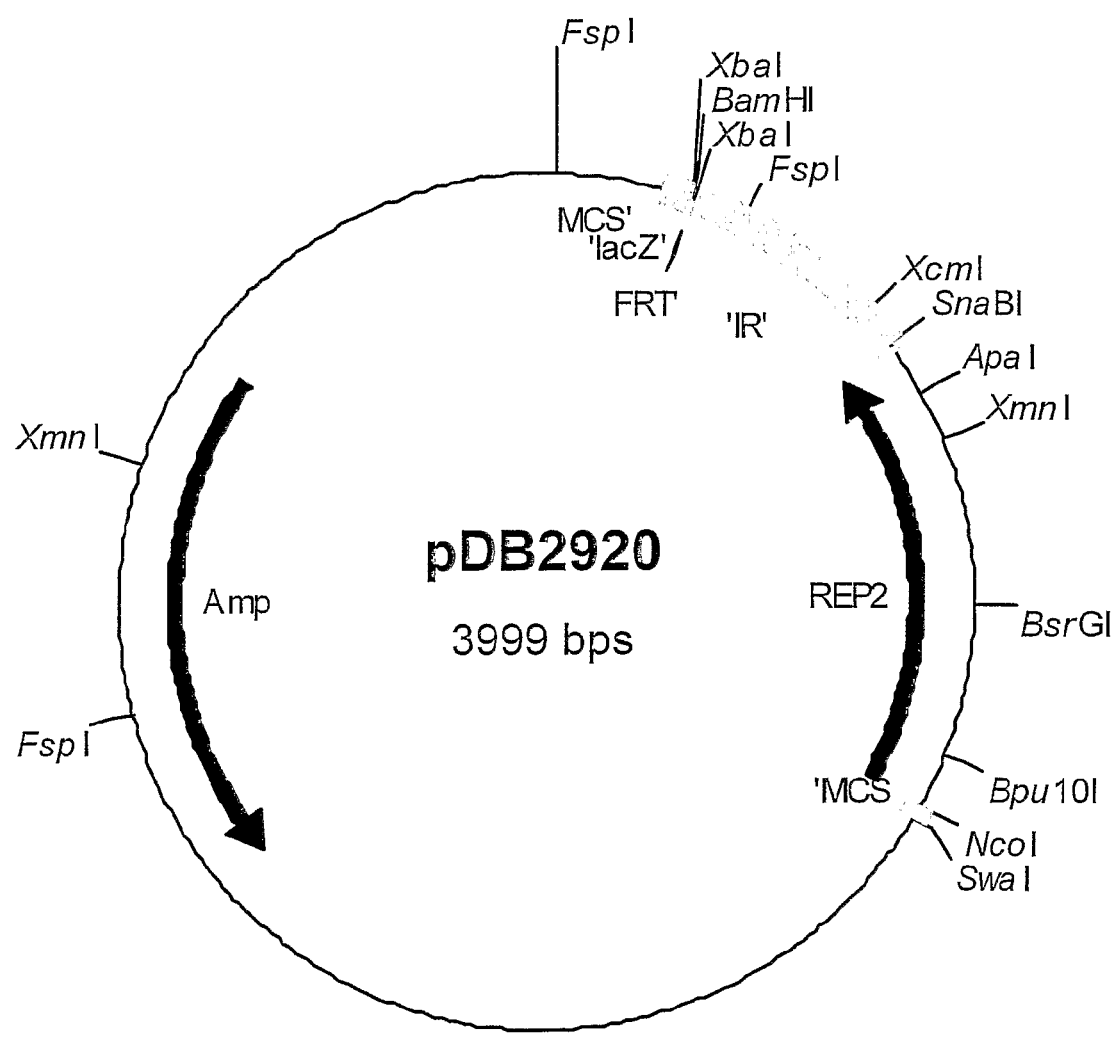

To construct pDB2938, the 1,085-bp NcoI-BamHI fragment from pDB2783 (FIG. 14) was first sub-cloned into pMCS5 (Hoheisel, 1994, Biotechniques, 17, 456), which had been digested with NcoI, BamHI and calf intestinal alkaline phosphatase. This produced pDB2809 (FIG. 39), which was subsequently mutated using oligonucleotides CF127 and CF128, to generate pDB2920 (FIG. 40).

```
The 51-bp mutagenic oligonucleotides CF127 and CF128
The SnaBI recognition sequence is underlined
CF127 5'-CGTAATACTTCTAGGGTATGA                            (SEQ ID NO: 43)
        TACGTATCCAATATCAAAGGAAATGATAGC-3'

CF128 5'-GCTATCATTTCCTTTGATATTGGA                         (SEQ ID NO: 44)
        TACGTATCATACCCTAGAAGTATTACG-3'
```

Oligonucleotide directed mutagenesis was performed according to the instruction manual of the Statagene's Quick-Change™ Site-Directed Mutagenesis Kit. SnaBI and HindIII restriction digestion of plasmid DNA was used to identify the ampicillin resistant E. coli transformants that contained pDB2920. The inserted 6-bp sequence of the SnaBI restriction site and the correct DNA sequence for the entire 1,091-bp NcoI-BamHI fragment was confirmed in pDB2920 by DNA sequencing using oligonucleotide primers CF98, CF99, CF129, CF130, CF131 and M13 forward and reverse primers (Table 1).

Figure 41:
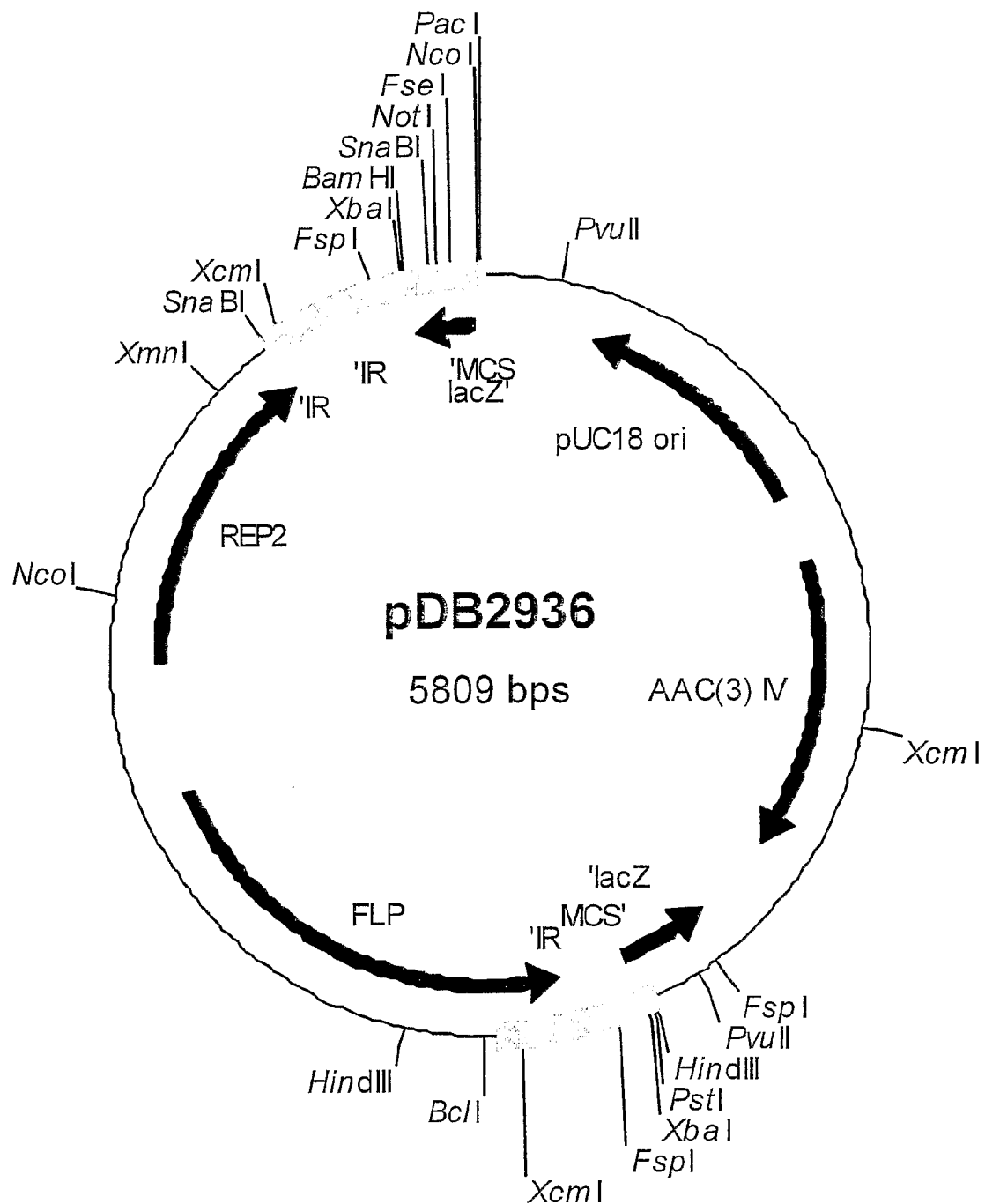

The 1,091-bp NcoI-BamHI fragment from pDB2920 was isolated by agarose gel purification and ligated with the approximately 4.7-kb NcoI-BamHI fragment from pDB2783 to produce pDB2936 (FIG. 41). The pDB2783 4.7-kb NcoI-BamHI fragment was isolated by complete BamHI digestion of pDB2783 DNA that had first been linearised by partial digestion with NcoI and purified by agarose gel electrophoresis. E. coli DH5α cells were transformed to apramycin resistance by the ligation products. pDB2936 was identified by SnaBI digestion of plasmid DNA isolated from the apramycin resistant clones.

Figure 42:
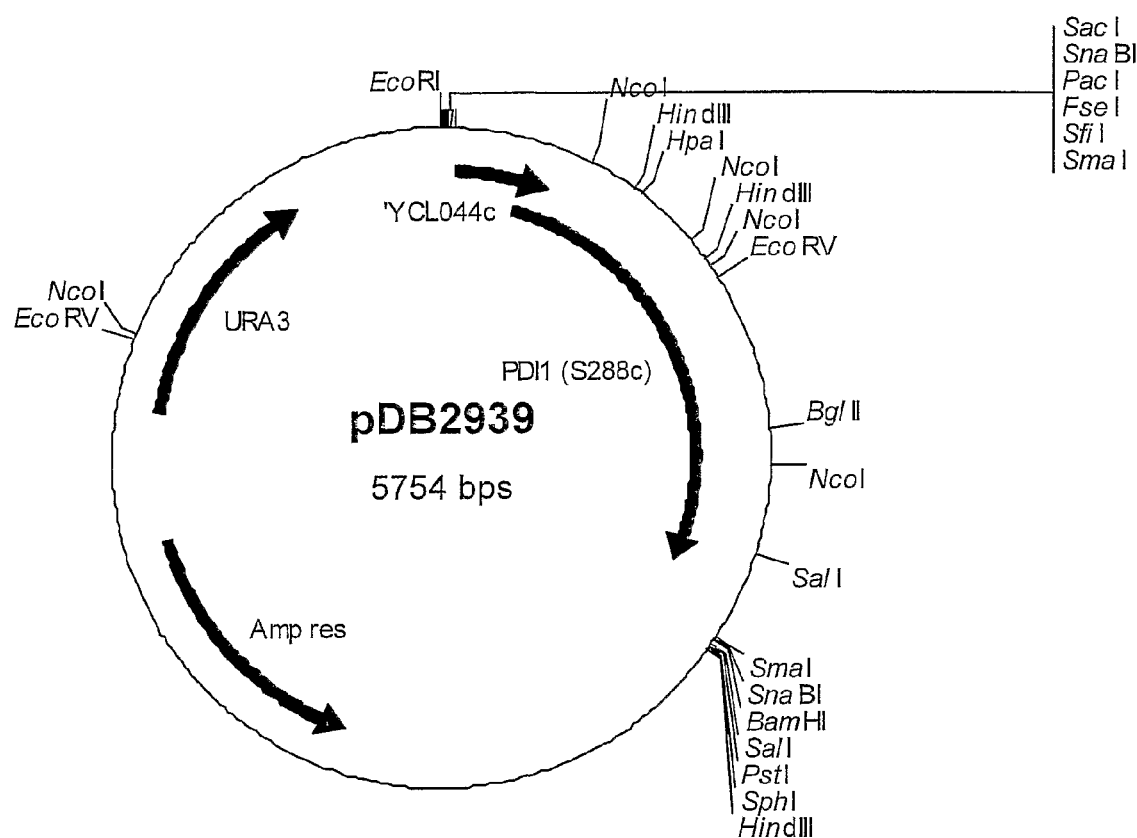
Figure 44:
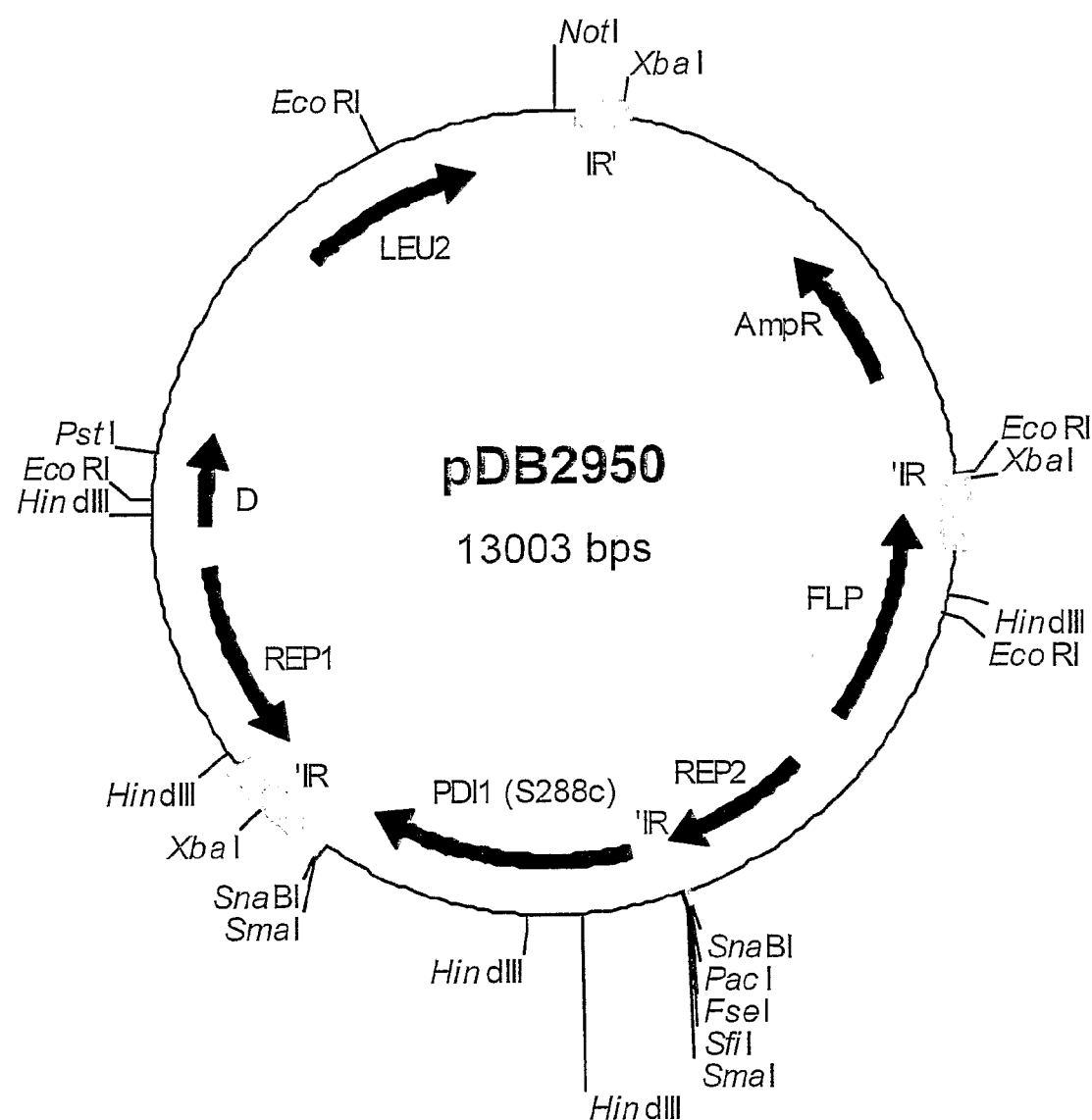

The 3,082-bp XbaI fragment from pDB2936 was subsequently ligated with a 7,961-bp pSAC35 fragment, which had been produced by partial XbaI digestion and treatment with calf intestinal alkaline phosphatase, to create the disintegration vector pDB2938 (2 μm B-form, FIG. 37)

pDB2938 was digested with SnaBI and calf intestinal phosphatase and ligated with an approximately 2-kb SnaBI fragment from pDB2939 (FIG. 42). pDB2939 was produced by PCR amplifying the PDI1 gene from S. cerevisiae S288c genomic DNA with oligonucleotide primers DS248 and DS250 (FIG. 43), followed by digesting the PCR products with EcoRI and BamHI and cloning the approximately 1.98-kb fragment into YIplac211 (Gietz & Sugino, 1988, Gene, 74, 527-534), that had been cut with EcoRI and BamHI. DNA sequencing of pDB2939 identified a missing 'G' from within the DS248 sequence, which is marked in bold in FIG. 43. The approximately 2-kb SnaBI fragment from pDB2939 was subsequently cloned into the unique SnaBI-site of pDB2938 to produce plasmid pDB2950 (FIG. 44). The PDI1 gene in pDB2950 is transcribed in the same direction as the REP2 gene.

pDB2950 was subsequently digested with SmaI and the approximately 11.1-kb DNA fragment was circularised to delete the S288c PDI1 sequence. This produced plasmid pDB2954 (FIG. 38) with the SnaBI-PacI-FseI/SfiI-SmaI-SnaBI linker located immediately after the TGA translation termination codon of REP2.

Figure 45:
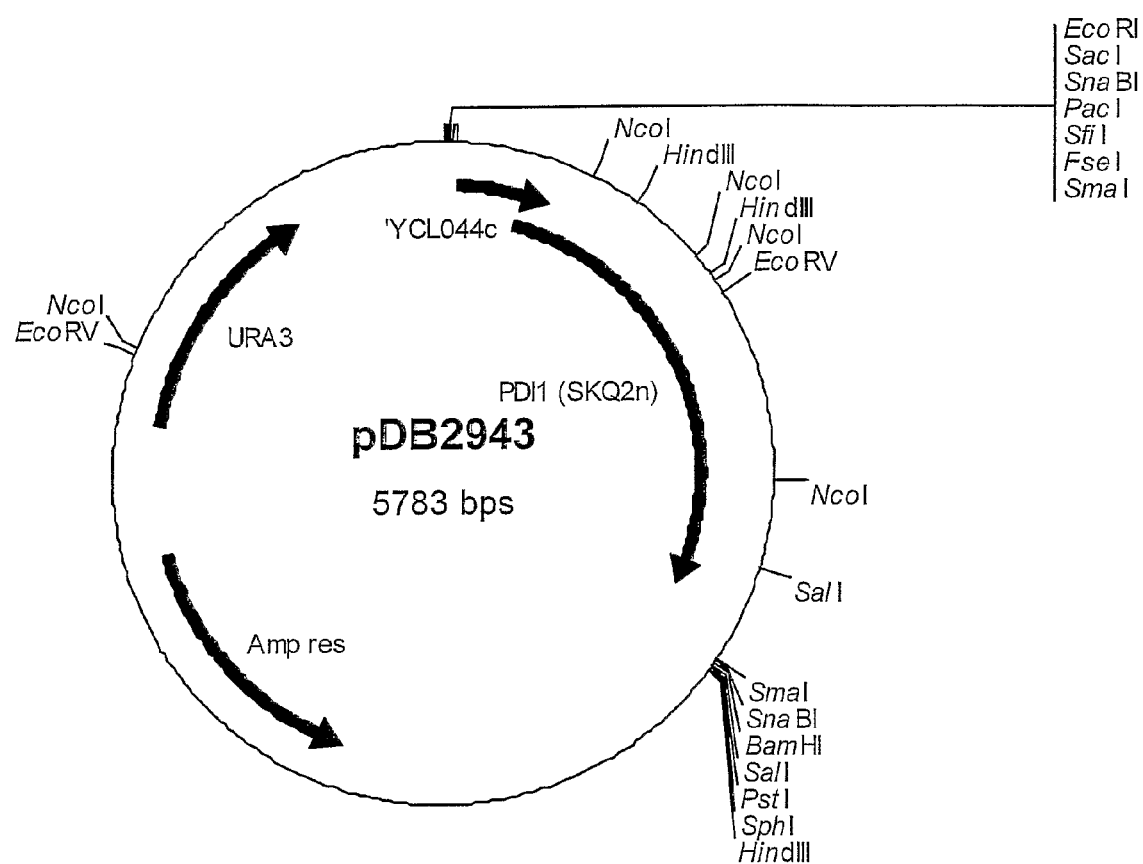
Figure 46:
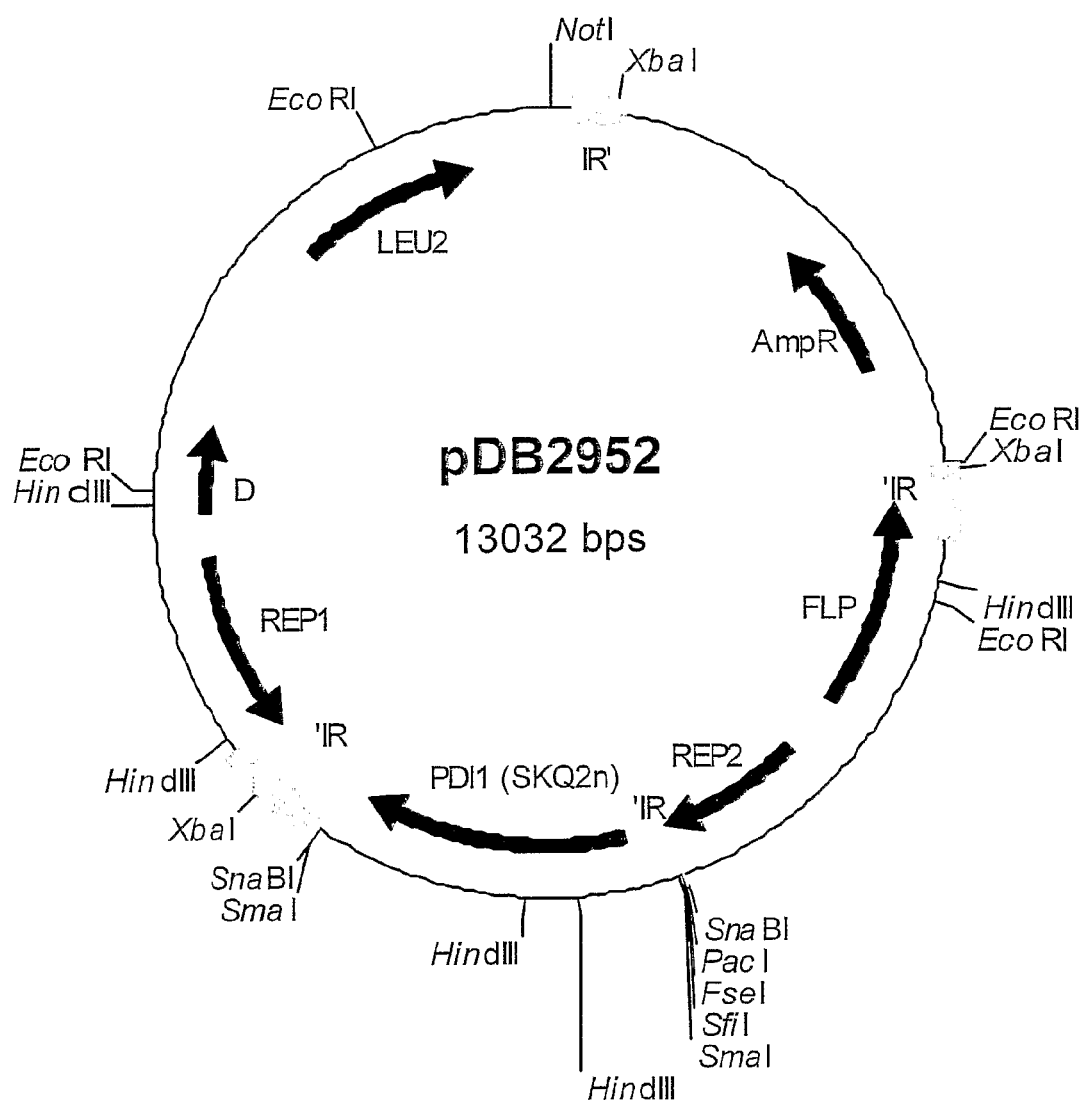

In addition to cloning the S. cerevisiae S288c PDI1 gene into the unique SnaBI-site of pDB2938, the S. cerevisiae SKQ2n PDI1 gene was similarly inserted at this site. The S. cerevisiae SKQ2n PDI1 gene sequence was PCR amplified from plasmid DNA containing the PDI1 gene from pMA3a:

C7 (U.S. Pat. No. 6,291,205), also known as Clone C7 (Crouzet & Tuite, 1987, supra; Farquhar et al, 1991, supra). The SKQ2n PDI1 gene was amplified using oligonucleotide primers DS248 and DS250 (FIG. 43). The approximately 2-kb PCR product was digested with EcoRI and BamHI and ligated into YIplac211 (Gietz & Sugino, 1988, Gene, 74, 527-534) that has been cut with EcoRI and BamHI, to produce plasmid pDB2943 (FIG. 45). The 5' end of the SKQ2n PDI1 sequence is analogous to a blunt-ended SpeI-site extended to include the EcoRI, SacI, SnaBI, PacI, FseI, SfiI and SmaI sites, the 3' end extends up to a site analogous to a blunt-ended Bsu36I site, extended to include a SmaI, SnaBI and BamHI sites. The PDI1 promoter length is approximately 210 bp. The entire DNA sequence was determined for the PDI1 fragment and shown to code for the PDI protein of S. cerevisiae strain SKQ2n sequence (NCBI accession number CAA38402), but with a serine residue at position 114 (not an arginine residue). Similarly to the S. cerevisiae S288c sequence in pDB2939, pDB2943 had a missing 'G' from within the DS248 sequence, which is marked in bold in FIG. 43. The approximately 1,989-bp SnaBI fragment from pDB2943 was subsequently cloned into the unique SnaBI-site in pDB2938. This produced plasmid pDB2952 (FIG. 46), in which the SKQ2n PDI1 gene is transcribed in the same direction as REP2.

Example 7

Relative Stabilities of the LEU2 Marker in Yeast Transformed with pSAC35-Like Plasmids Containing DNA Inserted Immediately after the Rep2 Gene The impact on plasmid stability from insertion of the linker sequence at the SnaBI-site introduced after the REP2 gene in pSAC35 was assessed for pDB2954. This was determined in the same S. cerevisiae strain as used in the earlier examples by loss of the LEU2 marker during non-selective growth on YEPS. The stability of pDB2954 was compared to the stabilities of pSAC35 (control plasmid), pDB2688 (XcmI-linker) and pDB2817 (XmnI-linker) by the method described in Example 1.

The yeast strain was transformed to leucine prototrophy using a modified lithium acetate method (Sigma yeast transformation kit, YEAST-1, protocol 2; (Ito et al, 1983, J. Bacteriol., 153, 163; Elble, 1992, Biotechniques, 13, 18)). Transformants were selected on BMMD-agar plates, and were subsequently patched out on BMMD-agar plates. Cryopreserved trehalose stocks were prepared from 10 mL BMMD shake flask cultures (24 hrs, 30° C., 200 rpm) by mixing with an equal volume of sterile 40% (w/v) trehalose and freezing aliquots at −80° C. (i.e. minus 80° C.).

For the determination of plasmid stability, a 1 mL cryopreserved stock was thawed and inoculated into 100 mL YEPS (initial $OD_{600}$~0.04-0.09) in a 250 mL conical flask and grown for approximately 72 hours (typically 70-74 hrs) at 30° C. in an orbital shaker (200 rpm, Innova 4300 incubator shaker, New Brunswick Scientific). Each strain was analysed in duplicate.

Samples were removed from each flask, diluted in YEPS-broth ($10^{-2}$ to $10^{-5}$ dilution), and 100 µL aliquots plated in duplicate onto YEPS-agar plates. Cells were grown at 30° C. for 3-4 days to allow single colonies to develop. For each yeast stock analysed, 100 random colonies were patched in replica onto BMMS-agar plates followed by YEPS-agar plates. After growth at 30° C. for 3-4 days the percentage of colonies growing on both BMMS-agar plates and YEPS-agar plates was determined as the measure of plasmid stability.

The results of the above analysis are shown below in Table 5A. These results indicate that pDB2954 is essentially as stable as the pSAC35 control and pDB2688. In this type of assay a low level of instability can occasionally be detected even with the pSAC35 control (see Table 4). Hence, the SnaBI-site artificially introduced into the inverted repeat sequence immediately after the translation termination codon of REP2 appeared to be equivalent to the XcmI-site in the inverted repeat for insertion of synthetic linker sequences. However, the XcmI-site appeared to be preferable to the SnaBI-site for insertion of the approximately 2-kb DNA fragment containing the PDI1 gene.

TABLE 5A

Relative stabilities of pSAC35-based vectors containing various DNA insertions

| Plasmid | Insertion site in US-Region | Gene inserted in US-Region | Gene(s) inserted at SnaBI/NotI-site in UL-Region | Relative Stability (%) |
|---------|-----|-----|-----|-----|
| pSAC35  | —     | —           | LEU2 | 100  |
| pDB2688 | XcmI  | —           | LEU2 | 99.5 |
| pDB2954 | SnaBI | —           | LEU2 | 99   |
| pDB2817 | XmnI  | —           | LEU2 | 27   |
| pDB2690 | XcmI  | PDI1 (SKQ2n) | LEU2 | 39.5 |
| pDB2952 | SnaBI | PDI1 (SKQ2n) | LEU2 | 0    |
| pDB2950 | SnaBI | PDI1 (S288c) | LEU2 | 0    |

A "zero percent stability" result of this assay for plasmids pDB2952 and pDB2950 was obtained in non-selective media, which gives an indication of the relative plasmid stabilities. This assay was optimised to compare the relative stabilities of the different linker inserts. In selective media, plasmids with PDI1 at the SnaBI-site (even when comprising an additional transferrin gene at the NotI site, which is known to further destabilise the plasmid (such as pDB2959 and pDB2960 as described below)) produced "precipitin halos" of secreted transferrin on both non-selective YEPD-agar and selective BMMD-agar plates containing anti-transferrin antibodies. Precipitin halos of secreted transferrin were not observed from pDB2961, without the PDI1 gene inserted at the SnaBI-site. These results demonstrate that the SnaBI-site is useful for the insertion of large genes such as PDI1, which can increase the secretion of heterologous proteins. These results were all generated in the control strain. An increase was also seen for Strain A containing pDB2959 and pDB2960, but in this case there was also a lower level of secretion observed with pDB2961 (because of the extra PDI1 gene in the genome of Strain A). Results from the control strain are summarised in Table 5B below. Antibody plates were used contained 100 µL of goat polyclonal anti-transferrin antiserum (Calbiochem) per 25 mL BMMD-agar or YEPD-agar. Strains were patched onto antibody plates and grown for 48-72 hours at 30° C., after which the precipitin "halos" were observed within the agar around colonies secreting high levels of recombinant transferrin. Very low levels of transferrin secretion are not observed in this assay.

Plasmids pDB2959, pDB2960 and pDB2961 were constructed from pDB2950 (FIG. 44), pDB2952 (FIG. 46) and pDB2954 (FIG. 38) respectively, by inserting the same 3.27-kb NotI cassette for rTf (N413Q, N611Q) as found in pDB2711 (FIG. 11), into the unique NotI-site, in the same orientation as pDB2711.

TABLE 5B

Increased transferrin secretion from the Control Strain transformed with pSAC35-based vectors containing various PDI1 gene insertions immediately-site after REP2

| Plasmid | Insertion site in US-Region | Gene inserted in US-Region | Gene(s) inserted at SnaBI/NotI-site in UL-Region | Transferrin secretion Detected on Anti-Transferrin Ab-plates | |
|---|---|---|---|---|---|
| | | | | BMMD-Anti Tf | YEPD-Anti Tf |
| pDB2960 | SnaBI | PDI1 (SKQ2n) | LEU2 + rTf | Yes | Yes |
| pDB2959 | SnaBI | PDI1 (S288c) | LEU2 + rTf | Yes | Yes |
| pDB2961 | SnaBI | — | LEU2 + rTf | No | No |

Example 8

Stabilities of the LEU2 Marker in Yeast Transformed with pSAC35-Like Plasmids Determined Over Thirty Generations of Growth in Non-Selective Conditions The stabilities of pSAC35-like plasmids with DNA inserted in the US-region were determined using a method analogous to that defined by Chinery & Hinchcliffe (1989, Curr. Genet., 16, 21-25) This was determined in the same S. cerevisiae strain as used in previous examples by loss of the LEU2 marker during logarithmic growth on non-selective YEPS medium over a defined number of generations. Thirty generations was suitable to show a difference between a control plasmid, pSAC35, or to shown comparable stability to the control plasmid. Plasmids selected for analysis by this assay were; pSAC35 (control), pDB2688 (XcmI-linker), pDB2812 (HgaI-linker), pDB2817 (XmnI-linker), pDB2960 (PDI1 gene inserted at XcmI site after REP2) and pDB2711 (PDI1 gene inserted at XcmI site after REP2 and a transferrin expression cassette inserted at the NotI-site in the UL-region).

Strains were grown to logarithmic phase in selective (BMMS) media at 30° C. and used to inoculate 100 mL non-selective (YEPS) media pre-warmed to 30° C. in 250 mL conical flasks, to give between $1.25 \times 10^5$ and $5 \times 10^5$ cells/ml. The number of cells inoculated into each flask was determined accurately by using a haemocytometer to count the number of cells in culture samples. Aliquots were also plated on non-selective (YEPS) agar and incubated at 30° C. for 3-4 days, after which for each stock analysed, 100 random colonies were replica plated on selective (BMMS) agar and non-selective (YEPS) agar to assess the proportion of cells retaining the plasmid. After growth at 30° C. for 3-4 days the percentage of colonies growing on both BMMS agar and YEPS agar plates was determined as a measure of plasmid stability.

Non-selective liquid cultures were incubated at 30° C. with shaking at 200 rpm for 24 hours to achieve approximately $1 \times 10^7$ cells/ml, as determined by haemocytometer counts. The culture was then re-inoculated into fresh pre-warmed non-selective media to give between $1.25 \times 10^5$ and $5 \times 10^5$ cells/ml. Aliquots were again plated on non-selective agar, and subsequently replicated plated on selective agar and non-selective agar to assess retention of the plasmid. Hence, it was possible to calculate the number of cell generations in non-selective liquid media. Exponential logarithmic growth was maintained for thirty generations in liquid culture, which was sufficient to show comparable stability to a control plasmid, such as pSAC35. Plasmid stability was defined as the percentage cells maintaining the selectable LEU2 marker.

Figure 47:
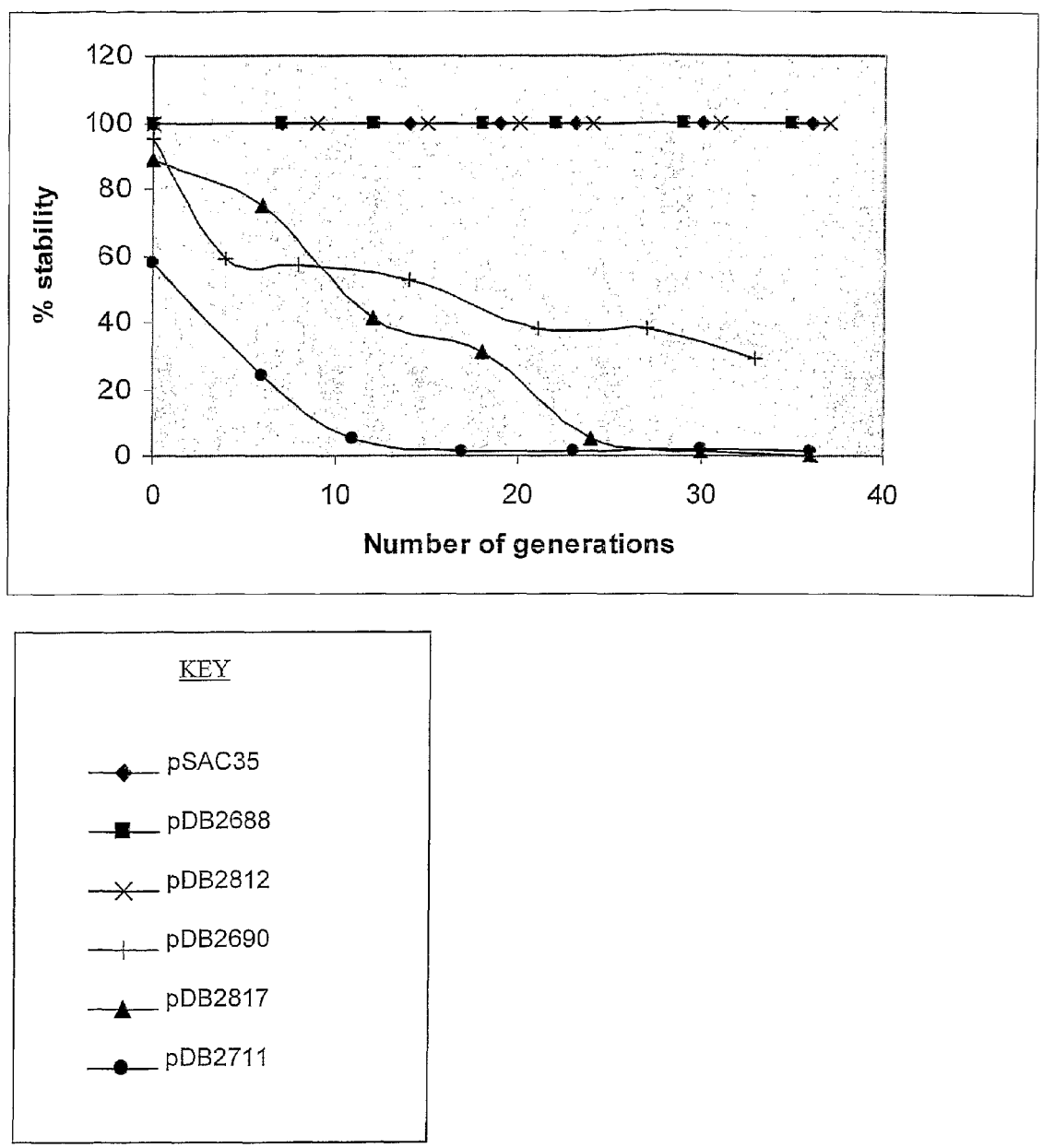
FIG. 47 shows plasmid stabilities with increasing number of generation growth in non-selective liquid culture for *S. cerevisiae* containing various pSAC35-derived plasmids.

Results of the above analysis to measure the retention of the plasmid-encoded phenotype through growth in non-selective media are shown in Table 6 and FIG. 47.

TABLE 6

The Relative Stabilities of Selected pSAC35-Like Plasmids in a S. cerevisiae Strain grown for Thirty Generations in Non-Selective Media

| Plasmid | Linker Insertion site in US-region | Gene inserted in US-region | Gene(s) inserted at SnaBI/NotI-site in UL-region | Percentage Stability after 30 generations |
|---|---|---|---|---|
| pSAC35 | — | — | LEU2 | 100 |
| pDB2688 | XcmI after REP2 | — | LEU2 | 100 |
| pDB2812 | HgaI after FLP | — | LEU2 | 100 |
| pDB2817 | XmnI in REP2 | — | LEU2 | 1 |
| pDB2690 | XcmI after REP2 | PDI1 (SKQ2n) | LEU2 | 33 |
| pDB2711 | XcmI after REP2 | PDI1 (SKQ2n) | LEU2 + rTf | 2 |

FIG. 47 shows the loss of the LEU2 marker with increasing number generation in non-selective liquid culture for each strain analysed.

The control plasmid pSAC35 remained 100% stable over the entire 30-generations of this assay. Plasmids pBD2688 and pDB2812 both appeared to be as stable as pSAC35. Therefore, insertion of the linker into the XcmI-site after REP2 or the HgaI-site after FLP respectively had no apparent effect on plasmid stability. In contrast, insertion of the XmnI-linker within the REP2 gene appeared to have reduced plasmid stability.

Plasmid pDB2690, which contains a S. cerevisiae PDI1 gene in the XcmI-linker after REP2, was approximately 33% stable after thirty generations growth, indicating that insertion of this large DNA fragment into the US-region of the 2 µm-based vector caused a decrease in plasmid stability. However, this decrease in stability was less than that observed with pDB2711, where insertion of the recombinant transferrin (N413Q, N611Q) expression cassette into the NotI-site within the large unique region of pSAC35 acted to further destabilise the plasmid. These observations are consistent with the results of Example 2 (see Table 2).

The stability of plasmid pDB2711 was assessed by the above method in an alternative strain of S. cerevisiae, and similar results were obtained (data not shown). This indicates that the stability of the plasmid is not strain dependent.

Example 9

PDI1 Gene Disruption, Combined with a PDI1 Gene on the 2 μm-Based Plasmid Enhanced Plasmid Stability Single stranded oligonucleotide DNA primers listed in Table 7 were designed to amplify a region upstream of the yeast PDI1 coding region and another a region downstream of the yeast PDI1 coding region.

TABLE 7

Oligonucleotide primers

| Primer | Description | Sequence |
|---|---|---|
| DS299 (SEQ ID NO: 45) | 5' PDI1 primer, 38 mer | 5'-CGTAGCGGCCGCCTGAAAGGGGTTGACCG TCCGTCGGC-3' |
| DS300 (SEQ ID NO: 46) | 5' PDI1 primer, 40 mer | 5'-CGTAAAGCTTCGCCGCCCGACAGGGTAAC ATATTATCAC-3' |
| DS301 (SEQ ID NO: 47) | 3' PDI1 primer, 38 mer | 5'-CGTAAAGCTTGACCACGTAGTAATAATAA GTGCATGGC-3' |
| DS302 (SEQ ID NO: 48) | 3' PDI1 primer, 41 mer | 5'-CGTACTGCAGATTGGATAGTGATTAGAGT GTATAGTCCCGG-3' |
| DS303 (SEQ ID NO: 49) | 18 mer | 5'-GGAGCGACAAACCTTTCG-3' |
| DS304 (SEQ ID NO: 50) | 20 mer | 5'-ACCGTAATAAAAGATGGCTG-3' |
| DS305 (SEQ ID NO: 51) | 24 mer | 5'-CATCTTGTGTGTGAGTATGGTCGG-3' |
| DS306 (SEQ ID NO: 52) | 14 mer | 5'-CCCAGGATAATTTTCAGG-3' |

Primers DS299 and DS300 amplified the 5' region of PDI1 by PCR, while primers DS301 and DS302 amplified a region 3' of PDI1, using genomic DNA derived S288c as a template. The PCR conditions were as follows: 1 μL S288c template DNA (at 0.01 ng/μL, 0.1 ng/μL, 1 ng/μL, 10 ng/μL and 100 ng/μL), 5 μL 10× Buffer (Fast Start Taq+Mg, (Roche)), 1 μL 10 mM dNTP's, 5 μL each primer (2 μM), 0.4 μL Fast Start Taq, made up to 50 μL with $H_2O$. PCRs were performed using a Perkin-Elmer Thermal Cycler 9700. The conditions were: denature at 95° C. for 4 min [HOLD], then [CYCLE] denature at 95° C. for 30 seconds, anneal at 45° C. for 30 seconds, extend at 72° C. for 45 seconds for 20 cycles, then [HOLD] 72° C. for 10 min and then [HOLD] 4° C. The 0.22 kbp PDI1 5' PCR product was cut with NotI and HindIII, while the 0.34 kbp PDI1 3' PCR product was cut with HindIII and PstI.

Figure 48:
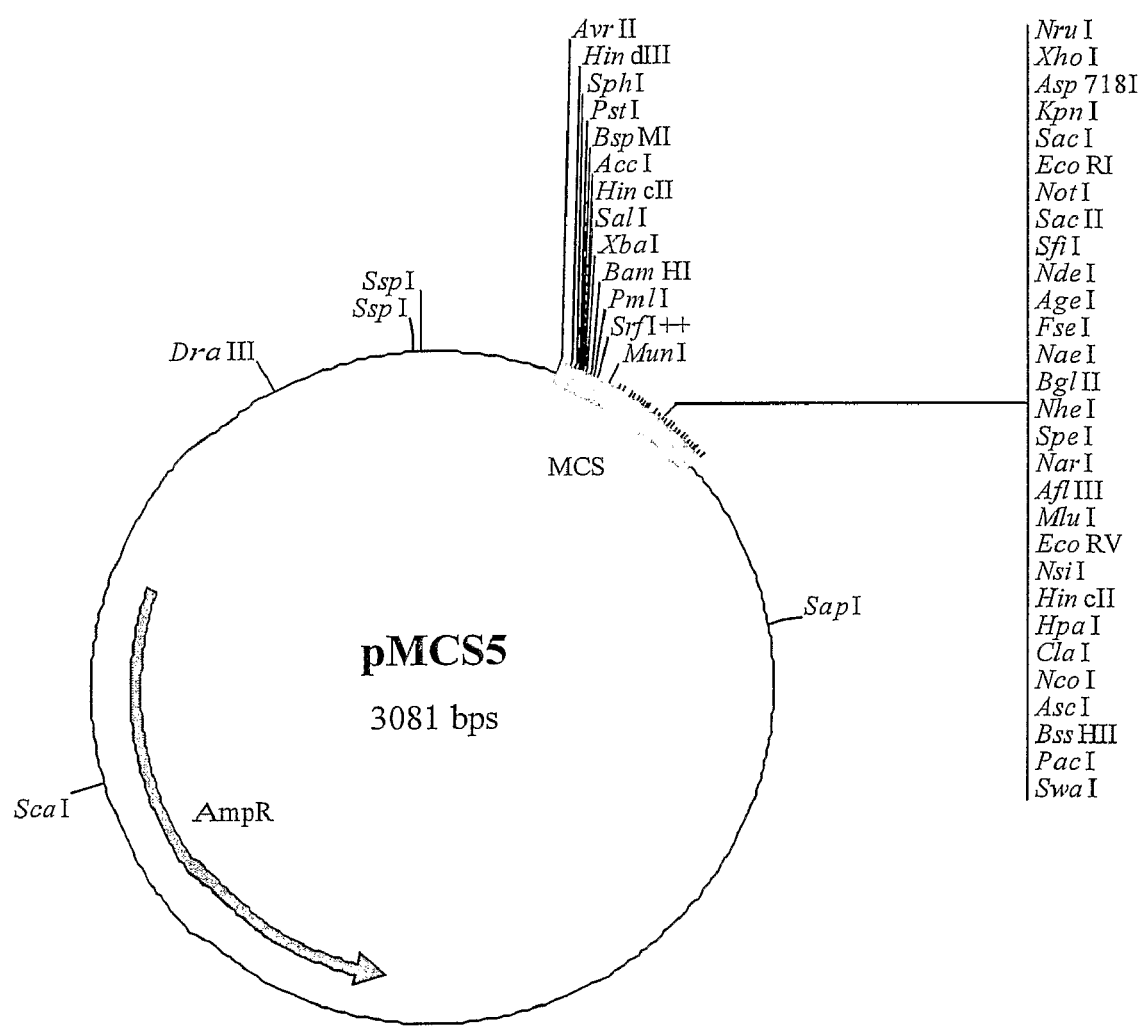
Figure 49:
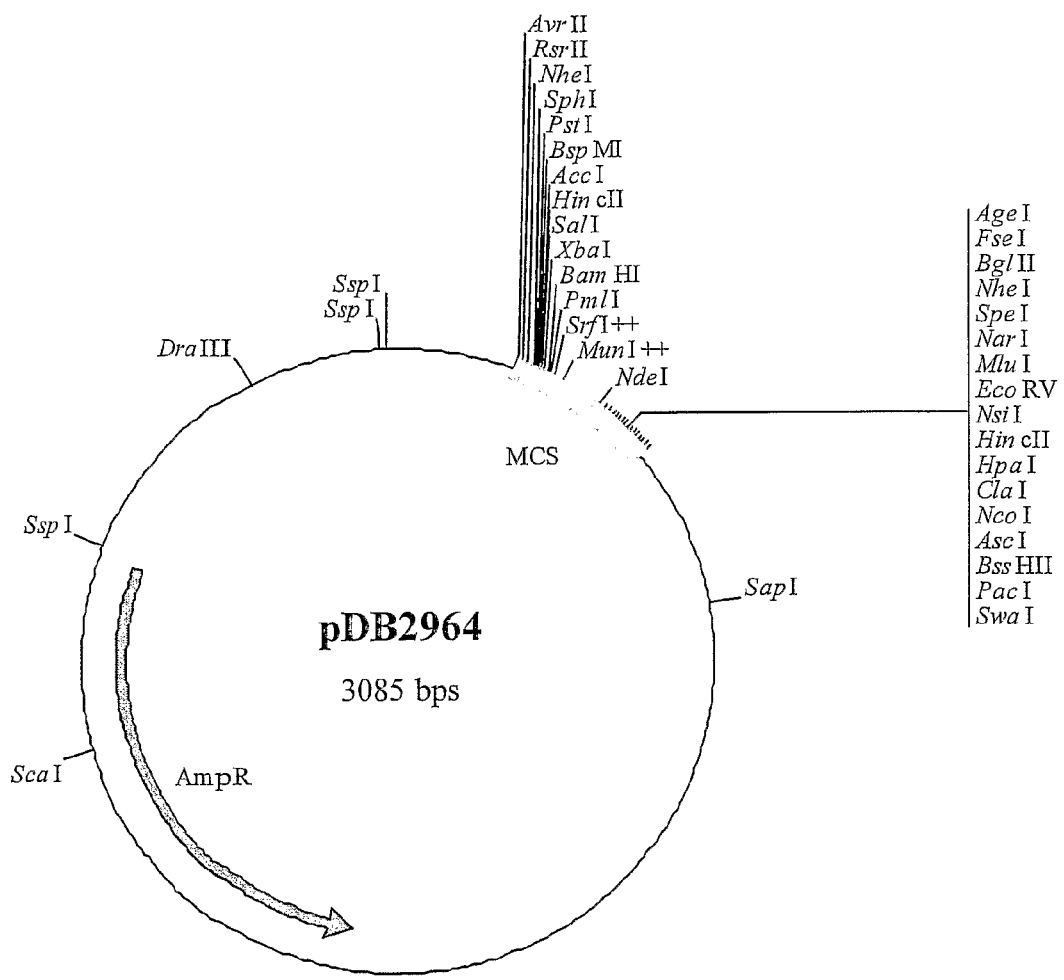

Plasmid pMCS5 (Hoheisel, 1994, *Biotechniques* 17, 456-460) (FIG. 48) was digested to completion with HindIII, blunt ended with T4 DNA polymerase plus dNTPs and religated to create pDB2964 (FIG. 49).

Figure 50:
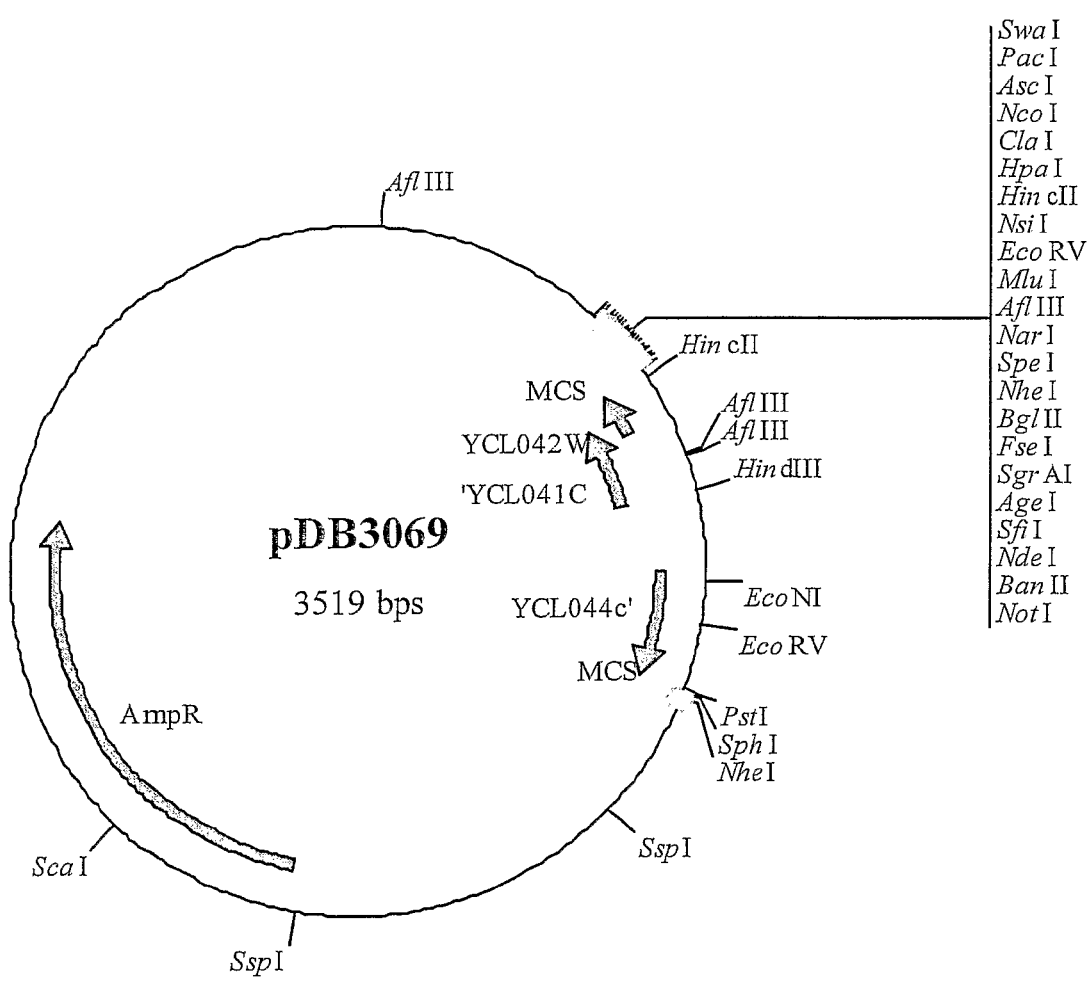

Plasmid pDB2964 was HindIII digested, treated with calf intestinal phosphatase, and ligated with the 0.22 kbp PDI1 5' PCR product digested with NotI and HindIII and the 0.34 kbp PDI1 3' PCR product digested with HindIII and PstI to create pDB3069 (FIG. 50) which was sequenced with forward and reverse universal primers and the DNA sequencing primers DS303, DS304, DS305 and DS306 (Table 7).

Figure 51:
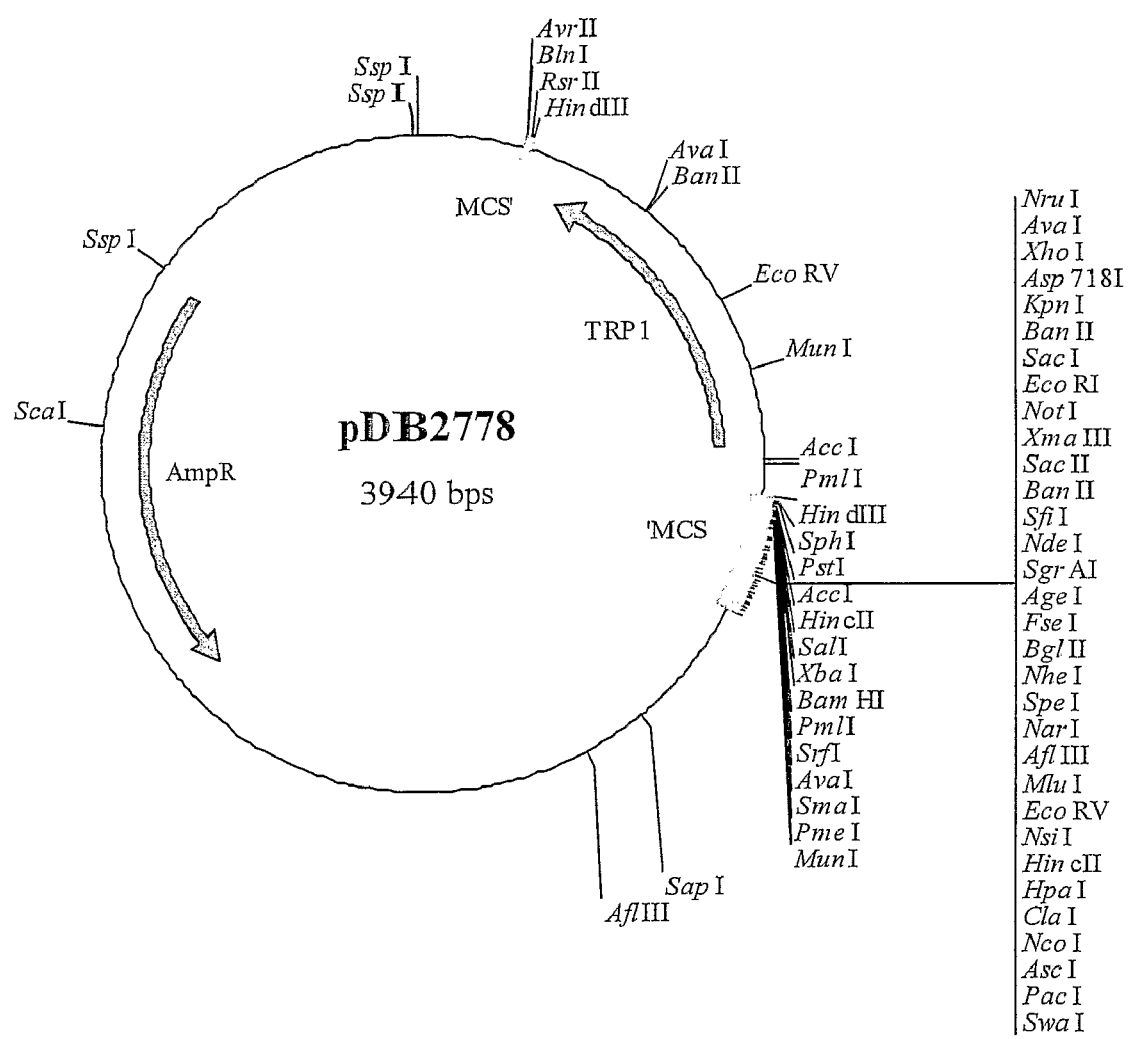

Primers DS234 and DS235 (Table 8) were used to amplify the modified TRP1 marker gene from YIplac204 (Gietz & Sugino, 1988, *Gene*, 74, 527-534), incorporating HindIII restriction sites at either end of the PCR product. The PCR conditions were as follows: 1 μL template YIplac204 (at 0.01 ng/μL, 0.1 ng/μL, 1 ng/μL, 10 ng/μL and 100 ng/μL), 5 μL 10× Buffer (Fast Start Taq+Mg, (Roche)), 1 μL 10 mM dNTP's, 5 μL each primer (2 μM), 0.4 μL Fast Start Taq, made up to 50 μL with $H_2O$. PCRs were performed using a Perkin-Elmer Thermal Cycler 9600. The conditions were: denature at 95° C. for 4 min [HOLD], then [CYCLE] denature at 95° C. for 30 seconds, anneal for 45 seconds at 45° C., extend at 72° C. for 90 sec for 20 cycles, then [HOLD] 72° C. for 10 min and then [HOLD] 4° C. The 0.86 kbp PCR product was digested with HindIII and cloned into the HindIII site of pMCS5 to create pDB2778 (FIG. 51). Restriction enzyme digestions and sequencing with universal forward and reverse primers as well as DS236, DS237, DS238 and DS239 (Table 8) confirmed that the sequence of the modified TRP1 gene was correct.

TABLE 8

Oligonucleotide primers

| Primer | Description | Sequence |
|---|---|---|
| DS230 (SEQ ID NO: 53) | TRP1 5' UTR | 5'-TAGCGAATTC AATCAGTAAAAATCAACG G-3' |
| DS231 (SEQ ID NO: 54) | TRP1 5' UTR | 5'-GTCAAAGCTTCAAAAAAGA AAAGCTCC GG-3' |
| DS232 (SEQ ID NO: 55) | TRP1 3' UTR | 5'-TAGCGGATCCGAATTCGGCGGTTGTTTGC AAGACCGAG-3' |
| DS233 (SEQ ID NO: 56) | TRP1 3' UTR | 5'-GTCAAAGCTTTAAAGATAATGCTAAATCA TTTGG-3' |
| DS234 (SEQ ID NO: 57) | TRP1 | 5'-TGACAAGCTTTCGGTCGAAAAAAGAAAG G AGAGG-3' |
| DS235 (SEQ ID NO: 58) | TRP1 | 5'-TGACAAGCTTGATCTTTTATGCTTGCTTT TC-3' |
| DS236 (SEQ ID NO: 59) | TRP1 | 5'-AATAGTTCAGGCACTCCG-3' |
| DS237 (SEQ ID NO: 60) | TRP1 | 5'-TGGAAGGCAAGAGAGCC-3' |

TABLE 8-continued

Oligonucleotide primers

| Primer | Description | Sequence |
|---|---|---|
| DS238 (SEQ ID NO: 61) | TRP1 | 5'-TAAAATGTAAGCTCTCGG-3' |
| DS239 (SEQ ID NO: 62) | TRP1 | 5'-CCAACCAAGTATTTCGG-3' |
| CED005 (SEQ ID NO: 63) | ΔTRP1 | 5'-GAGCTGACAGGGAAATGGTC-3' |
| CED006 (SEQ ID NO: 64) | ΔTRP1 | 5'-TACGAGGATACGGAGAGAGG-3' |

Figure 52:
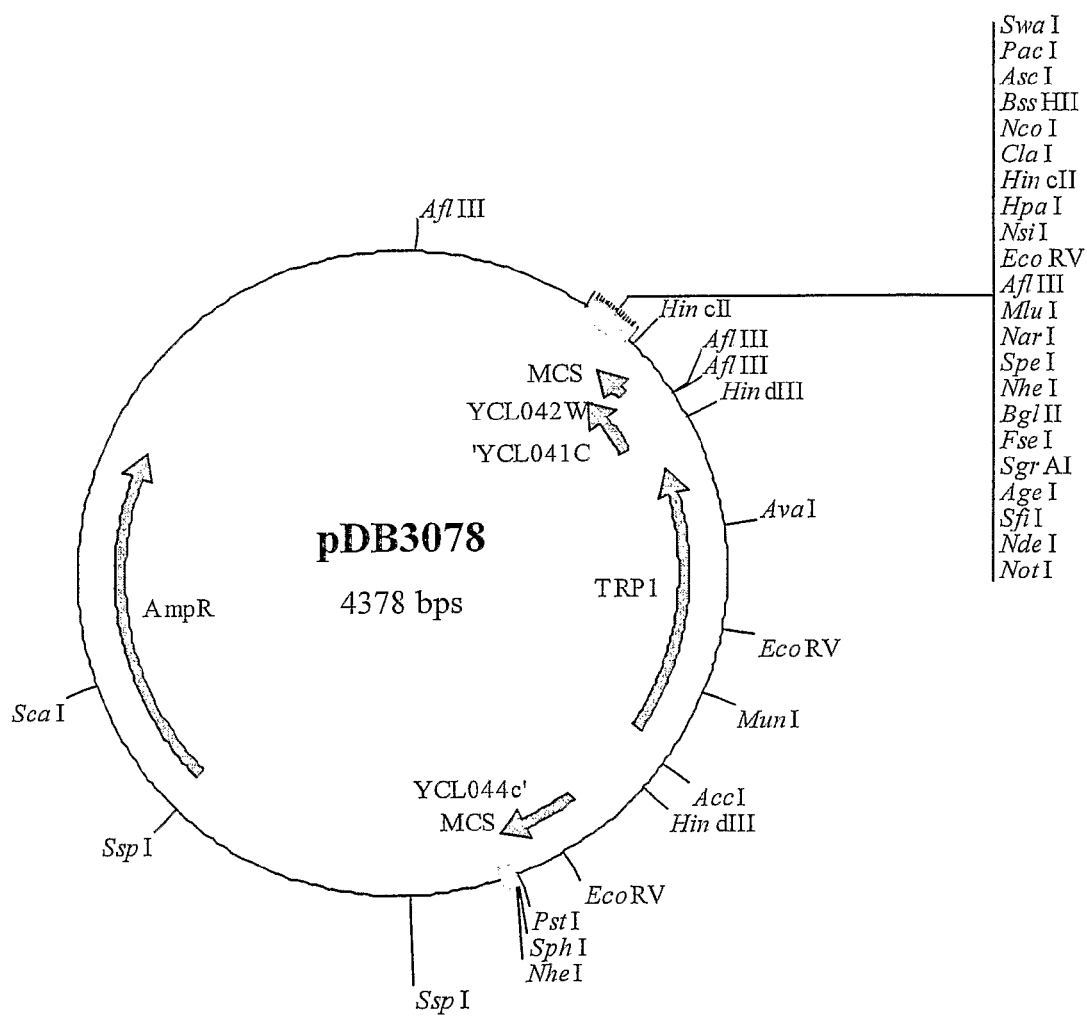
Figure 53:
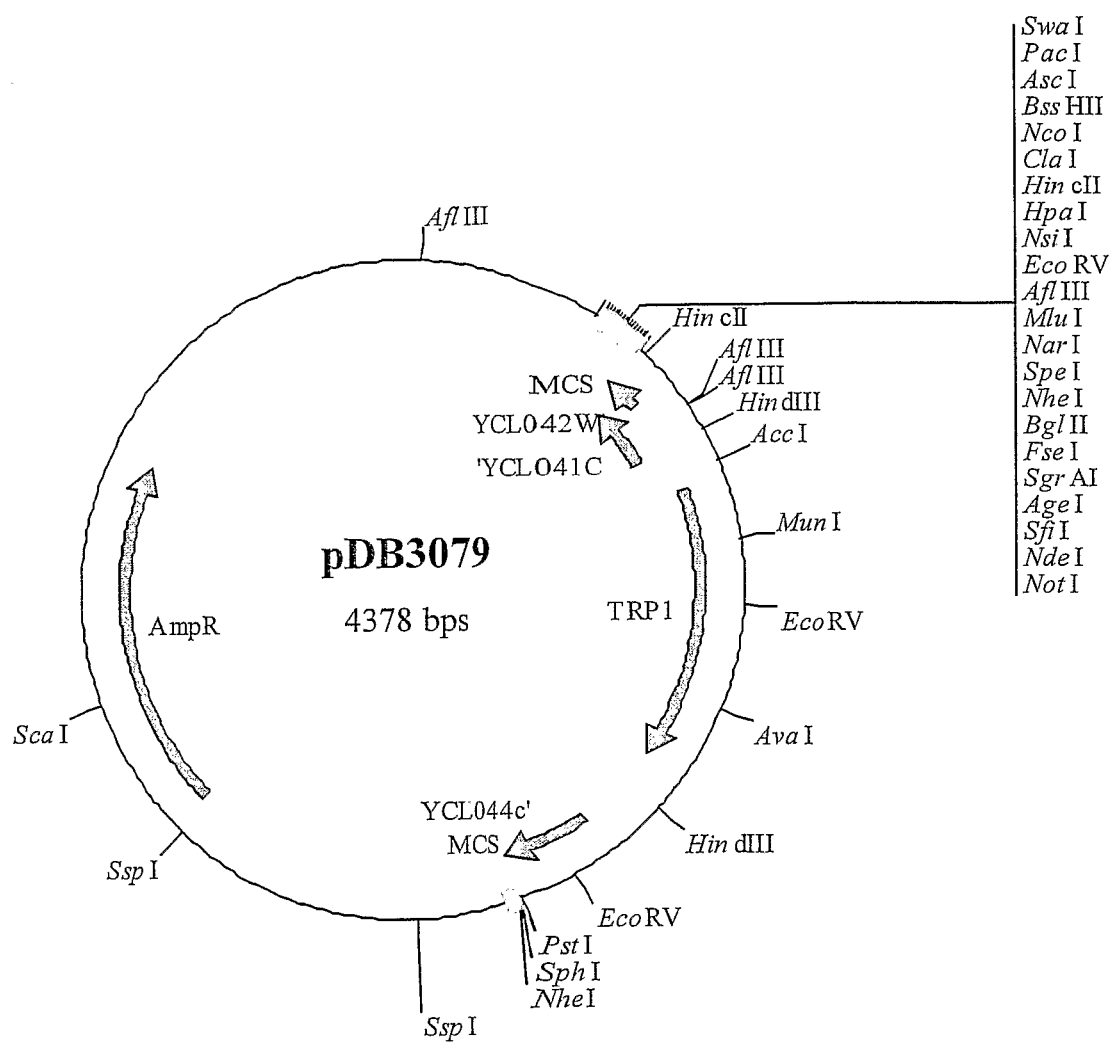

The 0.86 kbp TRP1 gene was isolated from pDB2778 by digestion with HindIII and cloned into the HindIII site of pDB3069 to create pDB3078 (FIG. 52) and pDB3079 (FIG. 53). A 1.41 kb pdi1::TRP1 disrupting DNA fragment was isolated from pDB3078 or pDB3079 by digestion with NotI/PstI.

Yeast strains incorporating a TRP1 deletion (trp1Δ) were to be constructed in such a way that no homology to the TRP1 marker gene (pDB2778) should left in the genome once the trp1Δ had been created, so preventing homologous recombination between future TRP1 containing constructs and the TRP1 locus. In order to achieve the total removal of the native TRP1 sequence from the genome of the chosen host strains, oligonucleotides were designed to amplify areas of the 5' UTR and 3' UTR of the TRP1 gene outside of TRP1 marker gene present on integrating vector YIplac204 (Gietz & Sugino, 1988, Gene, 74, 527-534). The YIplac204 TRP1 marker gene differs from the native/chromosomal TRP1 gene in that internal HindIII, PstI and XbaI sites were removed by site directed mutagenesis (Gietz & Sugino, 1988, Gene, 74, 527-534). The YIplac204 modified TRP1 marker gene was constructed from a 1.453 kbp blunt-ended genomic fragment EcoRI fragment, which contained the TRP1 gene and only 102 bp of the TRP1 promoter (Gietz & Sugino, 1988, Gene, 74, 527-534). Although this was a relatively short promoter sequence it was clearly sufficient to complement trp1 auxotrophic mutations (Gietz & Sugino, 1988, Gene, 74, 527-534). Only DNA sequences upstream of the EcoRI site, positioned 102 bp 5' to the start of the TRP1 ORF were used to create the 5' TRP1 UTR. The selection of the 3' UTR was less critical as long as it was outside the 3' end of the functional modified TRP1 marker, which was chosen to be 85 bp downstream of the translation stop codon.

Single stranded oligonucleotide DNA primers were designed and constructed to amplify the 5' UTR and 3' UTR regions of the TRP1 gene so that during the PCR amplification restriction enzyme sites would be added to the ends of the PCR products to be used in later cloning steps. Primers DS230 and DS231 (Table 8) amplified the 5' region of TRP1 by PCR, while primers DS232 and DS233 (Table 8) amplified a region 3' of TRP1, using S288c genomic DNA as a template. The PCR conditions were as follows: 1 µL template S288c genomic DNA (at 0.01 ng/µL, 0.1 ng/µL, 1 ng/µL, 10 ng/µL and 100 ng/µL), 5 µL 10× Buffer (Fast Start Taq+Mg, (Roche)), 1 µL 10 mM dNTP's, 5 µL each primer (2 µM), 0.4 µL Fast Start Taq, made up to 50 µL with $H_2O$. PCRs were performed using a Perkin-Elmer Thermal Cycler 9600. The conditions were: denature at 95° C. for 4 min [HOLD], then [CYCLE] denature at 95° C. for 30 seconds, anneal for 45 seconds at 45° C., extend at 72° C. for 90 sec for 20 cycles, then [HOLD] 72° C. for 10 min and then [HOLD] 4° C.

Figure 54:
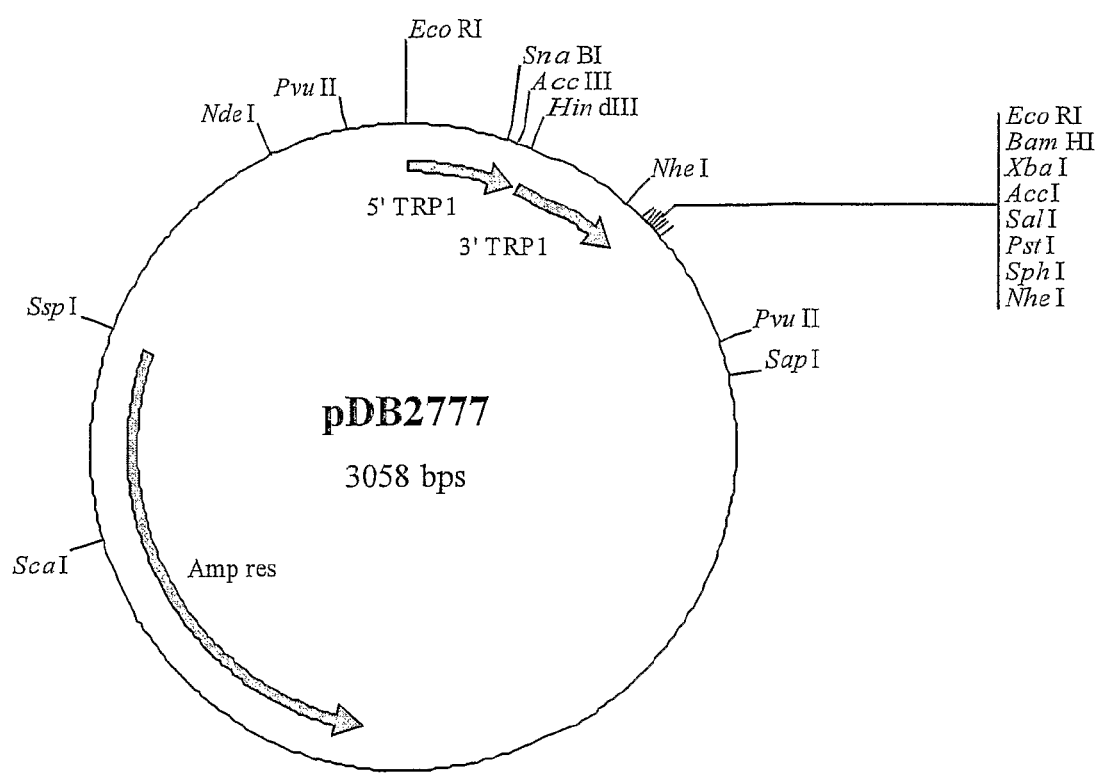

The 0.19 kbp TRP1 5' UTR PCR product was cut with EcoRI and HindIII, while the 0.2 kbp TRP1 3' UTR PCR product was cut with BamHI and HindIII and ligated into pAYE505 linearised with BamHI/EcoRI to create plasmid-pDB2777 (FIG. 54). The construction of pAYE505 is described in WO 95/33833. DNA sequencing using forward and reverse primers, designed to prime from the plasmid backbone and sequence the cloned inserts, confirmed that in both cases the cloned 5' and 3' UTR sequences of the TRP1 gene had the expected DNA sequence. Plasmid pDB2777 contained a TRP1 disrupting fragment that comprised a fusion of sequences derived from the 5' and 3' UTRs of TRP1. This 0.383 kbp TRP1 disrupting fragment was excised from pDB2777 by complete digestion with EcoRI.

Yeast strain DXY1 (Kerry-Williams et al., 1998, Yeast, 14, 161-169) was transformed to leucine prototrophy with the albumin expression plasmid pDB2244 using a modified lithium acetate method (Sigma yeast transformation kit, YEAST-1, protocol 2; (Ito et al, 1983, J. Bacteriol., 153, 163; Elble, 1992, Biotechniques, 13, 18)) to create yeast strain DXY1 [pDB2244]. The construction of the albumin expression plasmid pDB2244 is described in WO 00/44772. Transformants were selected on BMMD-agar plates, and were subsequently patched out on BMMD-agar plates. Cryopreserved trehalose stocks were prepared from 10 mL BMMD shake flask cultures (24 hrs, 30° C., 200 rpm).

DXY1 [pDB2244] was transformed to tryptophan autotrophy with the 0.383 kbp EcoRI TRP1 disrupting DNA fragment from pDB2777 using a nutrient agar incorporating the counter selective tryptophan analogue, 5-fluoroanthranilic acid (5-FAA), as described by Toyn et al., (2000 Yeast 16, 553-560). Colonies resistant to the toxic effects of 5-FAA were picked and streaked onto a second round of 5-FAA plates to confirm that they really were resistant to 5-FAA and to select away from any background growth. Those colonies which grew were then were re-patched onto BMMD and BMMD plus tryptophan to identify which were tryptophan auxotrophs.

Subsequently colonies that had been shown to be tryptophan auxotrophs were selected for further analysis by transformation with YCplac22 (Gietz & Sugino, 1988, Gene, 74, 527-534) to ascertain which isolates were trp1.

PCR amplification across the TRP1 locus was used to confirm that the trp⁻ phenotype was due to a deletion in this region. Genomic DNA was prepared from isolates identified as resistant to 5-FAA and unable to grow on minimal media without the addition of tryptophan. PCR amplification of the genomic TRP1 locus with primers CED005 and CED006 (Table 8) was achieved as follows: 1 µL template genomic DNA, 5 µL 10× Buffer (Fast Start Taq+Mg, (Roche)), 1 µL 10 mM dNTP's, 5 µL each primer (2 µM), 0.4 µL Fast Start Taq, made up to 50 µL with $H_2O$. PCRs were performed using a Perkin-Elmer Thermal Cycler 9600. The conditions were: denature at 94° C. for 10 min [HOLD], then [CYCLE] denature at 94-C for 30 seconds, anneal for 30 seconds at 55° C., extend at 72° C. for 120 sec for 40 cycles, then [HOLD] 72° C. for 10 min and then [HOLD] 4° C. PCR amplification of the wild type TRP1 locus resulted in a PCR product of 1.34 kbp in size, whereas amplification across the deleted TRP1 region resulted in a PCR product 0.84 kbp smaller at 0.50 kbp.

PCR analysis identified a DXY1 derived trp⁻ strain (DXY1 trp1Δ [pDB2244]) as having the expected deletion event.

The yeast strain DXY1 trp1Δ [pDB2244] was cured of the expression plasmid pDB2244 as described by Sleep et al., 1991, *Bio/Technology*, 9, 183-187. DXY1 trp1Δ cir⁰ was re-transformed the leucine prototrophy with either pDB2244, pDB2976, pDB2977, pDB2978, pDB2979, pDB2980 or pDB2981 (the production of pDB2976, pDB2977 and pDB2980 or pDB2981 is discussed further in Example 10) using a modified lithium acetate method (Sigma yeast transformation kit, YEAST-1, protocol 2; (Ito et al, 1983, *J. Bacteriol.*, 153, 163; Elble, 1992, *Biotechniques*, 13, 18)). Transformants were selected on BMMD-agar plates supplemented with tryptophan, and were subsequently patched out on BMMD-agar plates supplemented with tryptophan. Cryopreserved trehalose stocks were prepared from 10 mL BMMD shake flask cultures supplemented with tryptophan (24 hrs, 30° C., 200 rpm).

The yeast strains DXY1 trp1Δ [pDB2976], DXY1 trp1Δ [pDB2977], DXY1 trp1Δ [pDB3078], DXY1 trp1Δ [pDB3079], DXY1 trp1Δ [pDB2980] or DXY1 trp1Δ [pDB2981] was transformed to tryptophan prototrophy using the modified lithium acetate method (Sigma yeast transformation kit, YEAST-1, protocol 2; (Ito et al, 1983, *J. Bacteriol.*, 153, 163; Elble, 1992, *Biotechniques*, 13, 18)) with a 1.41 kb pdi1::TRP1 disrupting DNA fragment was isolated from pDB3078 by digestion with NotI/PstI. Transformants were selected on BMMD-agar plates and were subsequently patched out on BMMD-agar plates.

Six transformants of each strain were inoculated into 10 mL YEPD in 50 mL shake flasks and incubated in an orbital shaker at 30° C., 200 rpm for 4-days. Culture supernatants and cell biomass were harvested. Genomic DNA was prepared (Lee, 1992, *Biotechniques*, 12, 677) from the tryptophan prototrophs and DXY1 [pDB2244]. The genomic PDI1 locus amplified by PCR of with primers DS236 and DS303 (Table 7 and 8) was achieved as follows: 1 µL template genomic DNA, 5 µL 10× Buffer (Fast Start Taq+Mg, (Roche), 1 µL 10 mM dNTP's, 5 µL each primer (2 µM), 0.4 µL Fast Start Taq, made up to 50 µL with H₂O. PCRs were performed using a Perkin-Elmer Thermal Cycler 9700. The conditions were: denature at 94° C. for 4 min [HOLD], then [CYCLE] denature at 94° C. for 30 seconds, anneal for 30 seconds at 50° C., extend at 72° C. for 60 sec for 30 cycles, then [HOLD] 72° C. for 10 min and then [HOLD] 4° C. PCR amplification of the wild type PDI1 locus resulted in no PCR product, whereas amplification across the deleted PDI1 region resulted in a PCR product 0.65 kbp. PCR analysis identified that all 36 potential pdi1::TRP1 strains tested had the expected pdi1::TRP1 deletion.

Figure 55:
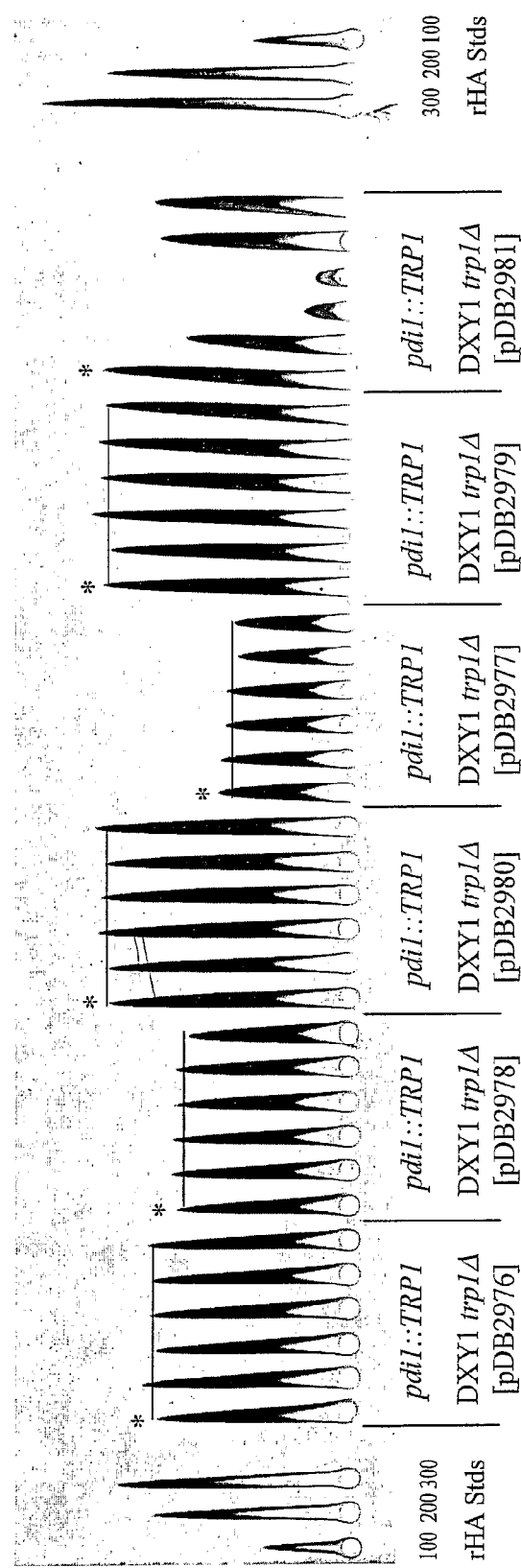
FIG. 55 shows the results of RIE. 10 mL YEPD shale flasks were inoculated with DXY1 trp1Δ [pDB2976], DXY1 trp1Δ [pDB2977], DXY1 trp1Δ [pDB2978], DXY1 trp1Δ [pDB2979], DXY1 trp1Δ [pDB2980] or DXY1 trp1Δ [pDB2981] transformed to tryptophan prototrophy with a 1.41 kb NotI/PstI pdi1::TRP1 disrupting DNA fragment was isolated from pDB3078. Transformants were grown for 4-days at 30° C., 200 rpm. 4 μL culture supernatant loaded per well of a rocket immunoelectrophoresis gel (Weeke, B. 1976. Rocket immunoelectrophoresis. In N. H. Azelsen, J. Kroll, and B. Weeke [eds.], A manual of quantitative immunoelectrophoresis. Methods and applications. Universitetsforlaget, Oslo, Norway). rHA standards concentrations are in μg/mL. 700 μL goat anti-HA (Sigma product A-1151 resuspended in 5 mL water)/50 mL agarose. Precipin was stained with Coomassie blue. Isolates selected for further analysis are indicated (*).

The recombinant albumin titres were compared by rocket immunoelectrophoresis (FIG. 55). Within each group, all six pdi1::TRP1 disruptants of DXY1 trp1Δ [pDB2976], DXY1 trp1Δ [pDB2978], DXY1 trp1Δ [pDB2980], DXY1 trp1Δ [pDB2977] and DXY1 trp1Δ [pDB2979] had very similar rHA productivities. Only the six pdi1::TRP1 disruptants of DXY1 trp1Δ [pDB2981] showed variation in rHA expression titre. The six pdi1::TRP1 disruptants indicated in FIG. 55 were spread onto YEPD agar to isolate single colonies and then re-patched onto BMMD agar.

Figure 56:
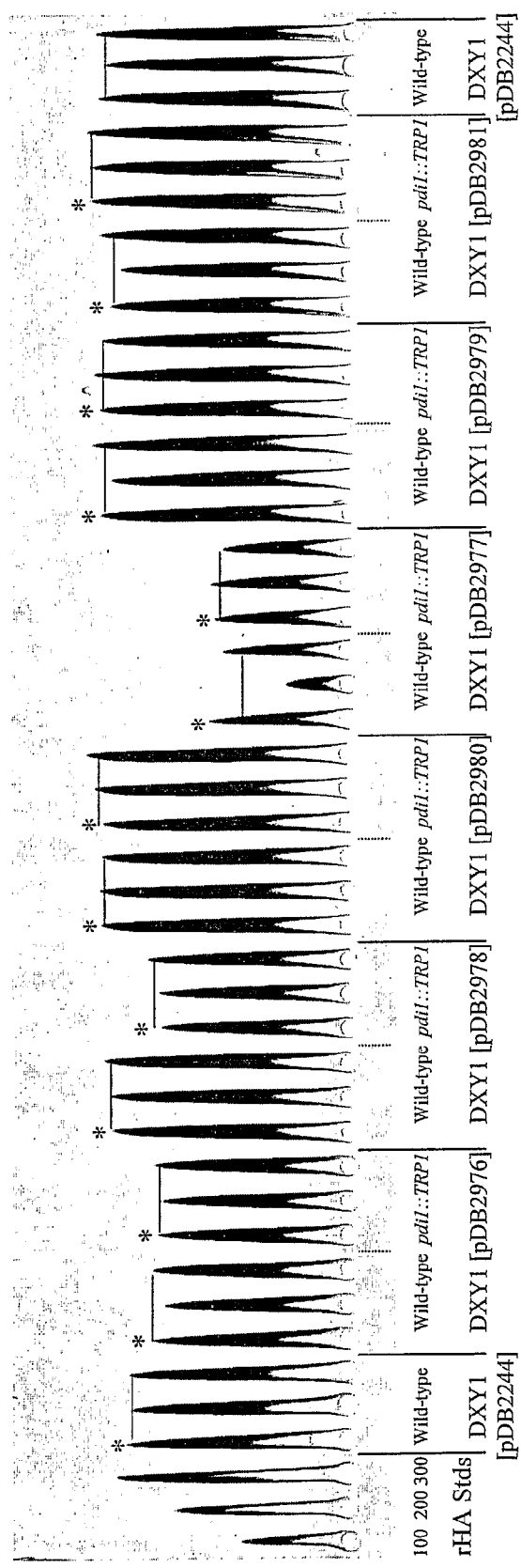
FIG. 56 shows the results of RIE. 10 mL YEPD shake flasks were inoculated with DXY1 [pDB2244], DXY1 [pDB2976], DXY1 trp1Δ pdi1::TRP1 [pDB2976], DXY1 [pDB2978], DXY1 trp1Δ pdi1::TRP1 [pDB2978], DXY1 [pDB2980], DXY1 trp1Δ pdi1::TRP1 [pDB2980], DXY1 [pDB2977], DXY1 trp1Δ pdi1::TRP1 [pDB2977], DXY1 [pDB2979] DXY1 trp1Δ pdi1::TRP1 [pDB2979], DXY1 [pDB2981] and DXY1 trp1Δ pdi1::TRP1 [pDB2981], and were grown for 4-days at 30° C., 200 rpm. 4 μL culture supernatant loaded per well of a rocket immunoelectrophoresis gel. rHA standards concentrations are in μg/mL. 800 μL goat anti-HA (Sigma product A-1151 resuspended in 5 mL water)/50 mL agarose. Precipin was stained with Coomassie blue. Isolates selected for further analysis are indicated (*)

Three single celled isolates of DXY1 trp1Δ pdi1::TRP1 [pDB2976], DXY1 trp1Δ pdi1::TRP1 [pDB2978], DXY1 trp1Δ pdi1::TRP1 [pDB2980], DXY1 trp1Δ pdi1::TRP1 [pDB2977], DXY1 trp1Δ pdi1::TRP1 [pDB2979] and DXY1 trp1Δ pdi1::TRP1 [pDB2981] along with DXY1 [pDB2244], DXY1 [pDB2976], DXY1 [pDB2978], DXY1 [pDB2980], DXY1 [pDB2977], DXY1 [pDB2979] and DXY1 [pDB2981] were inoculated into 10 mL YEPD in 50 mL shale flasks and incubated in an orbital shaker at 30° C., 200 rpm for 4-days. Culture supernatants were harvested and the recombinant albumin titres were compared by rocket immunoelectrophoresis (FIG. 56). The thirteen wild type PDI1 and pdi1::TRP1 disruptants indicated in FIG. 56 were spread onto YEPD agar to isolate single colonies. One hundred single celled colonies from each strain were then re-patched onto BMMD agar or YEPD agar containing a goat anti-HSA antibody to detect expression of recombinant albumin (Sleep et al., 1991, *Bio/Technology*, 9, 183-187) and the Leu+/rHA+, Leu+/rHA−, Leu−/rHA+ or Leu−/rHA− phenotype of each colony scored (Table 9).

TABLE 9

|  | PDI1 | | | | pdi1::TRP1 | | | |
| --- | --- | --- | --- | --- | --- | --- | --- | --- |
|  | Leu+ rHA+ | Leu− rHA+ | Leu+ rHA− | Leu− rHA− | Leu+ rHA+ | Leu− rHA+ | Leu+ rHA− | Leu− rHA− |
| pDB2244 | 100 | 0 | 0 | 0 |  |  |  |  |
| PDB2976 | 7 | 0 | 47 | 46 | 97 | 0 | 3 | 0 |
| pDB2978 | 86 | 0 | 0 | 14 | 100 | 0 | 0 | 0 |
| pDB2980 | 98 | 0 | 0 | 2 | 100 | 0 | 0 | 0 |
| pDB2977 | 0 | 0 | 4 | 96 | 100 | 0 | 0 | 0 |
| pDB2979 | 69 | 0 | 6 | 25 | 100 | 0 | 0 | 0 |
| pDB2981 | 85 | 0 | 0 | 15 | 92 | 0 | 0 | 8 |

These data indicate plasmid retention is increased when the PDI1 gene is used as a selectable marker on a plasmid in a host strain having no chromosomally encoded PDI, even in non-selective media such as this rich medium. These show that an "essential" chaperone (e.g. PDI1 or PSE1), or any other any "essential" gene product (e.g. PTK1 or FBA1) which, when deleted or inactivated, does not result in an auxotrophic (biosynthetic) requirement, can be used as a selectable marker on a plasmid in a host cell that, in the absence of the plasmid, is unable to produce that gene product, to achieve increased plasmid stability without the disadvantage of requiring the cell to be cultured under specific selective conditions. By "auxotrophic (biosynthetic) requirement" we include a deficiency, which can be complemented by additions or modifications to the growth medium. Therefore, "essential marker genes" in the context of the present invention are those that, when deleted or inactivated in a host cell, result in a deficiency which can not be complemented by additions or modifications to the growth medium.

Example 10

The Construction of Expression Vectors Containing Various PDI1 Genes and the Expression Cassettes for Various Heterologous Proteins on the Same 2 µm-Like Plasmid PCR Amplification and Cloning of PDI1 Genes into YIplac211

Figure 57:
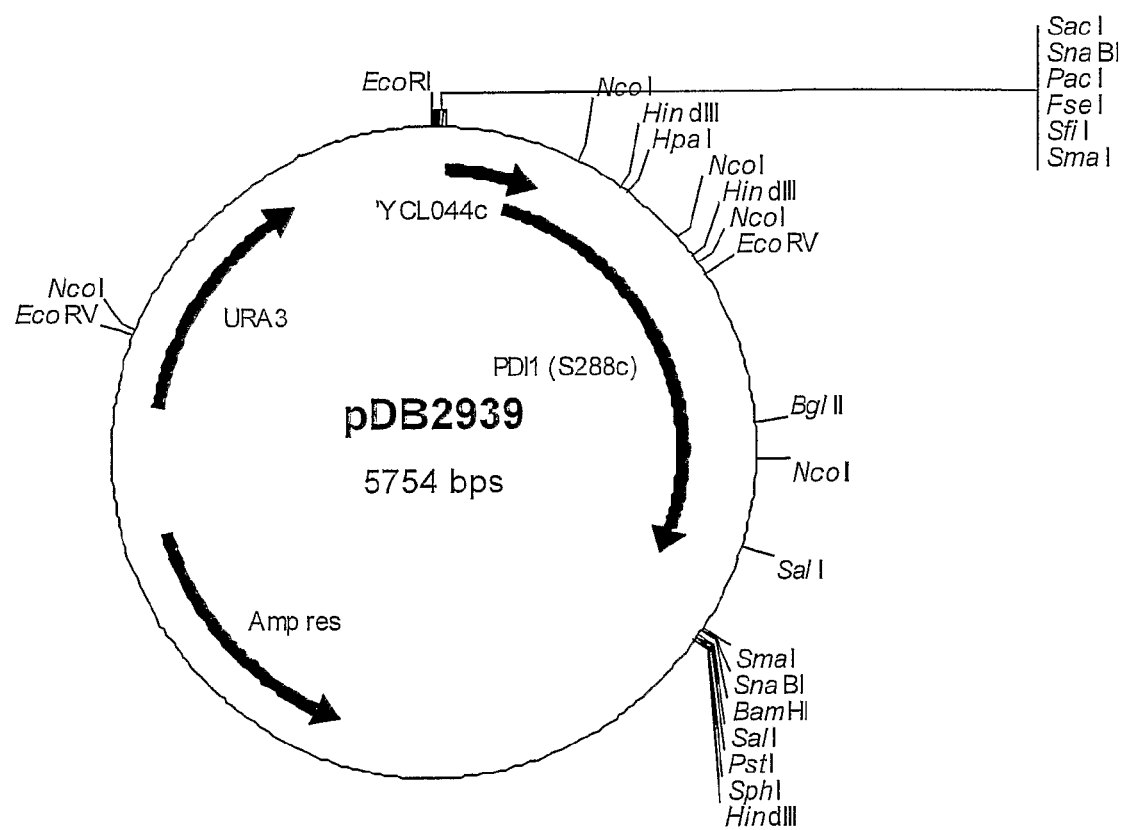

The PDI1 genes from *S. cerevisiae* S288c and *S. cerevisiae* SKQ2n were amplified by PCR to produce DNA fragments with different lengths of the 5'-untranslated region containing the promoter sequence. PCR primers were designed to permit cloning of the PCR products into the EcoRI and BamHI sites of YIplac211 (Gietz & Sugino, 1988, *Gene*, 74, 527-534). Additional restriction endonuclease sites were also incorporated into PCR primers to facilitate subsequent cloning. Table 10 describes the plasmids constructed and Table 11 gives the PCR primer sequences used to amplify the PDI1 genes. Differences in the PDI1 promoter length within these YIplac211-based plasmids are described in Table 10.

pDB2939 (FIG. 57) was produced by PCR amplification of the PDI1 gene from *S. cerevisiae* S288c genomic DNA with oligonucleotide primers DS248 and DS250 (Table 11), followed by digesting the PCR product with EcoRI and BamHI and cloning the approximately 1.98-kb fragment into YIplac211 (Gietz & Sugino, 1988, *Gene,* 74, 527-534), that had been cut with EcoRI and BamHI. DNA sequencing of pDB2939 identified a missing 'G' from within the DS248 sequence, which is marked in bold in Table 5. Oligonucleotide primers used for sequencing the PDI1 gene are listed in Table 6, and were designed from the published S288c PDI1 gene sequence (PDI1/YCL043C on chromosome III from coordinates 50221 to 48653 plus 1000 base pairs of upstream sequence and 1000 base pairs of downstream sequence. (http://www.yeastgenome.org/ Genebank Accession number NC001135).

TABLE 10

YIplac211-based Plasmids Containing PDI1 Genes

| Plasmid | Base | PDI1 Gene | | | PCR Primers |
| --- | --- | --- | --- | --- | --- |
| | | Source | Promoter | Terminator | |
| pDB2939 | YIplac211 | S288c | Long (~210-bp) | → Bsu36I | DS248 + DS250 |
| pDB2941 | YIplac211 | S288c | Medium (~140-bp) | → Bsu36I | DS251 + DS250 |
| pDB2942 | YIplac211 | S288c | Short (~80-bp) | → Bsu36I | DS252 + DS250 |
| pDB2943 | YIplac211 | SKQ2n | Long (~210-bp) | → Bsu36I | DS248 + DS250 |
| pDB2963 | YIplac211 | SKQ2n | Medium (~140-bp) | → Bsu36I | DS267 + DS250 |
| pDB2945 | YIplac211 | SKQ2n | Short (~80-bp) | → Bsu36I | DS252 + DS250 |

TABLE 11

Oligonucleotide Primers for PCR Amplification of *S. cerevisiae* PDI1 Genes

| Primer | Sequence |
| --- | --- |
| DS248 (SEQ ID NO: 65) | 5'-GTCAGAATTCGAGCTCTACGTATTAATTAAGGCCGGCCAGGCCCGGGCTAGTCTCTTTTTCCAATTTGCCACCGTGTAGCATTTTGTTGT3' |
| DS249 (SEQ ID NO: 66) | 5'-GTCAGGATCCTACGTACCCGGGGATATCATTATCATCTTTGTCGTGGTCATCTTGTGTG3' |
| DS250 (SEQ ID NO: 67) | 5'-GTCAGGATCCTACGTACCCGGGTAAGGCGTTCGTGCAGTGTGACGAATATAGCG-3' |
| DS251 (SEQ ID NO: 68) | 5'-GTCAGAATTCGAGCTCTACGTATTAATTAAGGCCGGCCAGGCCCGGGCCCGTATGGACATACATATATATATATATATATATATATTTTTGTTACGCG-3' |
| DS252 (SEQ ID NO: 69) | 5'-GTCAGAATTCGAGCTCTACGTATTAATTAAGGCCGGCCAGGCCCGGGCTTGTTGCAAGCAGCATGTCTAATTGGTAATTTTAAAGCTGCC-3' |
| sDS267 (SEQ ID NO: 70) | 5'-GTCAGAATTCGAGCTCTACGTATTAATTAAGGCCGGCCAGGCCCGGGCCCGTATGGACATACATATATATATATATATATATATATATATATTTTGTTACGCG-3' |

TABLE 12

Oligonucleotide Primers for DNA Sequencing *S. cerevisiae* PDI1 Genes

| Primer | Sequence |
| --- | --- |
| DS253 (SEQ ID NO: 71) | 5'-CCTCCCTGCTCCTCGCC-3' |
| DS254 (SEQ ID NO: 72) | 5'-CTGTAAGAACATGGCTCC-3' |
| DS255 (SEQ ID NO: 73) | 5'-CTCGATCGATTACGAGGG-3' |
| DS256 (SEQ ID NO: 74) | 5'-AAGAAAGCCGATATCGC-3' |

TABLE 12-continued

Oligonucleotide Primers for DNA Sequencing *S. cerevisiae* PDI1 Genes

| Primer | Sequence |
| --- | --- |
| DS257 (SEQ ID NO: 75) | 5'CAACTCTCTGAAGAGGCG-3' |
| DS258 (SEQ ID NO: 76) | 5'-CAACGCCACATCCGACG-3' |
| DS259 (SEQ ID NO: 77) | 5'-GTAATTCTGATCACTTTGG-3' |
| DS260 (SEQ ID NO: 78) | 5'-GCACTTATTATTACTACGTGG-3' |
| DS261 (SEQ ID NO: 79) | 5'-GTTTTCCTTGATGAAGTCG-3' |
| DS262 (SEQ ID NO: 80) | 5'-GTGACCACACCATGGGGC-3' |
| DS263 (SEQ ID NO: 81) | 5'-GTTGCCGGCGTGTCTGCC-3' |
| DS264 (SEQ ID NO: 82) | 5'-TTGAAATCATCGTCTGCG-3' |
| DS265 (SEQ ID NO: 83) | 5'-CGGCAGTTCTAGGTCCC-3' |
| DS266 (SEQ ID NO: 84) | 5'-CCACAGCCTCTTGTTGGG-3' |
| M13/pUC Primer (−40) (SEQ ID NO: 85) | 5'-GTTTTCCCAGTCACGAC-3' |

Figure 58:
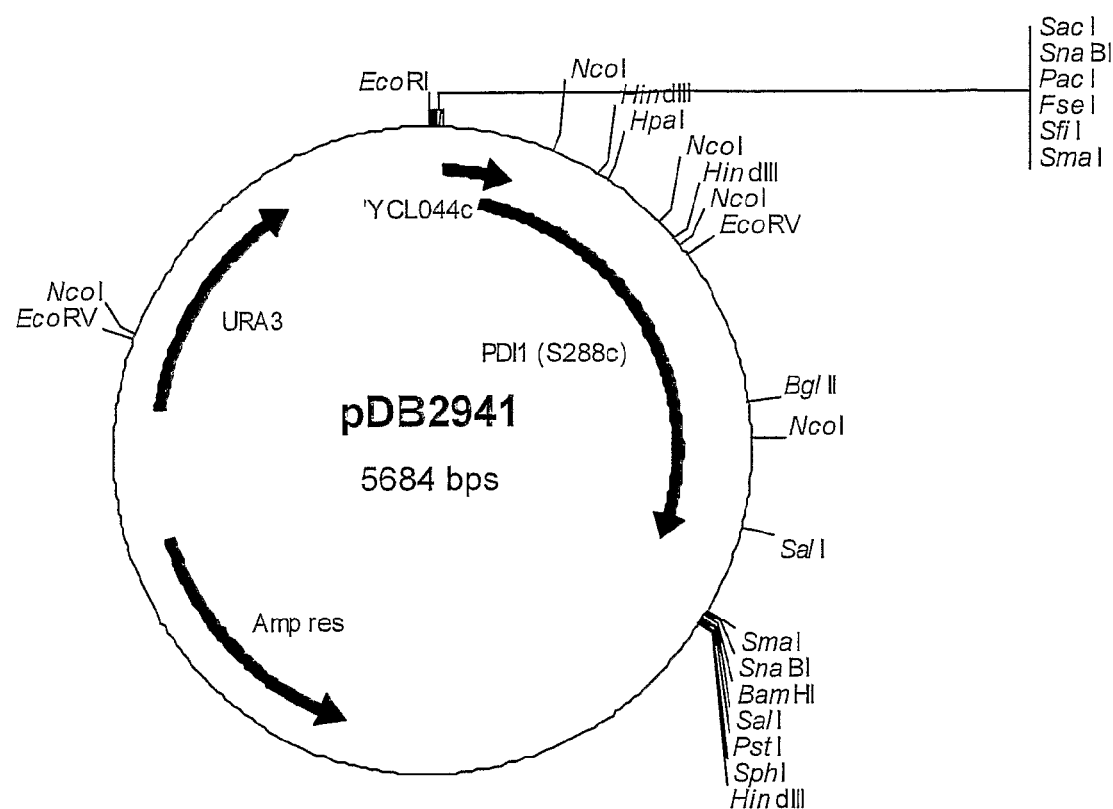
Figure 59:
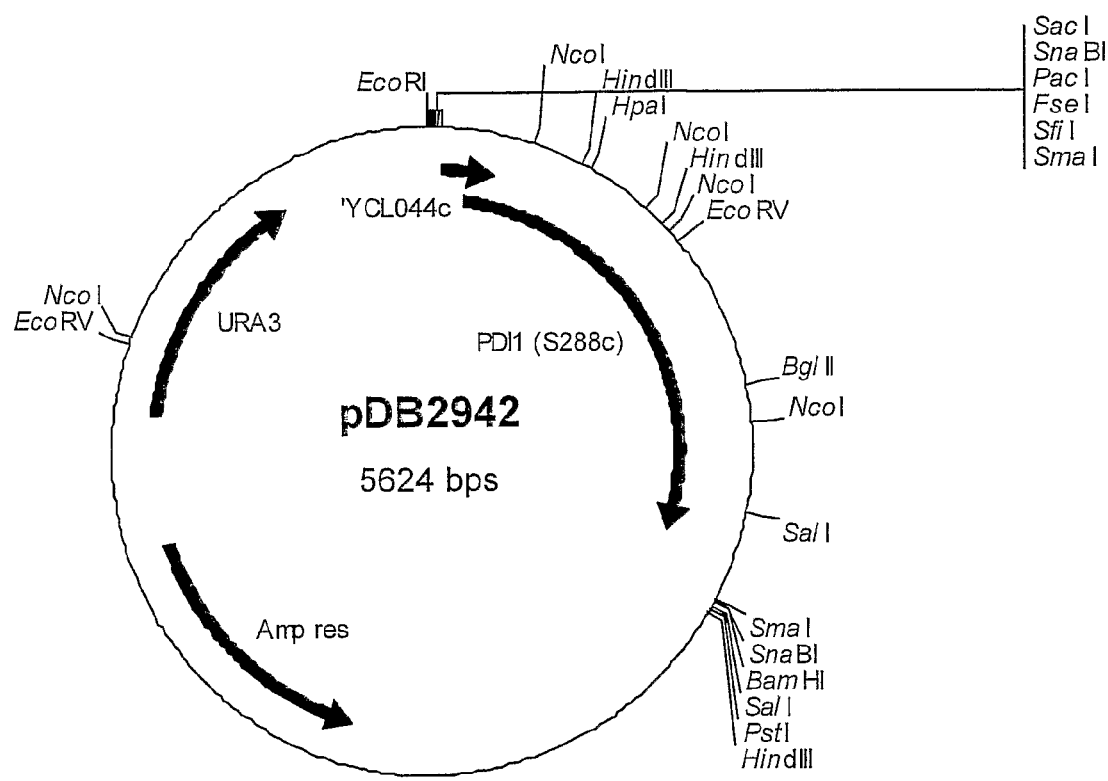

Plasmids pDB2941 (FIG. 58) and pDB2942 (FIG. 59) were constructed similarly using the PCR primers described in Tables 10 and 11, and by cloning the approximately 1.90-kb and 1.85-kb EcoRI-BamHI fragments, respectively, into YIplac211. The correct DNA sequences were confirmed for the PDI1 genes in pDB2941 and pDB2942.

Figure 60:
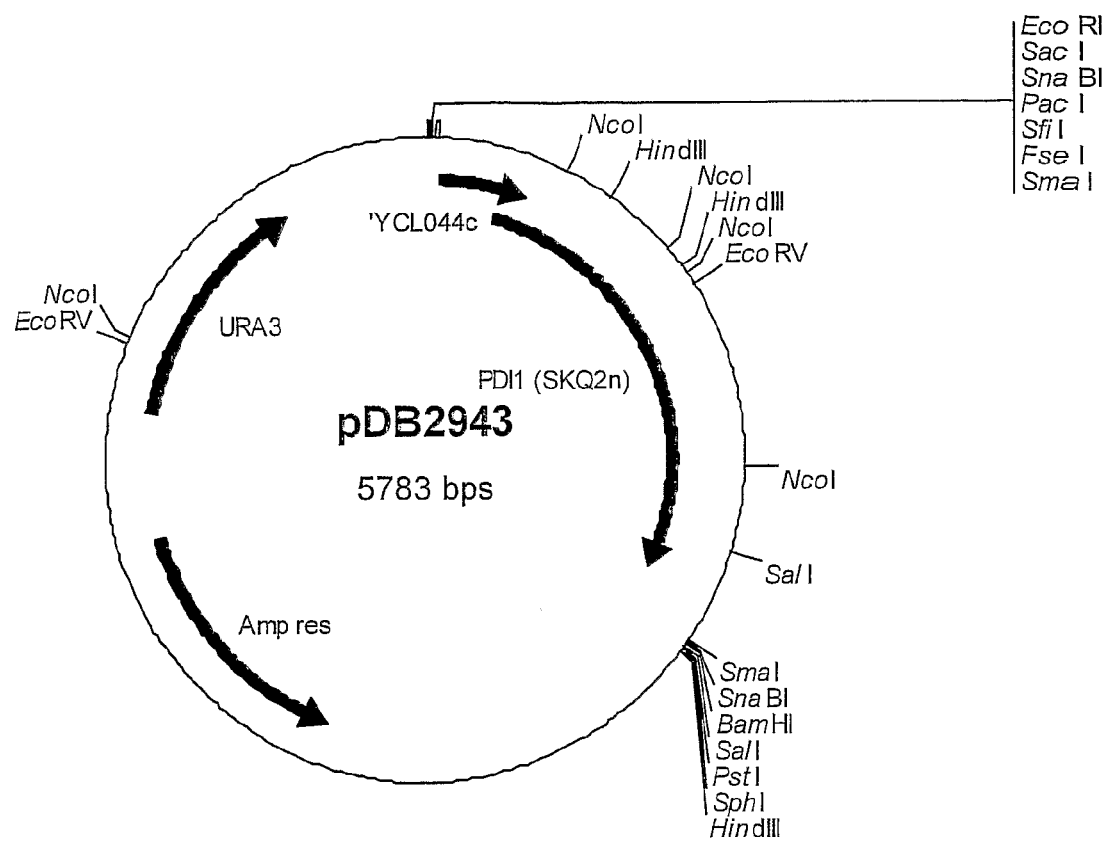

The *S. cerevisiae* SKQ2n PDI1 gene sequence was PCR amplified from plasmid DNA containing the PDI1 gene from pMA3a:C7 (U.S. Pat. No. 6,291,205), also known as Clone C7 (Crouzet & Tuite, 1987, supra; Farquhar et al., 1991, supra). The SKQ2n PDI1 gene was amplified using oligonucleotide primers DS248 and DS250 (Tables 10 and 11). The approximately 2.01-kb PCR product was digested with EcoRI and BamHI and ligated into YIplac211 (Gietz & Sugino, 1988, *Gene,* 74, 527-534) that has been cut with EcoRI and BamHI, to produce plasmid pDB2943 (FIG. 60). The 5' end of the SKQ2n PDI1 sequence is analogous to a blunt-ended SpeI-site extended to include the EcoRI, SacI, SnaBI, PacI, FseI, SfiI and SmaI sites, the 3' end extends up to a site analogous to a blunt-ended Bsu36I site, extended to include a SmaI, SnaBI and BamHI sites. The PDI1 promoter length is approximately 210 bp. The entire DNA sequence was determined for the PDI1 fragment using oligonucleotide primers given in Table 12. This confirmed the presence of a coding sequence for the PDI protein of *S. cerevisiae* strain SKQ2n (NCBI accession number CAA38402), but with a serine residue at position 114 (not an arginine residue as previously published). Similarly, in the same way as in the *S. cerevisiae* S288c sequence in pDB2939, pDB2943 also had a missing 'G' from within the DS248 sequence, which is marked in bold in Table 5.

Figure 61:
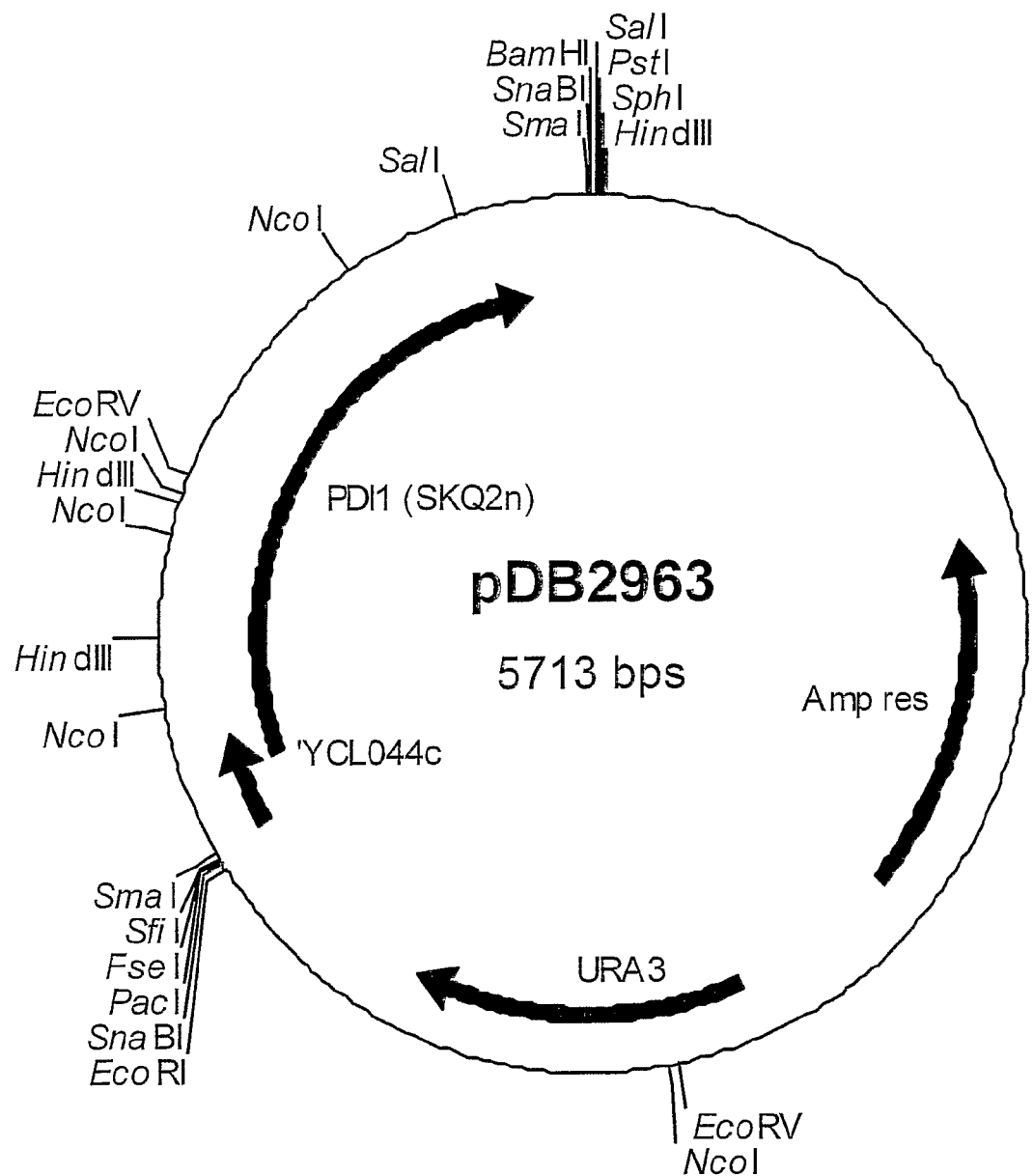
Figure 62:
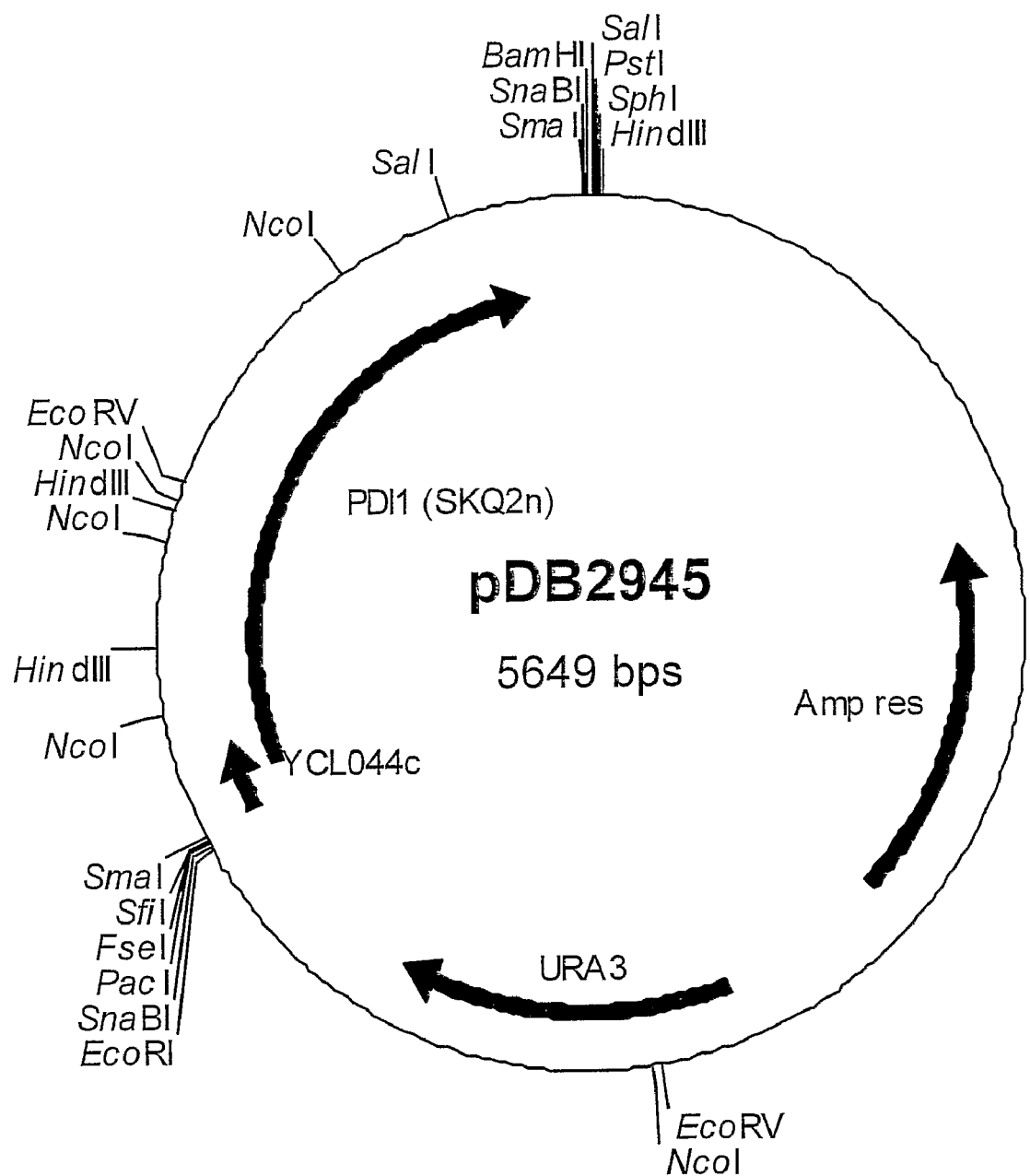

Plasmids pDB2963 (FIG. 61) and pDB2945 (FIG. 62) were constructed similarly using the PCR primers described in Tables 10 and 11, and by cloning the approximately 1.94-kb and 1.87-kb EcoRI-BamHI fragments, respectively, into YIplac211. The expected DNA sequences were confirmed for the PDI1 genes in pDB2963 and pDB2945, with a serine codon at the position of amino acid 114.

The Construction of pSAC35-Based rHA Expression Plasmids with Different PDI1 Genes Inserted at the XcmI-Site After REP2:

pSAC35-based plasmids were constructed for the co-expression of rHA with different PDI1 genes (Table 13).

TABLE 13 pSAC35-based plasmids for co-expression of rHA with different PDI1 genes

| Plasmid | Plasmid Base | PDI1 Gene at XcmI-site after REP2 | | | | Heterologous Protein Expression Cassette |
|---|---|---|---|---|---|---|
| | | Source | Promoter | Terminator | Orientation | (at NotI-site) |
| pDB2982 | pSAC35 | SKQ2n | Long | → Bsu36I | A | rHA |
| pDB2983 | pSAC35 | SKQ2n | Long | → Bsu36I | B | rHA |
| pDB2984 | pSAC35 | SKQ2n | Medium | → Bsu36I | A | rHA |
| pDB2985 | pSAC35 | SKQ2n | Medium | → Bsu36I | B | rHA |
| pDB2986 | pSAC35 | SKQ2n | Short | → Bsu36I | A | rHA |
| pDB2987 | pSAC35 | SKQ2n | Short | → Bsu36I | B | rHA |
| pDB2976 | pSAC35 | S288c | Long | → Bsu36I | A | rHA |
| pDB2977 | pSAC35 | S288c | Long | → Bsu36I | B | rHA |
| pDB2978 | pSAC35 | S288c | Medium | → Bsu36I | A | rHA |
| pDB2979 | pSAC35 | S288c | Medium | → Bsu36I | B | rHA |
| pDB2980 | pSAC35 | S288c | Short | → Bsu36I | A | rHA |
| pDB2981 | pSAC35 | S288c | Short | → Bsu36I | B | rHA |

Figure 63:
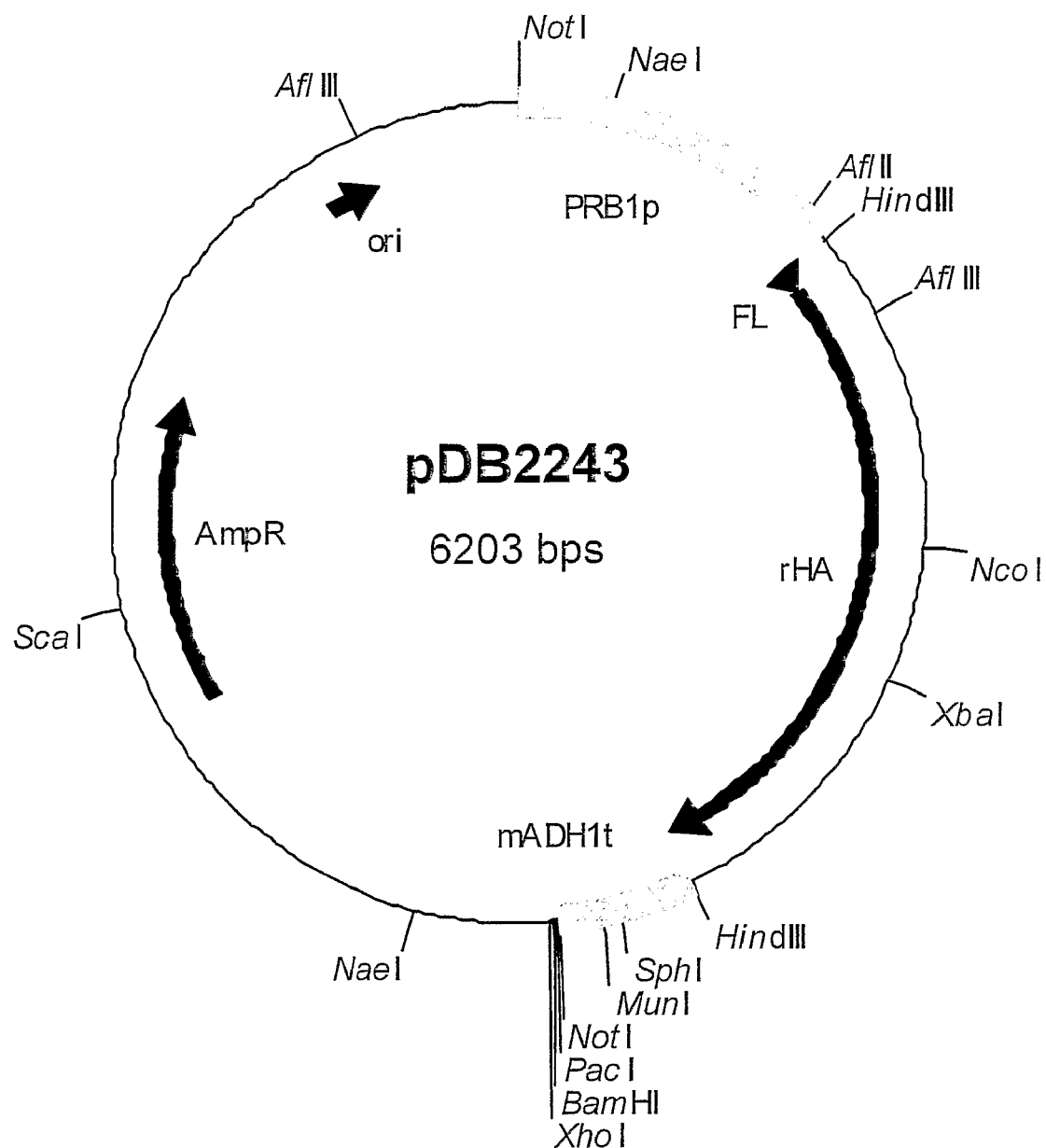
Figure 64:
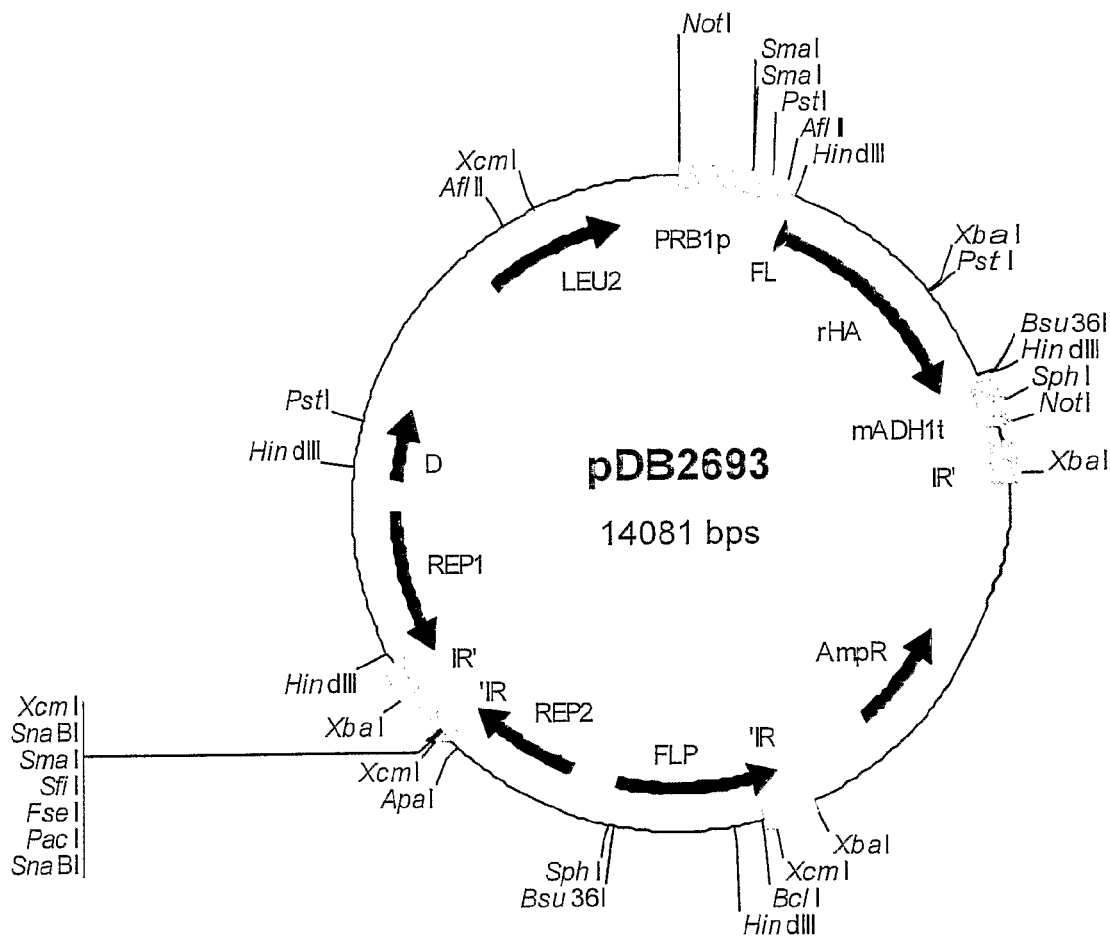
Figure 65:
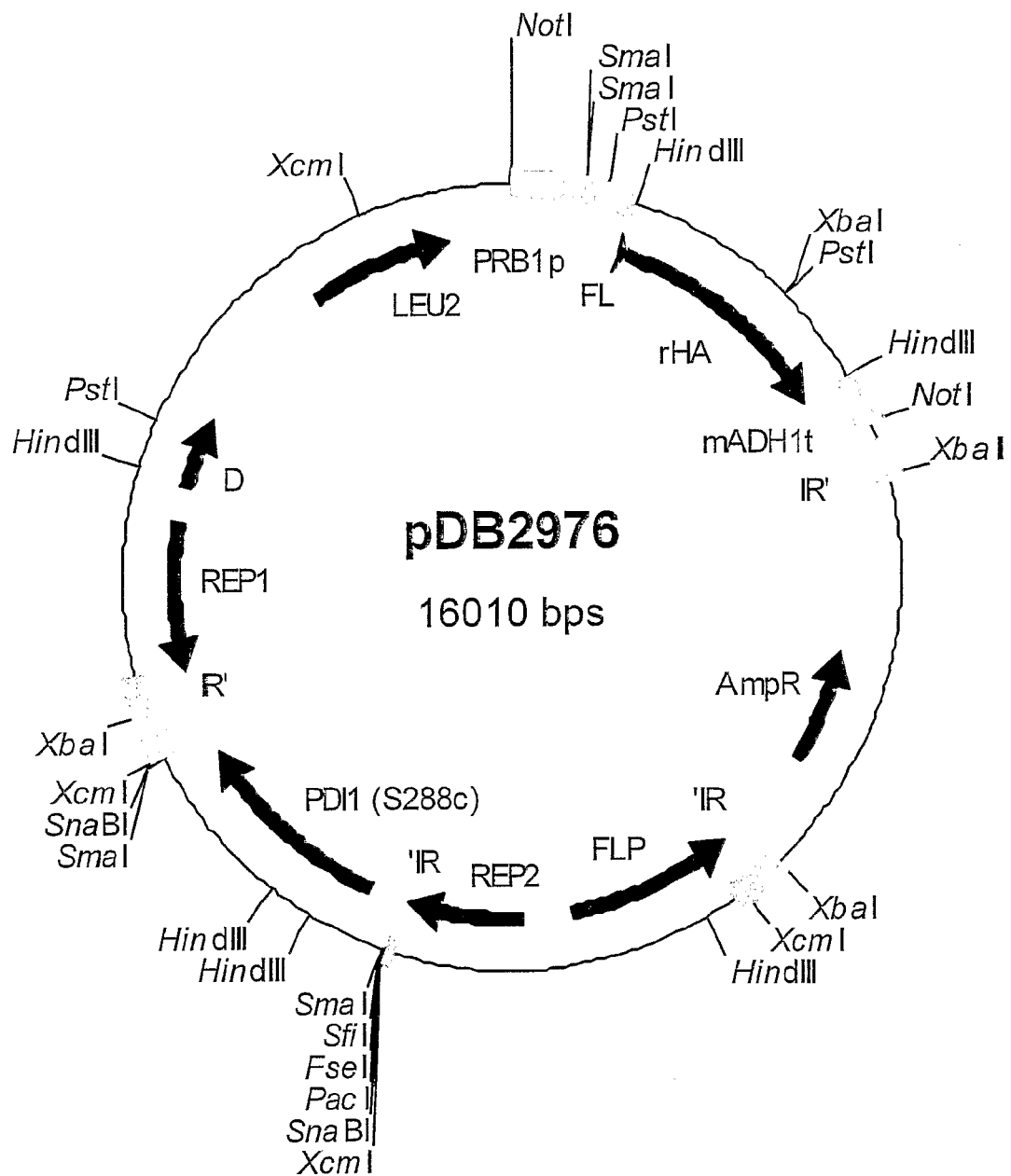
Figure 66:
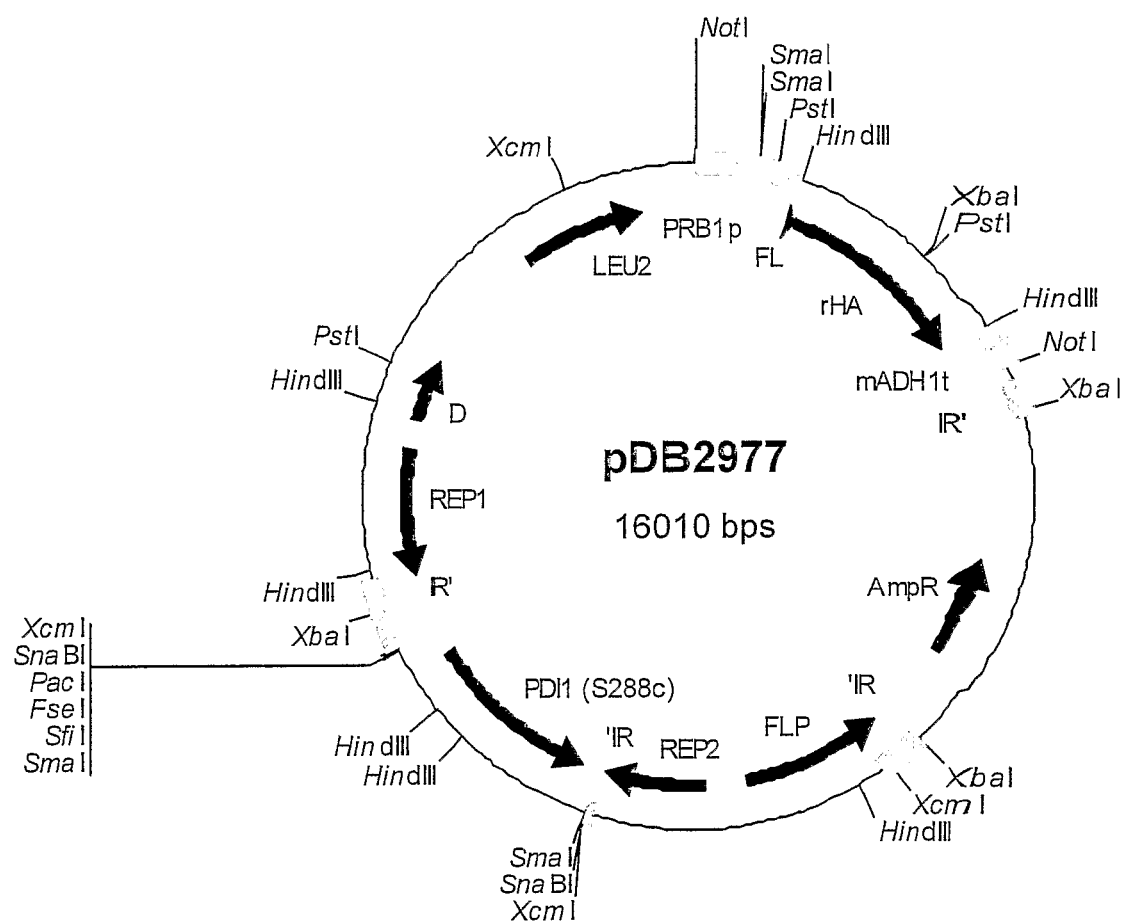
Figure 67:
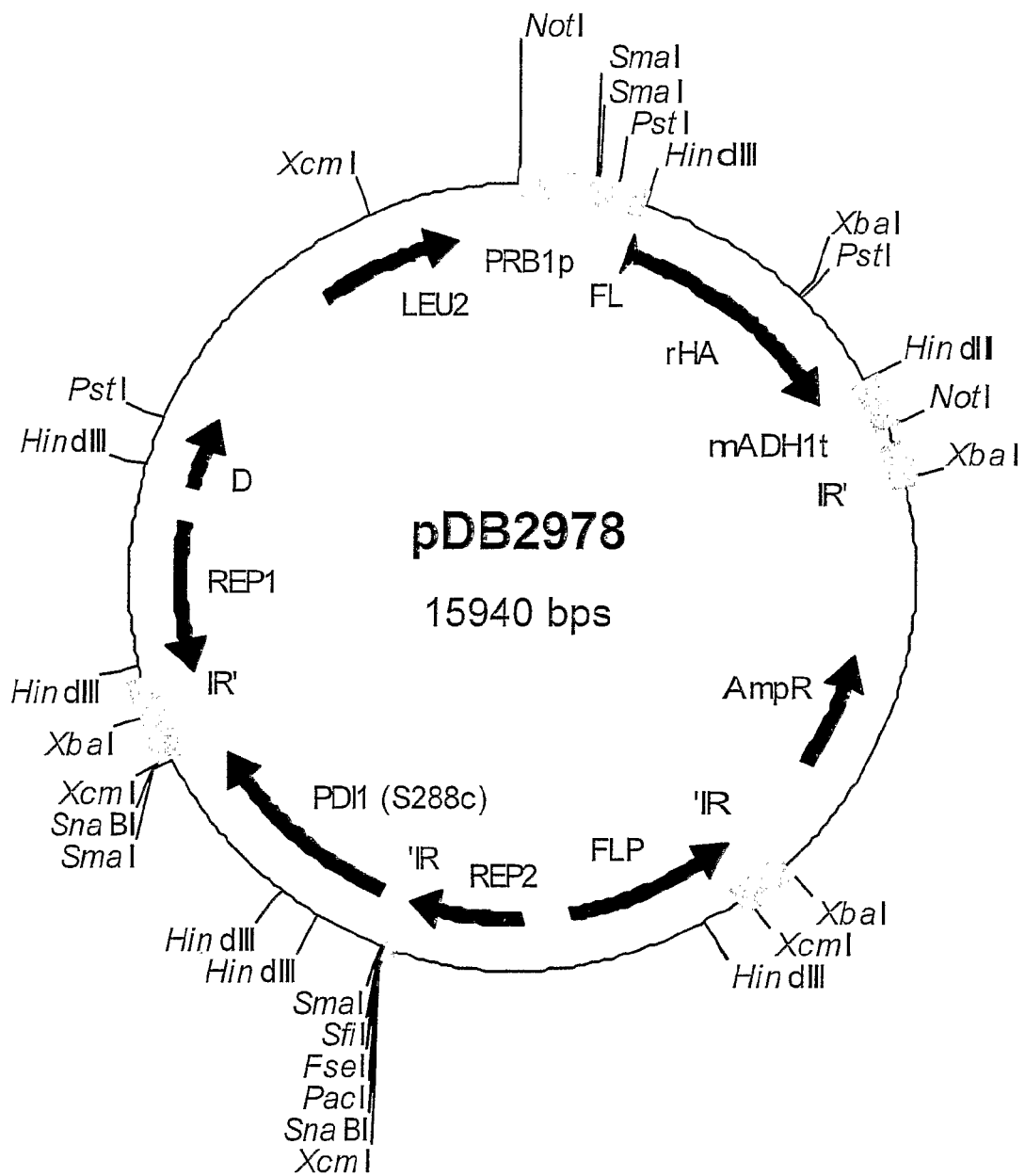
Figure 68:
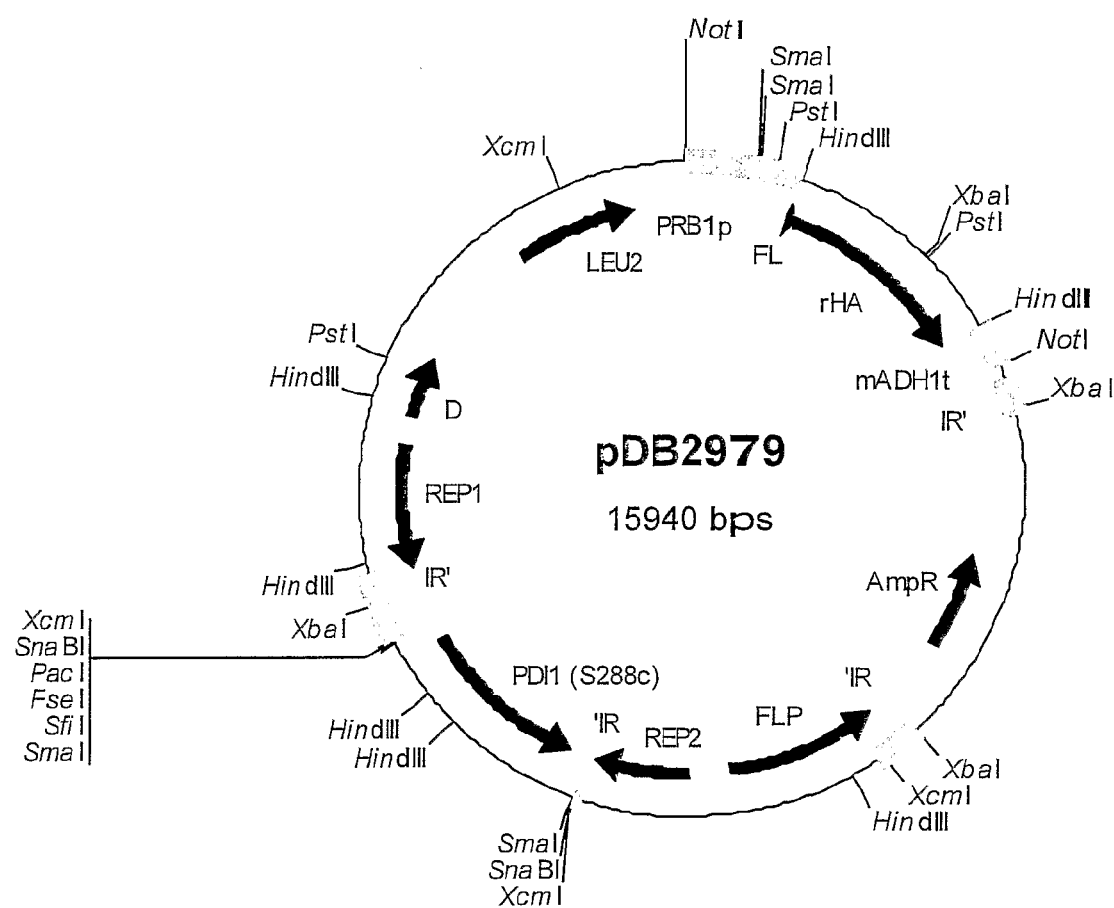
Figure 69:
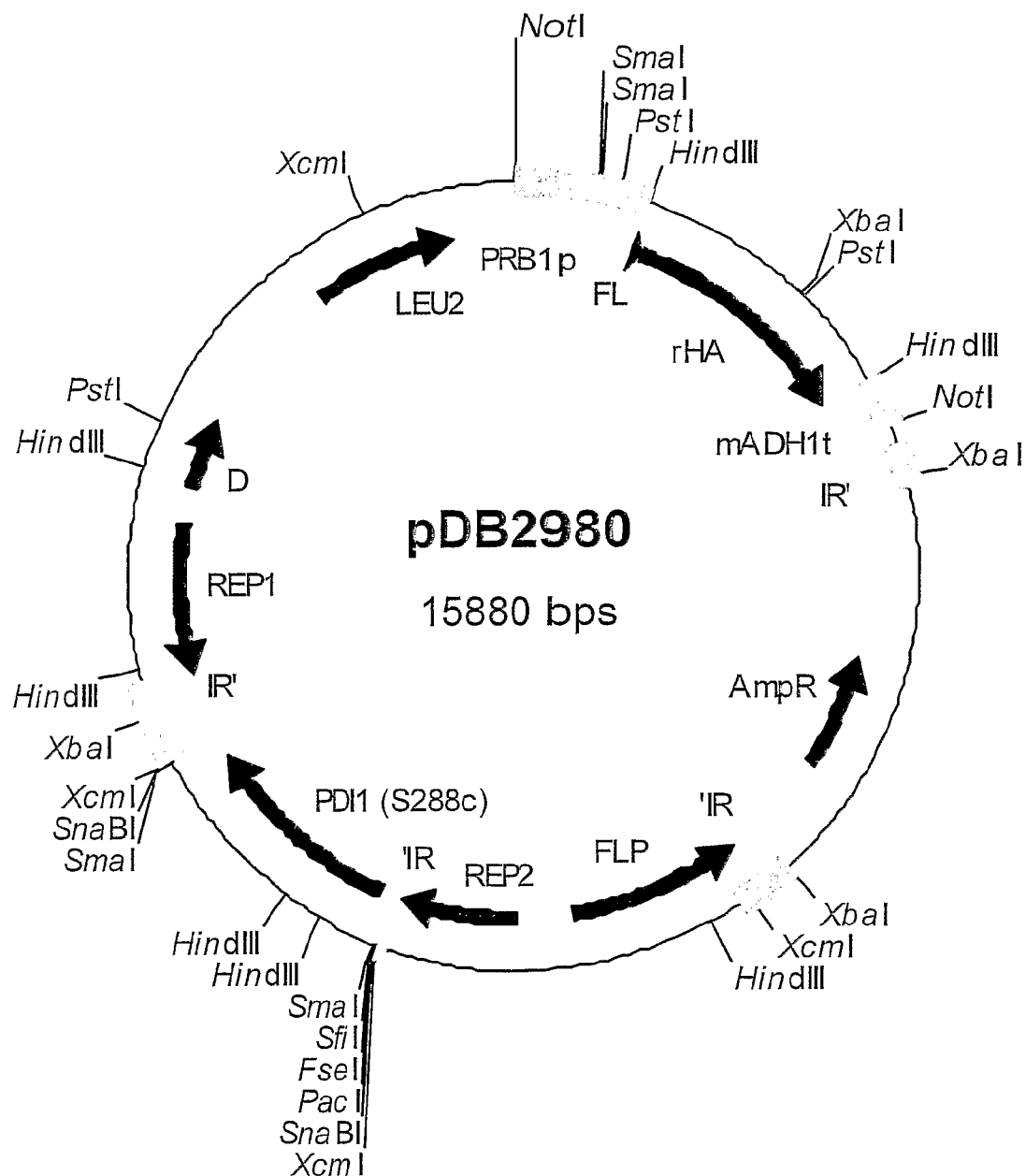
Figure 70:
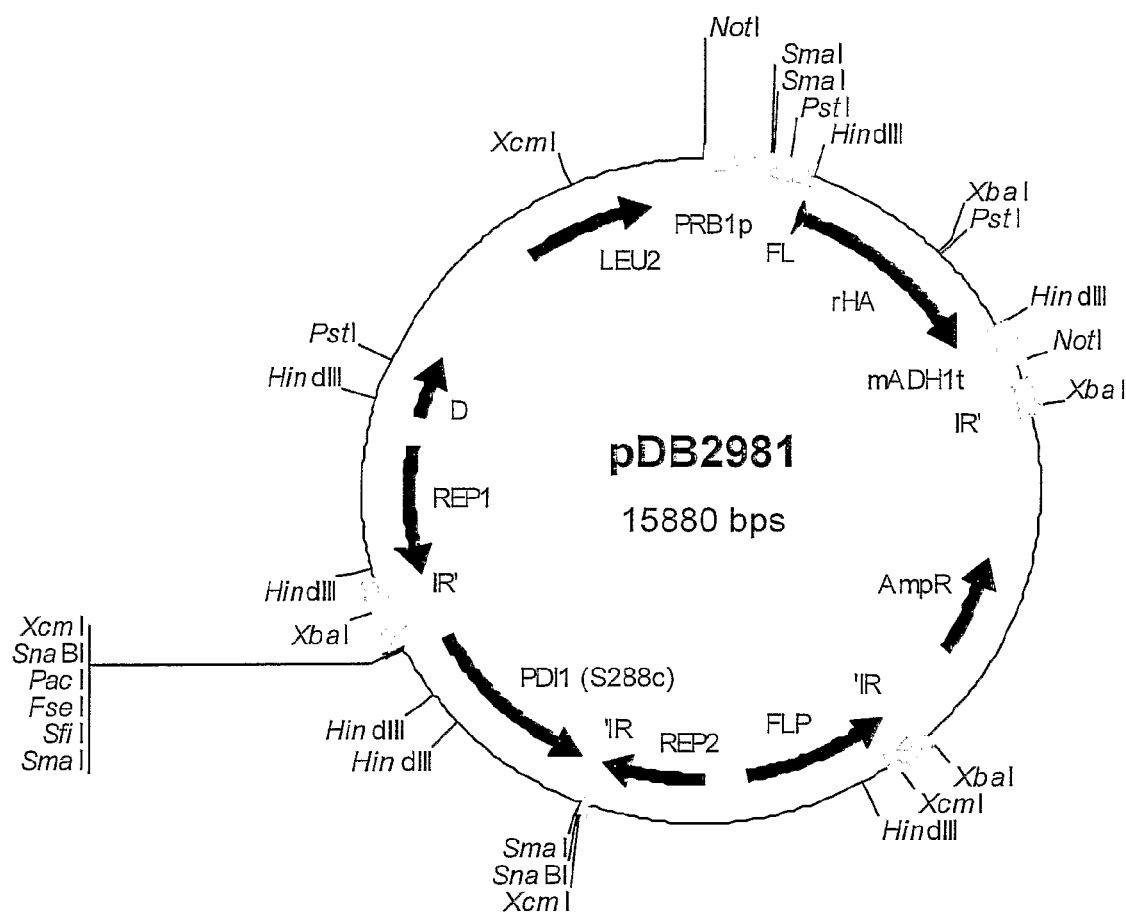
Figure 71:
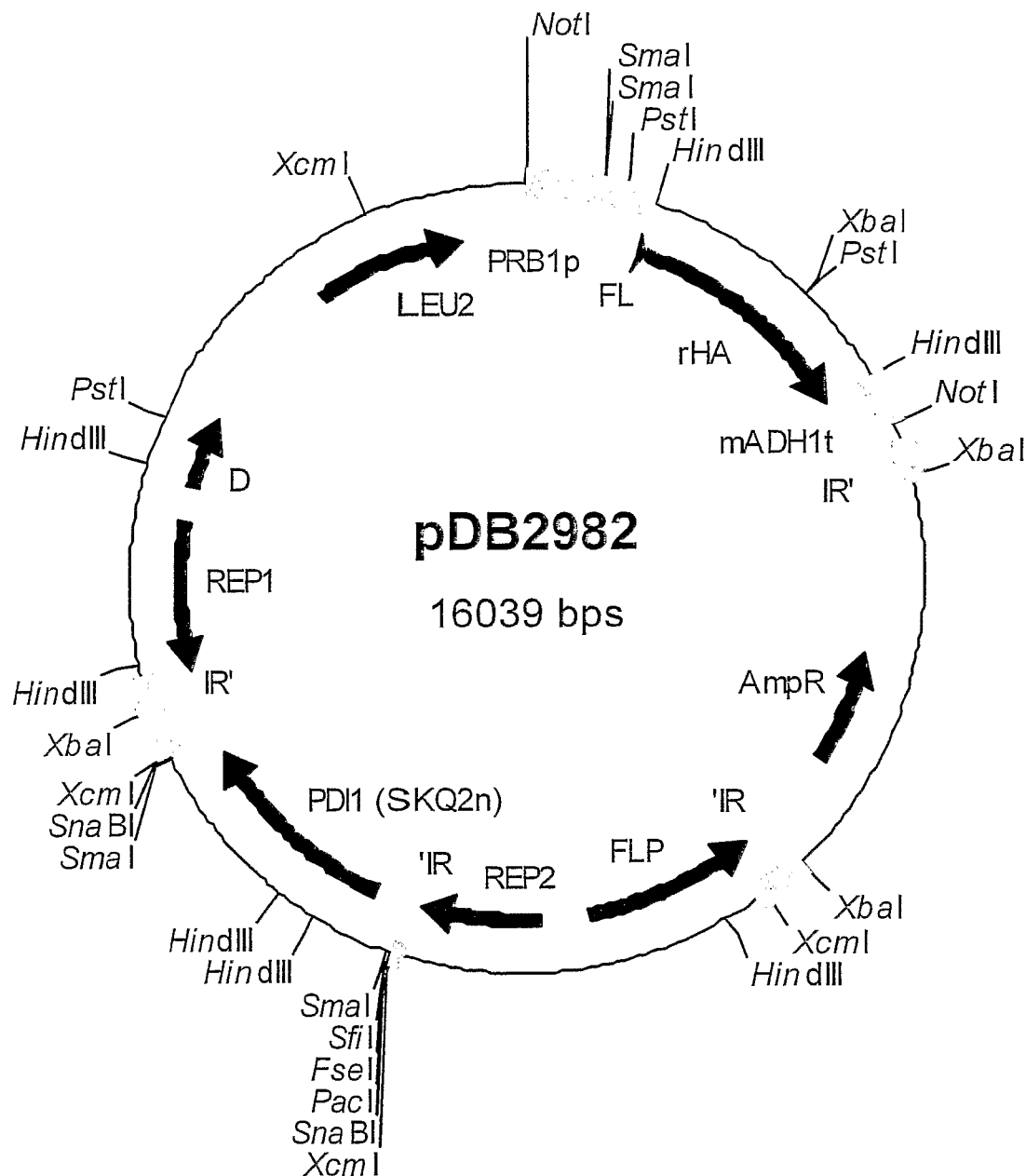
Figure 72:
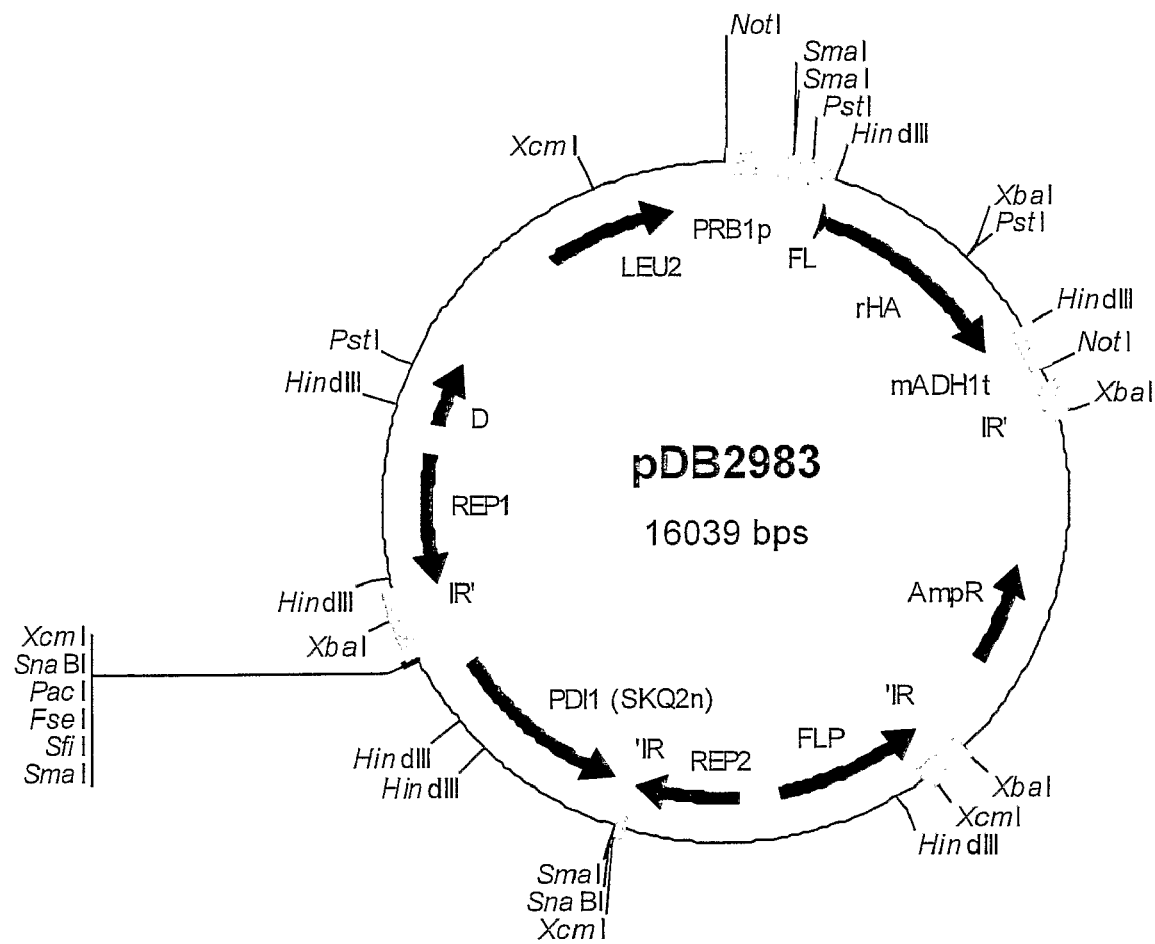
Figure 73:
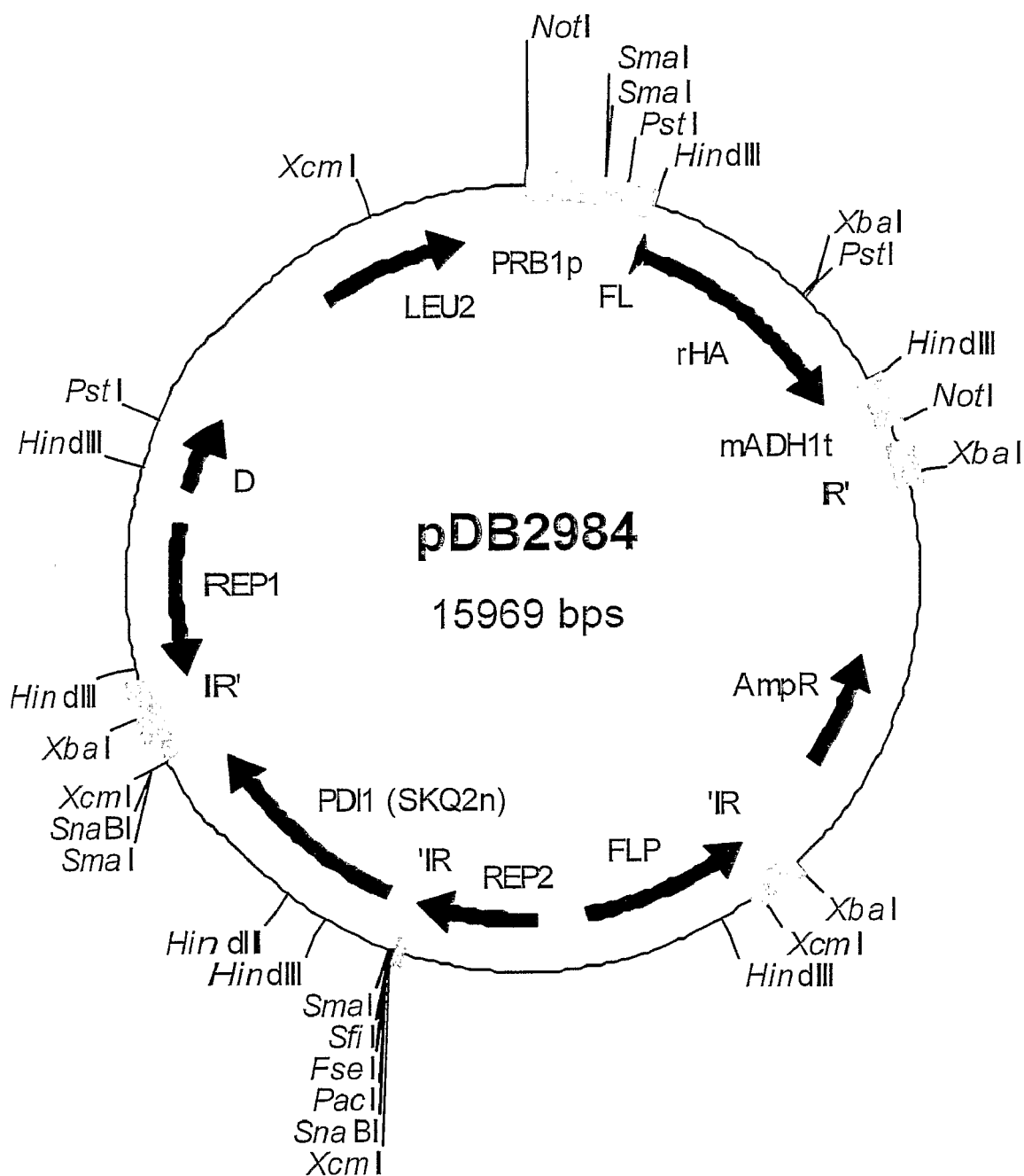
Figure 74:
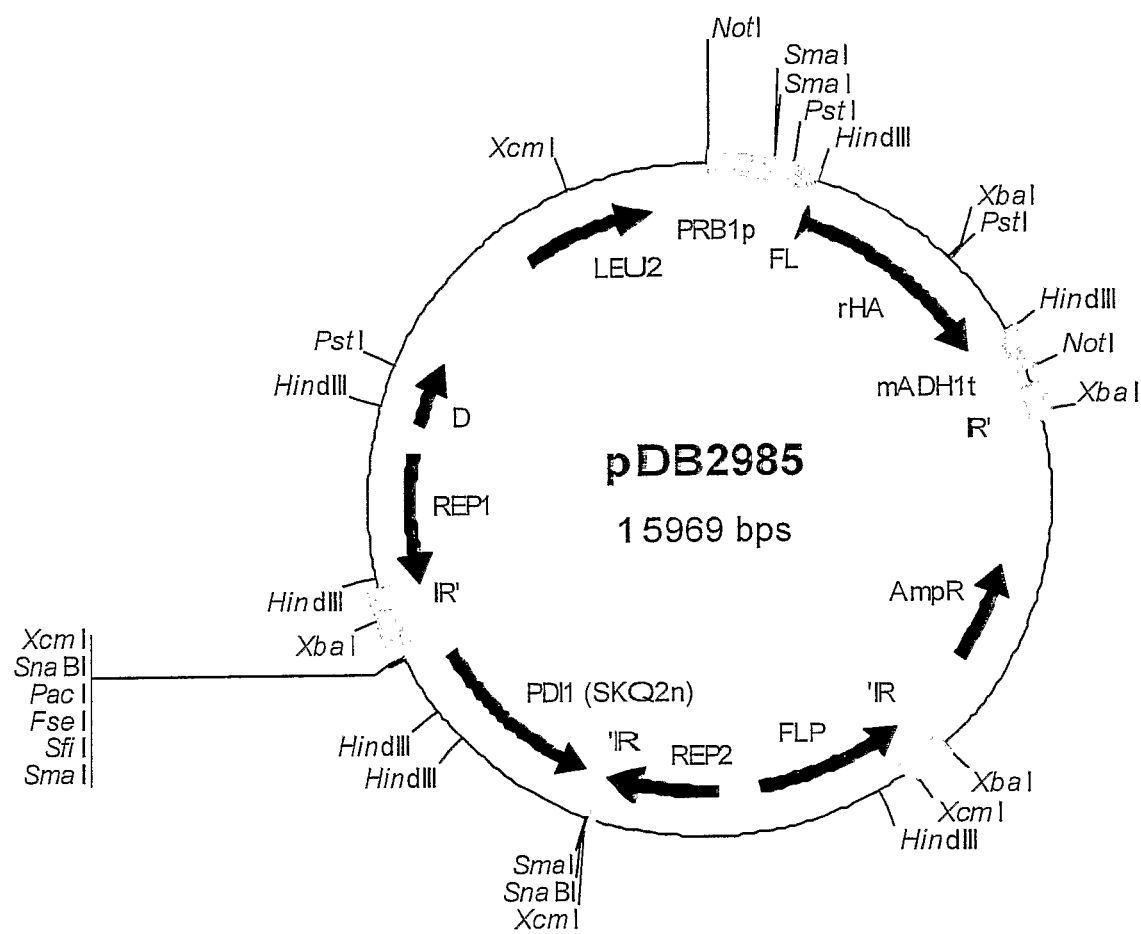
Figure 75:
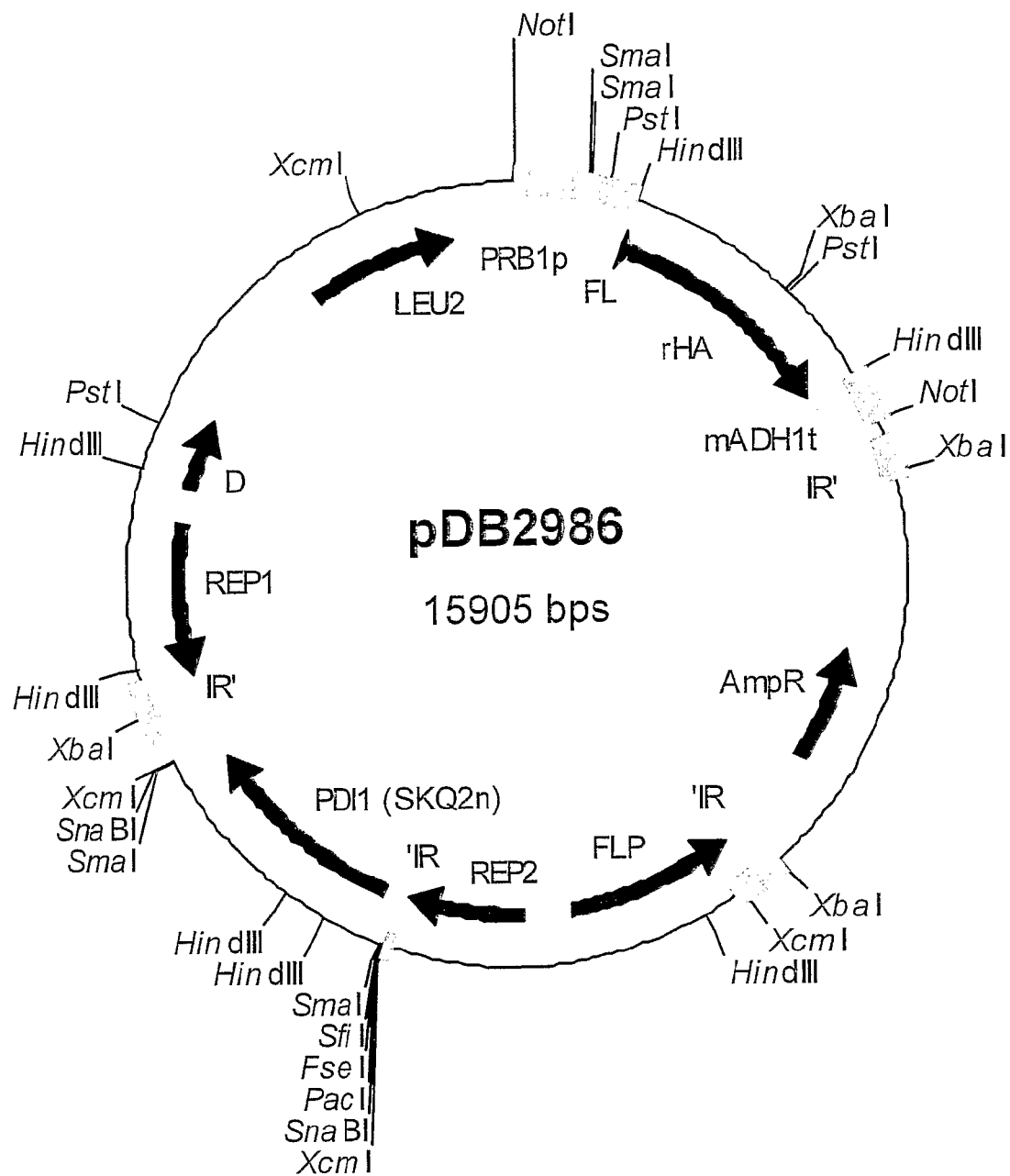
Figure 76:
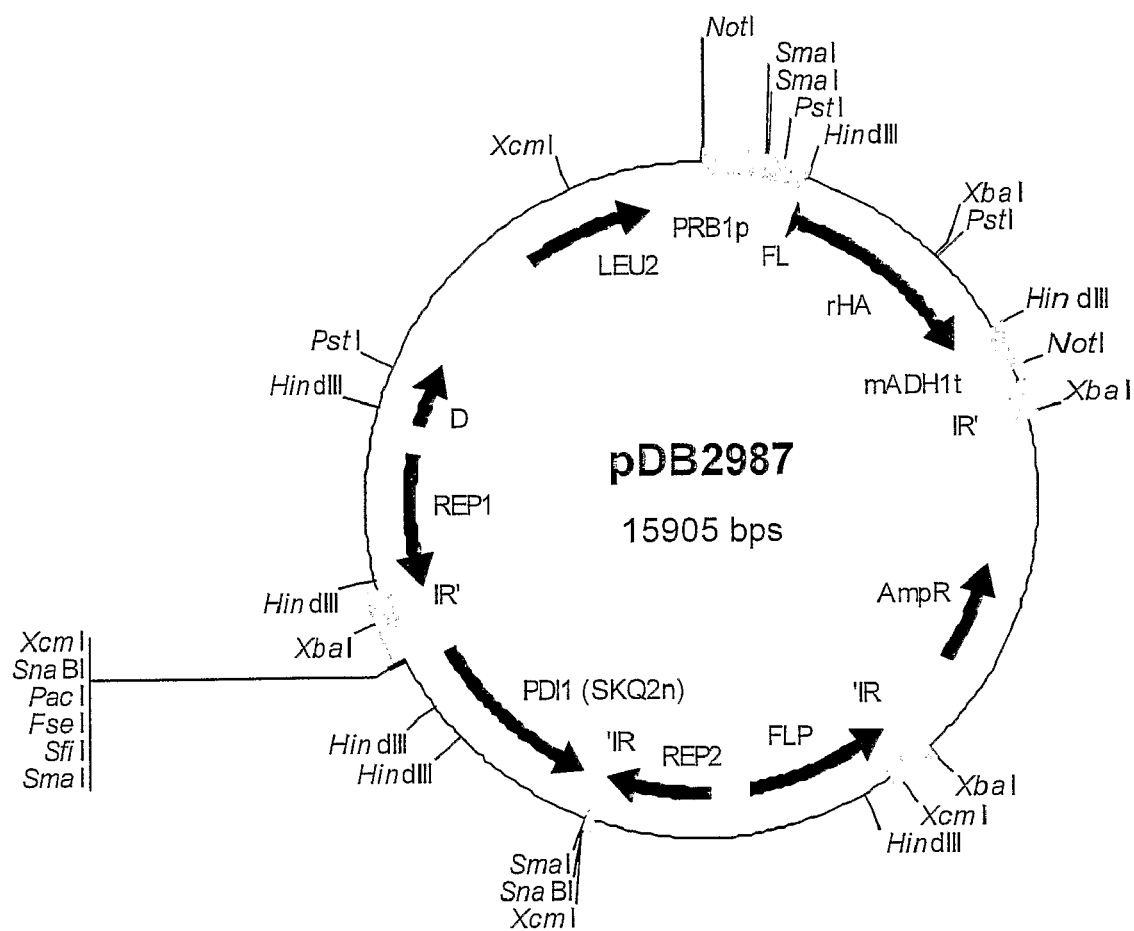

The rHA expression cassette from pDB2243 (FIG. 63, as described in WO 00/44772) was first isolated on a 2,992-bp NotI fragment, which subsequently was cloned into the NotI-site of pDB2688 (FIG. 4) to produce pDB2693 (FIG. 64). pDB2693 was digested with SnaBI, treated with calf intestinal alkaline phosphatase, and ligated with SnaBI fragments containing the PDI1 genes from pDB2943, pDB2963, pDB2945, pDB2939, pDB2941 and pDB2942. This produced plasmids pDB2976 to pDB2987 (FIGS. 65 to 76). PDI1 transcribed in the same orientation as REP2 was designated "orientation A", whereas PDI transcribed in opposite orientation to REP2 was designated "orientation B" (Table 13).

The invention claimed is:

1. A 2 μm-family plasmid comprising a polynucleotide sequence insertion, deletion and/or substitution between a first base after a last functional codon of at least one of either an REP2 gene or an FLP gene and a last base before an FRT site in an inverted repeat adjacent to said gene.

2. The 2 μm-family plasmid of claim 1 wherein, other than the polynucleotide sequence insertion, deletion and/or substitution, the FLP gene and/or the REP2 gene has the sequence of an FLP gene and/or an REP2 gene from a naturally occurring 2 μm-family plasmid.

3. The 2 μm-family plasmid of claim 1, wherein the plasmid comprises pSR1, pSB3 or pSB4 from *Zygosaccharomyces rouxii*, pSB1 from *Zygosaccharomyces bailli*, pSB2 from *Zygosaccharomyces balli*, pSM1 from *Zygosaccharomyces fermentati*, pKD1 from *Kluyveromyces drosophilarum*, pPM1 from *Pichia membranaefaciens*, or the 2 μm plasmid from *Saccharomyces cerevisiae*.

4. The 2 μm-family plasmid of claim 2 wherein the sequence of the inverted repeat adjacent to said FLP and/or REP2 gene is from the sequence of the corresponding inverted repeat in the same naturally occurring 2 μm-family plasmid as the sequence from which the gene is from.

5. The 2 μm-family plasmid of claim 2 wherein the naturally occurring 2 μm-family plasmid is the 2 μm plasmid as from *Saccharomyces cerevisiae*.

6. The 2 μm-family plasmid of claim 5 wherein the polynucleotide sequence insertion, deletion and/or substitution occurs at a position between a first base of codon 59 of the REP2 gene and the last base before the FRT site in the adjacent inverted repeat.

7. The 2 μm-family plasmid of claim 5 wherein, other than the polynucleotide sequence insertion, deletion and/or substitution, the sequence of the REP2 gene and the adjacent inverted repeat comprises the nucleotides of SEQ ID NO: 1, or a nucleotide sequence 95% identical to SEQ ID NO:1.

8. The 2 μm-family plasmid of claim 1 wherein polynucleotide sequence insertion, deletion and/or substitution occurs at a position between a first base of the inverted repeat and a last base before the FRT site.

9. The 2 μm-family plasmid of claim 1 wherein the polynucleotide sequence insertion, deletion and/or substitution occurs between a first base after the end of the REP2 coding sequence and the last base before the FRT site.

10. The 2 μm-family plasmid of claim 1 wherein, other than the polynucleotide sequence insertion, deletion and/or substitution, the inverted repeat that follows the REP2 coding sequence has a sequence from a corresponding region of the 2 μm plasmid from *Saccharomyces cerevisiae*.

11. The 2 μm-family plasmid of claim 5 wherein the polynucleotide sequence insertion, deletion and/or substitution occurs at a position between a first base of codon 344 of the FLP gene and the last base before the FRT site in the adjacent inverted repeat.

12. The 2 μm-family plasmid of claim 5 wherein, other than the polynucleotide sequence insertion, deletion and/or substitution, the sequence of the FLP coding sequence and the adjacent inverted repeat comprises the nucleotides of SEQ ID NO: 2, or a nucleotide sequence 95% identical to SEQ ID NO:2.

13. The 2 μm-family plasmid of claim 11 wherein the polynucleotide sequence insertion, deletion and/or substitution occurs at a position between a first base of the inverted repeat and the last base before the FRT site.

14. The 2 μm-family plasmid of claim 13 wherein the polynucleotide sequence insertion, deletion and/or substitution occurs at a position between a first base after the end of the FLP coding sequence and the last base before the FRT site.

15. The 2 μm-family plasmid of claim 14 wherein the polynucleotide sequence insertion, deletion and/or substitution occurs at a first base after the end of the FLP coding sequence.

16. The 2 μm-family plasmid of claim 11 wherein, other than the polynucleotide sequence insertion, deletion and/or substitution, the inverted repeat that follows the FLP gene has a sequence from a corresponding region of the 2 μm plasmid from *Saccharomyces cerevisiae*.

17. The 2 μm-family plasmid of claim 1 comprising polynucleotide sequence insertions, deletions and/or substitutions between a first base after the last functional codons of both of the REP2 gene and the FLP gene and a last base before the FRT sites in the inverted repeats adjacent to each of said genes, which polynucleotide sequence insertions, deletions and/or substitutions can be the same or different.

18. The 2 μm-family plasmid of claim 1, comprising a polynucleotide sequence insertion, deletion and/or substitution which is not between the first base and the last base.

19. The 2 μm-family plasmid of claim 18 wherein the polynucleotide sequence insertion, deletion and/or substitution occurs within an untranscribed region around an ARS sequence.

20. The 2 μm-family plasmid of claim 1 wherein the, or at least one, polynucleotide sequence insertion, deletion and/or substitution is a polynucleotide sequence insertion.

21. The 2 μm-family plasmid of claim 20 in which the polynucleotide sequence insertion encodes an open reading frame.

22. The 2 μm-family plasmid of claim 21 in which the open reading frame encodes a non-2 μm-family plasmid protein.

23. The 2 μm-family plasmid of claim 22 in which the non-2 μm-family plasmid protein comprises the sequence of a protein involved in protein folding, or which has chaperone activity or is involved in the unfolded protein response, albumin, a monoclonal antibody, an etoposide, a serum protein, antistasin, a tick anticoagulant peptide, transferrin, lactoferrin, endostatin, angiostatin, collagens, immunoglobulins or immunoglobulin-based molecules or fragments of either, a Kunitz domain protein, interferons, interleukins, IL 10, IL 11, IL2, interferon α species and sub-species, interferon β species and sub-species, interferon γ species and subspecies, leptin, CNTF, $CNTF_{Ax15}$, IL 1-receptor antagonist, erythropoietin (EPO) and EPO mimics, thrombopoietin (TPO) and TPO mimics, prosaptide, cyanovirin-N, 5-helix, T20 peptide, T1249 peptide, HIV gp4I, HIV gp120, urokinase, prourokinase, tPA, hirudin, platelet derived growth factor, parathyroid hormone, proinsulin, insulin, glucagon, glucagon-like peptides, insulin-like growth factor, calcitonin, growth hormone, transforming growth factor β, tumour necrosis factor, G-CSF, GM-CSF, M-CSF, FGF, coagulation factors in both pre and active forms, including but not limited to plasminogen, fibrinogen, thrombin, pre-thrombin, pro-thrombin, von Willebrand's factor, $α_1$-antitrypsin, plasminogen activators, Factor VII, Factor VIII, Factor IX, Factor X and Factor XIII, nerve growth factor, LACI, platelet-derived endothelial cell growth factor (PD-ECGF), glucose oxidase, serum cholinesterase, aprotinin, amyloid precursor protein, inter-alpha trypsin inhibitor, antithrombin III, apo-lipoprotein species, Protein C, or Protein S.

24. The 2 μm-family plasmid of claim 23 in which the 2 μm-family plasmid protein comprises the sequence of albumin.

25. The 2 μm-family plasmid of claim 23 in which the non-2 μm-family plasmid protein comprises the sequence of transferrin.

26. The 2 μm-family plasmid of claim 23 in which the non-2 μm-family plasmid protein comprises the sequence of lactoferrin.

27. The 2 μm-family plasmid of claim 23 in which the non-2 μm-family plasmid protein comprises the sequence of Fc.

28. The 2 μm-family plasmid of claim 23 in which the non-2 μm-family plasmid protein comprises the sequence of a protein involved in protein folding, or which has chaperone activity or is involved in the unfolded protein response as encoded by anyone of AHA1, CCT2, CCT3, CCT4, CCT5, CCT6, CCT7, CCT8, CNS1, CPR3, CPR6, EPS1, ERO1, EUG1, FMO1, HCH1, HSP10, HSP12, HSP104, HSP26, HSP30, HSP42, HSP60, HSP78, HSP82, JEM1, MDJ1, MDJ2, MPD1, PDI1, PFD1, ABC1, APJ1, ATP11, ATP12, BTT1, CDC37, CPR7, HSC82, KAR2, LHS1, MGE1, MRS11, NOB1, ECM10, SSA1, SSA2, SSA3, SSA4, SSC1, SSE2, SIL1, SLS1, UBI4, ORM1, ORM2, PER1, PTC2, PSE1 and HAC1 or a truncated intronless HAC1.

29. The 2 μm-family plasmid of claim 23 in which the chaperone is protein disulphide isomerase (PDI), or is a protein encoded by ORM2, SSA1 or PSE1.

30. The 2 μm-family plasmid of claim 22 in which the non-2 μm-family plasmid protein comprises a secretion leader sequence.

31. The 2 μm-family plasmid of claim 22 in which the non-2 μm-family plasmid protein comprises the sequence of a bacterial selectable marker and/or a yeast selectable marker.

32. The 2 μm-family plasmid of claim 31 in which the bacterial selectable marker is a β-lactamase gene and/or the yeast selectable marker is a LEU2 selectable marker.

33. The 2 μm-family plasmid according to claim 1, which plasmid comprises (i) a heterologous sequence encoding a non-2 μm-family plasmid protein; (ii) a heterologous sequence encoding a protein comprising the sequence of a protein involved in protein folding, a chaperone or a protein involved in the unfolded protein response; and (iii) a heterologous sequence encoding a protein comprising the sequence of a selectable marker; wherein at least one of the heterologous sequences occurs between the first base after the last functional codon of at least one of either the REP2 gene or the FLP gene and the last base before the FRT site in an inverted repeat adjacent to the gene.

34. A method of preparing a plasmid as defined by claim 1 comprising:
(a) providing a plasmid comprising the sequence of a REP2 gene and the inverted repeat that follows the REP2 gene, or a FLP gene and the inverted repeat that follows the FLP gene, in each case the inverted repeat comprising an FRT site;
(b) providing a polynucleotide sequence and inserting the polynucleotide sequence into the plasmid of claim 1 between the first base after the last functional codon of at least one of either the REP2 gene or the FLP gene and the last base before the FRT site in an inverted repeat adjacent to the gene; and/or
(c) deleting some or all of the nucleotide bases between the first base after the last functional codon of at least one of either the REP2 gene or the FLP gene and the last base before the FRT site in an inverted repeat adjacent to the gene of claim 1; and/or
(d) substituting some or all of the nucleotide bases between the first base after the last functional codon of at least one of either the REP2 gene or the FLP gene and the last base before the FRT site in an inverted repeat adjacent to the gene with alternative nucleotide bases.

35. A plasmid obtainable by the method of claim 34.

36. A host cell comprising a plasmid as defined by claim 1.

37. A host cell according to claim 36 which is a yeast cell.

38. A host cell according to claim 36 in which the plasmid is stable as a multicopy plasmid.

39. A host cell according to claim 38 in which the plasmid comprises a polynucleotide sequence insertion, deletion and/or substitution between a first base after a last functional codon of at least one of either an REP2 gene or an FLP gene and a last base before an FRT site in an inverted repeat adjacent to said gene.

40. A host cell according to claim 38 in which, if the plasmid contains, or is modified to contain, a selectable marker then stability, as measured by the loss of the marker, is at least 1%, 2%, 3%, 4%, 5%, 10%, 15%, 20%, 25%, 30%, 40%, 50%, 60%, 70%, 75%, 80%, 85%, 90%, 95%, 96%, 97%, 98%, 99%, 99.9% or 100% after 5 generations.

41. A method of producing a protein comprising the steps of—
(a) providing a plasmid as defined by claim 1;
(b) providing a suitable host cell;
(c) transforming the host cell with the plasmid; and
(d) culturing the transformed host cell in a culture medium;
(e) thereby to produce the protein.

42. A method of producing a protein comprising the steps of providing a host cell as defined by claim 36 which host cell comprises a plasmid comprising a polynucleotide sequence insertion, deletion and/or substitution between the first base after the last functional codon of at least one of either a REP2 gene or an FLP gene and the last base before the FRT site in an inverted repeat adjacent to said gene as and culturing the host cell in a culture medium thereby to produce the protein.

43. A method according to claim 41 further comprising the step of isolating the thus produced protein from the cultured host cell or the culture medium.

44. A method according to claim 43 further comprising the step of purifying the thus isolated protein.

45. A method according to claim 44 further comprising the step of formulating the thus purified protein with a carrier or diluent, and optionally presenting the thus formulated protein in a unit form.

46. A method according to claim 44 further comprising the step of formulating the purified protein with a pharmaceutically acceptable carrier or diluent and optionally presenting the thus formulated protein in a unit dosage form.

47. The 2 µm-family plasmid of claim 11, wherein the polynucleotide sequence insertion, deletion and/or substitution occurs at an HgaI site or an FspI site within the inverted repeat.

48. The 2 µm-family plasmid of claim 1, wherein the plasmid comprises a heterologous sequence encoding protein disulphide isomerase.

49. The 2 µm-family plasmid of claim 1, wherein the plasmid comprises a heterologous sequence encoding a protein of interest.

50. The 2 µm-family plasmid of claim 22 in which the non-2 µm-family plasmid protein comprises immunoglobulin-based molecules or fragments thereof selected from the group consisting of dAb, Fab', F(ab')2, scAb, scFv andor scFv.

51. A 2 µm-family plasmid comprising a polynucleotide sequence insertion between a first base after a last functional codon of at least one of either an REP2 gene or an FLP gene and a last base before an FRT site in an inverted repeat adjacent to said gene, wherein the polynucleotide sequence insertion encodes an open reading frame which encodes a non-2 µm-family plasmid protein comprising a secretion leader sequence.

* * * * *

SEQUENCE LISTING

<160> NUMBER OF SEQ ID NOS: 85

<210> SEQ ID NO 1
<211> LENGTH: 1485
<212> TYPE: DNA
<213> ORGANISM: Saccharomyces cerevisiae

<400> SEQUENCE: 1

```
atggacgaca ttgaaacagc caagaatctg acggtaaaag cacgtacagc ttatagcgtc    60
tgggatgtat gtcggctgtt tattgaaatg attgctcctg atgtagatat tgatatagag   120
agtaaacgta agtctgatga gctactcttt ccaggatatg tcataaggcc catggaatct   180
ctcacaaccg gtaggccgta tggtcttgat tctagcgcag aagattccag cgtatcttct   240
gactccagtg ctgaggtaat tttgcctgct gcgaagatgg ttaaggaaag gtttgattcg   300
attggaaatg gtatgctctc ttcacaagaa gcaagtcagg ctgccataga tttgatgcta   360
cagaataaca agctgttaga caatagaaag caactataca aatctattgc tataataata   420
ggaagattgc ccgagaaaga caagaagaga gctaccgaaa tgctcatgag aaaaatggat   480
tgtacacagt tattagtccc accagctcca acggaagaag atgttatgaa gctcgtaagc   540
gtcgttaccc aattgcttac tttagttcca ccagatcgtc aagctgcttt aataggtgat   600
ttattcatcc cggaatctct aaaggatata ttcaatagtt tcaatgaact ggcggcagag   660
aatcgtttac agcaaaaaaa gagtgagttg aaggaaggaa ctgaagtgaa ccatgctaat   720
acaaatgaag aagttccctc caggcgaaca agaagtagag acacaaatgc aagaggagca   780
tataaattac aaaacaccat cactgagggc cctaaagcgg ttcccacgaa aaaaaggaga   840
gtagcaacga gggtaagggg cagaaaatca cgtaatactt ctagggtatg atccaatatc   900
aaaggaaatg atagcattga aggatgagac taatccaatt gaggagtggc agcatataga   960
acagctaaag ggtagtgctg aaggaagcat acgataccc gcatggaatg ggataatatc  1020
acaggaggta ctagactacc tttcatccta cataaataga cgcatataag tacgcattta  1080
agcataaaca cgcactatgc cgttcttctc atgtatatat atatacaggc aacacgcaga  1140
tataggtgcg acgtgaacag tgagctgtat gtgcgcagct cgcgttgcat tttcggaaac  1200
gctcgttttc ggaaacgctt tgaagttcct attccgaagt tcctattctc tagaaagtat  1260
aggaacttca gagcgctttt gaaaaccaaa agcgctctga agacgcactt tcaaaaaacc  1320
aaaaacgcac cggactgtaa cgagctacta aaatattgcg aataccgctt ccacaaacat  1380
tgctcaaaag tatctctttg ctatatatct ctgtgctata tccctatata acctacccat  1440
ccacctttcg ctccttgaac ttgcatctaa actcgacctc tacat                  1485
```

<210> SEQ ID NO 2
<211> LENGTH: 1688
<212> TYPE: DNA
<213> ORGANISM: Saccharomyces cerevisiae

<400> SEQUENCE: 2

```
atgccacaat ttggtatatt atgtaaaaca ccacctaagg tgcttgttcg tcagtttgtg    60
gaaaggtttg aaagaccttc aggtgagaaa atagcattat gtgctgctga actaacctat   120
ttatgttgga tgattacaca taacggaaca gcaatcaaga gagccacatt catgagctat   180
aatactatca taagcaattc gctgagtttc gatattgtca ataaatcact ccagtttaaa   240
tacaagacgc aaaaagcaac aattctggaa gcctcattaa agaaattgat tcctgcttgg   300
gaatttacaa ttattcctta ctatggacaa aaacatcaat ctgatatcac tgatattgta   360
agtagtttgc aattacagtt cgaatcatcg gaagaagcag ataagggaaa tagccacagt   420
aaaaaaatgc ttaaagcact tctaagtgag ggtgaaagca tctgggagat cactgagaaa   480
atactaaatt cgtttgagta tacttcgaga tttacaaaaa caaaaacttt ataccaattc   540
ctcttcctag ctactttcat caattgtgga agattcagcg atattaagaa cgttgatccg   600
aaatcattta aattagtcca aaataagtat ctgggagtaa taatccagtg tttagtgaca   660
```

-continued

```
gagacaaaga caagcgttag taggcacata tacttcttta gcgcaagggg taggatcgat   720
ccacttgtat atttggatga attttgagg aattctgaac cagtcctaaa acgagtaaat   780
aggaccggca attcttcaag caataaacag gaataccaat tattaaaaga taacttagtc   840
agatcgtaca ataaagcttt gaagaaaaat gcgccttatt caatctttgc tataaaaaat   900
ggcccaaaat ctcacattgg aagacatttg atgacctcat ttctttcaat gaagggccta   960
acggagttga ctaatgttgt gggaaattgg agcgataagc gtgcttctgc cgtggccagg  1020
acaacgtata ctcatcagat aacagcaata cctgatcact acttcgcact agtttctcgg  1080
tactatgcat atgatccaat atcaaaggaa atgatagcat tgaaggatga gactaatcca  1140
attgaggagt ggcagcatat agaacagcta aagggtagtg ctgaaggaag catacgatac  1200
cccgcatgga atgggataat atcacaggag gtactagact acctttcatc ctacataaat  1260
agacgcatat aagtacgcat ttaagcataa acacgcacta tgccgttctt ctcatgtata  1320
tatatataca ggcaacacgc agatataggt gcgacgtgaa cagtgagctg tatgtgcgca  1380
gctcgcgttg cattttcgga agcgctcgtt ttcggaaacg ctttgaagtt cctattccga  1440
agttcctatt ctctagaaag tataggaact tcagagcgct tttgaaaacc aaaagcgctc  1500
tgaagacgca ctttcaaaaa accaaaaacg caccggactg taacgagcta ctaaaatatt  1560
gcgaataccg cttccacaaa cattgctcaa aagtatctct ttgctatata tctctgtgct  1620
atatccctat ataacctacc catccacctt tcgctccttg aacttgcatc taaactcgac  1680
ctctacat                                                          1688
```

```
<210> SEQ ID NO 3
<211> LENGTH: 522
<212> TYPE: PRT
<213> ORGANISM: Saccharomyces cerevisiae

<400> SEQUENCE: 3

Met Lys Phe Ser Ala Gly Ala Val Leu Ser Trp Ser Ser Leu Leu Leu
1               5                   10                  15

Ala Ser Ser Val Phe Ala Gln Gln Glu Ala Val Ala Pro Glu Asp Ser
            20                  25                  30

Ala Val Val Lys Leu Ala Thr Asp Ser Phe Asn Glu Tyr Ile Gln Ser
        35                  40                  45

His Asp Leu Val Leu Ala Glu Phe Phe Ala Pro Trp Cys Gly His Cys
    50                  55                  60

Lys Asn Met Ala Pro Glu Tyr Val Lys Ala Ala Glu Thr Leu Val Glu
65                  70                  75                  80

Lys Asn Ile Thr Leu Ala Gln Ile Asp Cys Thr Glu Asn Gln Asp Leu
                85                  90                  95

Cys Met Glu His Asn Ile Pro Gly Phe Pro Ser Leu Lys Ile Phe Lys
            100                 105                 110

Asn Ser Asp Val Asn Ser Ile Asp Tyr Glu Gly Pro Arg Thr Ala
        115                 120                 125

Glu Ala Ile Val Gln Phe Met Ile Lys Gln Ser Gln Pro Ala Val Ala
    130                 135                 140

Val Val Ala Asp Leu Pro Ala Tyr Leu Ala Asn Glu Thr Phe Val Thr
145                 150                 155                 160

Pro Val Ile Val Gln Ser Gly Lys Ile Asp Ala Asp Phe Asn Ala Thr
                165                 170                 175

Phe Tyr Ser Met Ala Asn Lys His Phe Asn Asp Tyr Asp Phe Val Ser
            180                 185                 190
```

-continued

Ala Glu Asn Ala Asp Asp Phe Lys Leu Ser Ile Tyr Leu Pro Ser
         195                 200                 205

Ala Met Asp Glu Pro Val Val Tyr Asn Gly Lys Lys Ala Asp Ile Ala
    210                 215                 220

Asp Ala Asp Val Phe Glu Lys Trp Leu Gln Val Glu Ala Leu Pro Tyr
225                 230                 235                 240

Phe Gly Glu Ile Asp Gly Ser Val Phe Ala Gln Tyr Val Ser Gly
             245                 250                 255

Leu Pro Leu Gly Tyr Leu Phe Tyr Asn Asp Glu Glu Leu Glu Glu
         260                 265                 270

Tyr Lys Pro Leu Phe Thr Glu Leu Ala Lys Lys Asn Arg Gly Leu Met
         275                 280                 285

Asn Phe Val Ser Ile Asp Ala Arg Lys Phe Gly Arg His Ala Gly Asn
    290                 295                 300

Leu Asn Met Lys Glu Gln Phe Pro Leu Phe Ala Ile His Asp Met Thr
305                 310                 315                 320

Glu Asp Leu Lys Tyr Gly Leu Pro Gln Leu Ser Glu Glu Ala Phe Asp
                325                 330                 335

Glu Leu Ser Asp Lys Ile Val Leu Glu Ser Lys Ala Ile Glu Ser Leu
            340                 345                 350

Val Lys Asp Phe Leu Lys Gly Asp Ala Ser Pro Ile Val Lys Ser Gln
        355                 360                 365

Glu Ile Phe Glu Asn Gln Asp Ser Ser Val Phe Gln Leu Val Gly Lys
    370                 375                 380

Asn His Asp Glu Ile Val Asn Asp Pro Lys Lys Asp Val Leu Val Leu
385                 390                 395                 400

Tyr Tyr Ala Pro Trp Cys Gly His Cys Lys Arg Leu Ala Pro Thr Tyr
                405                 410                 415

Gln Glu Leu Ala Asp Thr Tyr Ala Asn Ala Thr Ser Asp Val Leu Ile
            420                 425                 430

Ala Lys Leu Asp His Thr Glu Asn Asp Val Arg Gly Val Val Ile Glu
        435                 440                 445

Gly Tyr Pro Thr Ile Val Leu Tyr Pro Gly Gly Lys Lys Ser Glu Ser
    450                 455                 460

Val Val Tyr Gln Gly Ser Arg Ser Leu Asp Ser Leu Phe Asp Phe Ile
465                 470                 475                 480

Lys Glu Asn Gly His Phe Asp Val Asp Gly Lys Ala Leu Tyr Glu Glu
                485                 490                 495

Ala Gln Glu Lys Ala Ala Glu Ala Asp Ala Asp Ala Glu Leu Ala
            500                 505                 510

Asp Glu Glu Asp Ala Ile His Asp Glu Leu
        515                 520

<210> SEQ ID NO 4
<211> LENGTH: 530
<212> TYPE: PRT
<213> ORGANISM: Saccharomyces cerevisiae

<400> SEQUENCE: 4

Met Lys Phe Ser Ala Gly Ala Val Leu Ser Trp Ser Ser Leu Leu Leu
1               5                   10                  15

Ala Ser Ser Val Phe Ala Gln Gln Glu Ala Val Ala Pro Glu Asp Ser
            20                  25                  30

Ala Val Val Lys Leu Ala Thr Asp Ser Phe Asn Glu Tyr Ile Gln Ser
        35                  40                  45

His Asp Leu Val Leu Ala Glu Phe Phe Ala Pro Trp Cys Gly His Cys
 50                  55                  60

Lys Asn Met Ala Pro Glu Tyr Val Lys Ala Ala Glu Thr Leu Val Glu
 65                  70                  75                  80

Lys Asn Ile Thr Leu Ala Gln Ile Asp Cys Thr Glu Asn Gln Asp Leu
                 85                  90                  95

Cys Met Glu His Asn Ile Pro Gly Phe Pro Ser Leu Lys Ile Phe Lys
            100                 105                 110

Asn Arg Asp Val Asn Asn Ser Ile Asp Tyr Glu Gly Pro Arg Thr Ala
        115                 120                 125

Glu Ala Ile Val Gln Phe Met Ile Lys Gln Ser Gln Pro Ala Val Ala
    130                 135                 140

Val Val Ala Asp Leu Pro Ala Tyr Leu Ala Asn Glu Thr Phe Val Thr
145                 150                 155                 160

Pro Val Ile Val Gln Ser Gly Lys Ile Asp Ala Asp Phe Asn Ala Thr
                165                 170                 175

Phe Tyr Ser Met Ala Asn Lys His Phe Asn Asp Tyr Asp Phe Val Ser
            180                 185                 190

Ala Glu Asn Ala Asp Asp Phe Lys Leu Ser Ile Tyr Leu Pro Ser
        195                 200                 205

Ala Met Asp Glu Pro Val Val Tyr Asn Gly Lys Lys Ala Asp Ile Ala
    210                 215                 220

Asp Ala Asp Val Phe Glu Lys Trp Leu Gln Val Glu Ala Leu Pro Tyr
225                 230                 235                 240

Phe Gly Glu Ile Asp Gly Ser Val Phe Ala Gln Tyr Val Glu Ser Gly
                245                 250                 255

Leu Pro Leu Gly Tyr Leu Phe Tyr Asn Asp Glu Glu Leu Glu Glu
            260                 265                 270

Tyr Lys Pro Leu Phe Thr Glu Leu Ala Lys Lys Asn Arg Gly Leu Met
    275                 280                 285

Asn Phe Val Ser Ile Asp Ala Arg Lys Phe Gly Arg His Ala Gly Asn
290                 295                 300

Leu Asn Met Lys Glu Gln Phe Pro Leu Phe Ala Ile His Asp Met Thr
305                 310                 315                 320

Glu Asp Leu Lys Tyr Gly Leu Pro Gln Leu Ser Glu Glu Ala Phe Asp
                325                 330                 335

Glu Leu Ser Asp Lys Ile Val Leu Glu Ser Lys Ala Ile Glu Ser Leu
            340                 345                 350

Val Lys Asp Phe Leu Lys Gly Asp Ala Ser Pro Ile Val Lys Ser Gln
    355                 360                 365

Glu Ile Phe Glu Asn Gln Asp Ser Ser Val Phe Gln Leu Val Gly Lys
    370                 375                 380

Asn His Asp Glu Ile Val Asn Asp Pro Lys Lys Asp Val Leu Val Leu
385                 390                 395                 400

Tyr Tyr Ala Pro Trp Cys Gly His Cys Lys Arg Leu Ala Pro Thr Tyr
                405                 410                 415

Gln Glu Leu Ala Asp Thr Tyr Ala Asn Ala Thr Ser Asp Val Leu Ile
            420                 425                 430

Ala Lys Leu Asp His Thr Glu Asn Asp Val Arg Gly Val Val Ile Glu
        435                 440                 445

Gly Tyr Pro Thr Ile Val Leu Tyr Pro Gly Gly Lys Lys Ser Glu Ser
    450                 455                 460

Val Val Tyr Gln Gly Ser Arg Ser Leu Asp Ser Leu Phe Asp Phe Ile
465                 470                 475                 480

```
Lys Glu Asn Gly His Phe Asp Val Asp Gly Lys Ala Leu Tyr Glu Glu
                485                 490                 495

Ala Gln Glu Lys Ala Ala Glu Glu Ala Glu Ala Asp Ala Glu Ala Glu
            500                 505                 510

Ala Asp Ala Asp Ala Glu Leu Ala Asp Glu Glu Asp Ala Ile His Asp
        515                 520                 525

Glu Leu
    530

<210> SEQ ID NO 5
<211> LENGTH: 642
<212> TYPE: PRT
<213> ORGANISM: Saccharomyces cerevisiae

<400> SEQUENCE: 5

Met Ser Lys Ala Val Gly Ile Asp Leu Gly Thr Thr Tyr Ser Cys Val
1               5                   10                  15

Ala His Phe Ala Asn Asp Arg Val Asp Ile Ile Ala Asn Asp Gln Gly
            20                  25                  30

Asn Arg Thr Thr Pro Ser Phe Val Ala Phe Thr Asp Thr Glu Arg Leu
        35                  40                  45

Ile Gly Asp Ala Ala Lys Asn Gln Ala Ala Met Asn Pro Ser Asn Thr
    50                  55                  60

Val Phe Asp Ala Lys Arg Leu Ile Gly Arg Asn Phe Asn Asp Pro Glu
65                  70                  75                  80

Val Gln Ala Asp Met Lys His Phe Pro Phe Lys Leu Ile Asp Val Asp
                85                  90                  95

Gly Lys Pro Gln Ile Gln Val Glu Phe Lys Gly Glu Thr Lys Asn Phe
            100                 105                 110

Thr Pro Glu Gln Ile Ser Ser Met Val Leu Gly Lys Met Lys Glu Thr
        115                 120                 125

Ala Glu Ser Tyr Leu Gly Ala Lys Val Asn Asp Ala Val Val Thr Val
    130                 135                 140

Pro Ala Tyr Phe Asn Asp Ser Gln Arg Gln Ala Thr Lys Asp Ala Gly
145                 150                 155                 160

Thr Ile Ala Gly Leu Asn Val Leu Arg Ile Ile Asn Glu Pro Thr Ala
                165                 170                 175

Ala Ala Ile Ala Tyr Gly Leu Asp Lys Lys Gly Lys Glu Glu His Val
            180                 185                 190

Leu Ile Phe Asp Leu Gly Gly Gly Thr Phe Asp Val Ser Leu Leu Phe
        195                 200                 205

Ile Glu Asp Gly Ile Phe Glu Val Lys Ala Thr Ala Gly Asp Thr His
    210                 215                 220

Leu Gly Gly Glu Asp Phe Asp Asn Arg Leu Val Asn His Phe Ile Gln
225                 230                 235                 240

Glu Phe Lys Arg Lys Asn Lys Lys Asp Leu Ser Thr Asn Gln Arg Ala
                245                 250                 255

Leu Arg Arg Leu Arg Thr Ala Cys Glu Arg Ala Lys Arg Thr Leu Ser
            260                 265                 270

Ser Ser Ala Gln Thr Ser Val Glu Ile Asp Ser Leu Phe Glu Gly Ile
        275                 280                 285

Asp Phe Tyr Thr Ser Ile Thr Arg Ala Arg Phe Glu Glu Leu Cys Ala
    290                 295                 300

Asp Leu Phe Arg Ser Thr Leu Asp Pro Val Glu Lys Val Leu Arg Asp
305                 310                 315                 320
```

```
Ala Lys Leu Asp Lys Ser Gln Val Asp Glu Ile Val Leu Val Gly Gly
            325                 330                 335

Ser Thr Arg Ile Pro Lys Val Gln Lys Leu Val Thr Asp Tyr Phe Asn
            340                 345                 350

Gly Lys Glu Pro Asn Arg Ser Ile Asn Pro Asp Glu Ala Val Ala Tyr
            355                 360                 365

Gly Ala Ala Val Gln Ala Ala Ile Leu Thr Gly Asp Glu Ser Ser Lys
    370                 375                 380

Thr Gln Asp Leu Leu Leu Leu Asp Val Ala Pro Leu Ser Leu Gly Ile
385                 390                 395                 400

Glu Thr Ala Gly Gly Val Met Thr Lys Leu Ile Pro Arg Asn Ser Thr
                405                 410                 415

Ile Ser Thr Lys Lys Phe Glu Ile Phe Ser Thr Tyr Ala Asp Asn Gln
            420                 425                 430

Pro Gly Val Leu Ile Gln Val Phe Glu Gly Glu Arg Ala Lys Thr Lys
            435                 440                 445

Asp Asn Asn Leu Leu Gly Lys Phe Glu Leu Ser Gly Ile Pro Pro Ala
    450                 455                 460

Pro Arg Gly Val Pro Gln Ile Glu Val Thr Phe Asp Val Asp Ser Asn
465                 470                 475                 480

Gly Ile Leu Asn Val Ser Ala Val Glu Lys Gly Thr Gly Lys Ser Asn
                485                 490                 495

Lys Ile Thr Ile Thr Asn Asp Lys Gly Arg Leu Ser Lys Glu Asp Ile
            500                 505                 510

Glu Lys Met Val Ala Glu Ala Glu Lys Phe Lys Glu Glu Asp Glu Lys
            515                 520                 525

Glu Ser Gln Arg Ile Ala Ser Lys Asn Gln Leu Glu Ser Ile Ala Tyr
    530                 535                 540

Ser Leu Lys Asn Thr Ile Ser Glu Ala Gly Asp Lys Leu Glu Gln Ala
545                 550                 555                 560

Asp Lys Asp Thr Val Thr Lys Lys Ala Glu Glu Thr Ile Ser Trp Leu
                565                 570                 575

Asp Ser Asn Thr Thr Ala Ser Lys Glu Glu Phe Asp Asp Lys Leu Lys
            580                 585                 590

Glu Leu Gln Asp Ile Ala Asn Pro Ile Met Ser Lys Leu Tyr Gln Ala
            595                 600                 605

Gly Gly Ala Pro Gly Gly Ala Ala Gly Gly Ala Pro Gly Gly Phe Pro
    610                 615                 620

Gly Gly Ala Pro Pro Ala Pro Glu Ala Glu Gly Pro Thr Val Glu Glu
625                 630                 635                 640

Val Asp

<210> SEQ ID NO 6
<211> LENGTH: 1929
<212> TYPE: DNA
<213> ORGANISM: Saccharomyces cerevisiae

<400> SEQUENCE: 6
atgtcaaaag ctgtcggtat tgatttaggt acaacatact cgtgtgttgc tcactttgct      60
aatgatcgtg tggacattat tgccaacgat caaggtaaca gaaccactcc atcttttgtc     120
gctttcactg acactgaaag attgattggt gatgctgcta agaatcaagc tgctatgaat     180
ccttcgaata ccgttttcga cgctaagcgt ttgatcggta gaaacttcaa cgacccagaa     240
gtgcaggctg acatgaagca cttcccattc aagttgatcg atgttgacgg taagcctcaa     300
```

```
attcaagttg aatttaaggg tgaaaccaag aactttaccc cagaacaaat ctcctccatg      360
gtcttgggta agatgaagga aactgccgaa tcttacttgg gagccaaggt caatgacgct      420
gtcgtcactg tcccagctta cttcaacgat tctcaaagac aagctaccaa ggatgctggt      480
accattgctg gtttgaatgt cttgcgtatt attaacgaac ctaccgccgc tgccattgct      540 tacggttttgg acaagaaggg taaggaagaa cacgtcttga ttttcgactt gggtggtggt      600
actttcgatg tctctttgtt gttcattgaa gacggtatct ttgaagttaa ggccaccgct      660
ggtgacaccc atttgggtgg tgaagatttt gacaacagat tggtcaacca cttcatccaa      720
gaattcaaga gaaagaacaa gaaggacttg tctaccaacc aaagagcttt gagaagatta      780
agaaccgctt gtgaaagagc caagagaact ttgtcttcct ccgctcaaac ttccgttgaa      840
attgactctt tgttcgaagg tatcgatttc tacacttcca tcaccagagc cagattcgaa      900
gaattgtgtg ctgacttgtt cagatctact ttggacccag ttgaaaaggt cttgagagat      960
gctaaattgg acaaatctca agtcgatgaa attgtcttgg tcggtggttc taccagaatt     1020
ccaaaggtcc aaaaattggt cactgactac ttcaacggta aggaaccaaa cagatctatc     1080
aacccagatg aagctgttgc ttacggtgct gctgttcaag ctgctatttt gactggtgac     1140
gaatcttcca agactcaaga tctattgttg ttggatgtcg ctccattatc cttgggtatt     1200
gaaactgctg tggtgtcat gaccaagttg attccaagaa actctaccat ttcaacaaag     1260
aagttcgaga tcttttccac ttatgctgat aaccaaccag gtgtcttgat tcaagtcttt     1320
gaaggtgaaa gagccaagac taaggacaac aacttgttgg gtaagttcga attgagtggt     1380
attccaccag ctccaagagg tgtcccacaa attgaagtca ctttcgatgt cgactctaac     1440 ggtatttttga atgtttccgc cgtcgaaaag ggtactggta agtctaacaa gatcactatt     1500
accaacgaca agggtagatt gtccaaggaa gatatcgaaa agatggttgc tgaagccgaa     1560
aaattcaagg aagaagatga aaaggaatct caaagaattg cttccaagaa ccaattggaa     1620
tccattgctt actctttgaa gaacaccatt tctgaagctg gtgacaaatt ggaacaagct     1680
gacaaggaca ccgtcaccaa gaaggctgaa gagactattt cttggttaga cagcaacacc     1740
actgccagca aggaagaatt cgatgacaag ttgaaggagt gcaagacat tgccaaccca     1800 atcatgtcta agttgtacca agctggtggt gctccaggtg cgctgcagg tggtgctcca     1860 ggcggtttcc caggtggtgc tcctccagct ccagaggctg aaggtccaac cgttgaagaa     1920
gttgattaa                                                            1929

<210> SEQ ID NO 7
<211> LENGTH: 1089
<212> TYPE: PRT
<213> ORGANISM: Saccharomyces cerevisiae

<400> SEQUENCE: 7

Met Ser Ala Leu Pro Glu Glu Val Asn Arg Thr Leu Leu Gln Ile Val
1               5                   10                  15

Gln Ala Phe Ala Ser Pro Asp Asn Gln Ile Arg Ser Val Ala Glu Lys
            20                  25                  30

Ala Leu Ser Glu Glu Trp Ile Thr Glu Asn Asn Ile Glu Tyr Leu Leu
        35                  40                  45

Thr Phe Leu Ala Glu Gln Ala Ala Phe Ser Gln Asp Thr Thr Val Ala
    50                  55                  60

Ala Leu Ser Ala Val Leu Phe Arg Lys Leu Ala Leu Lys Ala Pro Pro
65                  70                  75                  80
```

```
Ser Ser Lys Leu Met Ile Met Ser Lys Asn Ile Thr His Ile Arg Lys
                85                  90                  95

Glu Val Leu Ala Gln Ile Arg Ser Ser Leu Leu Lys Gly Phe Leu Ser
            100                 105                 110

Glu Arg Ala Asp Ser Ile Arg His Lys Leu Ser Asp Ala Ile Ala Glu
            115                 120                 125

Cys Val Gln Asp Asp Leu Pro Ala Trp Pro Glu Leu Leu Gln Ala Leu
            130                 135                 140

Ile Glu Ser Leu Lys Ser Gly Asn Pro Asn Phe Arg Glu Ser Ser Phe
145                 150                 155                 160

Arg Ile Leu Thr Thr Val Pro Tyr Leu Ile Thr Ala Val Asp Ile Asn
                165                 170                 175

Ser Ile Leu Pro Ile Phe Gln Ser Gly Phe Thr Asp Ala Ser Asp Asn
            180                 185                 190

Val Lys Ile Ala Ala Val Thr Ala Phe Val Gly Tyr Phe Lys Gln Leu
            195                 200                 205

Pro Lys Ser Glu Trp Ser Lys Leu Gly Ile Leu Leu Pro Ser Leu Leu
            210                 215                 220

Asn Ser Leu Pro Arg Phe Leu Asp Asp Gly Lys Asp Ala Leu Ala
225                 230                 235                 240

Ser Val Phe Glu Ser Leu Ile Glu Leu Val Glu Leu Ala Pro Lys Leu
                245                 250                 255

Phe Lys Asp Met Phe Asp Gln Ile Ile Gln Phe Thr Asp Met Val Ile
            260                 265                 270

Lys Asn Lys Asp Leu Glu Pro Pro Ala Arg Thr Thr Ala Leu Glu Leu
            275                 280                 285

Leu Thr Val Phe Ser Glu Asn Ala Pro Gln Met Cys Lys Ser Asn Gln
            290                 295                 300

Asn Tyr Gly Gln Thr Leu Val Met Val Thr Leu Ile Met Met Thr Glu
305                 310                 315                 320

Val Ser Ile Asp Asp Asp Ala Ala Glu Trp Ile Glu Ser Asp Asp
                325                 330                 335

Thr Asp Asp Glu Glu Glu Val Thr Tyr Asp His Ala Arg Gln Ala Leu
            340                 345                 350

Asp Arg Val Ala Leu Lys Leu Gly Gly Glu Tyr Leu Ala Ala Pro Leu
            355                 360                 365

Phe Gln Tyr Leu Gln Gln Met Ile Thr Ser Thr Glu Trp Arg Glu Arg
            370                 375                 380

Phe Ala Ala Met Met Ala Leu Ser Ser Ala Ala Glu Gly Cys Ala Asp
385                 390                 395                 400

Val Leu Ile Gly Glu Ile Pro Lys Ile Leu Asp Met Val Ile Pro Leu
                405                 410                 415

Ile Asn Asp Pro His Pro Arg Val Gln Tyr Gly Cys Cys Asn Val Leu
            420                 425                 430

Gly Gln Ile Ser Thr Asp Phe Ser Pro Phe Ile Gln Arg Thr Ala His
            435                 440                 445

Asp Arg Ile Leu Pro Ala Leu Ile Ser Lys Leu Thr Ser Glu Cys Thr
450                 455                 460

Ser Arg Val Gln Thr His Ala Ala Ala Leu Val Asn Phe Ser Glu
465                 470                 475                 480

Phe Ala Ser Lys Asp Ile Leu Glu Pro Tyr Leu Asp Ser Leu Leu Thr
                485                 490                 495

Asn Leu Leu Val Leu Leu Gln Ser Asn Lys Leu Tyr Val Gln Glu Gln
            500                 505                 510
```

```
Ala Leu Thr Thr Ile Ala Phe Ile Ala Glu Ala Ala Lys Asn Lys Phe
        515                 520                 525

Ile Lys Tyr Tyr Asp Thr Leu Met Pro Leu Leu Leu Asn Val Leu Lys
        530                 535                 540

Val Asn Asn Lys Asp Asn Ser Val Leu Lys Gly Lys Cys Met Glu Cys
545                 550                 555                 560

Ala Thr Leu Ile Gly Phe Ala Val Gly Lys Glu Lys Phe His Glu His
                565                 570                 575

Ser Gln Glu Leu Ile Ser Ile Leu Val Ala Leu Gln Asn Ser Asp Ile
        580                 585                 590

Asp Glu Asp Asp Ala Leu Arg Ser Tyr Leu Glu Gln Ser Trp Ser Arg
        595                 600                 605

Ile Cys Arg Ile Leu Gly Asp Asp Phe Val Pro Leu Leu Pro Ile Val
        610                 615                 620

Ile Pro Pro Leu Leu Ile Thr Ala Lys Ala Thr Gln Asp Val Gly Leu
625                 630                 635                 640

Ile Glu Glu Glu Glu Ala Ala Asn Phe Gln Gln Tyr Pro Asp Trp Asp
                645                 650                 655

Val Val Gln Val Gln Gly Lys His Ile Ala Ile His Thr Ser Val Leu
        660                 665                 670

Asp Asp Lys Val Ser Ala Met Glu Leu Leu Gln Ser Tyr Ala Thr Leu
        675                 680                 685

Leu Arg Gly Gln Phe Ala Val Tyr Val Lys Glu Val Met Glu Glu Ile
        690                 695                 700

Ala Leu Pro Ser Leu Asp Phe Tyr Leu His Asp Gly Val Arg Ala Ala
705                 710                 715                 720

Gly Ala Thr Leu Ile Pro Ile Leu Leu Ser Cys Leu Leu Ala Ala Thr
                725                 730                 735

Gly Thr Gln Asn Glu Glu Leu Val Leu Leu Trp His Lys Ala Ser Ser
        740                 745                 750

Lys Leu Ile Gly Gly Leu Met Ser Glu Pro Met Pro Glu Ile Thr Gln
        755                 760                 765

Val Tyr His Asn Ser Leu Val Asn Gly Ile Lys Val Met Gly Asp Asn
        770                 775                 780

Cys Leu Ser Glu Asp Gln Leu Ala Ala Phe Thr Lys Gly Val Ser Ala
785                 790                 795                 800

Asn Leu Thr Asp Thr Tyr Glu Arg Met Gln Asp Arg His Gly Asp Gly
                805                 810                 815

Asp Glu Tyr Asn Glu Asn Ile Asp Glu Glu Asp Phe Thr Asp Glu
        820                 825                 830

Asp Leu Leu Asp Glu Ile Asn Lys Ser Ile Ala Ala Val Leu Lys Thr
        835                 840                 845

Thr Asn Gly His Tyr Leu Lys Asn Leu Glu Asn Ile Trp Pro Met Ile
        850                 855                 860

Asn Thr Phe Leu Leu Asp Asn Glu Pro Ile Leu Val Ile Phe Ala Leu
865                 870                 875                 880

Val Val Ile Gly Asp Leu Ile Gln Tyr Gly Gly Glu Gln Thr Ala Ser
                885                 890                 895

Met Lys Asn Ala Phe Ile Pro Lys Val Thr Glu Cys Leu Ile Ser Pro
                900                 905                 910

Asp Ala Arg Ile Arg Gln Ala Ala Ser Tyr Ile Ile Gly Val Cys Ala
        915                 920                 925

Gln Tyr Ala Pro Ser Thr Tyr Ala Asp Val Cys Ile Pro Thr Leu Asp
```

```
                930             935             940
Thr Leu Val Gln Ile Val Asp Phe Pro Gly Ser Lys Leu Glu Glu Asn
945                 950                 955                 960

Arg Ser Ser Thr Glu Asn Ala Ser Ala Ala Ile Ala Lys Ile Leu Tyr
            965                 970                 975

Ala Tyr Asn Ser Asn Ile Pro Asn Val Asp Thr Tyr Thr Ala Asn Trp
                980                 985                 990

Phe Lys Thr Leu Pro Thr Ile Thr Asp Lys Glu Ala Ala Ser Phe Asn
            995                 1000                1005

Tyr Gln Phe Leu Ser Gln Leu Ile Glu Asn Asn Ser Pro Ile Val Cys
    1010                1015                1020

Ala Gln Ser Asn Ile Ser Ala Val Val Asp Ser Val Ile Gln Ala Leu
1025                1030                1035                1040

Asn Glu Arg Ser Leu Thr Glu Arg Glu Gly Gln Thr Val Ile Ser Ser
                1045                1050                1055

Val Lys Lys Leu Leu Gly Phe Leu Pro Ser Ser Asp Ala Met Ala Ile
            1060                1065                1070

Phe Asn Arg Tyr Pro Ala Asp Ile Met Glu Lys Val His Lys Trp Phe
        1075                1080                1085

Ala

<210> SEQ ID NO 8
<211> LENGTH: 3270
<212> TYPE: DNA
<213> ORGANISM: Saccharomyces cerevisiae

<400> SEQUENCE: 8
atgtctgctt taccggaaga agttaataga acattacttc agattgtcca ggcgtttgct      60
tcccctgaca atcaaatacg ttctgtagct gagaaggctc ttagtgaaga atggattacc     120
gaaaacaata ttgagtatct tttaactttt ttggctgaac aagccgcttt ctcccaagat     180
acaacagttg cagcattatc tgctgttctg tttagaaaat tagcattaaa agctcccect     240 tcttcgaagc ttatgattat gtccaaaaat atcacacata ttaggaaaga agttcttgca     300
caaattcgtt cttcattgtt aaaagggttt tgtcggaaaa gagctgattc aattaggcac     360
aaactatctg atgctattgc tgagtgtgtt caagacgact accagcatgg ccagaatta     420 ctacaagctt taatagagtc tttaaaaagc ggtaacccaa attttagaga atccagtttt     480
agaattttga cgactgtacc ttatttaatt accgctgttg acatcaacag tatcttacca     540
atttttcaat caggctttac tgatgcaagt gataatgtca aaattgctgc agttacggct     600
ttcgtgggtt attttaagca actaccaaaa tctgagtggt ccaagttagg tattttatta     660
ccaagtcttt tgaatagttt accaagattt ttagatgatg gtaaggacga tgcccttgca     720 tcagttttg aatcgttaat tgagttggtg gaattggcac caaaactatt caaggatatg     780
tttgaccaaa taatacaatt cactgatatg gttataaaaa ataaggattt agaacctcca     840
gcaagaacca cagcactcga actgctaacc gttttcagcg agaacgctcc ccaaatgtgt     900
aaatcgaacc agaattacgg gcaaacttta gtgatggtta ctttaatcat gatgacggag     960
gtatccatag atgatgatga tgcagcagaa tggatagaat ctgacgatac cgatgatgaa    1020
gaggaagtta catatgacca cgctcgtcaa gctcttgatc gtgttgcttt aaagctgggt    1080
ggtgaatatt tggctgcacc attgttccaa tatttacagc aaatgatcac atcaaccgaa    1140
tggagagaaa gattcgcggc catgatggca ctttcctctg cagctgaggg ttgtgctgat    1200
gttctgatcg gcgagatccc aaaaatcctg gatatggtaa ttcccctcat caacgatcct    1260
```

```
catccaagag tacagtatgg atgttgtaat gttttgggtc aaatatctac tgattttca    1320 ccattcattc aaagaactgc acacgataga attttgccgg ctttaatatc taaactaacg    1380
tcagaatgca cctcaagagt tcaaacgcac gccgcagcgg ctctggttaa cttttctgaa    1440
ttcgcttcga aggatattct tgagccttac ttggatagtc tattgacaaa tttattagtt    1500
ttattacaaa gcaacaaact ttacgtacag aacaggccc taacaaccat tgcatttatt    1560
gctgaagctg caaagaataa atttatcaag tattacgata ctctaatgcc attattatta    1620
aatgttttga aggttaacaa taaagataat agtgttttga aggtaaatg tatggaatgt    1680 gcaactctga ttggttttgc cgttggtaag gaaaaatttc atgagcactc tcaagagctg    1740
atttctatat tggtcgcttt acaaaactca gatatcgatg aagatgatgc gctcagatca    1800
tacttagaac aaagttggag caggatttgc cgaattctgg gtgatgattt tgttccgttg    1860
ttaccgattg ttataccacc cctgctaatt actgccaaag caacgcaaga cgtcggttta    1920
attgaagaag aagaagcagc aaatttccaa caatatccag attgggatgt tgttcaagtt    1980
cagggaaaac acattgctat tcacacatcc gtccttgacg ataaagtatc agcaatggag    2040
ctattacaaa gctatgcgac acttttaaga ggccaaattg ctgtatatgt taaagaagta    2100
atggaagaaa tagctctacc atcgcttgac ttttacctac atgacggtgt tcgtgctgca    2160
ggagcaactt taattcctat tctattatct tgtttacttg cagccaccgg tactcaaaac    2220
gaggaattgg tattgttgtg gcataaagct tcgtctaaac taatcggagg cttaatgtca    2280
gaaccaatgc cagaaatcac gcaagtttat cacaactcgt tagtgaatgg tattaaagtc    2340
atgggtgaca attgcttaag cgaagaccaa ttagcggcat ttactaaggg tgtctccgcc    2400
aacttaactg cacttacga aaggatgcag gatcgccatg gtgatggtga tgaatataat    2460
gaaaatattg atgaagagga agactttact gacgaagatc ttctcgatga aatcaacaag    2520
tctatcgcgg ccgttttgaa aaccacaaat ggtcattatc taaagaattt ggagaatata    2580
tggcctatga taaacacatt cctttagat aatgaaccaa ttttagtcat ttttgcatta    2640
gtagtgattg gtgacttgat tcaatatggt ggcgaacaaa ctgctagcat gaagaacgca    2700
tttattccaa aggttaccga gtgcttgatt tctcctgacg ctcgtattcg ccaagctgct    2760
tcttatataa tcggtgtttg tgcccaatac gctccatcta catatgctga cgtttgcata    2820
ccgactttag atacacttgt tcagattgtc gatttccag gctccaaact ggaagaaaat    2880
cgttcttcaa cagagaatgc cagtgcagcc atcgccaaaa ttctttatgc atacaattcc    2940
aacattccta acgtagacac gtacacggct aattggttca aacgttacc aacaataact    3000 gacaaagaag ctgcctcatt caactatcaa tttttgagtc aattgattga aaataattcg    3060
ccaattgtgt gtgctcaatc taatatctcc gctgtagttg attcagtcat acaagccttg    3120
aatgagagaa gtttgaccga aagggaaggc caaacggtga taagttcagt taaaaagttg    3180
ttgggatttt tgccttctag tgatgctatg gcaattttca atagatatcc agctgatatt    3240
atggagaaag tacataaatg gtttgcataa                                     3270
```

<210> SEQ ID NO 9
<211> LENGTH: 216
<212> TYPE: PRT
<213> ORGANISM: Saccharomyces cerevisiae

<400> SEQUENCE: 9

Met Ile Asp Arg Thr Lys Asn Glu Ser Pro Ala Phe Glu Glu Ser Pro
1               5                   10                  15

```
Leu Thr Pro Asn Val Ser Asn Leu Lys Pro Phe Pro Ser Gln Ser Asn
         20                  25                  30

Lys Ile Ser Thr Pro Val Thr Asp His Arg Arg Arg Ser Ser Ser
         35                  40                  45

Val Ile Ser His Val Glu Gln Glu Thr Phe Glu Asp Glu Asn Asp Gln
 50                  55                  60

Gln Met Leu Pro Asn Met Asn Ala Thr Trp Val Asp Gln Arg Gly Ala
 65                  70                  75                  80

Trp Leu Ile His Ile Val Ile Val Leu Leu Arg Leu Phe Tyr Ser
             85                  90                  95

Leu Phe Gly Ser Thr Pro Lys Trp Thr Trp Thr Leu Thr Asn Met Thr
             100                 105                 110

Tyr Ile Ile Gly Phe Tyr Ile Met Phe His Leu Val Lys Gly Thr Pro
             115                 120                 125

Phe Asp Phe Asn Gly Gly Ala Tyr Asp Asn Leu Thr Met Trp Glu Gln
 130                 135                 140

Ile Asn Asp Glu Thr Leu Tyr Thr Pro Thr Arg Lys Phe Leu Leu Ile
145                 150                 155                 160

Val Pro Ile Val Leu Phe Leu Ile Ser Asn Gln Tyr Tyr Arg Asn Asp
             165                 170                 175

Met Thr Leu Phe Leu Ser Asn Leu Ala Val Thr Val Leu Ile Gly Val
             180                 185                 190

Val Pro Lys Leu Gly Ile Thr His Arg Leu Arg Ile Ser Ile Pro Gly
             195                 200                 205

Ile Thr Gly Arg Ala Gln Ile Ser
             210                 215

<210> SEQ ID NO 10
<211> LENGTH: 651
<212> TYPE: DNA
<213> ORGANISM: Saccharomyces cerevisiae

<400> SEQUENCE: 10
atgattgacc gcactaaaaa cgaatctcca gcttttgaag agtctccgct tacccccaat      60
gtgtctaacc tgaaaccatt cccttctcaa agcaacaaaa tatccactcc agtgaccgac     120
cataggagaa gacggtcatc cagcgtaata tcacatgtgg aacaggaaac cttcgaagac     180
gaaaatgacc agcagatgct tcccaacatg aacgctacgt gggtcgacca gcgaggcgcg     240
tggttgattc atatcgtcgt aatagtactc ttgaggctct tctactcctt gttcgggtcg     300
acgcccaaat ggacgtggac tttaacaaac atgacctaca tcatcggatt ctatatcatg     360
ttccaccttg tcaaaggtac gcccttcgac tttaacggtg gtgcgtacga caacctgacc     420
atgtgggagc agattaacga tgagactttg tacacaccca ctagaaaatt tctgctgatt     480
gtacccattg tgttgttcct gattagcaac cagtactacc gcaacgacat gacactattc     540
ctctccaacc tcgccgtgac ggtgcttatt ggtgtcgttc ctaagctggg aattacgcat     600
agactaagaa tatccatccc tggtattacg ggccgtgctc aaattagtta g             651

<210> SEQ ID NO 11
<211> LENGTH: 52
<212> TYPE: DNA
<213> ORGANISM: Artificial Sequence
<220> FEATURE:
<223> OTHER INFORMATION: CF86 oligonucleotide

<400> SEQUENCE: 11
ggagtggtac gtattaatta aggccggcca ggcccgggta cgtaccaatt ga              52
```

-continued

<210> SEQ ID NO 12
<211> LENGTH: 52
<212> TYPE: DNA
<213> ORGANISM: Artificial Sequence
<220> FEATURE:
<223> OTHER INFORMATION: CF87 oligonucleotide

<400> SEQUENCE: 12
caattggtac gtacccgggc ctggccggcc ttaattaata cgtaccactc ct        52

<210> SEQ ID NO 13
<211> LENGTH: 20
<212> TYPE: DNA
<213> ORGANISM: Artificial Sequence
<220> FEATURE:
<223> OTHER INFORMATION: CF88 primer

<400> SEQUENCE: 13
atcacgtaat acttctaggg        20

<210> SEQ ID NO 14
<211> LENGTH: 20
<212> TYPE: DNA
<213> ORGANISM: Artificial Sequence
<220> FEATURE:
<223> OTHER INFORMATION: CF98 primer

<400> SEQUENCE: 14
agagtgagtt ggaaggaagg        20

<210> SEQ ID NO 15
<211> LENGTH: 20
<212> TYPE: DNA
<213> ORGANISM: Artificial Sequence
<220> FEATURE:
<223> OTHER INFORMATION: CF99 primer

<400> SEQUENCE: 15
agctcgtaag cgtcgttacc        20

<210> SEQ ID NO 16
<211> LENGTH: 20
<212> TYPE: DNA
<213> ORGANISM: Artificial Sequence
<220> FEATURE:
<223> OTHER INFORMATION: CF90 primer

<400> SEQUENCE: 16
ctagtttctc ggtactatgc        20

<210> SEQ ID NO 17
<211> LENGTH: 20
<212> TYPE: DNA
<213> ORGANISM: Artificial Sequence
<220> FEATURE:
<223> OTHER INFORMATION: CF91 primer

<400> SEQUENCE: 17
gagttgacta atgttgtggg        20

<210> SEQ ID NO 18
<211> LENGTH: 20
<212> TYPE: DNA
<213> ORGANISM: Artificial Sequence
<220> FEATURE:
<223> OTHER INFORMATION: CF100 primer

<400> SEQUENCE: 18
aaagctttga agaaaaatgc                                                   20

<210> SEQ ID NO 19
<211> LENGTH: 20
<212> TYPE: DNA
<213> ORGANISM: Artificial Sequence
<220> FEATURE:
<223> OTHER INFORMATION: CF101 primer

<400> SEQUENCE: 19
gcaaggggta ggatcgatcc                                                   20

<210> SEQ ID NO 20
<211> LENGTH: 24
<212> TYPE: DNA
<213> ORGANISM: Artificial Sequence
<220> FEATURE:
<223> OTHER INFORMATION: CF123 primer

<400> SEQUENCE: 20
attcgagctc ggtacctacg tact                                              24

<210> SEQ ID NO 21
<211> LENGTH: 24
<212> TYPE: DNA
<213> ORGANISM: Artificial Sequence
<220> FEATURE:
<223> OTHER INFORMATION: CF126 primer

<400> SEQUENCE: 21
cccgggcacg tgggatcctc taga                                              24

<210> SEQ ID NO 22
<211> LENGTH: 17
<212> TYPE: DNA
<213> ORGANISM: Artificial Sequence
<220> FEATURE:
<223> OTHER INFORMATION: M13 Forward primer

<400> SEQUENCE: 22
gtaaaacgac ggccagt                                                      17

<210> SEQ ID NO 23
<211> LENGTH: 16
<212> TYPE: DNA
<213> ORGANISM: Artificial Sequence
<220> FEATURE:
<223> OTHER INFORMATION: M13 Reverse primer

<400> SEQUENCE: 23
aacagctatg accatg                                                       16

<210> SEQ ID NO 24
<211> LENGTH: 19
<212> TYPE: DNA
<213> ORGANISM: Artificial Sequence
<220> FEATURE:
<223> OTHER INFORMATION: CF129 primer

<400> SEQUENCE: 24
gtgtttatgc ttaaatgcg                                                    19

<210> SEQ ID NO 25
<211> LENGTH: 20

```
<212> TYPE: DNA
<213> ORGANISM: Artificial Sequence
<220> FEATURE:
<223> OTHER INFORMATION: CF130 primer

<400> SEQUENCE: 25
tcctcttgca tttgtgtctc                                          20

<210> SEQ ID NO 26
<211> LENGTH: 19
<212> TYPE: DNA
<213> ORGANISM: Artificial Sequence
<220> FEATURE:
<223> OTHER INFORMATION: CF131 primer

<400> SEQUENCE: 26
atcttcctat tattatagc                                           19

<210> SEQ ID NO 27
<211> LENGTH: 31
<212> TYPE: DNA
<213> ORGANISM: Artificial Sequence
<220> FEATURE:
<223> OTHER INFORMATION: CF104 oligonucleotide

<400> SEQUENCE: 27
gtattaatta aggccggcca ggcccgggta c                             31

<210> SEQ ID NO 28
<211> LENGTH: 31
<212> TYPE: DNA
<213> ORGANISM: Artificial Sequence
<220> FEATURE:
<223> OTHER INFORMATION: CF105 oligonucleotide

<400> SEQUENCE: 28
gtacccgggc ctggccggcc ttaattaata c                             31

<210> SEQ ID NO 29
<211> LENGTH: 45
<212> TYPE: DNA
<213> ORGANISM: Artificial Sequence
<220> FEATURE:
<223> OTHER INFORMATION: CF120 oligonucleotide

<400> SEQUENCE: 29
gtaataatac gtattaatta aggccggcca ggcccgggta cgtaa              45

<210> SEQ ID NO 30
<211> LENGTH: 45
<212> TYPE: DNA
<213> ORGANISM: Artificial Sequence
<220> FEATURE:
<223> OTHER INFORMATION: CF121 oligonucleotide

<400> SEQUENCE: 30
tacgtacccg ggcctggccg gccttaatta atacgtatta ttact              45

<210> SEQ ID NO 31
<211> LENGTH: 44
<212> TYPE: DNA
<213> ORGANISM: Artificial Sequence
<220> FEATURE:
<223> OTHER INFORMATION: CF108 oligonucleotide

<400> SEQUENCE: 31
ataataatac gtattaatta aggccggcca ggcccgggta cgta               44
```

<210> SEQ ID NO 32
<211> LENGTH: 44
<212> TYPE: DNA
<213> ORGANISM: Artificial Sequence
<220> FEATURE:
<223> OTHER INFORMATION: CF109 oligonucleotide

<400> SEQUENCE: 32
tacgtacccg ggcctggccg gccttaatta atacgtatta ttat                      44

<210> SEQ ID NO 33
<211> LENGTH: 24
<212> TYPE: DNA
<213> ORGANISM: Artificial Sequence
<220> FEATURE:
<223> OTHER INFORMATION: Fragment of REP2 coding sequence - Forward

<400> SEQUENCE: 33
accatcactg agggccctaa agcg                                            24

<210> SEQ ID NO 34
<211> LENGTH: 19
<212> TYPE: DNA
<213> ORGANISM: Artificial Sequence
<220> FEATURE:
<223> OTHER INFORMATION: Fragment of REP2 coding sequence - Reverse

<400> SEQUENCE: 34
tagggccctc agtgatggt                                                  19

<210> SEQ ID NO 35
<211> LENGTH: 50
<212> TYPE: DNA
<213> ORGANISM: Artificial Sequence
<220> FEATURE:
<223> OTHER INFORMATION: CF116 oligonucleotide

<400> SEQUENCE: 35
cttaataata cgtattaatt aaggccggcc aggcccgggt acgtagggcc                50

<210> SEQ ID NO 36
<211> LENGTH: 50
<212> TYPE: DNA
<213> ORGANISM: Artificial Sequence
<220> FEATURE:
<223> OTHER INFORMATION: CF117 oligonucleotide

<400> SEQUENCE: 36
ctacgtaccc gggcctggcc ggccttaatt aatacgtatt attaagggcc                50

<210> SEQ ID NO 37
<211> LENGTH: 43
<212> TYPE: DNA
<213> ORGANISM: Artificial Sequence
<220> FEATURE:
<223> OTHER INFORMATION: CF106 oligonucleotide

<400> SEQUENCE: 37
taataatacg tattaattaa ggccggccag gcccgggtac gta                       43

<210> SEQ ID NO 38
<211> LENGTH: 43
<212> TYPE: DNA
<213> ORGANISM: Artificial Sequence
<220> FEATURE:
<223> OTHER INFORMATION: CF107 oligonucleotide -continued

```
<400> SEQUENCE: 38
tacgtacccg ggcctggccg gccttaatta atacgtatta tta                43

<210> SEQ ID NO 39
<211> LENGTH: 49
<212> TYPE: DNA
<213> ORGANISM: Artificial Sequence
<220> FEATURE:
<223> OTHER INFORMATION: CF118 oligonucleotide

<400> SEQUENCE: 39
gatcactaat aatacgtatt aattaaggcc ggccaggccc gggtacgta           49

<210> SEQ ID NO 40
<211> LENGTH: 49
<212> TYPE: DNA
<213> ORGANISM: Artificial Sequence
<220> FEATURE:
<223> OTHER INFORMATION: CF119 oligonucleotide

<400> SEQUENCE: 40
gatctacgta cccgggcctg gccggcctta attaatacgt attattagt           49

<210> SEQ ID NO 41
<211> LENGTH: 47
<212> TYPE: DNA
<213> ORGANISM: Artificial Sequence
<220> FEATURE:
<223> OTHER INFORMATION: CF114 oligonucleotide

<400> SEQUENCE: 41
agtactataa tacgtattaa ttaaggccgg ccaggcccgg gtacgta             47

<210> SEQ ID NO 42
<211> LENGTH: 47
<212> TYPE: DNA
<213> ORGANISM: Artificial Sequence
<220> FEATURE:
<223> OTHER INFORMATION: CF115 oligonucleotide

<400> SEQUENCE: 42
gtacttacgt acccgggcct ggccggcctt aattaatacg tattata             47

<210> SEQ ID NO 43
<211> LENGTH: 51
<212> TYPE: DNA
<213> ORGANISM: Artificial Sequence
<220> FEATURE:
<223> OTHER INFORMATION: CF127 oligonucleotide

<400> SEQUENCE: 43
cgtaatactt ctagggtatg atacgtatcc aatatcaaag gaaatgatag c        51

<210> SEQ ID NO 44
<211> LENGTH: 51
<212> TYPE: DNA
<213> ORGANISM: Artificial Sequence
<220> FEATURE:
<223> OTHER INFORMATION: CF128 oligonucleotide

<400> SEQUENCE: 44
gcattatgaa gatcccatac tatgcatagg ttatagtttc ctttactatc g        51

<210> SEQ ID NO 45
<211> LENGTH: 38
```

-continued

```
<212> TYPE: DNA
<213> ORGANISM: Artificial Sequence
<220> FEATURE:
<223> OTHER INFORMATION: DS299 primer

<400> SEQUENCE: 45
cgtagcggcc gcctgaaagg ggttgaccgt ccgtcggc                              38

<210> SEQ ID NO 46
<211> LENGTH: 39
<212> TYPE: DNA
<213> ORGANISM: Artificial Sequence
<220> FEATURE:
<223> OTHER INFORMATION: DS300 primer

<400> SEQUENCE: 46
cgtaaagctt cgccgcccga cagggtaaca tattatcac                             39

<210> SEQ ID NO 47
<211> LENGTH: 38
<212> TYPE: DNA
<213> ORGANISM: Artificial Sequence
<220> FEATURE:
<223> OTHER INFORMATION: DS301 primer

<400> SEQUENCE: 47
cgtaaagctt gaccacgtag taataataag tgcatggc                              38

<210> SEQ ID NO 48
<211> LENGTH: 41
<212> TYPE: DNA
<213> ORGANISM: Artificial Sequence
<220> FEATURE:
<223> OTHER INFORMATION: DS302 primer

<400> SEQUENCE: 48
cgtactgcag attggatagt gattagagtg tatagtcccg g                          41

<210> SEQ ID NO 49
<211> LENGTH: 18
<212> TYPE: DNA
<213> ORGANISM: Artificial Sequence
<220> FEATURE:
<223> OTHER INFORMATION: DS303 primer

<400> SEQUENCE: 49
ggagcgacaa acctttcg                                                    18

<210> SEQ ID NO 50
<211> LENGTH: 20
<212> TYPE: DNA
<213> ORGANISM: Artificial Sequence
<220> FEATURE:
<223> OTHER INFORMATION: DS304 primer

<400> SEQUENCE: 50
accgtaataa aagatggctg                                                  20

<210> SEQ ID NO 51
<211> LENGTH: 24
<212> TYPE: DNA
<213> ORGANISM: Artificial Sequence
<220> FEATURE:
<223> OTHER INFORMATION: DS305 primer

<400> SEQUENCE: 51
catcttgtgt gtgagtatgg tcgg                                             24
```

<210> SEQ ID NO 52
<211> LENGTH: 18
<212> TYPE: DNA
<213> ORGANISM: Artificial Sequence
<220> FEATURE:
<223> OTHER INFORMATION: DS306 primer

<400> SEQUENCE: 52
cccaggataa ttttcagg                                                    18

<210> SEQ ID NO 53
<211> LENGTH: 29
<212> TYPE: DNA
<213> ORGANISM: Artificial Sequence
<220> FEATURE:
<223> OTHER INFORMATION: DS230 primer

<400> SEQUENCE: 53
tagcgaattc aatcagtaaa aatcaacgg                                        29

<210> SEQ ID NO 54
<211> LENGTH: 30
<212> TYPE: DNA
<213> ORGANISM: Artificial Sequence
<220> FEATURE:
<223> OTHER INFORMATION: DS231 primer

<400> SEQUENCE: 54
gtcaaagctt caaaaaaaga aaagctccgg                                       30

<210> SEQ ID NO 55
<211> LENGTH: 38
<212> TYPE: DNA
<213> ORGANISM: Artificial Sequence
<220> FEATURE:
<223> OTHER INFORMATION: DS232 primer

<400> SEQUENCE: 55
tagcggatcc gaattcggcg gttgtttgca agaccgag                              38

<210> SEQ ID NO 56
<211> LENGTH: 34
<212> TYPE: DNA
<213> ORGANISM: Artificial Sequence
<220> FEATURE:
<223> OTHER INFORMATION: DS233 primer

<400> SEQUENCE: 56
gtcaaagctt taaagataat gctaaatcat ttgg                                  34

<210> SEQ ID NO 57
<211> LENGTH: 35
<212> TYPE: DNA
<213> ORGANISM: Artificial Sequence
<220> FEATURE:
<223> OTHER INFORMATION: DS234 primer

<400> SEQUENCE: 57
tgacaagctt tcggtcgaaa aaagaaaagg agagg                                 35

<210> SEQ ID NO 58
<211> LENGTH: 31
<212> TYPE: DNA
<213> ORGANISM: Artificial Sequence
<220> FEATURE:
<223> OTHER INFORMATION: DS235 primer -continued

<400> SEQUENCE: 58
tgacaagctt gatcttttat gcttgctttt c                               31

<210> SEQ ID NO 59
<211> LENGTH: 18
<212> TYPE: DNA
<213> ORGANISM: Artificial Sequence
<220> FEATURE:
<223> OTHER INFORMATION: DS236 primer

<400> SEQUENCE: 59
aatagttcag gcactccg                                              18

<210> SEQ ID NO 60
<211> LENGTH: 17
<212> TYPE: DNA
<213> ORGANISM: Artificial Sequence
<220> FEATURE:
<223> OTHER INFORMATION: DS237 primer

<400> SEQUENCE: 60
tggaaggcaa gagagcc                                               17

<210> SEQ ID NO 61
<211> LENGTH: 18
<212> TYPE: DNA
<213> ORGANISM: Artificial Sequence
<220> FEATURE:
<223> OTHER INFORMATION: DS238 primer

<400> SEQUENCE: 61
taaaatgtaa gctctcgg                                              18

<210> SEQ ID NO 62
<211> LENGTH: 17
<212> TYPE: DNA
<213> ORGANISM: Artificial Sequence
<220> FEATURE:
<223> OTHER INFORMATION: DS239 primer

<400> SEQUENCE: 62
ccaaccaagt atttcgg                                               17

<210> SEQ ID NO 63
<211> LENGTH: 20
<212> TYPE: DNA
<213> ORGANISM: Artificial Sequence
<220> FEATURE:
<223> OTHER INFORMATION: CED005 primer

<400> SEQUENCE: 63
gagctgacag ggaaatggtc                                            20

<210> SEQ ID NO 64
<211> LENGTH: 20
<212> TYPE: DNA
<213> ORGANISM: Artificial Sequence
<220> FEATURE:
<223> OTHER INFORMATION: CED006 primer

<400> SEQUENCE: 64
tacgaggata cggagagagg                                            20

<210> SEQ ID NO 65
<211> LENGTH: 90

-continued

<212> TYPE: DNA
<213> ORGANISM: Artificial Sequence
<220> FEATURE:
<223> OTHER INFORMATION: DS248 primer

<400> SEQUENCE: 65
gtcagaattc gagctctacg tattaattaa ggccggccag cccgggcta gtctcttttt    60 ccaatttgcc accgtgtagc attttgttgt                                    90

<210> SEQ ID NO 66
<211> LENGTH: 59
<212> TYPE: DNA
<213> ORGANISM: Artificial Sequence
<220> FEATURE:
<223> OTHER INFORMATION: DS249 primer

<400> SEQUENCE: 66
gtcaggatcc tacgtacccg gggatatcat tatcatcttt gtcgtggtca tcttgtgtg    59

<210> SEQ ID NO 67
<211> LENGTH: 54
<212> TYPE: DNA
<213> ORGANISM: Artificial Sequence
<220> FEATURE:
<223> OTHER INFORMATION: DS250 primer

<400> SEQUENCE: 67
gtcaggatcc tacgtacccg ggtaaggcgt tcgtgcagtg tgacgaatat agcg          54

<210> SEQ ID NO 68
<211> LENGTH: 99
<212> TYPE: DNA
<213> ORGANISM: Artificial Sequence
<220> FEATURE:
<223> OTHER INFORMATION: DS251 primer

<400> SEQUENCE: 68
gtcagaattc gagctctacg tattaattaa ggccggccag cccgggccc gtatggacat    60 acatatatat atatatatat atatatattt tgttacgcg                          99

<210> SEQ ID NO 69
<211> LENGTH: 90
<212> TYPE: DNA
<213> ORGANISM: Artificial Sequence
<220> FEATURE:
<223> OTHER INFORMATION: DS252 primer

<400> SEQUENCE: 69
gtcagaattc gagctctacg tattaattaa ggccggccag cccgggctt gttgcaagca    60 gcatgtctaa ttggtaattt taaagctgcc                                    90

<210> SEQ ID NO 70
<211> LENGTH: 103
<212> TYPE: DNA
<213> ORGANISM: Artificial Sequence
<220> FEATURE:
<223> OTHER INFORMATION: DS267 primer

<400> SEQUENCE: 70
gtcagaattc gagctctacg tattaattaa ggccggccag cccgggccc gtatggacat    60 acatatatat atatatatat atatatatat attttgttac gcg                     103

<210> SEQ ID NO 71
<211> LENGTH: 17

<212> TYPE: DNA
<213> ORGANISM: Artificial Sequence
<220> FEATURE:
<223> OTHER INFORMATION: DS253 primer

<400> SEQUENCE: 71
cctccctgct gctcgcc                                                          17

<210> SEQ ID NO 72
<211> LENGTH: 18
<212> TYPE: DNA
<213> ORGANISM: Artificial Sequence
<220> FEATURE:
<223> OTHER INFORMATION: DS254 primer

<400> SEQUENCE: 72
ctgtaagaac atggctcc                                                         18

<210> SEQ ID NO 73
<211> LENGTH: 18
<212> TYPE: DNA
<213> ORGANISM: Artificial Sequence
<220> FEATURE:
<223> OTHER INFORMATION: DS255 primer

<400> SEQUENCE: 73
ctcgatcgat tacgaggg                                                         18

<210> SEQ ID NO 74
<211> LENGTH: 17
<212> TYPE: DNA
<213> ORGANISM: Artificial Sequence
<220> FEATURE:
<223> OTHER INFORMATION: DS256 primer

<400> SEQUENCE: 74
aagaaagccg atatcgc                                                          17

<210> SEQ ID NO 75
<211> LENGTH: 18
<212> TYPE: DNA
<213> ORGANISM: Artificial Sequence
<220> FEATURE:
<223> OTHER INFORMATION: DS257 primer

<400> SEQUENCE: 75
caactctctg aagaggcg                                                         18

<210> SEQ ID NO 76
<211> LENGTH: 17
<212> TYPE: DNA
<213> ORGANISM: Artificial Sequence
<220> FEATURE:
<223> OTHER INFORMATION: DS258 primer

<400> SEQUENCE: 76
caacgccaca tccgacg                                                          17

<210> SEQ ID NO 77
<211> LENGTH: 19
<212> TYPE: DNA
<213> ORGANISM: Artificial Sequence
<220> FEATURE:
<223> OTHER INFORMATION: DS259 primer

<400> SEQUENCE: 77
gtaattctga tcactttgg                                                        19

-continued

<210> SEQ ID NO 78
<211> LENGTH: 21
<212> TYPE: DNA
<213> ORGANISM: Artificial Sequence
<220> FEATURE:
<223> OTHER INFORMATION: DS260 primer

<400> SEQUENCE: 78
gcacttatta ttactacgtg g                                            21

<210> SEQ ID NO 79
<211> LENGTH: 19
<212> TYPE: DNA
<213> ORGANISM: Artificial Sequence
<220> FEATURE:
<223> OTHER INFORMATION: DS261 primer

<400> SEQUENCE: 79
gttttccttg atgaagtcg                                               19

<210> SEQ ID NO 80
<211> LENGTH: 18
<212> TYPE: DNA
<213> ORGANISM: Artificial Sequence
<220> FEATURE:
<223> OTHER INFORMATION: DS262 primer

<400> SEQUENCE: 80
gtgaccacac catggggc                                                18

<210> SEQ ID NO 81
<211> LENGTH: 18
<212> TYPE: DNA
<213> ORGANISM: Artificial Sequence
<220> FEATURE:
<223> OTHER INFORMATION: DS263 primer

<400> SEQUENCE: 81
gttgccggcg tgtctgcc                                                18

<210> SEQ ID NO 82
<211> LENGTH: 18
<212> TYPE: DNA
<213> ORGANISM: Artificial Sequence
<220> FEATURE:
<223> OTHER INFORMATION: DS264 primer

<400> SEQUENCE: 82
ttgaaatcat cgtctgcg                                                18

<210> SEQ ID NO 83
<211> LENGTH: 17
<212> TYPE: DNA
<213> ORGANISM: Artificial Sequence
<220> FEATURE:
<223> OTHER INFORMATION: DS265 primer

<400> SEQUENCE: 83
cggcagttct aggtccc                                                 17

<210> SEQ ID NO 84
<211> LENGTH: 18
<212> TYPE: DNA
<213> ORGANISM: Artificial Sequence
<220> FEATURE:
<223> OTHER INFORMATION: DS266 primer

```
<400> SEQUENCE: 84
ccacagcctc ttgttggg                                                      18

<210> SEQ ID NO 85
<211> LENGTH: 17
<212> TYPE: DNA
<213> ORGANISM: Artificial Sequence
<220> FEATURE:
<223> OTHER INFORMATION: M13/pUC primer (-40)

<400> SEQUENCE: 85
gttttcccag tcacgac                                                       17
```